US009498543B2

(12) United States Patent
Abrams et al.

(10) Patent No.: US 9,498,543 B2
(45) Date of Patent: Nov. 22, 2016

(54) ANTIBODY DRUG CONJUGATES

(71) Applicants: Tinya Abrams, Richmond, CA (US); Steven Bruce Cohen, San Diego, CA (US); Christie P. Fanton, Oakland, CA (US); Thomas Huber, Basel (CH); Kathy Miller, San Francisco, CA (US); Siew Ho Schleyer, El Cerrito, CA (US); Kathrin Ulrike Tissot-Daguette, Neuried (DE); Catrin Finner, Taxetweg (DE)

(72) Inventors: Tinya Abrams, Richmond, CA (US); Steven Bruce Cohen, San Diego, CA (US); Christie P. Fanton, Oakland, CA (US); Thomas Huber, Basel (CH); Kathy Miller, San Francisco, CA (US); Siew Ho Schleyer, El Cerrito, CA (US); Kathrin Ulrike Tissot-Daguette, Neuried (DE); Catrin Finner, Taxetweg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/205,915

(22) Filed: Mar. 12, 2014

(65) Prior Publication Data
US 2014/0271688 A1 Sep. 18, 2014

Related U.S. Application Data

(60) Provisional application No. 61/793,641, filed on Mar. 15, 2013.

(51) Int. Cl.
| *C07K 16/00* | (2006.01) |
| *A61K 47/48* | (2006.01) |
| *A61K 49/00* | (2006.01) |
| *A61K 51/10* | (2006.01) |
| *C07K 16/28* | (2006.01) |
| *A61K 45/06* | (2006.01) |
| *A61K 31/537* | (2006.01) |
| *A61K 47/12* | (2006.01) |
| *A61K 47/26* | (2006.01) |
| *C07K 16/32* | (2006.01) |
| *A61K 39/00* | (2006.01) |

(52) U.S. Cl.
CPC ....... *A61K 47/48561* (2013.01); *A61K 31/537* (2013.01); *A61K 45/06* (2013.01); *A61K 47/12* (2013.01); *A61K 47/26* (2013.01); *A61K 47/4863* (2013.01); *A61K 47/48376* (2013.01); *A61K 47/48384* (2013.01); *A61K 47/48446* (2013.01); *A61K 47/48592* (2013.01); *A61K 47/48615* (2013.01); *A61K 47/48715* (2013.01); *A61K 49/00* (2013.01); *A61K 51/103* (2013.01); *A61K 51/1093* (2013.01); *C07K 16/2803* (2013.01); *C07K 16/2863* (2013.01); *C07K 16/32* (2013.01); *A61K 2039/505* (2013.01); *C07K 2317/14* (2013.01); *C07K 2317/21* (2013.01); *C07K 2317/24* (2013.01); *C07K 2317/30* (2013.01); *C07K 2317/33* (2013.01); *C07K 2317/34* (2013.01); *C07K 2317/55* (2013.01); *C07K 2317/565* (2013.01); *C07K 2317/73* (2013.01); *C07K 2317/732* (2013.01); *C07K 2317/76* (2013.01); *C07K 2317/77* (2013.01); *C07K 2317/92* (2013.01)

(58) Field of Classification Search
CPC ...................................................... A61K 47/48
USPC ...................................................... 424/181.1
See application file for complete search history.

(56) References Cited

U.S. PATENT DOCUMENTS

| 3,896,111 A | 7/1975 | Kupchan |
| 4,137,230 A | 1/1979 | Hashimoto |
| 4,151,042 A | 4/1979 | Higashide |
| 4,248,870 A | 2/1981 | Miyashita |
| 4,256,746 A | 3/1981 | Miyashita |
| 4,260,608 A | 4/1981 | Miyashita |
| 4,265,814 A | 5/1981 | Hashimoto |
| 4,294,757 A | 10/1981 | Asai |
| 4,307,016 A | 12/1981 | Asai |
| 4,308,268 A | 12/1981 | Miyashita |
| 4,308,269 A | 12/1981 | Miyashita |
| 4,309,428 A | 1/1982 | Miyashita |
| 4,313,946 A | 2/1982 | Powell |
| 4,315,929 A | 2/1982 | Freedman |
| 4,317,821 A | 3/1982 | Miyashita |
| 4,322,348 A | 3/1982 | Asai |
| 4,331,598 A | 5/1982 | Hasegawa |
| 4,361,650 A | 11/1982 | Asai |
| 4,362,663 A | 12/1982 | Kida |
| 4,364,866 A | 12/1982 | Asai |
| 4,371,533 A | 2/1983 | Akimoto |
| 4,424,219 A | 1/1984 | Hashimoto |

(Continued)

FOREIGN PATENT DOCUMENTS

WO      WO 01/05950       1/2001

OTHER PUBLICATIONS

Kindblom et al., "Gastrointestinal Pacemaker Cell Tumor (GIPACT) Gastrointestinal Stromal Tumors Show Phenotypic Characteristics of the interstitial Cells of Cajal" *Am J. Path.* 1998 152(5):1259.

(Continued)

*Primary Examiner* — Yan Xiao
(74) *Attorney, Agent, or Firm* — David A. Carpenter

(57) ABSTRACT

The present invention relates to anti-cKIT antibodies, antibody fragments, antibody drug conjugates, and their uses for the treatment of cancer.

15 Claims, 45 Drawing Sheets

(56) References Cited

U.S. PATENT DOCUMENTS

| | | | |
|---|---|---|---|
| 4,450,254 | A | 5/1984 | Isley |
| 5,208,020 | A | 5/1993 | Chari |
| 5,489,516 | A | 2/1996 | Broudy |
| 5,545,533 | A | 8/1996 | Bartke |
| 5,808,002 | A | 9/1998 | Buhring |
| 6,441,163 | B1 | 8/2002 | Chari |
| 7,368,565 | B2 | 5/2008 | Chari |
| 7,811,572 | B2 | 10/2010 | Dai |
| 7,915,391 | B2 | 3/2011 | Ng |
| 8,163,888 | B2 | 4/2012 | Steeves |
| 8,436,150 | B2 | 5/2013 | Ng |
| 8,552,157 | B2 | 10/2013 | Amatulli |
| 2006/0182750 | A1 | 8/2006 | Chari |
| 2008/0145374 | A1 | 6/2008 | Steeves |
| 2011/0003969 | A1 | 1/2011 | Kellogg |
| 2011/0166319 | A1 | 7/2011 | Dai |
| 2012/0189633 | A1 | 7/2012 | Hadari |
| 2012/0253021 | A1 | 10/2012 | Li |
| 2012/0259100 | A1 | 10/2012 | Jin |
| 2012/0288506 | A1* | 11/2012 | Amatulli ............ A61K 31/404 424/139.1 |
| 2013/0011406 | A1 | 1/2013 | Hadari |
| 2014/0065168 | A1 | 3/2014 | Hadari et al. |

OTHER PUBLICATIONS

Besmer et al., "A New Acute Transforming Feline Retrovirus with fms Homology Specifies a C-terminally Truncated Version of the c-fms Protein that is Different from SM-Feline Sacreonla Virus v-fms Protein" *J. Virol.* 60(1):194-203, 1986.

Hirota et al. "Gain-of-Function Mutations of c-kit in Human Gastrointestinal Stromal Tumors" *Science* 279:577, 1998.

Espositio et al., "The Stem Cell Factor-c-kit System and Mast Cells in Human Pancreatic Cancer" *Laboratory Investigation* 82(11):1481, 2002.

Gadd et al., "A Murine Monoclonal Antibody Specific for a Cell-Surface Antigen Expressed by a Sub-Group of Human Myeloid Leukaemias" *Leukemia Research* 9(11):1329-1336, 1985.

Broudy et al., "Isolation and Characterization of a Monoclonal Antibody that Recognizes the Human c-kit Receptor" *Blood* 1992 79(2)338.

Edris et al,. "Anti-KIT Monoclonal Antibody inhibits Itnatinib-Resistant Gastroinestinal Stromal Tumor Growth" *Proc. Natl. Acad. Sci. USA* 110(9)3501-3506, Feb. 26, 2013.

Lambert, "Drug-Conjugated Monoclonal Antibodies for the Treatment of Cancer" *Current Opinion in Pharmacology* 5:543-549, 2005.

Chari et al., "Immunoconjugates Containing Novel Maytansinoids: Promising Anticancer Drugs" *Cancer Research* 52 :127-131, 1992.

Liu et al., "Eradicaton of Large Colon Tumor Xenografts by Targeted Delivery of Maytansinoids" *Proc. Natl. Acad. Sci.* 93:8618-8623, 1996.

Prassler et al., "In vitro Affinity Maturation of HuCAL Antibodies: Complementarity Determining Region Exchange and RapMAT Technology" *Future Med. Immuno.* 1(4):571-583, 2009.

Virnekas et al., "Trinucleotide Phosphoramidites: Ideal Reagents for the Synthesis of Mixed Oligonucleotides for Random Mutagenesis" *Nucleic Acids Research* 22(25):5600-5607, 1994.

Friquet et al., "Measurements of the True Affinity Constant in Solution of Antigen-Antibody Complexes by Enzyme-Linked Immunosorbent Assay" *Journal of Immunilogical Methods* 77:305-319, 1985.

Haenel et al., "Characterization of High-Affinity Antibodies by Electrochemiluminescence-Based Equilibrium Titration" *Anal. Biochem.* 339(1):182-184, 2005.

Abraham et al., "Determination of Binding Constants of Diabodies Directed Against Prostate-Specific Antigen Using Electrochemiluminescence-Based Immunoassays" *Journal of Molecular Recognition* 9:456-461, 1996.

Nagano et al., "Ultrastructural Analysis of Platelet-Like Particles from a Human Megakaryocytic Leukemia Cell Line (CMK11-5)" *International Journal of Hematology* 56:67-78, 1992.

Yuzawa et al., "Structural Basis for Activation of the Receptor Tyrosine Kinase KIT by Stem Cell Factor" *Cell* 130:323-334, 2007.

Saito et al, "Culture of Human Mast Cells from Peripheral Blood Progenitors" *Nature Protocols* 1(4):2178-2183, 2006.

Singh et al., "Antibody-Cytotoxic Agent Conjugates: Preparation and Characterization" *Therapeutic Antibodies: Methods and Protocols* 525:445-457, 2009.

Kawai et al., "Chemical Modification of Ansamitocins. III. Synthesis and Biological Effects of 3-Acyl Esters of Maytansinol" *Chem. Pharm. Bull.*, 32(9):3441-3451, 1984.

Saito et al., "Drug Delivery Strategy Utilizing Conjugation via Reversible Disulfide Linkages: Role and Site of Cellular Reducing Activities" *Advanced Drug Delivery Reviews* 55:199-215, 2003.

Trail et al., "Monoclonal Antibody Drug Immunoconjugates for Targeted Treatment of Cancer" *Cancer Immunol. Immunother.* 52:328-337, 2003.

Payne, "Progress in Immunoconjugate Cancer Therapeutics" *Cancer Cell* 3:207-212, 2003.

Allen, "Ligand-Targeted Therapeutic in Anticancer Therapy" *Nat. Rev. Cancer* 2:750-763, 2002.

Pastan and Kreitman, "Immunotoxins in Cancer Therapv" *Curr. Opin. Investig. Drugs* 3:1089-1091, 2002.

Senter and Springer, "Selective Activation of Anticancer Prodrugs by Monoclonal Antibody-Enzyme Conjugates" *Advanced Drug Delivery Reviews* 53:247-264, 2001.

DeNardo et al, "Comparison of 1,4,7,10-tetraazacyclododecane-N,N',N'',N'''-tetraacetic acid (DOTA)-peptide-ChL6, a Novel Immunoconjugate with Catabolizable Linker, to 2-iminothiolane-2-[p-(bromoacetamido)benzyl]-DOTA-ChL6 in Breast Cancer Xenografts" *Clinical Cancer Research* 4(10):2483-90, 1998.

Peterson et al., "Enzymatic Cleavage of Peptide-Linked Radiolabels from Immunoconjugates" *Bioconjugate Chemistry* 10(4):553-557, 1999.

Zimmerman et al., "A Triglycine Linker Improves Tumor Uptake and Biodistributions of 67-Cu-Labeled Anti-Neuroblastoma MAb chCE7 F9ab')$_2$ Fragments" *Nuclear Medicine Biolology* 26(8):943-950, 1999.

Trouet et al., "A Covalent Linkaze Between Daunorubicin and Proteins that is Stable in Serum and Reversible by Lysosomal Hydrolases, as Required for a Lysosomotropic Drug-Carrier Conjugate: In vitro and in vivo Studies" *Proc. Natl. Acad. Sci. USA* 79:626-629, 1982.

Umemoto et al., "Preparation and In vitro Cytotoxicity of a Methotrexate-anti-MM46 Monoclonal Antibody Conjugate via an Oligopeptide Spacer" *Int. J. Cancer* 43:677-684, 1989.

Knappik et al., "Fully Synthetic Human Combinatorial Antibody Libraries (HuCAL) Based on Modular Consensus Frameworks and CDRs Randomized with Trinucleotides" *J. Mol. Biol.* 296:57-86, 2000.

Reshetnyak et al., "Structural Basis for KIT Receptor Tyrosine Kinase Inhibition by Antibodies Targeting the D4 Membrane-Proximal Region" *Proc. Natl. Acad. Sci.* 110(44):17832-17837, Oct. 29, 2013.

Katz et al., "Anti-KIT Designer T Cells for the Treatment of Gastrointestinal Stromal Tumor" *Journal of Translational Medicine* 11:46, 2013.

* cited by examiner

FIGURE 1

Activity of c-Kit ADC on a panel of cell lines

| ADC | GIST T-1 | | GIST882 | | GIST430 | | NCI-H526 | | NCI-H1048 | | Kasumi-6 | | Kasumi-1 | | MDA-MB-453 (c-Kit neg) | |
|---|---|---|---|---|---|---|---|---|---|---|---|---|---|---|---|---|
| | IC50 nM | Amax % | IC50 nM | Amax % | IC50 nM | Amax % | IC50 nM | Amax % | IC50 nM | Amax % | IC50 nM | Amax % | IC50 nM | Amax % | IC50 nM | Amax % |
| IgG-MCC-DM1 | 13.622 | 82 | >68 | 27 | 33.121 | 53 | 35.738 | 99 | 12.141 | 98 | 19.200 | 78 | 8.300 | 99 | 11.383 | 95 |
| NEG024-MCC-DM1 | 0.021 | 72 | 0.721 | 66 | 0.038 | 53 | 0.074 | 99 | 0.737 | 98 | 5.262 | 78 | 8.493 | 99 | 22.772 | 92 |
| NEG085-MCC-DM1 | 0.009 | 76 | 0.471 | 71 | 0.036 | 59 | 0.026 | 99 | 0.547 | 98 | 0.637 | 80 | 4.824 | 99 | 46.827 | 90 |
| NEG086-MCC-DM1 | 0.013 | 74 | 0.430 | 69 | 0.056 | 54 | | | 0.828 | 98 | 0.522 | 80 | 4.223 | 99 | 16.922 | 91 |
| NEG087-MCC-DM1 | 0.008 | 78 | 0.411 | 70 | 0.046 | 57 | | | 1.503 | 98 | 3.242 | 80 | 6.073 | 99 | 45.431 | 90 |
| 20376-MCC-DM1 | 0.051 | 69 | 1.000 | 69 | 0.038 | 54 | 0.074 | 99 | 1.340 | 97 | 1.505 | 79 | 1.329 | 100 | 2.690 | 95 |

FIGURE 2

Comparison of different linkers/toxins on multiple cell lines

| Cell Line | Indication | 9P3-MCC-DM1 GI50 (nM) | 9P3-MCC-DM1 Amax (%) | 9P3-SPDB-DM4 GI50 (nM) | 9P3-SPDB-DM4 Amax (%) | 9P3-CX1-1-DM1 GI50 (nM) | 9P3-CX1-1-DM1 Amax (%) | cKit status |
|---|---|---|---|---|---|---|---|---|
| CMK11-5 | AML | 0.05 | 91 | 0.07 | 92 | nd | nd | WT |
| Hel92.1.7 | AML | 0.61 | 95 | 1.26 | 94 | 7.6 | 95 | WT |
| Kasumi-1 | AML | 4 | 100 | 0.83 | 100 | 0.02 | 100 | N822K/WT |
| Kasumi-6 | AML | 1.29 | 92 | 0.91 | 94 | nd | nd | WT |
| M-O7e | AML | 0.08 | 100 | 0.11 | 99 | nd | nd | WT |
| OCI-M1 | AML | 0.11 | 99 | 0.13 | 100 | nd | nd | WT |
| SKNO1 | AML | 3.8 | 99 | 1.6 | 99 | 5.2 | 100 | N822K/N822K |
| UKE.1 | AML | 1.8 | 99 | 5.6 | 100 | nd | nd | WT |
| GIST T1 | GIST | 0.02 | 75 | 0.045 | 75 | nd | nd | Ex11del |
| GIST430 | GIST | 0.08 | 60 | 0.17 | 65 | 0.04 | 55 | Ex11del, Ex13 |
| NCI-H526 | SCLC | 0.05 | 98 | 0.17 | 98 | nd | nd | WT |
| NCI-H889 | SCLC | 0.15 | 86 | 1.47 | 84 | nd | nd | Amp |
| NCI-H1048 | SCLC | 4.3 | 99 | 2.77 | 100 | 1.45 | 100 | WT |
| NCI-H1930 | SCLC | 0.09 | 87 | 0.3 | 88 | nd | nd | Amp | c-Kit ADC activity on GIST T1 cells c-Kit ADC activity on GIST 430 cells c-Kit ADC activity on NCI-H1048 cells c-Kit ADC activity on CMK-11-5 cells c-Kit ADC activity on Uke-1 cells

Activity of NEG085, NEG024, 20376 in Proliferation Assays In SCF-Dependent Cell Line Mo7e Activity of NEG085 in Proliferation Assays in Cell Line Mo7e, treated with GM-CSF NEG085 and 20376 do not mediate in vitro ADCC c-kit ADCs do not lead to apoptosis of human primary mast cells NEG085 and 20376 do not mediate mast cell degranulation on ex vivo primary human mast cells

FIGURE 20 (TA 1A)
Co-localization of IgG1 and mitotic arrest of NEG027-MCC-DM1 in GIST T1 xenograft model
(A) Hu IgG
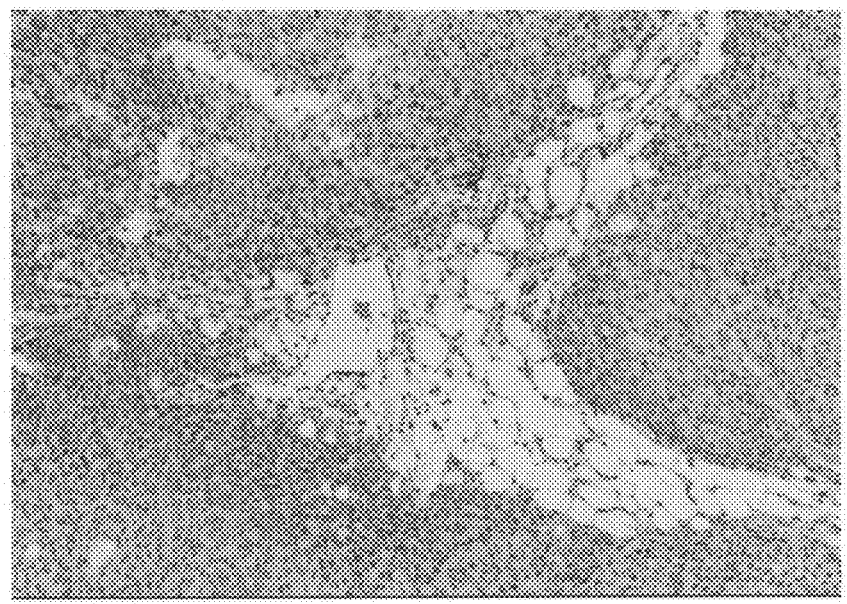
(B) P-Histone H3

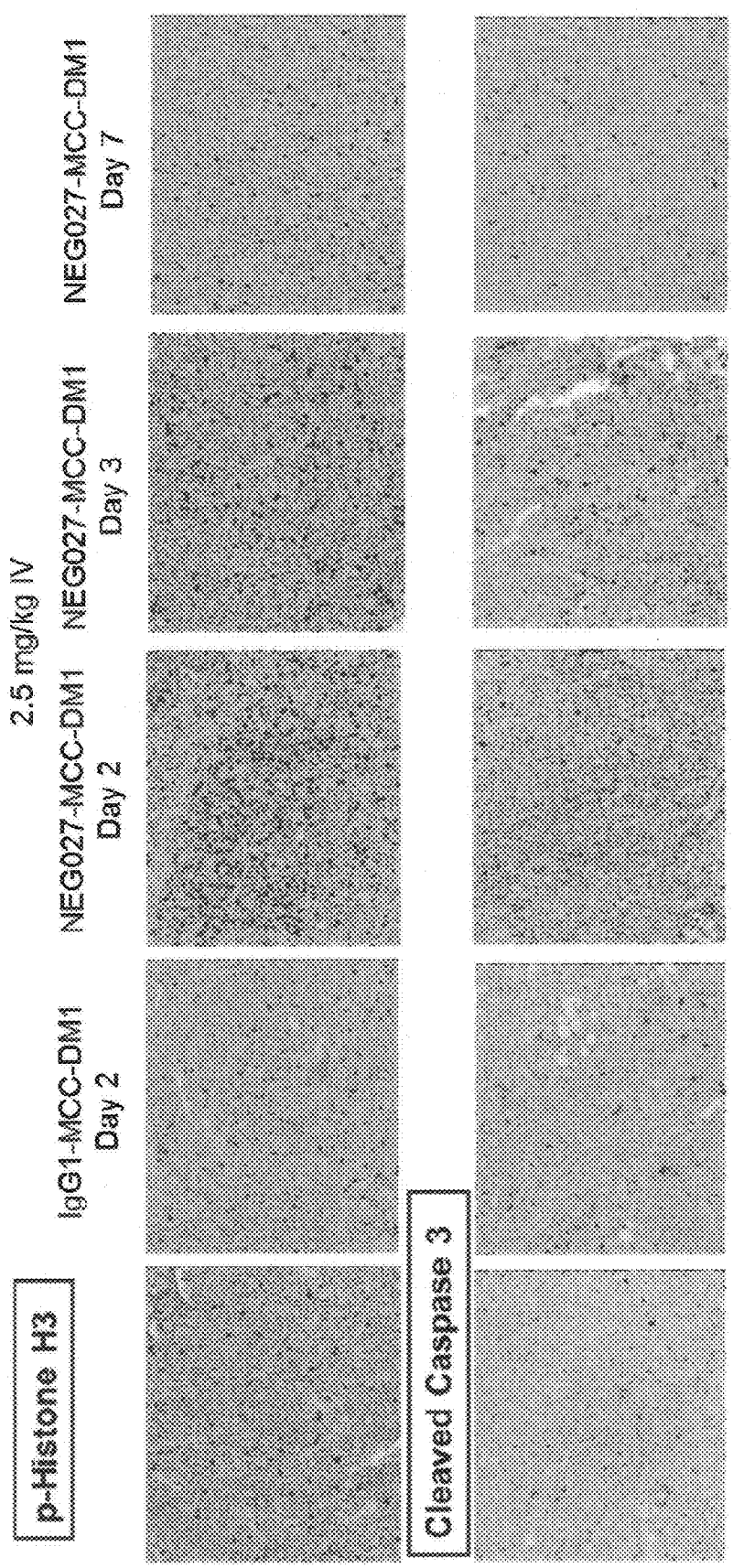

Mitotic arrest and apoptosis induction 8 days post single dose of c-Kit ADC

FIGURE 23
(A) Dose response efficacy in GIST T1 mouse xenograft
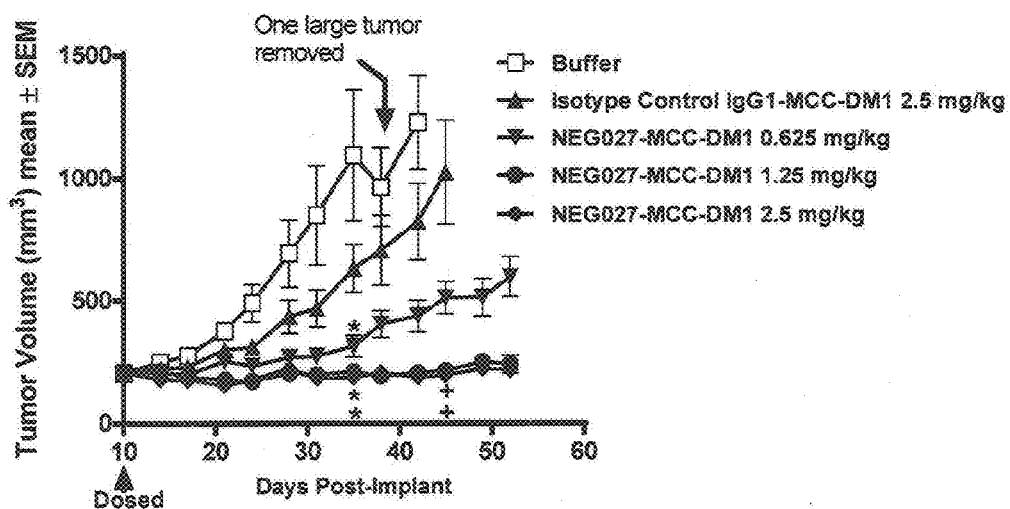
(B) *(figure legend of dosing in (A) applies to (B)), change in body weight over course of treatment
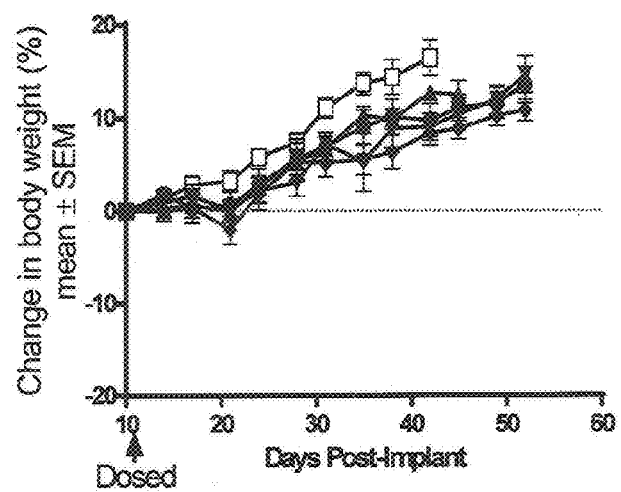

FIGURE 24 A/B
(A) anti-DM1 ELISA after dosing in a GIST T1 xenograft model
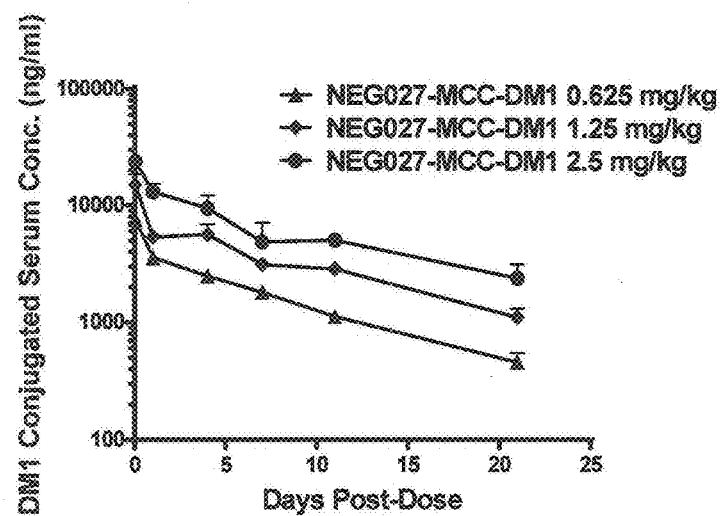
(B) anti-human IgG1 ELISA after dosing in a GIST T1 xenograft model
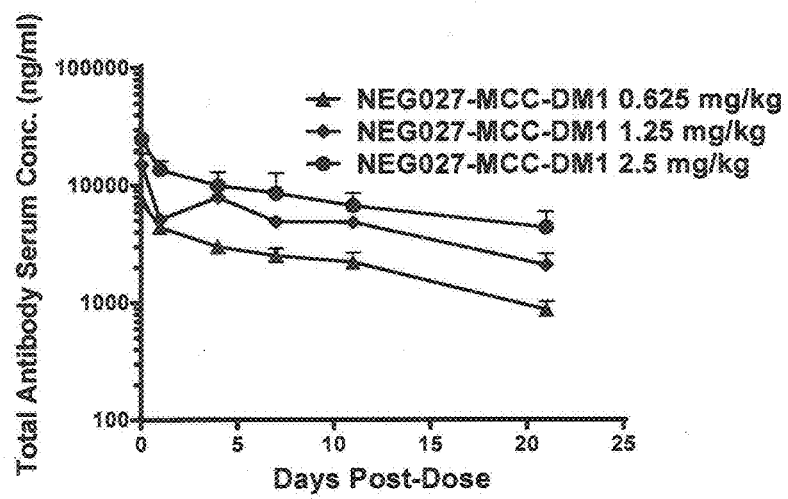

FIGURE 25

NEG027-MCC-DM1 dose response in a GIST T1 xenograft mouse model (Top graph)Day 35 data table ($p < 0.05$ vs vehicle, ANOVA/Tukey's Test) (Bottom graph Day 45 data table ($p < 0.05$ vs Grp 2 (IgG-DM1 control), ANOVA/Dun's Method)

| Group | Drug | Dose | Schedule | Mean change of tumor volume vs control (T/C) (%) | Regression (%) | Mean change of tumor volume (mm3 ± SEM) | Mean change of body weight (% ± SEM) | Survival (Survivors/ Total) |
|---|---|---|---|---|---|---|---|---|
| 1 | TBS | 0 mg/kg | single IV dose | 100 | - | 890 ± 270 | 13.7 ± 1.2 | 9/9 |
| 2 | IgG-MCC-DM1 | 2.5 mg/kg | single IV dose | 47 | - | 417 ± 95 | 10.2 ± 1.0 | 9/9 |
| 3 | NEG027-MCC-DM1 | 0.625 mg/kg | single IV dose | 12* | - | 109 ± 39 | 5.3 ± 3.2 | 9/9 |
| 4 | NEG027-MCC-DM1 | 1.25 mg/kg | single IV dose | 0* | - | 4 ± 15 | 9.0 ± 1.8 | 9/9 |
| 5 | NEG027-MCC-DM1 | 2.5 mg/kg | single IV dose | -2* | -8/1 | -18 ± 21 | 5.5 ± 1.8 | 9/9 |

| Group | Drug | Dose | Schedule | Mean change of tumor volume vs IgG control (T/C) (%) | Regression (%) | Mean change of tumor volume (mm3 ± SEM) | Mean change of body weight (% ± SEM) | Survival (Survivors/ Total) |
|---|---|---|---|---|---|---|---|---|
| 1 | TBS | 0 mg/kg | single IV dose | - | Down | 0 ± 0 | 0.0 ± 0.0 | 9/9 |
| 2 | IgG-MCC-DM1 | 2.5 mg/kg | single IV dose | - | - | 811 ± 214 | 12.5 ± 1.5 | 9/9 |
| 3 | NEG027-MCC-DM1 | 0.625 mg/kg | single IV dose | 50 | - | 381 ± 62 | 10.4 ± 1.7 | 8/9 (one removed from study on D38) |
| 4 | NEG027-MCC-DM1 | 1.25 mg/kg | single IV dose | 2* | - | 8 ± 19 | 11.1 ± 1.4 | 9/9 |
| 5 | NEG027-MCC-DM1 | 2.5 mg/kg | single IV dose | -2* | - | -14 ± 28 | 8.8 ± 1.1 | 8/9 (one removed from study D38) |

FIGURE 26
NEG027-MCC-DM1 dose response efficacy in GIST T1
(A) Group 4 pooled tumors
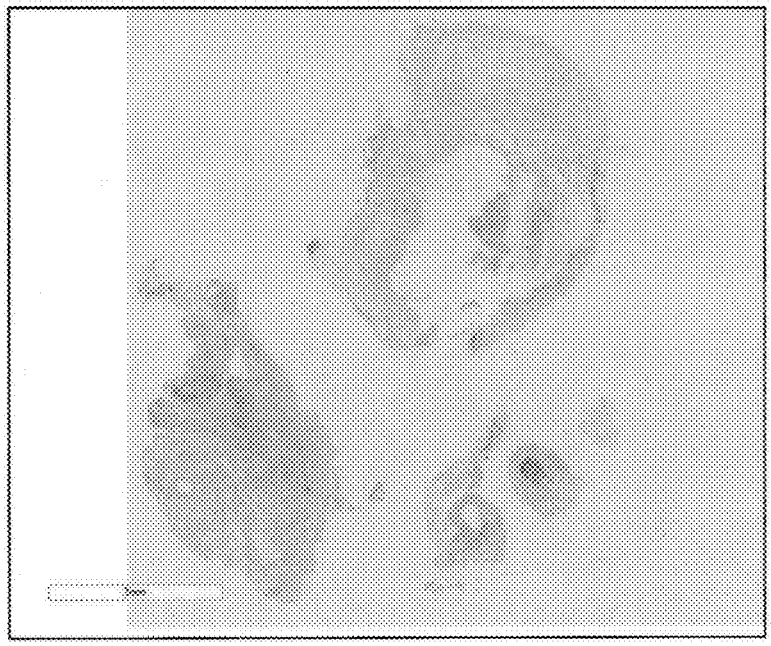
(B) Group 5 pooled tumors
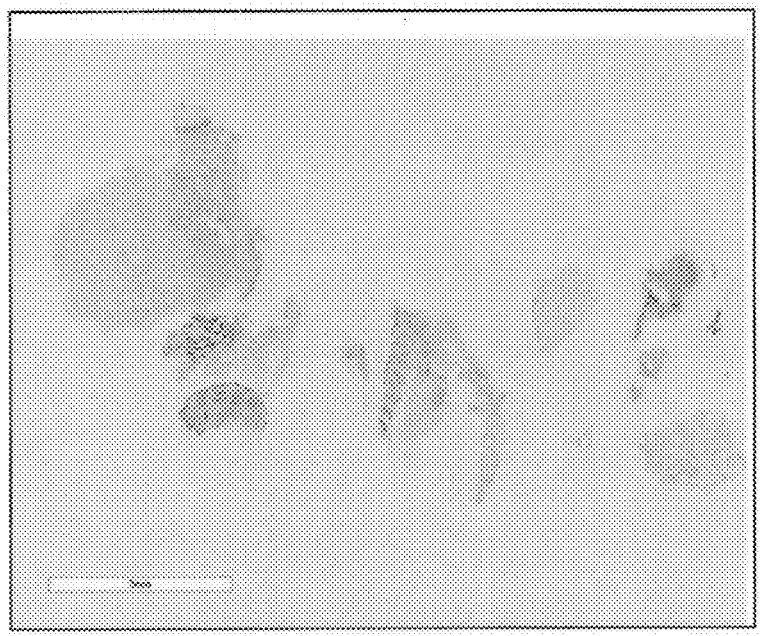

FIGURE 27
(A) Efficacy with 0.625mg/kg in a GIST T1 xenograft mouse model
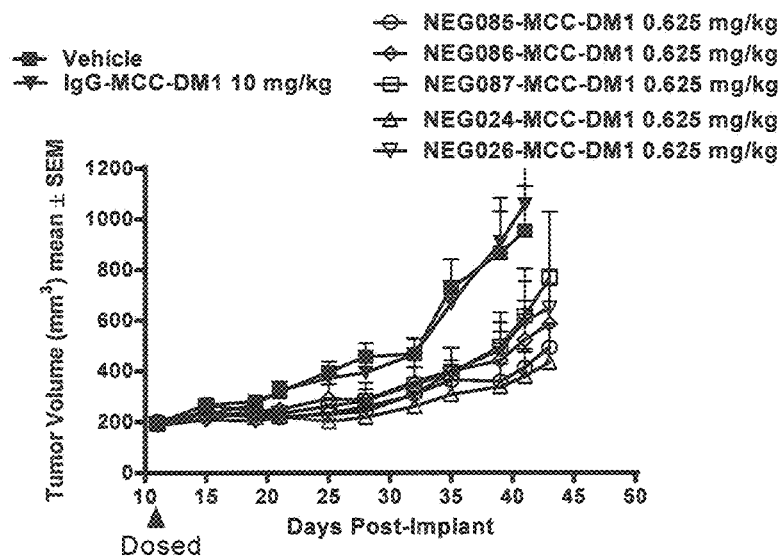
(B) change of tumor volume vs control (% T/C)
| ADC | % ΔT/ΔC (D41) |
|---|---|
| IgG1-DM1 | 114 |
| NEG085-DM1 | 28 |
| NEG086-DM1 | 43 |
| NEG087-DM1 | 56 |
| NEG024-DM1 | 23 |
| NEG026-DM1 | 54 |
(C) Change in body weight over course of treatment
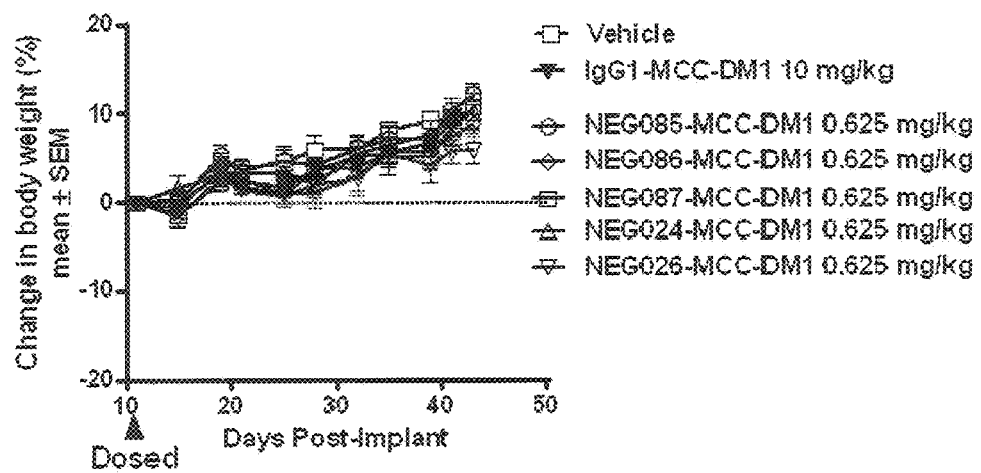

Day 41 after administration of single dose of anti-c-Kit ADC to a GIST T1 xenograft mouse

FIGURE 29

Anti-cKIT-ADC Efficacy Study (low dose) in GIST T1 Model in SCID-beige Mice

| Drug | Dose | Schedule | Tumor Response | | Host Response | |
|---|---|---|---|---|---|---|
| | | | Mean change of tumor volume vs control (T/C) (%) | Mean change of tumor volume (mm3 ± SEM) | Mean change of body weight (% ± SEM) | Survival (Survivors/total) |
| TBS | 0mg/kg | single dose IV | 100 | 757 ± 175 | 9.3 ± 1.0 | 8/8 |
| IgG-SMCC-DM1 | 10mg/kg | single dose IV | 114 | 861 ± 206 | 9.1 ± 1.0 | 8/8 |
| NEG085-SMCC-DM1 | 0.625mg/kg | single dose IV | 28 | 210 ± 56 | 10.3 ± 1.3 | 8/8 |
| NEG086-SMCC-DM1 | 0.625mg/kg | single dose IV | 43 | 325 ± 146 | 7.4 ± 1.4 | 8/8 |
| NEG087-SMCC-DM1 | 0.625mg/kg | single dose IV | 56 | 423 ± 188 | 8.4 ± 2.1 | 8/8 |
| NEG024-SMCC-DM1 | 0.625mg/kg | single dose IV | 23 | 176 ± 104 | 9.6 ± 2.0 | 8/8 |
| NEG026-SMCC-DM1 | 0.625mg/kg | single dose IV | 54 | 410 ± 166 | 5.7 ± 1.4 | 8/8 |

FIGURE 30 A/B
(A) Anti-c-Kit PK in a GIST T1 xenograft mouse model. (left panel is anti-DM1 ELISA)
(B) Right panel is anti-human IgG1 ELISA
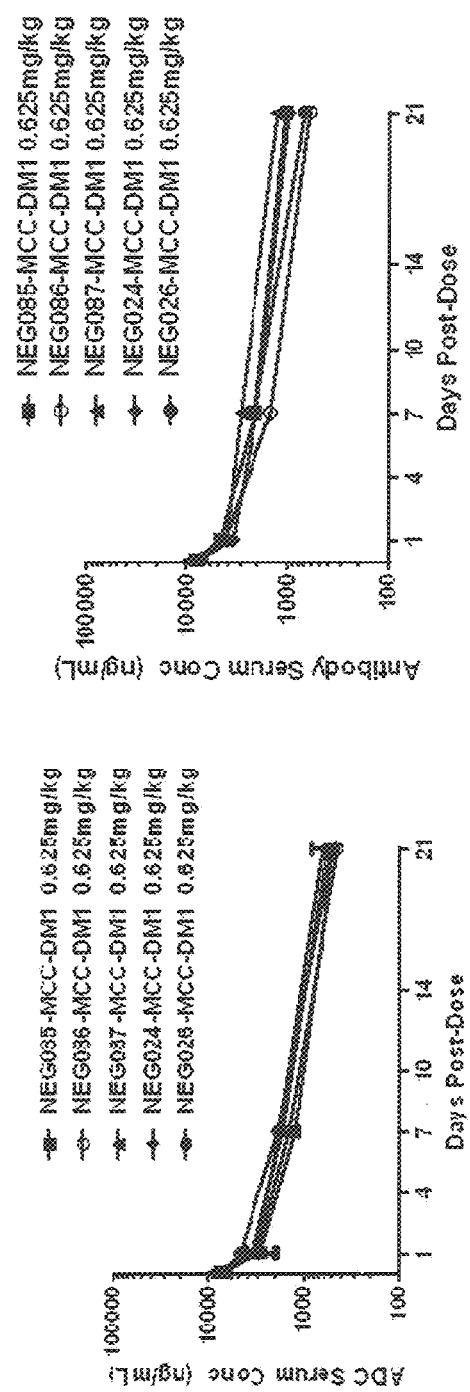

FIGURE 31A-C
(A) NEG085, NEG024 and NEG086 activity in a SCLC model
(B) change in body weight over course of treatment
(C) expression of c-Kit on tumor sample
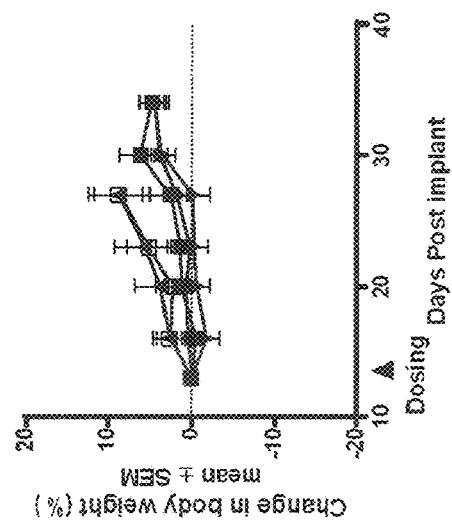
Body Weight
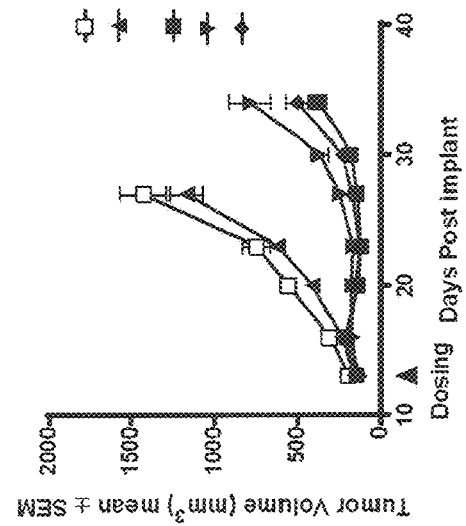
Efficacy in NCI-H1048 SCLC Model
- ○ Vehicle
- ▲ IgG1-MCC-DM1
- ■ NEG024-MCC-DM1 2 mg/kg*
- ▼ NEG085-MCC-DM1 2 mg/kg
- ◆ NEG086-MCC-DM1 2 mg/kg*
*P < 0.05, ANOVA/Fisher LSD Method
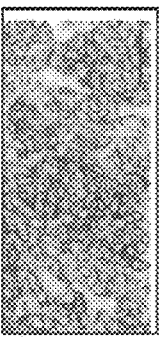
cKIT expression in NCI-H1048

FIGURE 32 anti-cKIT-ADC Efficacy Study in NCI-H1048 SCLC

| Drug | Dose | Schedule | Tumor Response | | | Host Response | |
|---|---|---|---|---|---|---|---|
| | | | Mean change of tumor volume vs control (T/C) (%) | Regression (%) | Mean change of tumor volume (mm3 ± SEM) | Mean change of body weight (% ± SEM) | Survival (Survivors/total) |
| Vehicle | 0mg/kg | single dose IV | 100 | - | 1234 ± 125 | 8.8 ± 3.7 | 8/8 |
| IgG1-MCC-DM1 | 2mg/kg | single dose IV | 82 | - | 1013 ± 91 | 8.8 ± 2.9 | 8/8 |
| NEG024-MCC-DM1 | 2mg/kg | single dose IV | - | -2.16* | -3 ± 18 | 2.5 ± 2.4 | 8/8 |
| NEG085-MCC-DM1 | 2mg/kg | single dose IV | 9 | - | 114 ± 42 | -0.2 ± 2.1 | 8/8 |
| NEG086-MCC-DM1 | 2mg/kg | single dose IV | 4* | - | 44 ± 22 | 1.8 ± 0.7 | 8/8 |

FIGURE 33 A/B
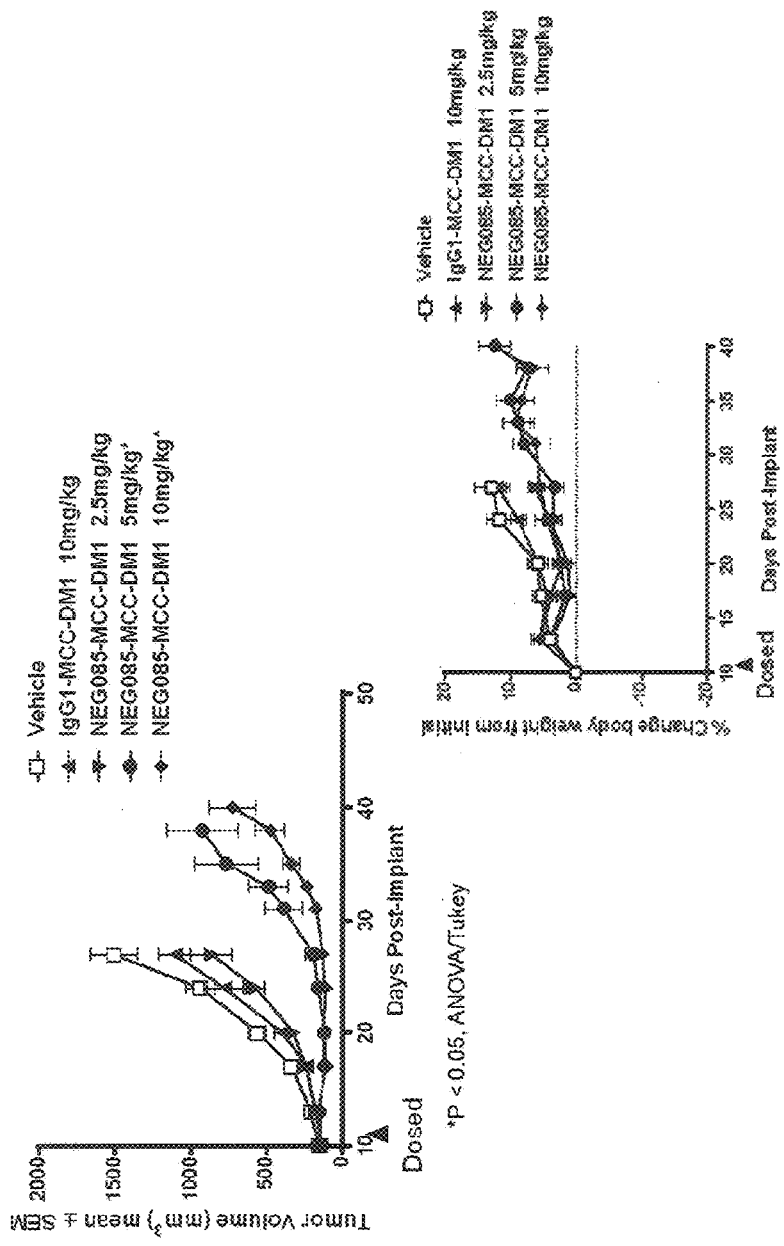
(A) NEG085-MCC-DM1 dose response in NCI-H1048 (SCLC) xenograft model
(B) Change in body weight over course of treatment

FIGURE 34

NEG085-MCC-DM1 efficacy study in NCI-1048 (SCLC) xenograft mouse model

Data Table Day 27

| Drug | Dose | Schedule | Tumor Response | | | Host Response | |
|---|---|---|---|---|---|---|---|
| | | | Mean change of tumor volume vs control (T/C) (%) | Regression (%) | Mean change of tumor volume (mm3 ± SEM) | Mean change of body weight (% ± SEM) | Survival (Survivors/total) |
| TBS | 0mg/kg | Single Dose IV | 100 | - | 1347 ± 164 | 12.9 ± 2.6 | 8/8 |
| IgG1-MCC-DM1 | 10mg/kg | Single Dose IV | 72 | - | 963 ± 113 | 12.0 ± 1.3 | 8/8 |
| NEG085-MCC-DM1 | 2.5mg/kg | Single Dose IV | 53 | - | 716 ± 141 | 6.3 ± 1.7 | 8/8 |
| NEG085-MCC-DM1 | 5mg/kg | Single Dose IV | 3* | - | 37 ± 55 | 6.0 ± 1.8 | 8/8 |
| NEG085-MCC-DM1 | 10mg/kg | Single Dose IV | - | -14.92* | -23 ± 14 | 5.5 ± 1.7 | 8/8 |

FIGURE 35 A-C
(A) Efficacy of 20376 and NEG024 in NCI-H526 (SCLC) xenograft mouse model
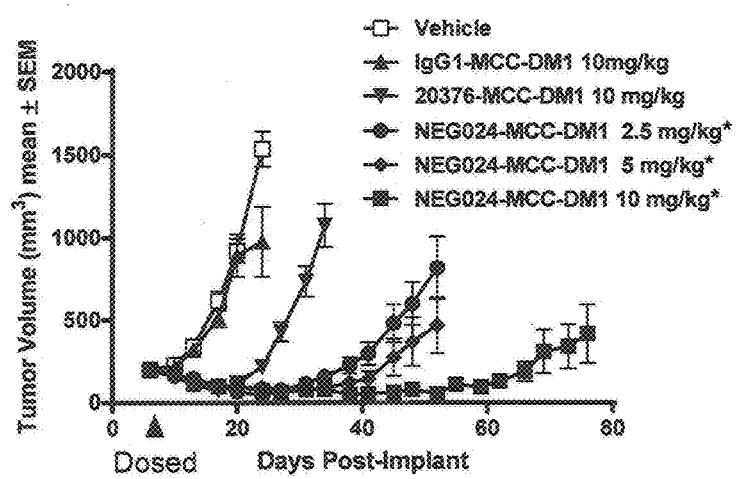
(B) Antibody serum concentration after dosing
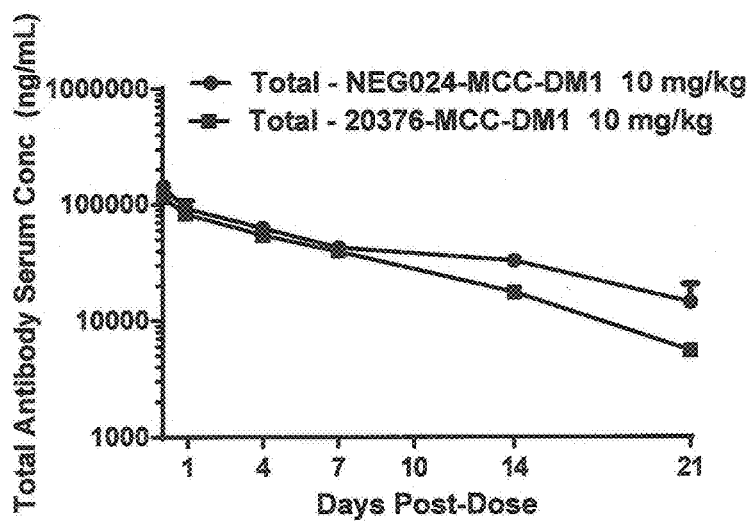
(C) IHC for c-Kit shows expression of cKIT levels on H526 tumor
cKIT IHC on H526 Tumor
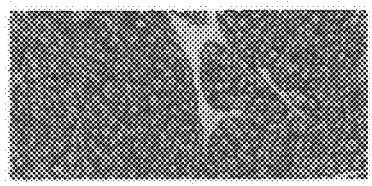

FIGURE 36

Anti-c-Kit ADC in a small cell lung cancer (SCLC) xenograft model (*p < 0.05, ANOVA/Dunn's)

| Drug | Dose | Schedule | Tumor Response | | | | Host Response | |
|---|---|---|---|---|---|---|---|---|
| | | | Mean change of tumor volume vs control (T/C) (%) | Regression (%) | Mean change of tumor volume (mm3 ± SEM) | Mean change of body weight (% ± SEM) | Survival (Survivors/total) | |
| TBS | 0mg/kg | Single Dose IV | 100 | - | 1338 ± 107 | 13.5 ± 3.6 | 9/9 | |
| IgG1-MCC-DM1 | 10mg/kg | Single Dose IV | 57 | - | 766 ± 208 | 6.6 ± 0.7 | 9/9 | |
| 20376-MCC-DM1 | 10mg/kg | Single Dose IV | 1 | - | 18 ± 28 | 4.1 ± 1.9 | 9/9 | |
| NEG024-MCC-DM1 | 2.5mg/kg | Single Dose IV | - | -76.14* | -148 ± 17 | 3.0 ± 1.1 | 9/9 | |
| NEG024-MCC-DM1 | 5mg/kg | Single Dose IV | - | -52.94* | -106 ± 15 | 3.3 ± 1.1 | 9/9 | |
| NEG024-MCC-DM1 | 10mg/kg | Single Dose IV | - | -63.04* | -123 ± 14 | -0.1 ± 2.2 | 9/9 | |

Efficacy in a HMC-1 mastocytosis xenograft mouse model

Control vs Treatment groups: Significant differences were measured using one-way ANOVA, posttest Tukey multiple comparison test, (*p<0.05)

FIGURE 39 A/B
Efficacy of mouse cross reactive 20376-MCC-DM1 in GIST T1 xenograft mouse model
A- Dosage and tumor volume
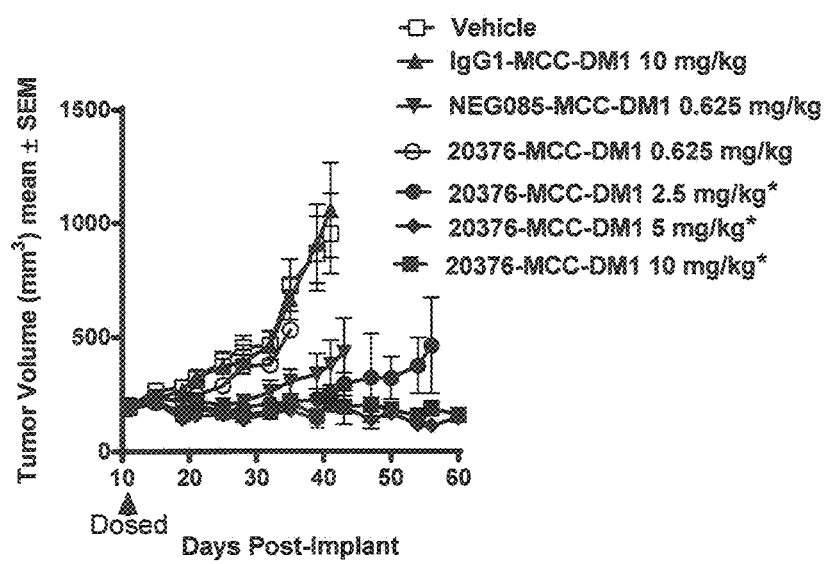
B- Change in body weight over course of treatment
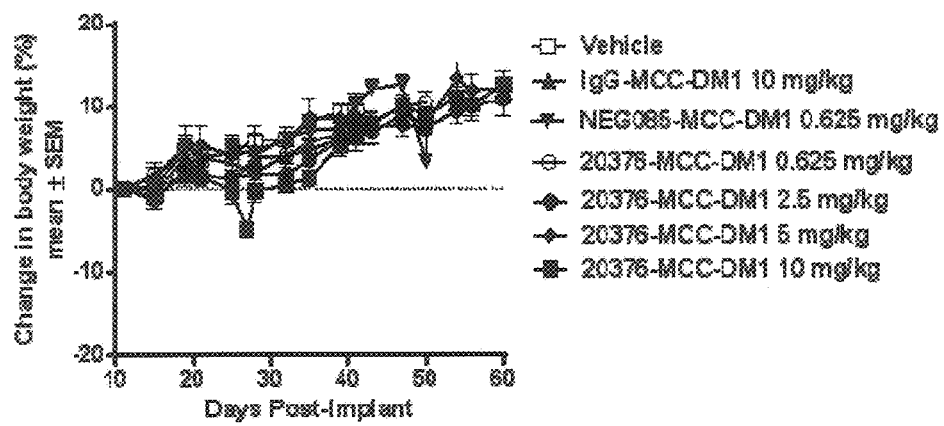

FIGURE 40 A/B
(A) Efficacy of mouse cross reactive 20376-MCC-DM1 in GIST T1 xenograft mouse model -PK
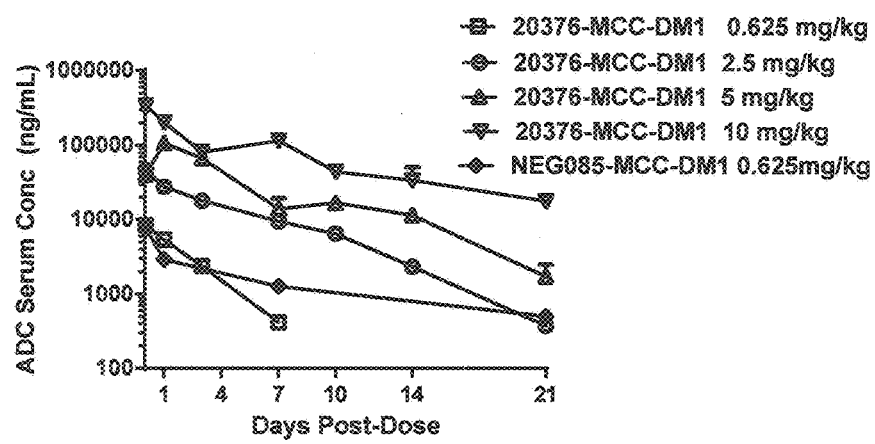
(B) Antibody serum concentration post dosing
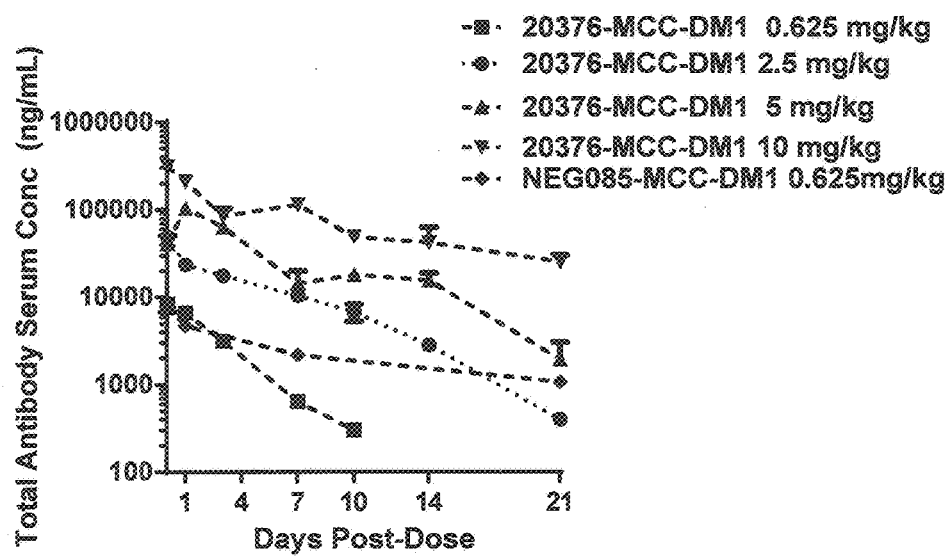

FIGURE 41

Dose response efficacy study in GIST T1 SCID-beige mice (Data Table 41)

| Drug | Dose | Schedule | Tumor Response | | | Host Response | |
|---|---|---|---|---|---|---|---|
| | | | Mean change of tumor volume vs control (T/C) (%) | Mean change of tumor volume (mm3 ± SEM) | | Mean change of body weight (% ± SEM) | Survival (Survivors/total) |
| Vehicle | 0mg/kg | single dose IV | 100 | 757 ± 175 | | 9.3 ± 1.0 | 8/8 |
| IgG-SMCC-DM1 | 10mg/kg | single dose IV | 114 | 861 ± 206 | | 8.1 ± 1.0 | 8/8 |
| NEO085-SMCC-DM1 | 0.625mg/kg | single dose IV | 28 | 210 ± 56 | | 10.3 ± 1.3 | 8/8 |
| 20376-SMCC-DM1 | 0.625mg/kg | single dose IV | 51 | 385 ± 106 | | 8.1 ± 1.0 | 8/9 (one mouse removed from study) |
| 20376-SMCC-DM1 | 2.5mg/kg | single dose IV | 9* | 66 ± 41 | | 7.2 ± 1.6 | 9/9 |
| 20376-SMCC-DM1 | 5mg/kg | single dose IV | 4* | 34 ± 62 | | 7.5 ± 1.2 | 9/9 |
| 20376-SMCC-DM1 | 10mg/kg | single dose IV | 3* | 22 ± 16 | | 6.1 ± 1.5 | 8/9 (one mouse removed from study) |

FIGURE 42A/B
(A) Efficacy in GIST T1 xenograft mouse model (no efficacy with unconjugated)
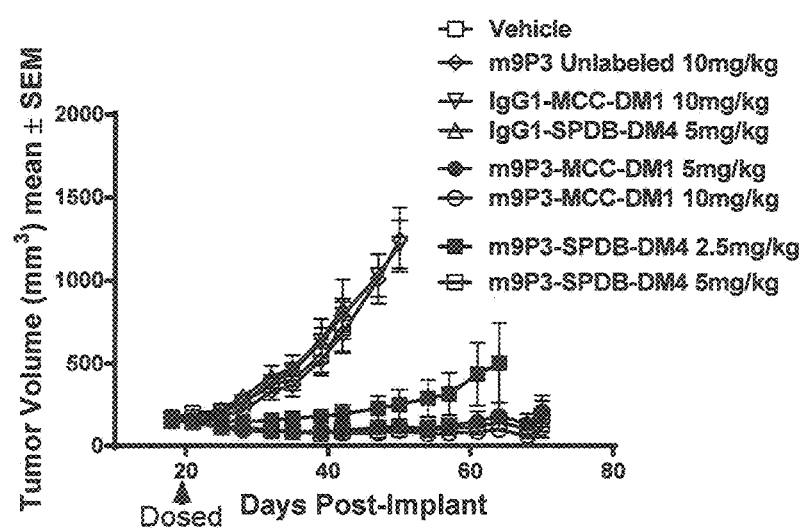
(B) Change in body weight over course of treatment
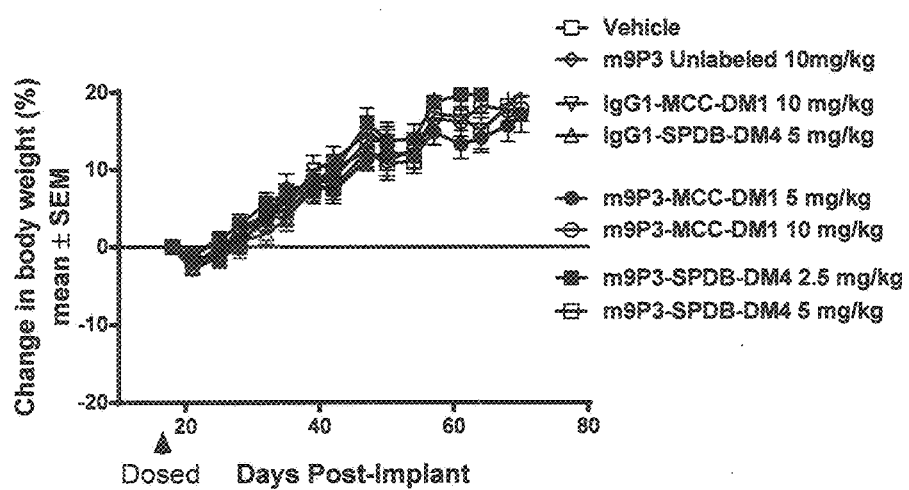

FIGURE 43

Efficacy in a GIST T1 mouse xenograft model (unlabeled/MCC-DM1/SPDB-DM4) (Data Table Day 42, p<0.05, ANOVA/Tukey

| Drug | Dose | Schedule | Tumor Response ||| Host Response ||
|---|---|---|---|---|---|---|---|
| | | | Mean change of tumor volume vs control (T/C) (%) | Regression (%) | Mean change of tumor volume (mm3 ± SEM) | Mean change of body weight (% ± SEM) | Survival (Survivors/ total) |
| Vehicle | 0mg/kg | single dose IV | 100 | - | 554 ± 148 | 9.5 ± 2.2 | 8/8 |
| 9P3 unlabeled | 10mg/kg | single dose IV | 95 | - | 525 ± 103 | 9.0 ± 1.9 | 8/8 |
| IgG1-MCC-DM1 | 5mg/kg | single dose IV | 113 | - | 624 ± 96 | 11.1 ± 1.9 | 9/9 |
| IgG1-SPDB-DM4 | 10mg/kg | single dose IV | 119 | - | 657 ± 176 | 10.0 ± 1.3 | 9/9 |
| 9P3-MCC-DM1 | 10mg/kg | single dose IV | - | -55.80 | -97 ± 23 | 10.2 ± 1.1 | 9/9 |
| 9P3-MCC-DM1 | 5mg/kg | single dose IV | - | -43.84 | -74 ± 28 | 7.2 ± 1.1 | 9/9 |
| 9P3-SPDB-DM4 | 5mg/kg | single dose IV | - | -43.24 | -67 ± 14 | 7.6 ± 2.0 | 9/9 |
| 9P3-SPDB-DM4 | 2.5mg/kg | single dose IV | 7 | - | 36 ± 58 | 9.6 ± 1.6 | 9/9 |

FIGURE 44 A/B
(A) Efficacy in a GIST 430 xenograft model comparing SPDB-DM4 and MCC-DM1
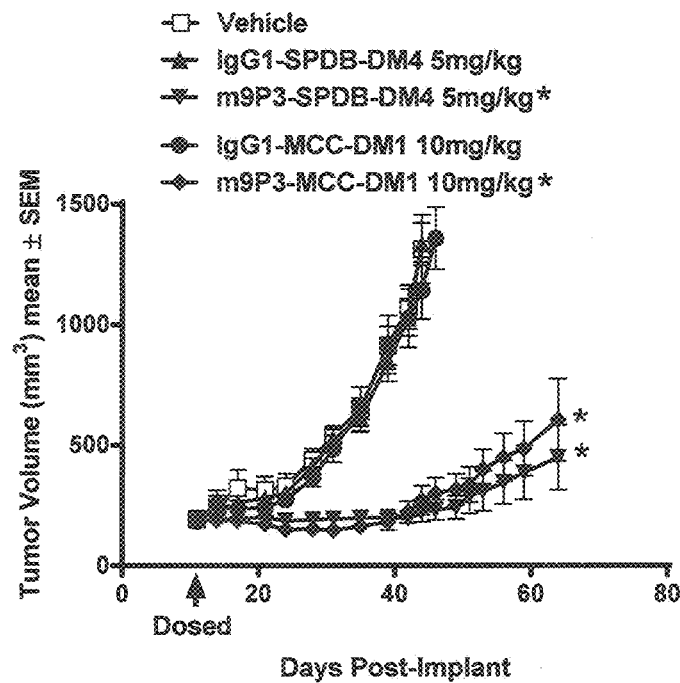
(B) Change in body weight over course of treatment
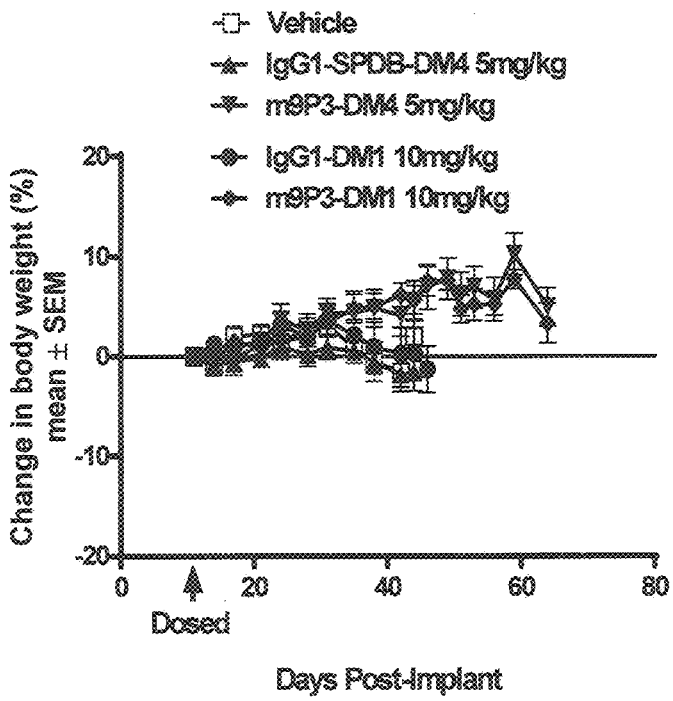

FIGURE 45

Efficacy in GIST 430 SCID-beige mouse model

| Drug | Dose (mg/kg) | Schedule | Tumor Response | | Host Response | |
|---|---|---|---|---|---|---|
| | | | Mean change of tumor volume vs control (T/C) (%) | Regression (%) | Mean change of tumor volume (mm3 ± SEM) | Mean change of body weight (% ± SEM) | Survival (Survivors/ total) |
| Vehicle | 0 | single dose IV | 100 | - | 1127 ± 161 | 2.1 ± 1.7 | 8/9 (cachexia w/ larger tumors) |
| IgG1-SPDB-DM4 | 5 | single dose IV | 101 | - | 1139 ± 91 | -1.6 ± 1.9 | 9/9 |
| 9P3-SPDB-DM4 | 5 | single dose IV | 3* | - | 34 ± 38 | 5.6 ± 2.0 | 9/9 |
| IgG1-MCC-DM1 | 10 | single dose IV | 85 | - | 959 ± 112 | 0.3 ± 2.5 | 9/9 |
| 9P3-MCC-DM1 | 10 | single dose IV | 7* | - (22% on D24) | 80 ± 51 | 5.7 ± 1.4 | 9/9 |

# ANTIBODY DRUG CONJUGATES

CROSS-REFERENCE TO RELATED APPLICATION

This application claims priority to provisional application Ser. No. 61/793,641, filed Mar. 15, 2013.

FIELD OF THE INVENTION

The present disclosure is directed to anti-cKIT antibodies, antibody fragments, antibody drug conjugates, and their uses for the treatment of cancer.

BACKGROUND OF THE INVENTION cKIT is a single transmembrane, receptor tyrosine kinase that binds the ligand Stem Cell Factor (SCF). SCF induces homodimerization of cKIT which activates its tyrosine kinase activity and signals through both the PI3-AKT and MAPK pathways (Kindblom et al., Am J. Path. 1998 152 (5):1259). cKIT was initially discovered as an oncogene as a truncated form expressed by a feline retrovirus (Besmer et al., 1986). Cloning of the corresponding human gene demonstrated that cKIT is a member of the type III class of receptor tyrosine kinases, which count among the family members; FLT3, CSF-1 receptor and PDGF receptor.

Mice that are mutant for cKIT have shown that cKIT is required for the development of hematopoietic cells, germ cells, mast cells and melanocytes. In the human, cKIT loss of function may lead to deafness and de-pigmentation of the skin and hair. A number of gain of function mutations for cKIT have been described in various cancers. Such cancers include gastro-intestinal-stromal tumors (GIST), acute myeloid leukemia (AML), small cell lung cancer (SCLC), mast cell leukemia (MCL) and pancreatic cancer (Hirota et al., Science 1998 (279):577; Esposito et al., Lab. Invets. 2002 82(11):1481).

Because of these preliminary indications that cKIT was an oncogene, an antibody was generated that identified cKIT as a marker of AML (Gadd et al., Leuk. Res. 1985 (9):1329). This murine monoclonal, known as YB5.8B, was generated by using leukemic blast cells from a human patient and bound cKIT, which was abundantly expressed on the surface of the AML cells, but did not detect cKIT on normal blood or bone marrow cells (Gadd et al., supra). A second cKIT antibody (SR-1) was generated that blocked the binding of SCF to cKIT and thus blocked cKIT signaling (Broudy et al., Blood 1992 79(2):338). The biological effect of the SR-1 antibody was to inhibit BFU-E and CFU-GM growth, and based on this evidence, suggested using it for further studies on hematopoiesis or tumor cell growth (Broudy et al., supra).

In further cancer studies, investigators found that treatment with Imatinib, a small molecule inhibitor of cKIT, would significantly reduce proliferation of GIST cell lines. However, Imatinib treated cells become resistant over time due to secondary mutations in cKIT (Edris et al., Proc. Nat. Acad. Sci. USA, Early On-line Edition 2013). However, if the GIST cells were treated with the SR-1 antibody as a second therapeutic, there was significant decrease in cell proliferation, and a decrease in cKIT expression on the cell surface (Edris et al., supra). Thus, a naked SR-1 antibody was efficacious in addressing the problem of Imatinib resistance in human GIST lines, suggesting that an Imatinib/anti-cKIT antibody combination may be useful.

Antibody Drug Conjugates

Antibody drug conjugates ("ADCs") have been used for the local delivery of cytotoxic agents in the treatment of cancer (see e.g., Lambert, Curr. Opinion In Pharmacology 5:543-549, 2005). ADCs allow targeted delivery of the drug moiety where maximum efficacy with minimal toxicity may be achieved. As more ADCs show promising clinical results, there is an increased need to develop new therapeutics for cancer therapy.

SUMMARY OF THE INVENTION

The present disclosure is directed to an antibody drug conjugate of the formula $Ab-(L-(D)_m)_n$ or a pharmaceutically acceptable salt thereof; wherein Ab is an antibody or antigen binding fragment thereof that specifically binds to an epitope of human cKIT; L is a linker; D is a drug moiety; m is an integer from 1 to 8; and n is an integer from 1 to 10.

The antibody drug conjugate wherein said n is 3 or 4.

The antibody drug conjugate, wherein said antibody or antigen binding fragment thereof specifically binds the extracellular domain of cKIT (SEQ ID NO. 160).

The antibody drug conjugate, wherein said antibody or antigen binding fragment specifically binds to an epitope of human cKIT at domains 1-3 (SEQ ID NO. 155).

The antibody drug conjugate, wherein said antibody or antigen binding fragment thereof specifically binds human cKIT at SEQ ID NO. 161 or SEQ ID NO. 162.

The antibody drug conjugate wherein said antibody or antigen binding fragment thereof comprises a heavy chain variable region that comprises: (a) a VH CDR1 of SEQ ID NO: 3, (b) a VH CDR2 of SEQ ID NO: 4, (c) a VH CDR3 of SEQ ID NO: 5; and a light chain variable region that comprises: (d) a VL CDR1 of SEQ ID NO: 12, (e) a VL CDR2 of SEQ ID NO: 13, and (f) a VL CDR3 of SEQ ID NO: 14.

The antibody drug conjugate wherein said antibody or antigen binding fragment thereof comprises a heavy chain variable region that comprises: (a) a VH CDR1 of SEQ ID NO: 22, (b) a VH CDR2 of SEQ ID NO: 23, (c) a VH CDR3 of SEQ ID NO: 24; and a light chain variable region that comprises: (d) a VL CDR1 of SEQ ID NO: 31, (e) a VL CDR2 of SEQ ID NO: 32, and (f) a VL CDR3 of SEQ ID NO: 33.

The antibody drug conjugate wherein said antibody or antigen binding fragment thereof comprises a heavy chain variable region that comprises: (a) a VH CDR1 of SEQ ID NO: 40, (b) a VH CDR2 of SEQ ID NO: 41, (c) a VH CDR3 of SEQ ID NO: 42; and a light chain variable region that comprises: (d) a VL CDR1 of SEQ ID NO: 49, (e) a VL CDR2 of SEQ ID NO: 50, and (f) a VL CDR3 of SEQ ID NO: 51.

The antibody drug conjugate wherein said antibody or antigen binding fragment thereof comprises a heavy chain variable region that comprises: (a) a VH CDR1 of SEQ ID NO: 58, (b) a VH CDR2 of SEQ ID NO: 59, (c) a VH CDR3 of SEQ ID NO: 60; and a light chain variable region that comprises: (d) a VL CDR1 of SEQ ID NO: 67, (e) a VL CDR2 of SEQ ID NO: 68, and (f) a VL CDR3 of SEQ ID NO: 69.

The antibody drug conjugate wherein said antibody or antigen binding fragment thereof comprises a heavy chain variable region that comprises: (a) a VH CDR1 of SEQ ID NO: 76, (b) a VH CDR2 of SEQ ID NO: 77, (c) a VH CDR3 of SEQ ID NO: 78; and a light chain variable region that comprises: (d) a VL CDR1 of SEQ ID NO: 85, (e) a VL CDR2 of SEQ ID NO: 86, and (f) a VL CDR3 of SEQ ID NO: 87.

The antibody drug conjugate wherein said antibody or antigen binding fragment thereof comprises a heavy chain variable region that comprises: (a) a VH CDR1 of SEQ ID NO: 94, (b) a VH CDR2 of SEQ ID NO: 95, (c) a VH CDR3 of SEQ ID NO: 96; and a light chain variable region that comprises: (d) a VL CDR1 of SEQ ID NO: 103, (e) a VL CDR2 of SEQ ID NO: 104, and (f) a VL CDR3 of SEQ ID NO: 105.

The antibody drug conjugate wherein said antibody or antigen binding fragment thereof comprises a heavy chain variable region that comprises: (a) a VH CDR1 of SEQ ID NO: 112, (b) a VH CDR2 of SEQ ID NO: 113, (c) a VH CDR3 of SEQ ID NO: 114; and a light chain variable region that comprises: (d) a VL CDR1 of SEQ ID NO: 121, (e) a VL CDR2 of SEQ ID NO: 122, and (f) a VL CDR3 of SEQ ID NO: 123.

The antibody drug conjugate wherein said antibody or antigen binding fragment thereof comprises a heavy chain variable region that comprises: (a) a VH CDR1 of SEQ ID NO: 130, (b) a VH CDR2 of SEQ ID NO: 131, (c) a VH CDR3 of SEQ ID NO: 132; and a light chain variable region that comprises: (d) a VL CDR1 of SEQ ID NO: 139, (e) a VL CDR2 of SEQ ID NO: 140, and (f) a VL CDR3 of SEQ ID NO: 141.

The antibody drug conjugate wherein said linker is selected from the group consisting of a cleavable linker, a non-cleavable linker, a hydrophilic linker, a procharged linker and a dicarboxylic acid based linker.

The antibody drug conjugate wherein the linker is derived from a cross-linking reagent selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

The antibody drug conjugate wherein said linker is derived from the cross-linking reagent N-succinimidyl 4-(maleimidomethyl)cyclohexanecarboxylate (SMCC).

The antibody drug conjugate wherein the cytotoxic agent is a maytansinoid.

The antibody drug conjugate wherein the maytansinoid is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

An antibody drug conjugate of the formula

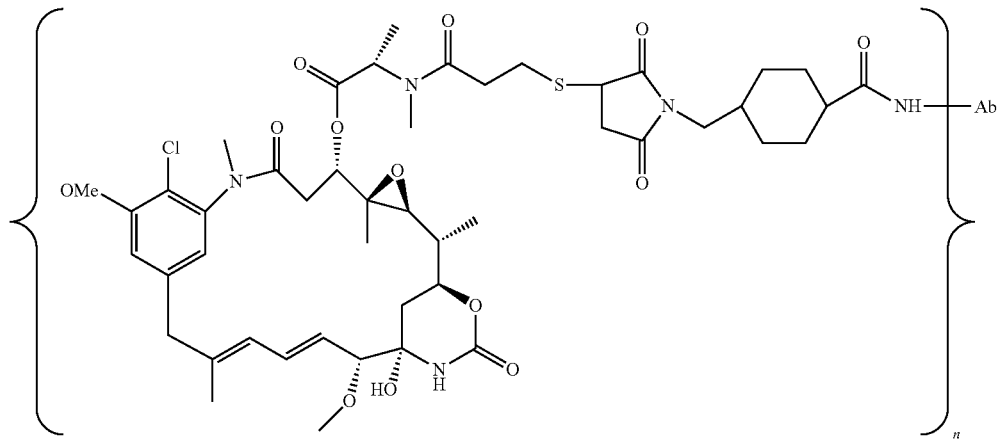

or a pharmaceutically acceptable salt thereof; wherein Ab is an antibody or antigen binding fragment thereof that specifically binds to human cKIT, and comprises at least n number of primary amines; and n is an integer from 1 to 10.

The antibody drug conjugate wherein said Ab is an antibody or antigen binding fragment thereof comprises a heavy chain variable region that comprises: (a) a VH CDR1 of SEQ ID NO: 3, (b) a VH CDR2 of SEQ ID NO: 4, (c) a VH CDR3 of SEQ ID NO: 5; and a light chain variable region that comprises: (d) a VL CDR1 of SEQ ID NO: 12, (e) a VL CDR2 of SEQ ID NO: 13, and (f) a VL CDR3 of SEQ ID NO: 14.

The antibody drug conjugate wherein said Ab is an antibody or antigen binding fragment thereof comprises a heavy chain variable region that comprises: (a) a VH CDR1 of SEQ ID NO: 22, (b) a VH CDR2 of SEQ ID NO: 23, (c) a VH CDR3 of SEQ ID NO: 24; and a light chain variable region that comprises: (d) a VL CDR1 of SEQ ID NO: 31, (e) a VL CDR2 of SEQ ID NO: 32, and (f) a VL CDR3 of SEQ ID NO: 33.

The antibody drug conjugate wherein said Ab is an antibody or antigen binding fragment thereof comprises a heavy chain variable region that comprises: (a) a VH CDR1 of SEQ ID NO: 40, (b) a VH CDR2 of SEQ ID NO: 41, (c) a VH CDR3 of SEQ ID NO: 42; and a light chain variable region that comprises: (d) a VL CDR1 of SEQ ID NO: 49, (e) a VL CDR2 of SEQ ID NO: 50, and (f) a VL CDR3 of SEQ ID NO: 51.

The antibody drug conjugate wherein said Ab is an antibody or antigen binding fragment thereof comprises a heavy chain variable region that comprises: (a) a VH CDR1 of SEQ ID NO: 58, (b) a VH CDR2 of SEQ ID NO: 59, (c) a VH CDR3 of SEQ ID NO: 60; and a light chain variable region that comprises: (d) a VL CDR1 of SEQ ID NO: 67, (e) a VL CDR2 of SEQ ID NO: 68, (f) a VL CDR3 of SEQ ID NO: 69.

The antibody drug conjugate wherein said Ab is an antibody or antigen binding fragment thereof comprises a heavy chain variable region that comprises: (a) a VH CDR1 of SEQ ID NO: 76, (b) a VH CDR2 of SEQ ID NO: 77, (c) a VH CDR3 of SEQ ID NO: 78; and a light chain variable region that comprises: (d) a VL CDR1 of SEQ ID NO: 85, (e) a VL CDR2 of SEQ ID NO: 86, and (f) a VL CDR3 of SEQ ID NO: 87.

The antibody drug conjugate wherein said Ab is an antibody or antigen binding fragment thereof comprises a heavy chain variable region that comprises: (a) a VH CDR1 of SEQ ID NO: 94, (b) a VH CDR2 of SEQ ID NO: 95, (c) a VH CDR3 of SEQ ID NO: 96; and a light chain variable region that comprises: (d) a VL CDR1 of SEQ ID NO: 103, (e) a VL CDR2 of SEQ ID NO: 104, and (f) a VL CDR3 of SEQ ID NO: 105.

The antibody drug conjugate wherein said Ab is an antibody or antigen binding fragment thereof comprises a heavy chain variable region that comprises: (a) a VH CDR1 of SEQ ID NO: 112, (b) a VH CDR2 of SEQ ID NO: 113, (c) a VH CDR3 of SEQ ID NO: 114; and a light chain variable region that comprises: (d) a VL CDR1 of SEQ ID NO: 121, (e) a VL CDR2 of SEQ ID NO: 122, and (f) a VL CDR3 of SEQ ID NO: 123.

The antibody drug conjugate wherein said Ab is an antibody or antigen binding fragment thereof comprises a heavy chain variable region that comprises: (a) a VH CDR1 of SEQ ID NO: 130, (b) a VH CDR2 of SEQ ID NO: 131, (c) a VH CDR3 of SEQ ID NO: 132; and a light chain variable region that comprises: (d) a VL CDR1 of SEQ ID NO: 139, (e) a VL CDR2 of SEQ ID NO: 140, and (f) a VL CDR3 of SEQ ID NO: 141.

The antibody drug conjugate wherein said m is 1.

The antibody drug conjugate wherein said n is 3 or 4.

The antibody drug conjugate wherein said antibody is a human antibody.

The antibody drug conjugate wherein said antibody is a monoclonal antibody.

The antibody drug conjugate wherein said linker is selected from the group consisting of a cleavable linker, a non-cleavable linker, a hydrophilic linker, a procharged linker and a dicarboxylic acid based linker.

The antibody drug conjugate wherein the linker is derived from a cross-linking reagent selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

The antibody drug conjugate wherein said linker is N-succinimidyl 4-(maleimidomethyl)cyclohexanecarboxylate (SMCC).

The antibody drug conjugate wherein said drug moiety is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

The antibody drug conjugate wherein the cytotoxic agent is a maytansinoid.

The antibody drug conjugate wherein the maytansinoid is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

A pharmaceutical composition comprising the antibody drug conjugate of any one of the antibody drug conjugates herein and a pharmaceutically acceptable carrier.

The pharmaceutical composition wherein said composition is prepared as a lyophilisate.

The pharmaceutical composition wherein said lyophilisate comprises the antibody drug conjugate, sodium succinate, and polysorbate 20.

A method of treating an cKIT positive cancer in a patient in need thereof, comprising administering to said patient any of antibody drug conjugates or pharmaceutical compositions disclosed herein.

The method wherein said cancer is selected from the group consisting of gastrointestinal stromal tumors (GIST), small cell lung cancer (SCLC), acute myelod leukemia (AML), melanoma, mast cell leukemia (MCL), mastocytosis, neurofibromatosis, breast cancer, non-small cell lung cancer (NSCLC) and pancreatic cancer.

An antibody drug conjugate for use as a medicament.

An antibody drug conjugate or pharmaceutical composition for use in the treatment of a cKIT positive cancer.

The antibody or antigen binding fragment wherein said antibody or antigen binding fragment is a single chain antibody (scFv).

A nucleic acid that encodes the antibody or antigen binding fragment.

A vector comprising the nucleic acid.

A host cell comprising the vector.

A process for producing an antibody or antigen binding fragment comprising cultivating the host cell and recovering the antibody from the culture.

A process for producing an anti-cKIT antibody drug conjugate comprising: (a) chemically linking SMCC to a drug moiety DM-1; (b) conjugating said linker-drug to the antibody recovered from the cell culture of claim 49; and (c) purifying the antibody drug conjugate.

The antibody drug conjugate having an average maytansinoid to antibody ratio (MAR), measured with a UV spectrophotometer, of about 3.5.

A diagnostic reagent comprising the antibody or antigen binding fragment thereof which is labeled.

The diagnostic reagent wherein the label is selected from the group consisting of a radiolabel, a fluorophore, a chromophore, an imaging agent, and a metal ion.

DEFINITIONS

Unless stated otherwise, the following terms and phrases as used herein are intended to have the following meanings:

The term "alkyl" refers to a monovalent saturated hydrocarbon chain having the specified number of carbon atoms. For example, $C_{1-6}$ alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)).

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time-1) divided by the association rate constant (ka, time-1, M-1). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an antibody drug conjugate of the present disclosure. In some aspects, the phrase "consisting essentially of" expressly excludes the inclusion of one or more additional active agents other than an antibody drug conjugate of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "immunoconjugate" or "antibody drug conjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the immunoconjugate.

Additionally, the immunoconjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "toxin," "cytotoxin" or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated to an antibody or antigen binding fragment, and can include any therapeutic or diagnostic agent, for example, an anti-cancer, anti-inflammatory, anti-infective (e.g., anti-fungal, antibacterial, anti-parasitic, anti-viral), or an anesthetic agent. In certain aspects, a drug moiety is selected from a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Methods for attaching each of these to a linker compatible with the antibodies and method of the present disclosure are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

The term "maytansinoid drug moiety" means the substructure of an antibody-drug conjugate that has the structure of a maytansinoid compound. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256, 746; 4,260,608; 4,265,814; 4,294,757; 4,307,016; 4,308, 268; 4,308,269; 4,309,428; 4,313,946; 4,315,929; 4,317, 821; 4,322,348; 4,331,598; 4,361,650; 4,364,866; 4,424, 219; 4,450,254; 4,362,663; and 4,371,533, and Kawai et al (1984) Chem. Pharm. Bull. 3441-3451), each of which are expressly incorporated by reference. Specific examples of maytansinoids useful for conjugation include DM1, DM3 and DM4.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is to show a decline in growth rate of tumor cells, tumor size stasis or tumor size reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "cKIT" refers to a tyrosine kinase receptor that is a member of the receptor tyrosine kinase III family. The nucleic acid and amino acid sequences of cKIT are known, and have been published in GenBank Accession Nos. X06182.1, EU826594.1, GU983671.1, HM015525.1, HM015526.1, AK304031.1 and BC071593.1. See also SEQ ID NO:1 for the human cKIT cDNA sequence and SEQ ID NO. 2 for the human cKIT protein sequence. Structurally, cKIT receptor is a type I transmembrane protein and contains a signal peptide, 5 Ig-like C2 domains in the extracellular domain and has a protein kinase domain in its intracellular domain and has over its full length at least about 90%, 91%, 92%, 93%, 94%, 95%, 96%, 97%, 98%, 99%, or 100% sequence identity with the amino acid sequence of SEQ ID NO. 2. Structurally, a cKIT nucleic acid sequence has over its full length at least about 90%, 91%, 92%, 93%, 94%, 95%, 96%, 97%, 98%, 99%, or 100% sequence identity with the nucleic acid sequence of SEQ ID NO 1.

The terms "cKIT expressing cancer" or "cKIT positive cancer" refers to a cancer that express cKIT and/or a mutant form of cKIT on the surface of cancer cells.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both. In yet another aspect, "treat," "treating," or "treatment" refers to preventing or delaying the onset or development or progression of the disease or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated with cancer.

The term "co-administer" refers to the simultaneous presence of two active agents in the blood of an individual. Active agents that are co-administered can be concurrently or sequentially delivered.

BRIEF DESCRIPTION OF THE DRAWINGS

FIG. 1 shows activity of c-Kit-MCC-DM1 ADCs in a subset of cancer cell lines.

FIG. 2 depicts activity of 9P3-MCC-DM1, 9P3-SPDB-DM4 and 9P3-CX1-1-DM1 in a subset of cancer cell lines.

FIG. 20 shows co-localization of IgG1 and mitotic arrest of NEG027-MCC-DM1 in GIST T1 xenograft model.

FIG. 21 shows tissue sections of mitotic arrest (p-histone H3) and apoptosis (caspase 3) after single dose of c-Kit ADC.

FIG. 23 shows (A) Dose response efficacy in GIST T1 mouse xenograft and (B), change in body weight over course of treatment.

FIG. 24 graphically depicts (A) anti-DM1 ELISA after dosing in a GIST T1 xenograft model and (B) anti-human IgG1 ELISA after dosing in a GIST T1 xenograft model.

FIG. 25 is a table of NEG027-MCC-DM1 dose response in a GIST T1 xenograft mouse model.

FIG. 26 are histology sections of NEG027-MCC-DM1 dose response efficacy in GIST T1. (A) is Group 4 pooled tumors, (B) Group 5 pooled tumors.

FIG. 27 depicts (A) Efficacy with 0.625 mg/kg in a GIST T1 xenograft mouse model, (B) change of tumor volume vs control (% T/C) and (C) change in body weight over course of treatment.

FIG. 29 is a table of cKIT ADC efficacy at low effective dose in GIST T1 xenograft model.

FIG. 30 shows (A) Anti-c-Kit PK in a GIST T1 xenograft mouse model, (left panel is anti-DM1 ELISA) (B) Right panel is anti-human IgG1 ELISA.

FIG. 31A-C shows (A) NEG085, NEG024 and NEG086 activity in a SCLC model (B) change in body weight over course of treatment (C) expression of c-Kit on tumor sample.

FIG. 32 is a table of an anti-cKIT-ADC Efficacy Study in NCI-H1048 SCLC

FIG. 33 A-B shows (A) NEG085-MCC-DM1 dose response in NCI-H1048 (SCLC) xenograft model, (B) Change in body weight over course of treatment.

FIG. 34 is a table showing a NEG085-MCC-DM1 efficacy study in a NCI-1048 (SCLC) xenograft mouse model.

FIG. 35 A-C shows (A) Efficacy of 20376 and NEG024 in NCI-H526 (SCLC) xenograft mouse model, (B) Antibody serum concentration after dosing and (C) IHC for c-Kit shows expression of cKIT levels on H526 tumor.

FIG. 36 shows anti-cKIT ADC in a small cell lung cancer (SCLC) xenograft model.

FIG. 39 A/B shows efficacy of mouse cross reactive 20376-MCC-DM1 in GIST T1 xenograft mouse model with (A) dosage and tumor volume and (B) change in body weight over course of treatment.

FIG. 40 A/B shows (A) Efficacy of mouse cross reactive 20376-MCC-DM1 in GIST T1 xenograft mouse model-PK and (B) Antibody serum concentration post dosing.

FIG. 41 shows dose response efficacy study in GIST T1 SCID-beige mice.

FIG. 42 A/B shows (A) efficacy in GIST T1 xenograft mouse model (no efficacy with unconjugated) and (B) change in body weight over course of treatment.

FIG. 43 is a comparison of efficacy in a GIST T1 mouse xenograft model (unlabeled/MCC-DM1/SPDB-DM4).

FIG. 44 A/B shows (A) Efficacy in a GIST 430 xenograft model comparing SPDB-DM4 and MCC-DM1 and (B) Change in body weight over course of treatment FIG. 45 shows efficacy in GIST 430 SCID-beige mouse model.

DETAILED DESCRIPTION

Figure 3:
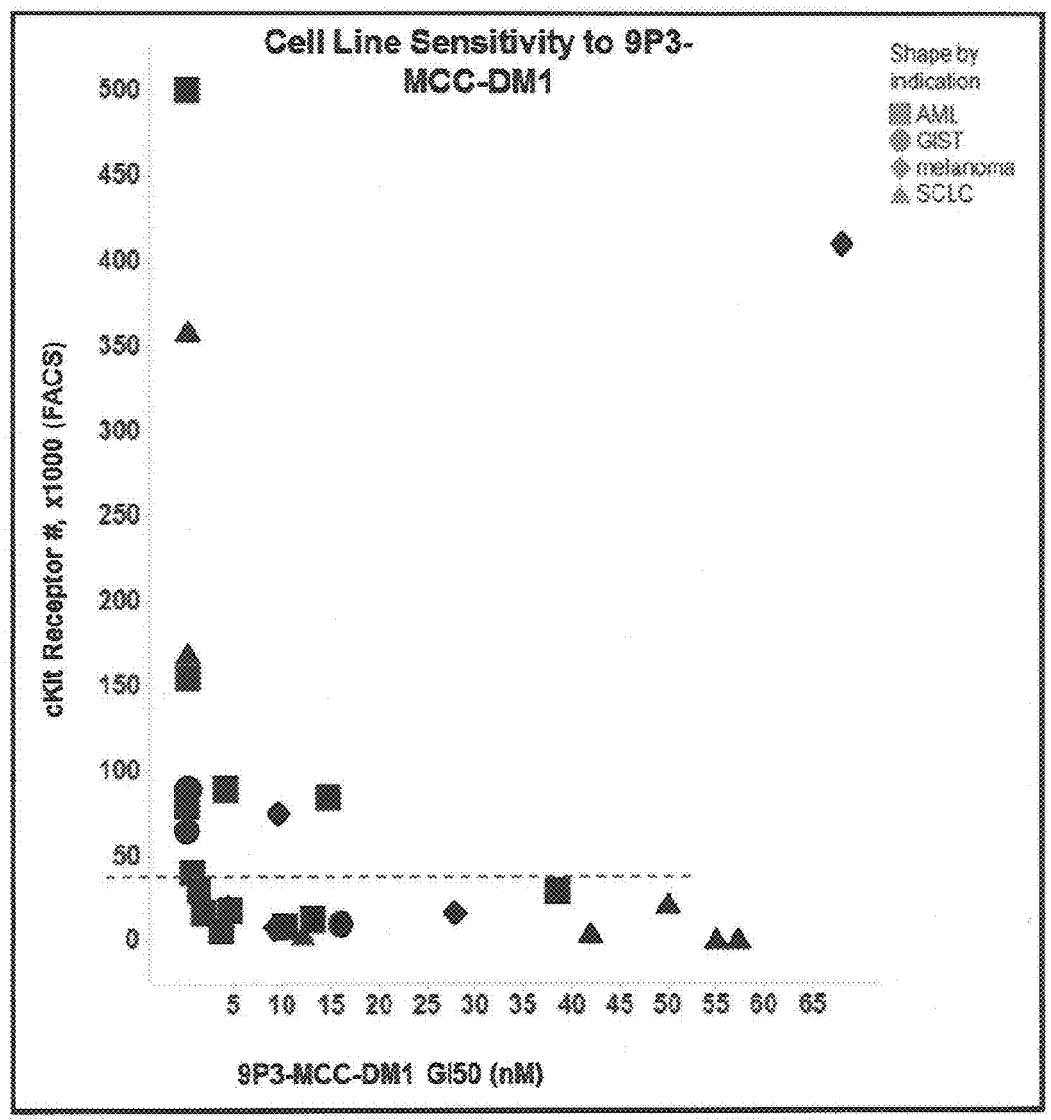
FIG. 3 shows the activity of 9P3-MCC-DM1 in a panel of AML, GIST, melanoma and SCLC cell lines with varying levels of c-Kit surface receptor expression.

The present disclosure provides for antibodies, antibody fragments (e.g., antigen binding fragments), and antibody drug conjugates that bind to cKIT. In particular, the present disclosure is directed to antibodies and antibody fragments (e.g., antigen binding fragments) that bind to cKIT, and internalize upon such binding. The antibodies and antibody fragments (e.g., antigen binding fragments) of the present disclosure can be used for producing antibody drug conjugates. Furthermore, the present disclosure provides antibody drug conjugates that have desirable pharmacokinetic characteristics and other desirable attributes, and thus can be used for treating cancer expressing cKIT, without limitation, for example: gastrointestinal stromal tumors (GIST), small cell lung cancer (SCLC), acute myelod leukemia (AML), melanoma, mast cell leukemia (MCL), mastocytosis, neurofibromatosis, breast cancer, non-small cell lung cancer (NSCLC) and pancreatic cancer. The present disclosure further provides pharmaceutical compositions comprising the antibody drug conjugates, and methods of making and using such pharmaceutical compositions for the treatment of cancer.

Antibody Drug Conjugates

The present disclosure provides antibody drug conjugates, where an antibody, antigen binding fragment or its functional equivalent that specifically binds to cKIT is linked to a drug moiety. In one aspect, the antibodies, antigen binding fragments or their functional equivalents are linked, via covalent attachment by a linker, to a drug moiety that is an anti-cancer agent. The antibody drug conjugates can selectively deliver an effective dose of an anti-cancer agent (e.g., a cytotoxic agent) to tumor tissues expressing cKIT, whereby greater selectivity (and lower efficacious dose) may be achieved.

In one aspect, the disclosure provides for an immunoconjugate of Formula (I):

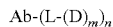

Wherein Ab represents an cKIT binding antibody or antibody fragment (e.g., antigen binding fragment) described herein;
L is a linker;
D is a drug moiety;
m is an integer from 1-8; and
n is an integer from 1-20. In one aspect, n is an integer from 1 to 10, 2 to 8, or 2 to 5. In a specific aspect, n is 3 to 4. In some aspects, m is 1. In some aspects, m is 2, 3 or 4.

While the drug to antibody ratio has an exact value for a specific conjugate molecule (e.g., n multiplied by m in Formula (I)), it is understood that the value will often be an average value when used to describe a sample containing many molecules, due to some degree of inhomogeneity, typically associated with the conjugation step. The average loading for a sample of an immunoconjugate is referred to herein as the drug to antibody ratio, or "DAR." In the aspect of maytansinoids, this can be referred to as maytansinoid to antibody ratio or "MAR." In some aspects, the DAR is between about 1 and about 5, and typically is about 3, 3.5, 4, 4.5, or 5. In some aspects, at least 50% of a sample by weight is compound having the average DAR plus or minus 2, and preferably at least 50% of the sample is a conjugate that contains the average DAR plus or minus 1. Other aspects include immunoconjugates wherein the DAR is about 3.5. In some aspects, a DAR of 'about n' means the measured value for DAR is within 20% of n.

The present disclosure provides immunoconjugates comprising the antibodies, antibody fragments (e.g., antigen binding fragments) and their functional equivalents as disclosed herein, linked or conjugated to a drug moiety. In one aspect, the drug moiety D is a maytansinoid drug moiety, including those having the structure:

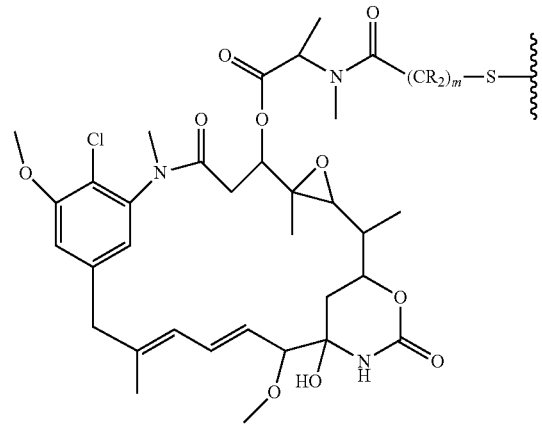

where the wavy line indicates the covalent attachment of the sulfur atom of the maytansinoid to a linker of an antibody drug conjugate. R at each occurrence is independently H or a $C_1$-$C_6$ alkyl. The alkylene chain attaching the amide group to the sulfur atom may be methanyl, ethanyl, or proyl, i.e. m is 1, 2, or 3. (U.S. Pat. No. 633,410, U.S. Pat. No. 5,208,020, Chari et al. (1992) Cancer Res. 52; 127-131, Lui et al. (1996) Proc. Natl. Acad. Sci. 93:8618-8623).

All stereoisomers of the maytansinoid drug moiety are contemplated for the immunoconjugates disclosed, i.e. any combination of R and S configurations at the chiral carbons of the maytansinoid. In one aspect the maytansinoid drug moiety has the following stereochemistry.

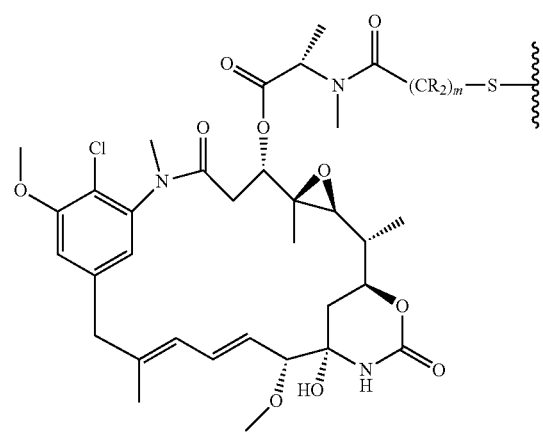

In one aspect, the maytansinoid drug moiety is $N^{2'}$-deacetyl-$N^{2'}$-(3-mercapto-1-oxopropyl)-maytansine (also known as DM1). DM1 is represented by the following structural formula.

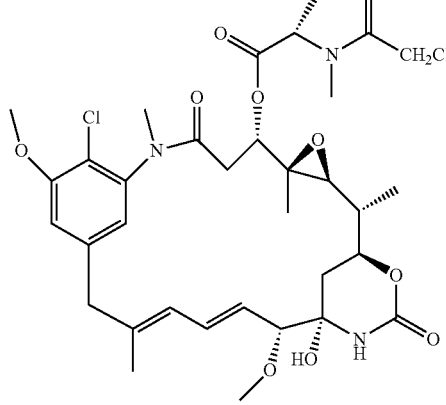

DM1

In another aspect the maytansinoid drug moiety is $N^{2'}$-deacetyl-$N^{2'}$-(4-mercapto-1-oxopentyl)-maytansine (also known as DM3). DM3 is represented by the following structural formula.

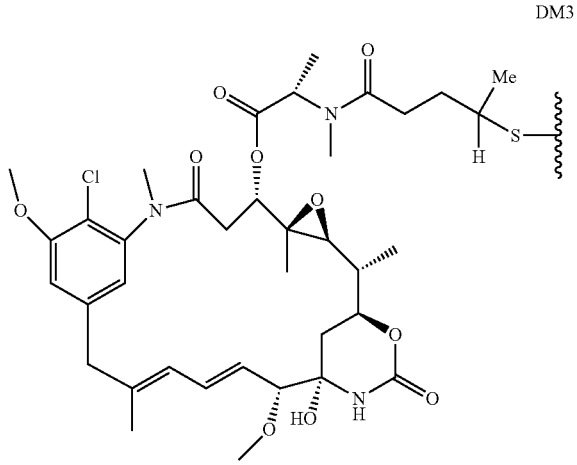 [SMILES: *SC(C)CCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

DM3

In another aspect the maytansinoid drug moiety is $N^{2'}$-deacetyl-$N^{2'}$-(4-methyl-4-mercapto-1-oxopentyl)-maytansine (also known as DM4). DM4 is represented by the following structural formula.

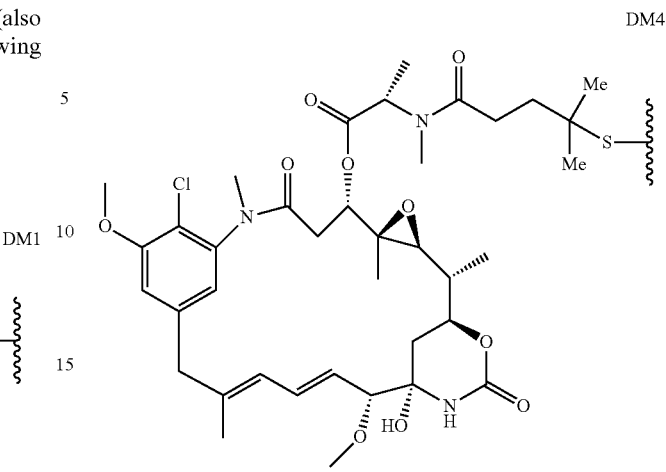

DM4

The drug moiety D can be linked to the antibody through a linker L. L is any chemical moiety that is capable of linking the antibody Ab to the drug moiety D. The linker, L attaches the antibody Ab to the drug D through covalents bond(s). The linker reagent is a bifunctional or multifunctional moiety which can be used to link a drug moiety D and an antibody Ab to form antibody drug conjugates. Antibody drug conjugates can be prepared using a linker having a reactive functionality for binding to the drug moiety D and to the antibody Ab. A cysteine, thiol or an amine, e.g. N-terminus or amino acid side chain such as lysine of the antibody can form a bond with a functional group of a linker reagent.

In one aspect, L is a cleavable linker. In another aspect, L is a non-cleavable linker. In some aspects, L is an acid-labile linker, photo-labile linker, peptidase cleavable linker, esterase cleavable linker, a disulfide bond reducible linker, a hydrophilic linker, a procharged linker, or a dicarboxylic acid based linker.

Suitable cross-linking reagents that form a non-cleavable linker between the drug moiety D, for example maytansinoid, and the antibody Ab are well known in the art, and can form non-cleavable linkers that comprise a sulfur atom (such as SMCC) or those that are without a sulfur atom. Preferred cross-linking reagents that form non-cleavable linkers between the drug moiety D, for example maytansinoid, and the antibody Ab comprise a maleimido- or haloacetyl-based moiety. According to the present disclosure, such non-cleavable linkers are said to be derived from maleimido- or haloacetyl-based moieties.

Cross-linking reagents comprising a maleimido-based moiety include but not limited to, N-succinimidyl-4-(maleimidomethyl)cyclohexanecarboxylate (SMCC), sulfosuccinimidyl 4-(N-maleimidomethyl)cyclohexane-1-carboxylate (sulfo-SMCC), N-succinimidyl-4-(maleimidomethyl)cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-succinimidyl ester (EMCS), m-maleimidobenzoyl-N-hydroxysuccinimide ester (MBS), N-(α-maleimidoacetoxy)-succinimide ester (AMSA), succinimidyl-6-(β-maleimidopropionamido)hexanoate (SMPH), N-succinimidyl-4-(p-maleimidophenyl)-butyrate (SMPB), N-(-p-maleomidophenyl)isocyanate (PMIP) and maleimido-based cross-linking reagents containing a polyethylene glycol spacer, such as MAL-PEG-NHS. These cross-linking reagents form non-cleavable linkers derived from maleimido-based moieties. Representative structures of maleimido-based cross-linking reagents are shown below.

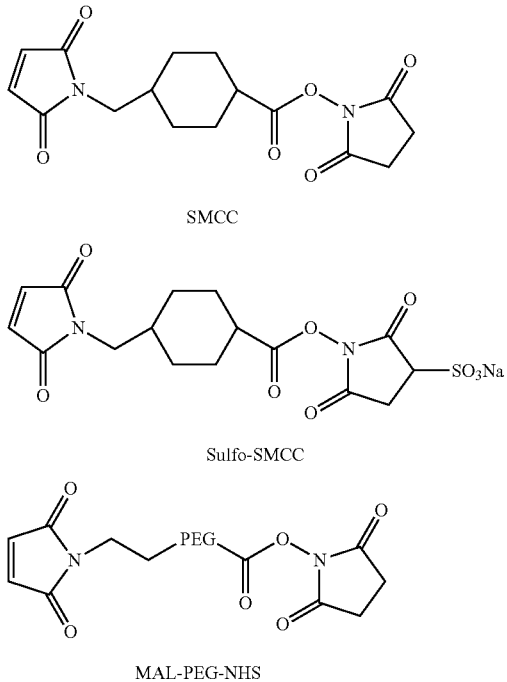

In another aspect, the linker L is derived from N-succinimidyl-4-(maleimidomethyl)cyclohexanecarboxylate (SMCC), sulfosuccinimidyl 4-(N-maleimidomethyl)cyclohexane-1-carboxylate (sulfo-SMCC) or MAL-PEG-NHS.

Cross-linking reagents comprising a haloacetyle-based moiety include N-succinimidyl iodoacetate (SIA), N-succinimidyl(4-iodoacetyl)aminobenzoate (SIAB), N-succinimidyl bromoacetate (SBA) and N-succinimidyl 3-(bromoacetamido)propionate (SBAP). These cross-linking reagents form a non-cleavable linker derived from haloacetyl-based moieties. Representative structures of haloacetyl-based cross-linking reagents are shown below.

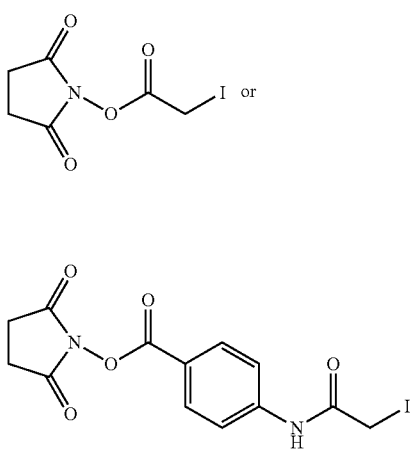

In one aspect, the linker L is derived from N-succinimidyl iodoacetate (SIA) or N-succinimidyl(4-iodoacetyl)aminobenzoate (SIAB).

Suitable cross-linking reagents that form a cleavable linker between the drug moiety D, for example maytansinoid, and the antibody Ab are well known in the art. Disulfide containing linkers are linkers cleavable through disulfide exchange, which can occur under physiological conditions. According to the present disclosure, such cleavable linkers are said to be derived from disulfide-based moieties. Suitable disulfide cross-linking reagents include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB) and N-succinimidyl-4-(2-pyridyldithio)-2-sulfo-butanoate (sulfo-SPDB), the structures of which are shown below. These disulfide cross-linking reagents form a cleavable linker derived from disulfide-based moieties.

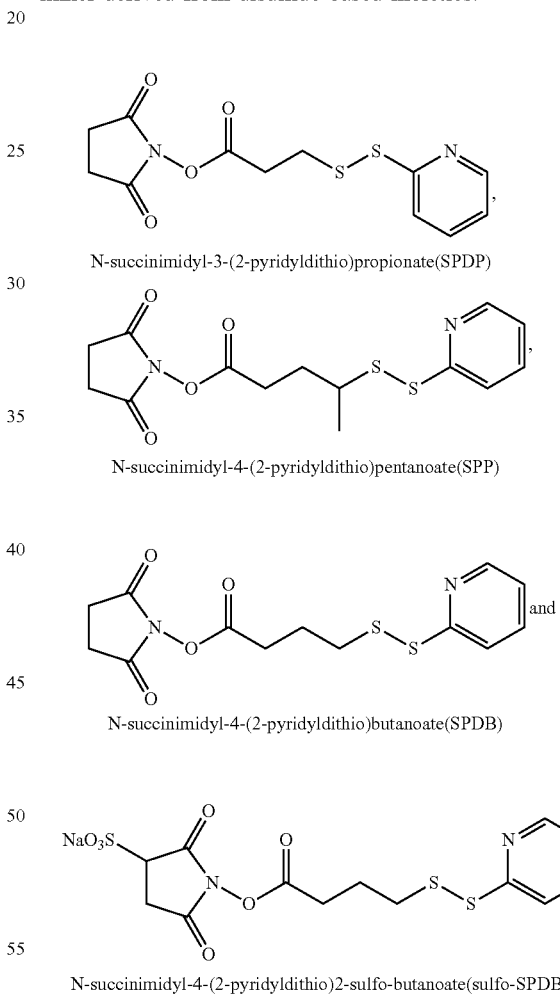

In one aspect, the linker L is derived from N-succinimidyl-4-(2-pyridyldithio)butanoate (SPDB).

Suitable cross-linking reagents that form a charged linker between the drug moiety D, for example maytansinoid, and the antibody Ab are known as procharged cross-linking reagents. In one aspect, the linker L is derived from the procharged cross-linking reagent is CX1-1. The structure of CX1-1 is below.

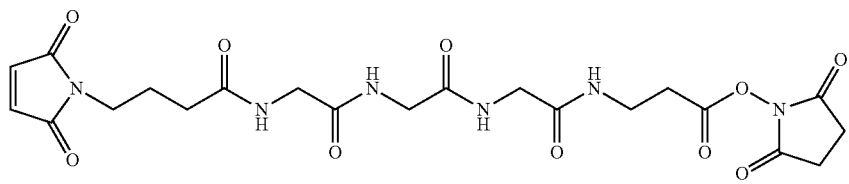
2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate(CX-1-1)
In one aspect provided by the disclosure, the conjugate is represented by any one of the following structural formulae:
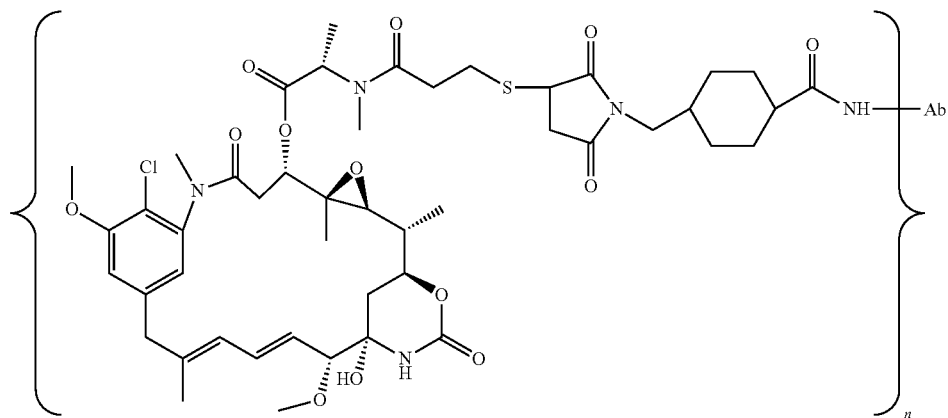
Ab-SMCC-DM1
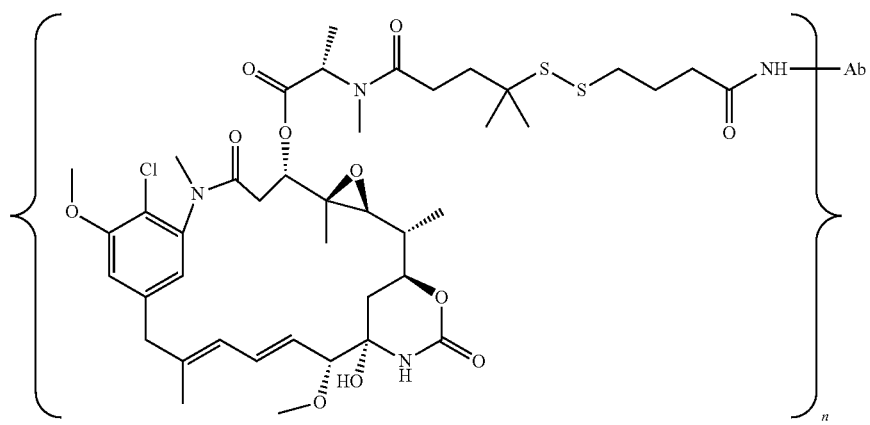
Ab-SPDB-DM4

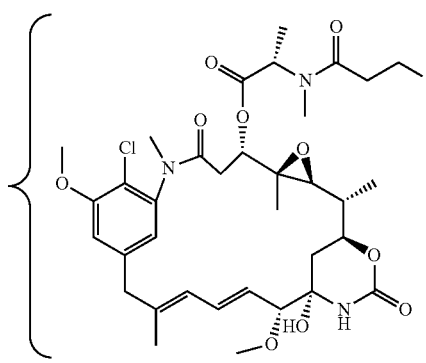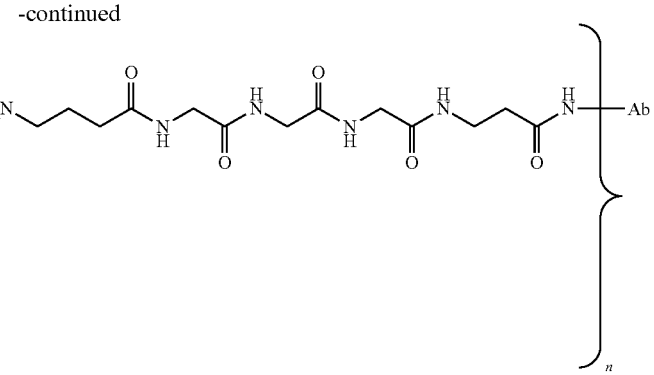

Ab-CX1-1-DM1 wherein:

Ab is an antibody or antigen binding fragment thereof that specifically binds to human cKIT;

n, which indicates the number of D-L groups attached the Ab through the formation of an amide bond with a primary amine of the Ab, is an integer from 1 to 20. In one aspect, n is an integer from 1 to 10, 2 to 8 or 2 to 5. In a specific aspect, n is 3 or 4.

In one aspect, the average molar ratio of drug (e.g., DM1 or DM4) to the antibody in the conjugate (i.e., average w value, also known as Maytanisnoid Antibody Ratio (MAR)) is about 1 to about 10, about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 8.1), about 2.5 to about 7, about 3 to about 5, about 2.5 to about 4.5 (e.g., about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

In one aspect provided by the disclosure, the conjugate has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug (e.g., DM1 or DM4) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent).

As used herein, the term "unconjugated linker" refers to the antibody that is covalently linked with a linker derived from a cross-linking reagent (e.g., SMCC, Sulfo-SMCC, SPDB, Sulfo-SPDB or CX1-1), wherein the antibody is not covalently coupled to the drug (e.g., DM1 or DM4) through a linker (i.e., the "unconjugated linker" can be represented by Ab-SMCC, Ab-SPDB, or Ab-CX1-1).

1. Drug Moiety

The present disclosure provides immunoconjugates that specifically bind to cKIT. The immunoconjugates of the present disclosure comprise anti-cKIT antibodies, antibody fragments (e.g., antigen binding fragments) or functional equivalents that are conjugated to a drug moiety, e.g., an anti-cancer agent, anti-hematological disorder agent, an autoimmune treatment agent, an anti-inflammatory agent, an antifungal agent, an antibacterial agent, an anti-parasitic agent, an anti-viral agent, or an anesthetic agent. The antibodies, antibody fragments (e.g., antigen binding fragments) or functional equivalents can be conjugated to several identical or different drug moieties using any methods known in the art.

In certain aspects, the drug moiety of the immunoconjugates of the present disclosure is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, proteasome inhibitors, an inhibitor of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

In one aspect, the drug moiety of the immunoconjugates of the present disclosure is a maytansinoid drug moiety, such as but not limited to, DM1, DM3, or DM4.

Further, the antibodies, antibody fragments (e.g., antigen binding fragments) or functional equivalents of the present disclosure may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one aspect, the antibodies, antibody fragments (e.g., antigen binding fragments) or functional equivalents of the present disclosure are conjugated to a drug moiety, such as a cytotoxin, a drug (e.g., an immunosuppressant) or a radiotoxin. Examples of cytotoxin include but are not limited to, taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood (2003) (electronic publication prior to print publication), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698), taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of cytotoxins that can be conjugated to the antibodies, antibody fragments (antigen binding fragments) or functional equivalents of the present disclosure include duocarmycins, calicheamicins, maytansines and auristatins, and derivatives thereof.

Various types of cytotoxins, linkers and methods for conjugating therapeutic agents to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

The antibodies, antibody fragments (e.g., antigen binding fragments) or functional equivalents of the present disclosure can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, and lutetium-177. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies disclosed herein. In certain aspects, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

The antibodies, antibody fragments (e.g., antigen binding fragments) or functional equivalents of the present disclosure can also conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the present disclosure provides fusion proteins comprising an antibody fragment (e.g., antigen binding fragment) described herein (e.g., a Fab fragment, Fd fragment, Fv fragment, F(ab)2 fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the present disclosure or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the antibodies, antibody fragments (e.g., antigen binding fragments) or functional equivalents of the present disclosure can be conjugated to marker sequences, such as a peptide, to facilitate purification. In preferred aspects, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., (1989) Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al., J. Biochem. Biophys. Methods 49: 455-465, 2001). As described in the present disclosure, antibodies or antigen binding fragments can also be conjugated to tumor-penetrating peptides in order to enhance their efficacy.

In other aspects, the antibodies, antibody fragments (e.g., antigen binding fragments) or functional equivalents of the present disclosure are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{32}$P, $^{153}$Gd, $^{169}$Yb, $^{51}$Cr, $^{54}$Mn, $^{75}$Se, $^{64}$Cu, $^{113}$Sn, and $^{117}$Sn; and positron emitting metals using various positron emission tomographies, and non-radioactive paramagnetic metal ions.

The antibodies, antibody fragments (e.g., antigen binding fragments) or functional equivalents of the present disclosure may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

2. Linker

As used herein, a "linker" is any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid based linker.

In one aspect, the linker used is derived from a crosslinking reagent such as N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), sulfosuccinimidyl-4-(2-pyridyldithio)butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1). In another aspect, the linker used is derived from a cross-linking agent such as N-succinimidyl-3-(2-pyridyldithio)propionate (SPDP), N-succinimidyl 4-(maleimidomethyl)cyclohexanecarboxylate (SMCC), N-sulfosuccinimidyl 4-(maleimidomethyl)cyclohexanecarboxylate (sulfo-SMCC), sulfosuccinimidyl-4-(2-pyridyldithio)butanoate (sulfo-SPDB) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

Non-cleavable linkers are any chemical moiety capable of linking a drug, such as a maytansinoid, to an antibody in a stable, covalent manner and does not fall off under the categories listed above for cleaveable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which the drug, such as maytansionoid or the antibody does not lose its activity.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e. peptidase cleavable linkers. Only certain peptides are readily cleaved inside or outside cells, see e.g. Trout et al., 79 Proc. Natl. Acad. Sci. USA, 626-629 (1982) and Umemoto et al. 43 Int. J. Cancer, 677-684 (1989). Furthermore, peptides are composed of α-amino acids and peptidic bonds, which chemically are amide bonds between the carboxylate of one amino acid and the amino group of a second amino acid. Other amide bonds, such as the bond between a carboxylate and the ε-amino group of lysine, are understood not to be peptidic bonds and are considered non-cleavable.

Some linkers can be cleaved by esterases, i.e. esterase cleavable linkers. Again, only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

Procharged linkers are derived from charged cross-linking reagents that retain their charge after incorporation into an antibody drug conjugate. Examples of procharged linkers can be found in US 2009/0274713.

3. Conjugation and Preparation of ADCs

The conjugates of the present disclosure can be prepared by any methods known in the art, such as those described in U.S. Pat. Nos. 7,811,572, 6,411,163, 7,368,565, and 8,163,888, and US application publications 2011/0003969, 2011/0166319, 2012/0253021 and 2012/0259100. The entire teachings of these patents and patent application publications are herein incorporated by reference.

One-Step Process

In one aspect, the conjugates of the present disclosure can be prepared by a one-step process. The process comprises combining the antibody, drug and cross-linking agent in a substantially aqueous medium, optionally containing one or more co-solvents, at a suitable pH. In one aspect, the process comprises the step of contacting the antibody of the present disclosure with a drug (e.g., DM1 or DM4) to form a first mixture comprising the antibody and the drug, and then contacting the first mixture comprising the antibody and the drug with a cross-linking agent (e.g., SMCC, Sulfo-SMCC, SPDB, Sulfo-SPDB or CX1-1) in a solution having a pH of about 4 to about 9 to provide a mixture comprising (i) the conjugate (e.g., Ab-SMCC-DM1, Ab-SPDB-DM4, or Ab-CX1-1-DM1), (ii) free drug (e.g., DM1 or DM4), and (iii) reaction by-products.

In one aspect, the one-step process comprises contacting the antibody with the drug (e.g., DM1 or DM4) and then the cross-linking agent (e.g., SMCC, Sulfo-SMCC, SPDB, Sulfo-SPDB or CX1-1) in a solution having a pH of about 6 or greater (e.g., about 6 to about 9, about 6 to about 7, about 7 to about 9, about 7 to about 8.5, about 7.5 to about 8.5, about 7.5 to about 8.0, about 8.0 to about 9.0, or about 8.5 to about 9.0). For example, the process comprises contacting a cell-binding agent with the drug (DM1 or DM4) and then the cross-linking agent (e.g., SMCC, Sulfo-SMCC, SPDB, Sulfo-SPDB or CX1-1) in a solution having a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In another aspect, the process comprises contacting a cell-binding agent with the drug (e.g., DM1 or DM4) and then the cross-linking agent (e.g., SMCC, Sulfo-SMCC, SPDB, Sulfo-SPDB or CX1-1) in a solution having a pH of about 7.8 (e.g., a pH of 7.6 to 8.0 or a pH of 7.7 to 7.9).

The one-step process (i.e., contacting the antibody with the drug (e.g., DM1 or DM4) and then the cross-linking agent (e.g., SMCC, Sulfo-SMCC, SPDB, Sulfo-SPDB or CX1-1) can be carried out at any suitable temperature known in the art. For example, the one-step process can occur at about 20° C. or less (e.g., about −10° C. (provided that the solution is prevented from freezing, e.g., by the presence of organic solvent used to dissolve the cytotoxic agent and the bifunctional crosslinking reagent) to about 20° C., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one aspect, the one-step process occurs at a temperature of about 16° C. to about 24° C. (e.g., about 16° C., about 17° C., about 18° C., about 19° C., about 20° C., about 21° C., about 22° C., about 23° C., about 24° C., or about 25° C.). In another aspect, the one-step process is carried out at a temperature of about 15° C. or less (e.g., about −10° C. to about 15° C., or about 0° C. to about 15° C.). For example, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., about 0° C., about −1° C., about −2° C., about −3° C., about −4° C., about −5° C., about −6° C., about −7° C., about −8° C., about −9° C., or about −10° C., provided that the solution is prevented from freezing, e.g., by the presence of organic solvent(s) used to dissolve the cross-linking agent (e.g., SMCC, Sulfo-SMCC, Sulfo-SPDB SPDB, or CX1-1). In one aspect, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about −10° C. to about 15° C., about 0° C. to about 15° C., about 0° C. to about 10° C., about 0° C. to about 5° C., about 5° C. to about 15° C., about 10° C. to about 15° C., or about 5° C. to about 10° C. In another aspect, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 10° C. (e.g., a temperature of 8° C. to 12° C. or a temperature of 9° C. to 11° C.).

In one aspect, the contacting described above is effected by providing the antibody, then contacting the antibody with the drug (e.g., DM1 or DM4) to form a first mixture comprising the antibody and the drug (e.g., DM1 or DM4), and then contacting the first mixture comprising the antibody and the drug (e.g., DM1 or DM4) with the cross-linking agent (e.g., SMCC, Sulfo-SMCC, SPDB, Sulfo-SPDB or CX1-1). For example, in one aspect, the antibody is provided in a reaction vessel, the drug (e.g., DM1 or DM4) is added to the reaction vessel (thereby contacting the antibody), and then the cross-linking agent (e.g., SMCC, Sulfo-SMCC, SPDB, Sulfo-SPDB or CX1-1) is added to the mixture comprising the antibody and the drug (e.g., DM1 or DM4) (thereby contacting the mixture comprising the antibody and the drug). In one aspect, the antibody is provided in a reaction vessel, and the drug (e.g., DM1 or DM4) is added to the reaction vessel immediately following providing the antibody to the vessel. In another aspect, the antibody is provided in a reaction vessel, and the drug (e.g., DM1 or DM4) is added to the reaction vessel after a time interval following providing the antibody to the vessel (e.g., about 5 minutes, about 10 minutes, about 20 minutes, about 30 minutes, about 40 minutes, about 50 minutes, about 1 hour, about 1 day or longer after providing the cell-binding agent to the space). The drug (e.g., DM1 or DM4) can be added quickly (i.e., within a short time interval, such as about 5 minutes, about 10 minutes) or slowly (such as by using a pump).

The mixture comprising the antibody and the drug (e.g., DM1 or DM4) can then be contacted with the cross-linking agent (e.g., SMCC, Sulfo-SMCC, SPDB, Sulfo-SPDB or CX1-1) either immediately after contacting the antibody with the drug (e.g., DM1 or DM4) or at some later point (e.g., about 5 minutes to about 8 hours or longer) after contacting the antibody with the drug (e.g., DM1 or DM4). For example, in one aspect, the cross-linking agent (e.g., SMCC, Sulfo-SMCC, SPDB, Sulfo-SPDB or CX1-1) is added to the mixture comprising the antibody and the drug (e.g., DM1 or DM4) immediately after the addition of the drug (e.g., DM1 or DM4) to the reaction vessel comprising the antibody. Alternatively, the mixture comprising the antibody and the drug (e.g., DM1 or DM4) can be contacted with the cross-linking agent (e.g., SMCC, Sulfo-SMCC, SPDB, Sulfo-SPDB or CX1-1) at about 5 minutes, about 10 minutes, about 20 minutes, about 30 minutes, about 1 hour, about 2 hours, about 3 hours, about 4 hours, about 5 hours, about 6 hours, about 7 hours, about 8 hours, or longer after contacting the antibody with the drug (e.g., DM1 or DM4).

After the mixture comprising the antibody and the drug (e.g., DM1 or DM4) is contacted with the cross-linking agent (e.g., SMCC, Sulfo-SMCC, SPDB, Sulfo-SPDB or CX1-1) the reaction is allowed to proceed for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer (e.g., about 30 hours, about 35 hours, about 40 hours, about 45 hours, or about 48 hrs).

In one aspect, the one-step process further comprises a quenching step to quench any unreacted drug (e.g., DM1 or DM4) and/or unreacted cross-linking agent (e.g., SMCC, Sulfo-SMCC, SPDB, Sulfo-SPDB or CX1-1). The quenching step is typically performed prior to purification of the conjugate. In one aspect, the mixture is quenched by contacting the mixture with a quenching reagent. As used herein, the "quenching reagent" refers to a reagent that reacts with the free drug (e.g., DM1 or DM4) and/or cross-linking agent (e.g., SMCC, Sulfo-SMCC, SPDB, Sulfo-SPDB or CX1-1). In one aspect, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the drug (e.g., DM1 or DM4) is quenched. The quenching step can help prevent the dimerization of the drug (e.g., DM1). The dimerized DM1 can be difficult to remove. Upon quenching with polar, charged thiol-quenching reagents (such as 4-maleimidobutyric acid or 3-maleimidopropionic acid), the excess, unreacted DM1 is converted into a polar, charged, water-soluble adduct that can be easily separated from the covalently-linked conjugate during the purification step. Quenching with non-polar and neutral thiol-quenching reagents can also be used. In one aspect, the mixture is quenched by contacting the mixture with a quenching reagent that reacts with the unreacted cross-linking agent (e.g., SMCC, Sulfo-SMCC, SPDB, Sulfo-SPDB or CX1-1). For example, nucleophiles can be added to the mixture in order to quench any unreacted SMCC. The nucleophile preferably is an amino group containing nucleophile, such as lysine, taurine and hydroxylamine.

In another aspect, the reaction (i.e., contacting the antibody with the drug (e.g., DM1 or DM4) and then cross-linking agent (e.g., SMCC, Sulfo-SMCC, SPDB, Sulfo-SPDB or CX1-1)) is allowed to proceed to completion prior to contacting the mixture with a quenching reagent. In this regard, the quenching reagent is added to the mixture about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

Alternatively, the mixture is quenched by lowering the pH of the mixture to about 5.0 (e.g., 4.8, 4.9, 5.0, 5.1 or 5.2). In another aspect, the mixture is quenched by lowering the pH to less than 6.0, less than 5.5, less than 5.0, less than 4.8, less than 4.6, less than 4.4, less than 4.2, less than 4.0. Alternatively, the pH is lowered to about 4.0 (e.g., 3.8, 3.9, 4.0, 4.1 or 4.2) to about 6.0 (e.g., 5.8, 5.9, 6.0, 6.1 or 6.2), about 4.0 to about 5.0, about 4.5 (e.g., 4.3, 4.4, 4.5, 4.6 or 4.7) to about 5.0. In one aspect, the mixture is quenched by lowering the pH of the mixture to 4.8. In another aspect, the mixture is quenched by lowering the pH of the mixture to 5.5.

In one aspect, the one-step process further comprises a holding step to release the unstably bound linkers from the antibody. The holding step comprises holding the mixture prior to purification of the conjugate (e.g., after the reaction step, between the reaction step and the quenching step, or after the quenching step). For example, the process comprises (a) contacting the antibody with the drug (e.g., DM1 or DM4) to form a mixture comprising the antibody and the drug (e.g., DM1 or DM4); and then contacting the mixture comprising the antibody and drug (e.g., DM1 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate (e.g., Ab-SMCC-DM1, Ab-SPDB-DM4 or Ab-CX1-1-DM1), (ii) free drug (e.g., DM1 or DM4), and (iii) reaction by-products, (b) holding the mixture prepared in step (a) to release the unstably bound linkers from the cell-binding agent, and (c) purifying the mixture to provide a purified conjugate.

In another aspect, the process comprises (a) contacting the antibody with the drug (e.g., DM1 or DM4) to form a mixture comprising the antibody and the drug (e.g., DM1 or DM4); and then contacting the mixture comprising the antibody and the drug (e.g., DM1 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate, (ii) free drug (e.g., DM1 or DM4), and (iii) reaction by-products, (b) quenching the mixture prepared in step (a) to quench any unreacted drug (e.g., DM1 or DM4) and/or unreacted cross-linking agent (e.g., SMCC, Sulfo-SMCC, SPDB, Sulfo-SPDB or CX1-1), (c) holding the mixture prepared in step (b) to release the unstably bound linkers from the cell-binding agent, and (d) purifying the mixture to provide a purified conjugate (e.g., Ab-SMCC-DM1, Ab-SPDB-DM4 or Ab-CX1-1-DM1).

Alternatively, the holding step can be performed after purification of the conjugate, followed by an additional purification step.

In another aspect, the reaction is allowed to proceed to completion prior to the holding step. In this regard, the holding step can be about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 24 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

The holding step comprises maintaining the solution at a suitable temperature (e.g., about 0° C. to about 37° C.) for a suitable period of time (e.g., about 1 hour to about 1 week, about 1 hour to about 24 hours, about 1 hour to about 8 hours, or about 1 hour to about 4 hours) to release the unstably bound linkers from the antibody while not substantially releasing the stably bound linkers from the antibody. In one aspect, the holding step comprises maintaining the solution at about 20° C. or less (e.g., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one aspect, the holding step comprises maintaining the solution at a temperature of about 16° C. to about 24° C. (e.g., about 15° C., about 16° C., about 17° C., about 18° C., about 19° C., about 20° C., about 21° C., about 22° C., about 23° C., about 24° C., or about 25° C.). In another aspect, the holding step comprises maintaining the solution at a temperature of about 2° C. to about 8° C. (e.g., about 0° C., about 1° C., about 2° C., about 3° C., about 4° C., about 5° C., about 6° C., about 7° C., about 8° C., about 9° C., or about 10° C.). In another aspect, the holding step comprises maintaining the solution at a temperature of about 37° C.

(e.g., about 34° C., about 35° C., about 36° C., about 37° C., about 38° C., about 39° C., or about 40° C.).

The duration of the holding step depends on the temperature and the pH at which the holding step is performed. For example, the duration of the holding step can be substantially reduced by performing the holding step at elevated temperature, with the maximum temperature limited by the stability of the cell-binding agent-cytotoxic agent conjugate. The holding step can comprise maintaining the solution for about 1 hour to about 1 day (e.g., about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours), about 10 hours to about 24 hours, about 12 hours to about 24 hours, about 14 hours to about 24 hours, about 16 hours to about 24 hours, about 18 hours to about 24 hours, about 20 hours to about 24 hours, about 5 hours to about 1 week, about 20 hours to about 1 week, about 12 hours to about 1 week (e.g., about 12 hours, about 16 hours, about 20 hours, about 24 hours, about 2 days, about 3 days, about 4 days, about 5 days, about 6 days, or about 7 days), or about 1 day to about 1 week.

In one aspect, the holding step comprises maintaining the solution at a temperature of about 2° C. to about 8° C. for a period of at least about 12 hours for up to a week. In another aspect, the holding step comprises maintaining the solution at a temperature of about 2° C. to about 8° C. overnight (e.g., about 12 to about 24 hours, preferably about 20 hours).

The pH value for the holding step preferably is about 4 to about 10. In one aspect, the pH value for the holding step is about 4 or more, but less than about 6 (e.g., 4 to 5.9) or about 5 or more, but less than about 6 (e.g., 5 to 5.9). In another aspect, the pH values for the holding step range from about 6 to about 10 (e.g., about 6.5 to about 9, about 6 to about 8). For example, pH values for the holding step can be about 6, about 6.5, about 7, about 7.5, about 8, about 8.5, about 9, about 9.5, or about 10.

In other aspects, the holding step can comprise incubating the mixture at 25° C. at a pH of about 6-7.5 for about 12 hours to about 1 week, incubating the mixture at 4° C. at a pH of about 4.5-5.9 for about 5 hours to about 5 days, or incubating the mixture at 25° C. at a pH of about 4.5-5.9 for about 5 hours to about 1 day.

The one-step process can optionally include the addition of sucrose to the reaction step to increase solubility and recovery of the conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to about 10% (w/v) (e.g., about 0.5% (w/v), about 1% (w/v), about 1.5% (w/v), about 2% (w/v), about 3% (w/v), about 4% (w/v), about 5% (w/v), about 6% (w/v), about 7% (w/v), about 8% (w/v), about 9% (w/v), about 10% (w/v), or about 11% (w/v)). In addition, the reaction step also can comprise the addition of a buffering agent. Any suitable buffering agent known in the art can be used. Suitable buffering agents include, for example, a citrate buffer, an acetate buffer, a succinate buffer, and a phosphate buffer. In one aspect, the buffering agent is selected from the group consisting of HEPPSO(N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

The one-step process can further comprise the step of purifying the mixture to provide purified conjugate (e.g., Ab-SMCC-DM1, Ab-SPDB-DM4 or Ab-CX1-1-DM1). Any purification methods known in the art can be used to purify the conjugates of the present disclosure. In one aspect, the conjugates of the present disclosure use tangential flow filtration (TFF), non-adsorptive chromatography, adsorptive chromatography, adsorptive filtration, selective precipitation, or any other suitable purification process, as well as combinations thereof. In another aspect, prior to subjecting the conjugates to purification process described above, the conjugates are first filtered through one or more PVDF membranes. Alternatively, the conjugates are filtered through one or more PVDF membranes after subjecting the conjugates to the purification process described above. For example, in one aspect, the conjugates are filtered through one or more PVDF membranes and then purified using tangential flow filtration. Alternatively, the conjugates are purified using tangential flow filtration and then filtered through one or more PVDF membranes.

Any suitable TFF systems may be utilized for purification, including a Pellicon® type system (Millipore, Billerica, Mass.), a Sartocon® Cassette system (Sartorius AG, Edgewood, N.Y.), and a Centrasette® type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel® hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel® resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-Prep® Methyl and Macro-Prep® t-Butyl resins (Biorad Laboratories, Hercules, Calif.). Examples of suitable ion exchange resins include SP-Sepharose®, Sepharose®, and Q-Sepharose® resins (all from GE Healthcare, Piscataway, N.J.), and Unosphere® S resin (Bio-Rad Laboratories, Hercules, Calif.). Examples of suitable mixed mode ion exchangers include Bakerbond® ABx resin (JT Baker, Phillipsburg N.J.). Examples of suitable IMAC resins include Chelating Sepharose® resin (GE Healthcare, Piscataway, N.J.) and Profinity® IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.) and lectin affinity resins, e.g. Lentil Lectin Sepharose® resin (GE Healthcare, Piscataway, N.J.), where the antibody bears appropriate lectin binding sites. Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

Two-Step Process and One-Pot Process

In one aspect, the conjugates of the present disclosure can be prepared as described in the U.S. Pat. No. 7,811,572 and U.S. Patent Application Publication No. 2006/0182750. The process comprises the steps of (a) contacting the antibody of the present disclosure with the cross-linking agent (e.g., SMCC, Sulfo-SMCC, SPDB, Sulfo-SPDB or CX1-1) to covalently attach the linker (i.e., Ab-SMCC, Ab-SPDB or Ab-CX1-1) to the antibody and thereby prepare a first mixture comprising the antibody having the linker bound thereto; (b) optionally subjecting the first mixture to a purification process to prepare a purified first mixture of the antibody having the linker bound thereto; (c) conjugating the drug (e.g., DM1 or DM4) to the antibody having the linker bound thereto in the first mixture by reacting the antibody having the linker bound thereto with the drug (e.g., DM1 or DM4) in a solution having a pH of about 4 to about 9 to prepare a second mixture comprising (i) conjugate (e.g., Ab-SMCC-DM1, Ab-SPDB-DM4 or Ab-CX1-1-DM1), (ii) free drug (e.g., DM1 or DM4); and (iii) reaction by-products; and (d) subjecting the second mixture to a purification process to purify the conjugate from the other components of the second mixture. Alternatively, the purification step (b) can be omitted. Any purification methods described herein can be used for steps (b) and (d). In one embodiment, TFF is used for both steps (b) and (d). In another embodiment, TFF is used for step (b) and absorptive chromatography (e.g., CHT) is used for step (d).

One-Step Reagent and In-Situ Process

In one aspect, the conjugates of the present disclosure can be prepared by conjugating pre-formed drug-linker compound (e.g., SMCC-DM1, Sulfo-SMCC-DM1, SPDB-DM4 or CX1-1-DM1) to the antibody of the present disclosure, as described in U.S. Pat. No. 6,441,163 and U.S. Patent Application Publication Nos. 2011/0003969 and 2008/0145374, followed by a purification step. Any purification methods described herein can be used. The drug-linker compound is prepared by reacting the drug (e.g., DM1 or DM4) with the cross-linking agent (e.g., SMCC, Sulfo-SMCC, SPDB, Sulfo-SPDB or CX1-1). The drug-linker compound (e.g., SMCC-DM1, Sulfo-SMCC-DM1, SPDB-DM4 or CX1-1-DM1) is optionally subjected to purification before being conjugated to the antibody.

4. Characterization and Selection of Desirable Antibodies and Antibody Drug-Conjugates The antibodies, antibody fragments (e.g., antigen binding fragments) or antibody drug conjugates of the present disclosure can be characterized and selected for their physical/chemical properties and/or biological activities by various assays known in the art.

For example, an antibody of the present disclosure can be tested for its antigen binding activity by known methods such as ELISA, FACS, Biacore or Western blot.

Transgenic animals and cell lines are particularly useful in screening antibody drug conjugates (ADCs) that have potential as prophylactic or therapeutic treatments of cancer overexpression of tumor-associated antigens and cell surface receptors. Screening for a useful ADC may involve administering a candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. The candidate ADC may be screened serially and individually, or in parallel under medium or high-throughput screening format.

One aspect is a screening method comprising (a) transplanting cells from a stable cancer cell line or human patient tumor expressing cKIT (e.g., a GIST cell line or tumor fragment, a melanoma cell line or tumor fragment) into a non-human animal, (b) administering an ADC drug candidate to the non-human animal and (c) determining the ability of the candidate to inhibit the growth of tumors from the transplanted cell line. The present disclosure also encompasses a method of screening ADC candidates for the treatment of a disease or disorder characterized by the overexpression of cKIT comprising (a) contacting cells from a stable cancer cell line expressing cKIT with a drug candidate, and (b) evaluating the ability of the ADC candidate to inhibit the growth of the stable cell line.

Another aspect is a screening method comprising (a) contacting cells from a stable cancer cell line expressing cKIT with an ADC drug candidate and (b) evaluating the ability of the ADC candidate to block ligand activation of cKIT. In another aspect the ability of the ADC candidate to block ligand-stimulated tyrosine phosphorylation is evaluated.

A further aspect is a screening method comprising (a) contacting cells from a stable cancer cell line expressing cKIT with an ADC drug candidate and (b) evaluating the ability of the ADC candidate to induce cell death. In one aspect the ability of the ADC candidate to induce apoptosis is evaluated.

Candidate ADC can be screened by being administered to the transgenic animal over a range of doses, and evaluating the animal's physiological response to the compounds over time. In some cases, it can be appropriate to administer the compound in conjunction with co-factors that would enhance the efficacy of the compound. If cell lines derived from the subject transgenic animals are used to screen for ADCs useful in treating various disorders associated with overexpression of cKIT, the test ADCs are added to the cell culture medium at an appropriate time, and the cellular response to the ADCs is evaluated over time using the appropriate biochemical and/or histological assays.

Thus, the present disclosure provides assays for identifying ADC which specifically target and bind to cKIT, and cKIT overexpression on tumor cells.

cKIT Antibodies

The present disclosure provides for antibodies or antibody fragments (e.g., antigen binding fragments) that specifically bind to human cKIT. Antibodies or antibody fragments (e.g., antigen binding fragments) of the present disclosure include, but are not limited to, the human monoclonal antibodies or fragments thereof, isolated as described, in the Examples below.

The present disclosure in certain aspects provides antibodies or antibody fragments (e.g., antigen binding fragments) that specifically bind cKIT, said antibodies or antibody fragments (e.g., antigen binding fragments) comprise a VH domain having an amino acid sequence of SEQ ID NO: 9, 28, 46, 64, 82, 100, 118 or 136 (Table 1). The present disclosure also provides antibodies or antibody fragments (e.g., antigen binding fragments) that specifically bind to cKIT, said antibodies or antibody fragments (e.g., antigen binding fragments) comprise a VH CDR having an amino acid sequence of any one of the VH CDRs listed in Table 1. In particular aspects, the present disclosure provides antibodies or antibody fragments (e.g., antigen binding fragments) that specifically bind to cKIT, said antibodies comprising (or alternatively, consist of) one, two, three, four, five or more VH CDRs having an amino acid sequence of any of the VH CDRs listed in Table 1, infra.

The present disclosure provides antibodies or antibody fragments (e.g., antigen binding fragments) that specifically bind to cKIT, said antibodies or antibody fragments (e.g., antigen binding fragments) comprise a VL domain having an amino acid sequence of SEQ ID NO: 18, 37, 55, 73, 91, 109, 127 or 145 (Table1). The present disclosure also provides antibodies or antibody fragments (e.g., antigen binding fragments) that specifically bind to cKIT, said antibodies or antibody fragments (e.g., antigen binding fragments) comprise a VL CDR having an amino acid sequence of any one of the VL CDRs listed in Table 1, infra. In particular, the disclosure provides antibodies or antibody fragments (e.g., antigen binding fragments) that specifically bind to cKIT, said antibodies or antibody fragments (e.g., antigen binding fragments) comprise (or alternatively, consist of) one, two, three or more VL CDRs having an amino acid sequence of any of the VL CDRs listed in Table 1.

Other antibodies or antibody fragments (e.g., antigen binding fragments) of the present disclosure include amino acids that have been mutated, yet have at least 60, 70, 80, 90 or 95 percent identity in the CDR regions with the CDR regions depicted in the sequences described in Table 1. In some aspects, it includes mutant amino acid sequences wherein no more than 1, 2, 3, 4 or 5 amino acids have been mutated in the CDR regions when compared with the CDR regions depicted in the sequence described in Table 1.

The present disclosure also provides nucleic acid sequences that encode VH, VL, the full length heavy chain, and the full length light chain of the antibodies that specifically bind to cKIT. Such nucleic acid sequences can be optimized for expression in mammalian cells.

TABLE 1

Examples of anti- cKIT Antibodies

9P3

| | | | |
|---|---|---|---|
| SEQ ID NO 3: | (Kabat) | HCDR1 | DYYMA |
| SEQ ID NO 4: | (Kabat) | HCDR2 | NINYDGSSTYYLDSLKS |
| SEQ ID NO 5: | (Kabat) | HCDR3 | GDYYGTTYWYFDV |
| SEQ ID NO 6: | (Chothia) | HCDR1 | GFTFSDY |
| SEQ ID NO 7: | (Chothia) | HCDR2 | NYDGSS |
| SEQ ID NO 8: | (Chothia) | HCDR3 | GDYYGTTYWYFDV |
| SEQ ID NO 9: | | VH | EVRLVESEGGLVQPRSSMKLSCTASGFTFSDYYMAWVRQVPEKG LEWVANINYDGSSTYYLDSLKSRFIISRDNAKNILYLQMSSLKSED TATYYCARGDYYGTTYWYFDVWGTGTTVTVSS |
| SEQ ID NO 10 | | Constant heavy chain | VAAPSVFIFPPSDEQLKSGTASVVCLLNNFYPREAKVQWKVDNAL QSGNSQESVTEQDSKDSTYSLSSTLTLSKADYEKHKVYACEVTHQ GLSSPVTKSFNRGEC |
| SEQ ID NO 11: | | Heavy Chain (humanized) | EVQLVESGGGLVQPGGSLRLSCAASGFTFSDYYMAWVRQAPGKG LEWVANINYDGSSTYYLDSVKGRFTISRDNAKNSLYLQMNSLRA EDTAVYYCARGDYYGTTYWYFDVWGQGTTYTVSSASTKGPSVF PLAPSSKSTSGGTAALGCLVKDYFPEPVTVSWNSGALTSGVHTFP AVLQSSGLYSLSSVVTVPSSSLGTQTYICNVNHKPSNTKVDKRVEP KSCDKTHTCPPCPAPELLGGPSVFLFPPKPKDTLMISRTPEVTCVV VDVSHEDPEVKFNWYVDGVEVHNAKTKPREEQYNSTYRVVSVL TVLHQDWLNGKEYKCKVSNKALPAPIEKTISKAKGQPREPQVYTL PPSREEMTKNQVSLTCLVKGFYPSDIAVEWESNGQPENNYKTTPP VLDSDGSFFLYSKLTVDKSRWQQGNVFSCSVMHEALHNHYTQKS LSLSPGK |
| SEQ ID NO 12: | (Kabat) | LCDR1 | RASQDISNYLN |
| SEQ ID NO 13: | (Kabat) | LCDR2 | YTSRLQS |
| SEQ ID NO 14: | (Kabat) | LCDR3 | QQGKKLWS |
| SEQ ID NO 15: (Chothia) | | LCDR1 | SQDISNY |
| SEQ ID NO 16: (Chothia) | | LCDR2 | YTS |
| SEQ ID NO 17: (Chothia) | | LCDR3 | GKKLW |
| SEQ ID NO 18: | | VL | DIQMTQTTSSLSASLGDRVTISCRASQDISNYLNWYQQKPDGTVK LLIYYTSRLQSGVPSRFSGSGSGTDYSLTISNLEQEDIATYFCQQGK KLWSFGGGTKLEIKR |

TABLE 1-continued

Examples of anti- cKIT Antibodies

| | | |
|---|---|---|
| SEQ ID NO:19 | Constant light chain | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKRVEPKSCDKTHTCPPCPAPELLGGPSVELFTPKPKDTLMIS RTPEVTCVVVDVSHEDPEVKFNWYVDGVEVHNAKTKPREEQYN STYRVVSVLTVLHQDWLNGKEYKCKVSNKALPAPIEKTISKAKG QPREPQVYTLPPSREEMTKNQVSLTCLVKGFYPSDIAVEWESNGQ PENNYKTTPPVLDSDGSFFLYSKLTVDKSRWQQGNVFSCSVMHE ALHNHYTQKSLSLSPGK |
| SEQ ID NO 20: | Light Chain (humanized VK1) | DIQMTQSPSSLSASVGDRVTITCRASQSISSYLNWYQQKPGKAPKL LIYYTSRLQSGVPSRFSGSGSGTDYTLTISSLQPEDFATYYCQQGK KLWSFGGGTKVEIKRTVAAPSVFIFPPSDEQLKSGTASVVCLLNNF YPREAKVQWKVDNALQSGNSQESVTEQDSKDSTYSLSSTLTLSK ADYEKHKVYACEVTHQGLSSPVTKSFNRGEC |
| SEQ ID NO 21: | DNA Light Chain (humanized VK3 NEG009) | EIVMTQSPATLSLSPGERATLSCRASQDISNYLNWYQQKPGQAPR LLIYYTSRLQSGIPARFSGSGSGTDYTLTISSLEPEDFAVYYCQQGK KLWSFGGGTKVEIKRTVAAPSVFIFPPSDEQLKSGTASVVCLLNNF YPREAKVQWKVDNALQSGNSQESVTEQDSKDSTYSLSSTLTLSK ADYEKHKVYACEVTHQGLSSPVTKSFNRGEC |

NEG024

| | | |
|---|---|---|
| SEQ ID NO 22: (Kabat) | HCDR1 | DYYMA |
| SEQ ID NO 23: (Kabat) | HCDR2 | NINQIAGSTYYLDSVRG |
| SEQ ID NO 24: (Kabat) | HCDR3 | GDYYGTTYWYFDV |
| SEQ ID NO 25: (Chothia) | HCDR1 | GFTFSDY |
| SEQ ID NO 26: (Chothia) | HCDR2 | NQIAGS |
| SEQ ID NO 27: (Chothia) | HCDR3 | GDYYGTTYWYFDV |
| SEQ ID NO 28: | VH | EVQLVESGGGLVQPGGSLRLSCAASGFTFSDYYMAWVRQAPGKG LEWVANINQIAGSTYYLDSVRGRFTISRDNAKNSLYLQMNSLRAE DTAVYYCARGDYYGTTYWYFDVWGQGTTVTVSS |
| SEQ ID NO 29: | Heavy Chain | EVQLVESGGGLVQPGGSLRLSCAASGFTFSDYYMAWVRQAPGKG LEWVANINQIAGSTYYLDSVRGRFTISRDNAKNSLYLQMNSLRAE DTAVYYCARGDYYGTTYWYFDVWGQGTTVTVSSASTKGPSVFP LAPSSKSTSGGTAALGCLVKDYFPEPVTVSWNSGALTSGVHTFPA VLQSSGLYSLSSVVTVPSSSLGTQTYICNVNHKPSNTKVDKRVEPK SCDKTHTCPPCPAPELLGGPSVFLFPPKPKDTLMISRTPEVTCVVV DVSHEDPEVKFNWYVDGVEVHNAKTKPREEQYNSTYRVVSVLT VLHQDWLNGKEYKCKVSNKALPAPIEKTISKAKGQPREPQVYTLP PSREEMTKNQVSLTCLVKGFYPSDIAVEWESNGQPENNYKTTPPV LDSDGSFFLYSKLTVDKSRWQQGNVFSCSVMHEALHNHYTQKSL SLSPGK |
| SEQ ID NO 30: | DNA Heavy Chain | GAAGTGCAATTGGTGGAAAGCGGCGGAGGCCTGGTGCAGCCT GGCGGCTCTCTGAGACTGAGCTGTGCCGCCAGCGGCTTCACCT TCAGCGACTACTACATGGCCTGGGTCCGACAGGCCCCTGGCAA GGGCCTGGAATGGGTGGCCAATATCAACCAAATCGCCGGCAGC ACCTACTACCTGGACAGCGTGAGAGGCCGGTTCACCATCAGCC GGGACAACGCCAAGAACAGCCTGTACCTGCAGATGAACAGCC TGCGGGCCGAGGACACCGCCGTGTACTACTGCGCCAGAGGCGA TTACTACGGCACCACCTACTGGTACTTCGACGTGTGGGGCCAG GGCACCACCGTGACCGTCAGCTCAGCTAGCACCAAGGGCCCCA GCGTGTTCCCCCTGGCCCCCAGCAGCAAGAGCACCAGCGGCGG CACAGCCGCCCTGGGCTGCCTGGTGAAGGACTACTTCCCCGAG CCCGTGACCGTGTCCTGGAACAGCGGAGCCCTGACCTCCGGCG TGCACACCTTCCCCGCCGTGCTGCAGAGCAGCGGCCTGTACAG CCTGTCCAGCGTGGTGACAGTGCCCAGCAGCAGCCTGGGCACC CAGACCTACATCTGCAACGTGAACCACAAGCCCAGCAACACCA AGGTGGACAAGAGAGTGGAGCCCAAGAGCTGCGACAAGACCC ACACCTGCCCCCCTGCCCAGCCCCAGAGCTGCTGGGCGGACC CTCCGTGTTCCTGTTCCCCCCCAAGCCCAAGGACACCCTGATGA TCAGCAGGACCCCCGAGGTGACCTGCGTGGTGGTGGACGTGAG CCACGAGGACCCAGAGGTGAAGTTCAACTGGTACGTGGACGG CGTGGAGGTGCACAACGCCAAGACCAAGCCCAGAGAGGAGCA GTACAACAGCACCTACAGGGTGGTGTCCGTGCTGACCGTGCTG CACCAGGACTGGCTGAACGGCAAGGAATACAAGTGCAAGGTC |

TABLE 1-continued

Examples of anti- cKIT Antibodies

| | | |
|---|---|---|
| | | TCCAACAAGGCCCTGCCAGCCCCCATCGAAAAGACCATCAGCA<br>AGGCCAAGGGCCAGCCACGGGAGCCCCAGGTGTACACCCTGC<br>CCCCCTCCCGGGAGGAGATGACCAAGAACCAGGTGTCCCTGAC<br>CTGTCTGGTGAAGGGCTTCTACCCCAGCGACATCGCCGTGGAG<br>TGGGAGAGCAACGGCCAGCCCGAGAACAACTACAAGACCACC<br>CCCCCAGTGCTGGACAGCGACGGCAGCTTCTTCCTGTACAGCA<br>AGCTGACCGTGGACAAGTCCAGGTGGCAGCAGGGCAACGTGTT<br>CAGCTGCAGCGTGATGCACGAGGCCCTGCACAACCACTACACC<br>CAGAAGAGCCTGAGCCTGTCCCCCGGCAAG |
| SEQ ID NO 31: (Kabat) | LCDR1 | RASQDISNYLN |
| SEQ ID NO 32: (Kabat) | LCDR2 | YTSRLQS |
| SEQ ID NO 33: (Kabat) | LCDR3 | QQGKKLWS |
| SEQ ID NO 34:<br>(Chothia) | LCDR1 | SQDISNY |
| SEQ ID NO 35:<br>(Chothia) | LCDR2 | YTS |
| SEQ ID NO 36:<br>(Chothia) | LCDR3 | GKKLW |
| SEQ ID NO 37: | VL | EIVMTQSPATLSLSPGERATLSCRASQDISNYLNWYQQKPGQAPR<br>LLIYYTSRLQSGIPARFSGSGSGTDYTLTISSLEPEDFAVYYCQQGK<br>KLWSFGGGTKVEIK |
| SEQ ID NO 38: | Light<br>Chain | EIVMTQSPATLSLSPGERATLSCRASQDISNYLNWYQQKPGQAPR<br>LLIYYTSRLQSGIPARFSGSGSGTDYTLTISSLEPEDFAVYYCQQGK<br>KLWSFGGGTKVEIKRTVAAPSVFIFPPSDEQLKSGTASVVCLLNNF<br>YPREAKVQWKVDNALQSGNSQESVTEQDSKDSTYSLSSTLTLSK<br>ADYEKHKVYACEVTHQGLSSPVTKSFNRGEC |
| SEQ ID NO 39: | DNA<br>Light<br>Chain | GAGATCGTGATGACCCAGAGCCCCGCCACCCTGAGCCTGAGCC<br>CTGGCGAAAGAGCCACCCTGTCCTGCAGAGCCAGCCAGGACAT<br>CAGCAACTACCTGAACTGGTATCAGCAGAAGCCCGGCCAGGCC<br>CCCAGACTGCTGATCTACTACACCAGCCGGCTGCAGAGCGGCA<br>TCCCCGCCAGATTTTCTGGCAGCGGCAGCGGCACCGACTACAC<br>CCTGACCATCAGCAGCCTGGAACCCGAGGACTTCGCCGTGTAC<br>TACTGCCAGCAGGGCAAGAAGCTGTGGTCCTTCGGCGGAGGCA<br>CCAAGGTGGAAATCAAGCGTACGGTGGCCGCTCCCAGCGTGTT<br>CATCTTCCCCCCCAGCGACGAGCAGCTGAAGAGCGGCACCGCC<br>AGCGTGGTGTGCCTGCTGAACAACTTCTACCCCCGGGAGGCCA<br>AGGTGCAGTGGAAGGTGGACAACGCCCTGCAGAGCGGCAACA<br>GCCAGGAGAGCGTCACCGAGCAGGACAGCAAGGACTCCACCT<br>ACAGCCTGAGCAGCACCCTGACCCTGAGCAAGGCCGACTACGA<br>GAAGCATAAGGTGTACGCCTGCGAGGTGACCCACCAGGGCCTG<br>TCCAGCCCCGTGACCAAGAGCTTCAACAGGGGCGAGTGC |
| | NEG026 | |
| SEQ ID NO 40: (Kabat) | HCDR1 | DYYMA |
| SEQ ID NO 41: (Kabat) | HCDR2 | NINQNTGSTYYVDSVQG |
| SEQ ID NO 42: (Kabat) | HCDR3 | GDYYGTTYWYFDV |
| SEQ ID NO 43:<br>(Chothia) | HCDR1 | GFTFSDY |
| SEQ ID NO 44:<br>(Chothia) | HCDR2 | NQNTGS |
| SEQ ID NO 45:<br>(Chothia) | HCDR3 | GDYYGTTYWYFDV |
| SEQ ID NO 46: | VH | EVQLVESGGGLVQPGGSLRLSCAASGFTFSDYYMAWVRQAPGKG<br>LEWVANINQNTGSTYYVDSVQGRFTISRDNAKNSLYLQMNSLRA<br>EDTAVYYCARGDYYGTTYWYFDVWGQGTTVTVSS |
| SEQ ID NO 47: | Heavy<br>Chain | EVQLVESGGGLVQPGGSLRLSCAASGFTFSDYYMAWVRQAPGKG<br>LEWVANINQNTGSTYYVDSVQGRFTISRDNAKNSLYLQMNSLRA<br>EDTAVYYCARGDYYGTTYWYFDVWGQGTTVTVSSASTKGPSVF<br>PLAPSSKSTSGGTAALGCLVKDYFPEPVTVSWNSGALTSGVHTFP<br>AVLQSSGLYSLSSVVTVPSSSLGTQTYICNVNHKPSNTKVDKRVEP<br>KSCDKTHTCPPCPAPELLGGPSVFLFPPKPKDTLMISRTPEVTCVV |

TABLE 1-continued

Examples of anti- cKIT Antibodies

| | | |
|---|---|---|
| | | VDVSHEDPEVKFNWYVDGVEVHNAKTKPREEQYNSTYRVVSVL<br>TVLHQDWLNGKEYKCKVSNKALPAPIEKTISKAKGQPREPQVYTL<br>PPSREEMTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK |
| SEQ ID NO 48: | DNA<br>Heavy<br>Chain | GAAGTGCAATTGGTGGAAAGCGGCGGAGGCCTGGTGCAGCCT<br>GGCGGCTCTCTGAGACTGAGCTGTGCCGCCAGCGGCTTCACCT<br>TCAGCGACTACTACATGGCCTGGGTCCGACAGGCCCCTGGCAA<br>GGGCCTGGAATGGGTGGCCAATATCAACCAAAACACCGGCAG<br>CACCTACTACGTGGACAGCGTGCAAGGCCGGTTCACCATCAGC<br>CGGGACAACGCCAAGAACAGCCTGTACCTGCAGATGAACAGC<br>CTGCGGGCCGAGGACACCGCCGTGTACTACTGCGCCAGAGGCG<br>ATTACTACGGCACCACCTACTGGTACTTCGACGTGTGGGGCCA<br>GGGCACCACCGTGACCGTCAGCTCAGCTAGCACCAAGGGCCCC<br>AGCGTGTTCCCCCTGGCCCCCAGCAGCAAGAGCACCAGCGGCG<br>GCACAGCCGCCCTGGGCTGCCTGGTGAAGGACTACTTCCCCGA<br>GCCCGTGACCGTGTCCTGGAACAGCGGAGCCCTGACCTCCGGC<br>GTGCACACCTTCCCCGCCGTGCTGCAGAGCAGCGGCCTGTACA<br>GCCTGTCCAGCGTGGTGACAGTGCCCAGCAGCAGCCTGGGCAC<br>CCAGACCTACATCTGCAACGTGAACCACAAGCCCAGCAACACC<br>AAGGTGGACAAGAGAGTGGAGCCCAAGAGCTGCGACAAGACC<br>CACACCTGCCCCCCCTGCCCAGCCCCAGAGCTGCTGGGCGGAC<br>CCTCCGTGTTCCTGTTCCCCCCCAAGCCCAAGGACACCCTGATG<br>ATCAGCAGGACCCCCGAGGTGACCTGCGTGGTGGTGGACGTGA<br>GCCACGAGGACCCAGAGGTGAAGTTCAACTGGTACGTGGACG<br>GCGTGGAGGTGCACAACGCCAAGACCAAGCCCAGAGAGGAGC<br>AGTACAACAGCACCTACAGGGTGGTGTCCGTGCTGACCGTGCT<br>GCACCAGGACTGGCTGAACGGCAAGGAATACAAGTGCAAGGT<br>CTCCAACAAGGCCCTGCCAGCCCCCATCGAAAAGACCATCAGC<br>AAGGCCAAGGGCCAGCCACGGGAGCCCCAGGTGTACACCCTG<br>CCCCCCTCCCGGGAGGAGATGACCAAGAACCAGGTGTCCCTGA<br>CCTGTCTGGTGAAGGGCTTCTACCCCAGCGACATCGCCGTGGA<br>GTGGGAGAGCAACGGCCAGCCCGAGAACAACTACAAGACCAC<br>CCCCCCAGTGCTGGACAGCGACGGCAGCTTCTTCCTGTACAGC<br>AAGCTGACCGTGGACAAGTCCAGGTGGCAGCAGGGCAACGTG<br>TTCAGCTGCAGCGTGATGCACGAGGCCCTGCACAACCACTACA<br>CCCAGAAGAGCCTGAGCCTGTCCCCCGGCAAG |
| SEQ ID NO 49: (Kabat) | LCDR1 | RASQDISNYLN |
| SEQ ID NO 50: (Kabat) | LCDR2 | YTSRLQS |
| SEQ ID NO 51: (Kabat) | LCDR3 | QQGKKLWS |
| SEQ ID NO 52:<br>(Chothia) | LCDR1 | SQDISNY |
| SEQ ID NO 53:<br>(Chothia) | LCDR2 | YTS |
| SEQ ID NO 54:<br>(Chothia) | LCDR3 | GKKLW |
| SEQ ID NO 55: | VL | EIVMTQSPATLSLSPGERATLSCRASQDISNYLNWYQQKPGQAPR<br>LLIYYTSRLQSGIPARFSGSGSGTDYTLTISSLEPEDFAVYYCQQGK<br>KLWSFGGGTKVEIK |
| SEQ ID NO 56: | Light<br>Chain | EIVMTQSPATLSLSPGERATLSCRASQDISNYLNWYQQKPGQAPR<br>LLIYYTSRLQSGIPARFSGSGSGTDYTLTISSLEPEDFAVYYCQQGK<br>KLWSFGGGTKVEIKRTVAAPSVFIFPP SDEQLKSGTASVVCLLNNF<br>YPREAKVQWKVDNALQSGNSQE<br>SVTEQDSKDSTYSLSSTLTLSKADYEKHKVYACEVTHQGLSSPVT<br>KSFNRGEC |
| SEQ ID NO 57: | DNA<br>Light<br>Chain | GAGATCGTGATGACCCAGAGCCCCGCCACCCTGAGCCTGAGCC<br>CTGGCGAAAGAGCCACCCTGTCCTGCAGAGCCAGCCAGGACAT<br>CAGCAACTACCTGAACTGGTATCAGCAGAAGCCCGGCCAGGCC<br>CCCAGACTGCTGATCTACTACACCAGCCGGCTGCAGAGCGGCA<br>TCCCCGCCAGATTTTCTGGCAGCGGCAGCGGCACCGACTACAC<br>CCTGACCATCAGCAGCCTGGAACCCGAGGACTTCGCCGTGTAC<br>TACTGCCAGCAGGGCAAGAAGCTGTGGTCCTTCGGCGGAGGCA<br>CCAAGGTGGAAATCAAGCGTACGGTGGCCGCTCCCAGCGTGTT<br>CATCTTCCCCCCCAGCGACGAGCAGCTGAAGAGCGGCACCGCC<br>AGCGTGGTGTGCCTGCTGAACAACTTCTACCCCCGGGAGGCCA<br>AGGTGCAGTGGAAGGTGGACAACGCCCTGCAGAGCGGCAACA |

TABLE 1-continued

Examples of anti-cKIT Antibodies

```
GCCAGGAGAGCGTCACCGAGCAGGACAGCAAGGACTCCACCT
ACAGCCTGAGCAGCACCCTGACCCTGAGCAAGGCCGACTACGA
GAAGCATAAGGTGTACGCCTGCGAGGTGACCCACCAGGGCCTG
TCCAGCCCCGTGACCAAGAGCTTCAACAGGGGCGAGTGC
```

NEG027

| | | | |
|---|---|---|---|
| SEQ ID NO 58: (Kabat) | HCDR1 | DYYMA | |
| SEQ ID NO 59: (Kabat) | HCDR2 | SINQNTGSTYYLDSVRG | |
| SEQ ID NO 60: (Kabat) | HCDR3 | GDYYGTTYWYFDV | |
| SEQ ID NO 61: (Chothia) | HCDR1 | GFTFSDY | |
| SEQ ID NO 62: (Chothia) | HCDR2 | NQNTGS | |
| SEQ ID NO 63: (Chothia) | HCDR3 | GDYYGTTYWYFDV | |
| SEQ ID NO 64: | VH | EVQLVESGGGLVQPGGSLRLSCAASGFTFSDYYMAWVRQAPGKG LEWVASINQNTGSTYYLDSVRGRFTISRDNAKNSLYLQMNSLRAE DTAVYYCARGDYYGTTYWYFDVWGQGTTVTVSS | |
| SEQ ID NO 65: | Heavy Chain | EVQLVESGGGLVQPGGSLRLSCAASGFTFSDYYMAWVRQAPGKG LEWVASINQNTGSTYYLDSVRGRFTISRDNAKNSLYLQMNSLRAE DTAVYYCARGDYYGTTYWYFDVWGQGTTVTVSSASTKGPSVFP LAPSSKSTSGGTAALGCLVKDYFPEPVTVSWNSGALTSGVHTFPA VLQSSGLYSLSSVVTVPSSSLGTQTYICNVNHKPSNTKVDKRVEPK SCDKTHTCPPCPAPELLGGPSVFLFPPKPKDTLMISRTPEVTCVVV DVSHEDPEVKFNWYVDGVEVHNAKTKPREEQYNSTYRVVSVLT VLHQDWLNGKEYKCKVSNKALPAPIEKTISKAKGQPREPQVYTLP PSREEMTKNQVSLTCLVKGFYPSDIAVEWESNGQPENNYKTTPPV LDSDGSFFLYSKLTVDKSRWQQGNVFSCSVMHEALHNHYTQKSL SLSPGK | |
| SEQ ID NO 66: | DNA Heavy Chain | GAAGTGCAATTGGTGGAAAGCGGCGGAGGCCTGGTGCAGCCT GGCGGCTCTCTGAGACTGAGCTGTGCCGCCAGCGGCTTCACCT TCAGCGACTACTACATGGCCTGGGTCCGACAGGCCCCTGGCAA GGGCCTGGAATGGGTGGCCAGTATCAACCAAAACACCGGCAG CACCTACTACCTGGACAGCGTGCGAGGCCGGTTCACCATCAGC CGGGACAACGCCAAGAACAGCCTGTACCTGCAGATGAACAGC CTGCGGGCCGAGGACACCGCCGTGTACTACTGCGCCAGAGGCG ATTACTACGGCACCACCTACTGGTACTTCGACGTGTGGGGCCA GGGCACCACCGTGACCGTCAGCTCAGCTAGCACCAAGGGCCCC AGCGTGTTCCCCCTGGCCCCCAGCAGCAAGAGCACCAGCGGCG GCACAGCCGCCCTGGGCTGCCTGGTGAAGGACTACTTCCCCGA GCCCGTGACCGTGTCCTGGAACAGCGGAGCCCTGACCTCCGGC GTGCACACCTTCCCCGCCGTGCTGCAGAGCAGCGGCCTGTACA GCCTGTCCAGCGTGGTGACAGTGCCCAGCAGCAGCCTGGGCAC CCAGACCTACATCTGCAACGTGAACCACAAGCCCAGCAACACC AAGGTGGACAAGAGAGTGGAGCCCAAGAGCTGCGACAAGACC CACACCTGCCCCCCCTGCCCAGCCCCAGAGCTGCTGGGCGGAC CCTCCGTGTTCCTGTTCCCCCCCAAGCCCAAGGACACCCTGATG ATCAGCAGGACCCCCGAGGTGACCTGCGTGGTGGTGGACGTGA GCCACGAGGACCCAGAGGTGAAGTTCAACTGGTACGTGGACG GCGTGGAGGTGCACAACGCCAAGACCAAGCCCAGAGAGGAGC AGTACAACAGCACCTACAGGGTGGTGTCCGTGCTGACCGTGCT GCACCAGGACTGGCTGAACGGCAAGGAATACAAGTGCAAGGT CTCCAACAAGGCCCTGCCAGCCCCCATCGAAAAGACCATCAGC AAGGCCAAGGGCCAGCCACGGGAGCCCCAGGTGTACACCCTG CCCCCCTCCCGGGAGGAGATGACCAAGAACCAGGTGTCCCTGA CCTGTCTGGTGAAGGGCTTCTACCCCAGCGACATCGCCGTGGA GTGGGAGAGCAACGGCCAGCCCGAGAACAACTACAAGACCAC CCCCCCAGTGCTGGACAGCGACGGCAGCTTCTTCCTGTACAGC AAGCTGACCGTGGACAAGTCCAGGTGGCAGCAGGGCAACGTG TTCAGCTGCAGCGTGATGCACGAGGCCCTGCACAACCACTACA CCCAGAAGAGCCTGAGCCTGTCCCCCGGCAAG | |
| SEQ ID NO 67: (Kabat) | LCDR1 | RASQDISNYLN | |
| SEQ ID NO 68: (Kabat) | LCDR2 | YTSRLQS | |
| SEQ ID NO 69: (Kabat) | LCDR3 | QQGKKLWS | |

TABLE 1-continued

Examples of anti- cKIT Antibodies

| SEQ ID NO 70: (Chothia) | LCDR1 | SQDISNY |
|---|---|---|
| SEQ ID NO 71: (Chothia) | LCDR2 | YTS |
| SEQ ID NO 72: (Chothia) | LCDR3 | GKKLW |
| SEQ ID NO 73: | VL | EIVMTQSPATLSLSPGERATLSCRASQDISNYLNWYQQKPGQAPR LLIYYTSRLQSGIPARFSGSGSGTDYTLTISSLEPEDFAVYYCQQGK KLWSFGGGTKVEIK |
| SEQ ID NO 74: | Light Chain | EIVMTQSPATLSLSPGERATLSCRASQDISNYLNWYQQKPGQAPR LLIYYTSRLQSGIPARFSGSGSGTDYTLTISSLEP EDFAVYYCQQGKKLWSFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| SEQ ID NO 75: | DNA Light Chain | GAGATCGTGATGACCCAGAGCCCCGCCACCCTGAGCCTGAGCC CTGGCGAAAGAGCCACCCTGTCCTGCAGAGCCAGCCAGGACAT CAGCAACTACCTGAACTGGTATCAGCAGAAGCCCGGCCAGGCC CCCAGACTGCTGATCTACTACACCAGCCGGCTGCAGAGCGGCA TCCCCGCCAGATTTTCTGGCAGCGGCAGCGGCACCGACTACAC CCTGACCATCAGCAGCCTGGAACCCGAGGACTTCGCCGTGTAC TACTGCCAGCAGGGCAAGAAGCTGTGGTCCTTCGGCGGAGGCA CCAAGGTGGAAATCAAGCGTACGGTGGCCGCTCCCAGCGTGTT CATCTTCCCCCCCAGCGACGAGCAGCTGAAGAGCGGCACCGCC AGCGTGGTGTGCCTGCTGAACAACTTCTACCCCCGGGAGGCCA AGGTGCAGTGGAAGGTGGACAACGCCCTGCAGAGCGGCAACA GCCAGGAGAGCGTCACCGAGCAGGACAGCAAGGACTCCACCT ACAGCCTGAGCAGCACCCTGACCCTGAGCAAGGCCGACTACGA GAAGCATAAGGTGTACGCCTGCGAGGTGACCCACCAGGGCCTG TCCAGCCCCGTGACCAAGAGCTTCAACAGGGGCGAGTGC |

NEG085

| SEQ ID NO 76: (Kabat) | HCDR1 | GYYMA |
|---|---|---|
| SEQ ID NO 77: (Kabat) | HCDR2 | NINYPGSSTYYLDSVKG |
| SEQ ID NO 78: (Kabat) | HCDR3 | GDYYGTTYWYFDV |
| SEQ ID NO 79: (Chothia) | HCDR1 | GFAFSGY |
| SEQ ID NO 80: (Chothia) | HCDR2 | NYPGSS |
| SEQ ID NO 81: (Chothia) | HCDR3 | GDYYGTTYWYFDV |
| SEQ ID NO 82: | VH | EVQLVESGGGLVQPGGSLRLSCAASGFAFSGYYMAWVRQAPGK GLEWVANINYPGSSTYYLDSVKGRFTISRDNAKNSLYLQMNSLRA EDTAVYYCARGDYYGTTYWYFDVWGQGTTVTSS |
| SEQ ID NO 83: | Heavy Chain | EVQLVESGGGLVQPGGSLRLSCAASGFAFSGYYMAWVRQAPGK GLEWVANINYPGSSTYYLDSVKGRFTISRDNAKNSLYLQMNSLRA EDTAVYYCARGDYYGTTYWYFDVWGQGTTVTSSASTKGPSVF PLAPSSKSTSGGTAALGCLVKDYFPEPVTVSWNSGALTSGVHTFP AVLQSSGLYSLSSVVTVPSSSLGTQTYICNVNHKPSNTKVDKRVEP KSCDKTHTCPPCPAPELLGGPSVFLFPPKPKDTLMISRTPEVTCVV VDVSHEDPEVKFNWYVDGVEVHNAKTKPREEQYNSTYRVVSVL TVLHQDWLNGKEYKCKVSNKALPAPIEKTISKAKGQPREPQVYTL PPSREEMTKNQVSLTCLVKGFYPSDIAVEWESNGQPENNYKTTPP VLDSDGSFFLYSKLTVDKSRWQQGNVFSCSVMHEALHNHYTQKS LSLSPGK |
| SEQ ID NO 84: | DNA Heavy Chain | GAAGTGCAATTGGTGGAAAGCGGCGGAGGCCTGGTGCAGCCT GGCGGCTCTCTGAGACTGAGCTGTGCCGCCAGCGGCTTCGCCT TCAGCGGCTACTACATGGCCTGGGTCCGACAGGCCCCTGGCAA GGGCCTGGAATGGGTGGCCAACATCAACTACCCCGGCAGCAGC ACCTACTACCTGGACAGCGTGAAGGGCCGGTTCACCATCAGCC GGGACAACGCCAAGAACAGCCTGTACCTGCAGATGAACAGCC TGCGGGCCGAGGACACCGCCGTGTACTACTGCGCCAGAGGCGA TTACTACGGCACCACCTACTGGTACTTCGACGTGTGGGGCCAG GGCACCACCGTGACCGTCAGCTCAGCTAGCACCAAGGGCCCCA GCGTGTTCCCCCTGGCCCCCAGCAGCAAGAGCACCAGCGGCGG |

TABLE 1-continued

Examples of anti- cKIT Antibodies

| | | | |
|---|---|---|---|
| | | | CACAGCCGCCCTGGGCTGCCTGGTGAAGGACTACTTCCCCGAG<br>CCCGTGACCGTGTCCTGGAACAGCGGAGCCCTGACCTCCGGCG<br>TGCACACCTTCCCCGCCGTGCTGCAGAGCAGCGGCCTGTACAG<br>CCTGTCCAGCGTGGTGACAGTGCCCAGCAGCAGCCTGGGCACC<br>CAGACCTACATCTGCAACGTGAACCACAAGCCCAGCAACACCA<br>AGGTGGACAAGAGAGTGGAGCCCAAGAGCTGCGACAAGACCC<br>ACACCTGCCCCCCCTGCCCAGCCCCAGAGCTGCTGGGCGGACC<br>CTCCGTGTTCCTGTTCCCCCCCAAGCCCAAGGACACCCTGATGA<br>TCAGCAGGACCCCCGAGGTGACCTGCGTGGTGGTGGACGTGAG<br>CCACGAGGACCCAGAGGTGAAGTTCAACTGGTACGTGGACGG<br>CGTGGAGGTGCACAACGCCAAGACCAAGCCCAGAGAGGAGCA<br>GTACAACAGCACCTACAGGGTGGTGTCCGTGCTGACCGTGCTG<br>CACCAGGACTGGCTGAACGGCAAGGAATACAAGTGCAAGGTC<br>TCCAACAAGGCCCTGCCAGCCCCCATCGAAAAGACCATCAGCA<br>AGGCCAAGGGCCAGCCACGGGAGCCCCAGGTGTACACCCTGC<br>CCCCCTCCCGGGAGGAGATGACCAAGAACCAGGTGTCCCTGAC<br>CTGTCTGGTGAAGGGCTTCTACCCCAGCGACATCGCCGTGGAG<br>TGGGAGAGCAACGGCCAGCCCGAGAACAACTACAAGACCACC<br>CCCCCAGTGCTGGACAGCGACGGCAGCTTCTTCCTGTACAGCA<br>AGCTGACCGTGGACAAGTCCAGGTGGCAGCAGGGCAACGTGTT<br>CAGCTGCAGCGTGATGCACGAGGCCCTGCACAACCACTACACC<br>CAGAAGAGCCTGAGCCTGTCCCCCGGCAAG |
| SEQ ID NO 85: (Kabat) | LCDR1 | RASQSISSYLN | |
| SEQ ID NO 86: (Kabat) | LCDR2 | YTSRLQS | |
| SEQ ID NO 87: (Kabat) | LCDR3 | QQGRRLWS | |
| SEQ ID NO 88:<br>(Chothia) | LCDR1 | SQSISSY | |
| SEQ ID NO 89:<br>(Chothia) | LCDR2 | YTS | |
| SEQ ID NO 90:<br>(Chothia) | LCDR3 | GRRLW | |
| SEQ ID NO 91: | VL | DIQMTQSPSSLSASVGDRVTITCRASQSISSYLNWYQQKPGKAPKL<br>LIYYTSRLQSGVPSRFSGSGSGTDFTLTISSLQPEDFATYYCQQGRR<br>LWSFGGGTKVEIK | |
| SEQ ID NO 92: | Light<br>Chain | DIQMTQSPSSLSASVGDRVTITCRASQSISSYLNWYQQKPGKAPKL<br>LIYYTSRLQSGVPSRFSGSGSGTDFTLTISSLQPEDFATYYCQQGRR<br>LWSFGGGTKVEIKRTVAAPSVFIFPPSDEQLKSGTASVVCLLNNFY<br>PREAKVQWKVDNALQSGNSQESVTEQDSKDSTYSLSSTLTLSKA<br>DYEKHKVYACEVTHQGLSSPVTKSFNRGEC | |
| SEQ ID NO 93: | DNA<br>Light<br>Chain | GATATCCAGATGACCCAGAGCCCCAGCAGCCTGAGCGCCAGCG<br>TGGGCGACAGAGTGACCATCACCTGTCGGGCCAGCCAGAGCAT<br>CAGCAGCTACCTGAACTGGTATCAGCAGAAGCCCGGCAAGGCC<br>CCCAAGCTGCTGATCTACTACACCAGCCGGCTGCAGAGCGGCG<br>TGCCCAGCAGATTTTCTGGCAGCGGCAGCGGCACCGACTTCAC<br>CCTGACCATCAGCAGCCTGCAGCCCGAGGACTTCGCCACCTAC<br>TACTGCCAGCAGGGCCGCCGCCTGTGGTCCTTCGGCGGAGGCA<br>CCAAGGTGGAAATCAAGCGTACGGTGGCCGCTCCCAGCGTGTT<br>CATCTTCCCCCCCAGCGACGAGCAGCTGAAGAGCGGCACCGCC<br>AGCGTGGTGTGCCTGCTGAACAACTTCTACCCCCGGGAGGCCA<br>AGGTGCAGTGGAAGGTGGACAACGCCCTGCAGAGCGGCAACA<br>GCCAGGAGAGCGTCACCGAGCAGGACAGCAAGGACTCCACCT<br>ACAGCCTGAGCAGCACCCTGACCCTGAGCAAGGCCGACTACGA<br>GAAGCATAAGGTGTACGCCTGCGAGGTGACCCACCAGGGCCTG<br>TCCAGCCCCGTGACCAAGAGCTTCAACAGGGGCGAGTGC | |
| | | NEG086 | |
| SEQ ID NO 94: (Kabat) | HCDR1 | DYYMA | |
| SEQ ID NO 95: (Kabat) | HCDR2 | NINQIAGSTYYVDSVQG | |
| SEQ ID NO 96: (Kabat) | HCDR3 | GDYYGTTYWYFDV | |
| SEQ ID NO 97:<br>(Chothia) | HCDR1 | GFTFSDY | |
| SEQ ID NO 98:<br>(Chothia) | HCDR2 | NQIAGS | |

TABLE 1-continued

Examples of anti- cKIT Antibodies

| | | |
|---|---|---|
| SEQ ID NO 99: (Chothia) | HCDR3 | GDYYGTTYWYFDV |
| SEQ ID NO 100: | VH | EVQLVESGGGLVQPGGSLRLSCAASGFTFSDYYMAWVRQAPGKG<br>LEWVANINQIAGSTYYVDSVQGRFTISRDNAKNSLYLQMNSLRAE<br>DTAVYYCARGDYYGTTYWYFDVWGQGTTVTVSS |
| SEQ ID NO 101: | Heavy Chain | EVQLVESGGGLVQPGGSLRLSCAASGFTFSDYYMAWVRQAPGKG<br>LEWVANINQIAGSTYYVDSVQGRFTISRDNAKNSLYLQMNSLRAE<br>DTAVYYCARGDYYGTTYWYFDVWGQGTTVTVSSASTKGPSVFP<br>LAPSSKSTSGGTAALGCLVKDYFPEPVTVSWNSGALTSGVHTFPA<br>VLQSSGLYSLSSVVTVPSSSLGTQTYICNVNHKPSNTKVDKRVEPK<br>SCDKTHTCPPCPAPELLGGPSVFLFPPKPKDTLMISRTPEVTCVVV<br>DVSHEDPEVKFNWYVDGVEVHNAKTKPREEQYNSTYRVVSVLT<br>VLHQDWLNGKEYKCKVSNKALPAPIEKTISKAKGQPREPQVYTLP<br>PSREEMTKNQVSLTCLVKGFYPSDIAVEWESNGQPENNYKTTPPV<br>LDSDGSFFLYSKLTVDKSRWQQGNVFSCSVMHEALHNHYTQKSL<br>SLSPGK |
| SEQ ID NO 102: | DNA Heavy Chain | GAAGTGCAATTGGTGGAAAGCGGCGGAGGCCTGGTGCAGCCT<br>GGCGGCTCTCTGAGACTGAGCTGTGCCGCCAGCGGCTTCACCT<br>TCAGCGACTACTACATGGCCTGGGTCCGACAGGCCCCTGGCAA<br>GGGCCTGGAATGGGTGGCCAATATCAACCAAATCGCCGGCAGC<br>ACCTACTACGTGGACAGCGTGCAAGGCCGGTTCACCATCAGCC<br>GGGACAACGCCAAGAACAGCCTGTACCTGCAGATGAACAGCC<br>TGCGGGCCGAGGACACCGCCGTGTACTACTGCGCCAGAGGCGA<br>TTACTACGGCACCACCTACTGGTACTTCGACGTGTGGGGCCAG<br>GGCACCACCGTGACCGTCAGCTCAGCTAGCACCAAGGGCCCCA<br>GCGTGTTCCCCCTGGCCCCCAGCAGCAAGAGCACCAGCGGCGG<br>CACAGCCGCCCTGGGCTGCCTGGTGAAGGACTACTTCCCCGAG<br>CCCGTGACCGTGTCCTGGAACAGCGGAGCCCTGACCTCCGGCG<br>TGCACACCTTCCCCGCCGTGCTGCAGAGCAGCGGCCTGTACAG<br>CCTGTCCAGCGTGGTGACAGTGCCCAGCAGCAGCCTGGGCACC<br>CAGACCTACATCTGCAACGTGAACCACAAGCCCAGCAACACCA<br>AGGTGGACAAGAGAGTGGAGCCCAAGAGCTGCGACAAGACCC<br>ACACCTGCCCCCCCTGCCCAGCCCCAGAGCTGCTGGGCGGACC<br>CTCCGTGTTCCTGTTCCCCCCCAAGCCCAAGGACACCCTGATGA<br>TCAGCAGGACCCCCGAGGTGACCTGCGTGGTGGTGGACGTGAG<br>CCACGAGGACCCAGAGGTGAAGTTCAACTGGTACGTGGACGG<br>CGTGGAGGTGCACAACGCCAAGACCAAGCCCAGAGAGGAGCA<br>GTACAACAGCACCTACAGGGTGGTGTCCGTGCTGACCGTGCTG<br>CACCAGGACTGGCTGAACGGCAAGGAATACAAGTGCAAGGTC<br>TCCAACAAGGCCCTGCCAGCCCCCATCGAAAAGACCATCAGCA<br>AGGCCAAGGGCCAGCCACGGGAGCCCCAGGTGTACACCCTGC<br>CCCCCTCCCGGGAGGAGATGACCAAGAACCAGGTGTCCCTGAC<br>CTGTCTGGTGAAGGGCTTCTACCCCAGCGACATCGCCGTGGAG<br>TGGGAGAGCAACGGCCAGCCCGAGAACAACTACAAGACCACC<br>CCCCCAGTGCTGGACAGCGACGGCAGCTTCTTCCTGTACAGCA<br>AGCTGACCGTGGACAAGTCCAGGTGGCAGCAGGGCAACGTGTT<br>CAGCTGCAGCGTGATGCACGAGGCCCTGCACAACCACTACACC<br>CAGAAGAGCCTGAGCCTGTCCCCCGGCAAG |
| SEQ ID NO 103: (Kabat) | LCDR1 | RASQSISSYLN |
| SEQ ID NO 104: (Kabat) | LCDR2 | YTSRLQS |
| SEQ ID NO 105: (Kabat) | LCDR3 | QQGRRLWS |
| SEQ ID NO 106: (Chothia) | LCDR1 | SQSISSY |
| SEQ ID NO 107: (Chothia) | LCDR2 | YTS |
| SEQ ID NO 108: (Chothia) | LCDR3 | GRRLW |
| SEQ ID NO 109: | VL | DIQMTQSPSSLSASVGDRVTITCRASQSISSYLNWYQQKPGKAPKL<br>LIYYTSRLQSGVPSRFSGSGSGTDFTLTISSLQPEDFATYYCQQGRR<br>LWSFGGGTKVEIK |
| SEQ ID NO 110: | Light Chain | DIQMTQSPSSLSASVGDRVTITCRASQSISSYLNWYQQKPGKAPKL<br>LIYYTSRLQSGVPSRFSGSGSGTDFTLTISSLQPEDFATYYCQQGRR<br>LWSFGGGTKVEIKRTVAAPSVFIFPPSDEQLKSGTASVVCLLNNFY<br>PREAKVQWKVDNALQSGNSQESVTEQDSKDSTYSLSSTLTLSKA<br>DYEKHKVYACEVTHQGLSSPVTKSFNRGEC |

TABLE 1-continued

Examples of anti-cKIT Antibodies

| | | |
|---|---|---|
| SEQ ID NO 111: | DNA Light Chain | GATATCCAGATGACCCAGAGCCCCAGCAGCCTGAGCGCCAGCG TGGGCGACAGAGTGACCATCACCTGTCGGGCCAGCCAGAGCAT CAGCAGCTACCTGAACTGGTATCAGCAGAAGCCCGGCAAGGCC CCCAAGCTGCTGATCTACTACACCAGCCGGCTGCAGAGCGGCG TGCCCAGCAGATTTTCTGGCAGCGGCAGCGGCACCGACTTCAC CCTGACCATCAGCAGCCTGCAGCCCGAGGACTTCGCCACCTAC TACTGCCAGCAGGGCCGCCGCCTGTGGTCCTTCGGCGGAGGCA CCAAGGTGGAAATCAAGCGTACGGTGGCCGCTCCCAGCGTGTT CATCTTCCCCCCCAGCGACGAGCAGCTGAAGAGCGGCACCGCC AGCGTGGTGTGCCTGCTGAACAACTTCTACCCCCGGGAGGCCA AGGTGCAGTGGAAGGTGGACAACGCCCTGCAGAGCGGCAACA GCCAGGAGAGCGTCACCGAGCAGGACAGCAAGGACTCCACCT ACAGCCTGAGCAGCACCCTGACCCTGAGCAAGGCCGACTACGA GAAGCATAAGGTGTACGCCTGCGAGGTGACCCACCAGGGCCTG TCCAGCCCCGTGACCAAGAGCTTCAACAGGGGCGAGTGC |

NEG087

| | | |
|---|---|---|
| SEQ ID NO 112: (Kabat) | HCDR1 | DYYMA |
| SEQ ID NO 113: (Kabat) | HCDR2 | SINQNTGSTYYLDSVRG |
| SEQ ID NO 114: (Kabat) | HCDR3 | GDYYGTTYWYFDV |
| SEQ ID NO 115: (Chothia) | HCDR1 | GFTFSDY |
| SEQ ID NO 116: (Chothia) | HCDR2 | NQNTGS |
| SEQ ID NO 117: (Chothia) | HCDR3 | GDYYGTTYWYFDV |
| SEQ ID NO 118: | VH | EVQLVESGGGLVQPGGSLRLSCAASGFTFSDYYMAWVRQAPGKG LEWVASINQNTGSTYYLDSVRGRFTISRDNAKNSLYLQMNSLRAE DTAVYYCARGDYYGTTYWYFDVWGQGTTVTVSS |
| SEQ ID NO 119: | Heavy Chain | EVQLVESGGGLVQPGGSLRLSCAASGFTFSDYYMAWVRQAPGKG LEWVASINQNTGSTYYLDSVRGRFTISRDNAKNSLYLQMNSLRAE DTAVYYCARGDYYGTTYWYFDVWGQGTTVTVSSASTKGPSVFP LAPSSKSTSGGTAALGCLVKDYFPEPVTVSWNSGALTSGVHTFPA VLQSSGLYSLSSVVTVPSSSLGTQTYICNVNHKPSNTKVDKRVEPK SCDKTHTCPPCPAPELLGGPSVFLFPPKPKDTLMISRTPEVTCVVV DVSHEDPEVKFNWYVDGVEVHNAKTKPREEQYNSTYRVVSVLT VLHQDWLNGKEYKCKVSNKALPAPIEKTISKAKGQPREPQVYTLP PSREEMTKNQVSLTCLVKGFYPSDIAVEWESNGQPENNYKTTPPV LDSDGSFFLYSKLTVDKSRWQQGNVFSCSVMHEALHNHYTQKSL SLSPGK |
| SEQ ID NO 120: | DNA Heavy Chain | GAAGTGCAATTGGTGGAAAGCGGCGGAGGCCTGGTGCAGCCT GGCGGCTCTCTGAGACTGAGCTGTGCCGCCAGCGGCTTCACCT TCAGCGACTACTACATGGCTTGGGTCCGACAGGCCCCTGGCAA GGGCCTGGAATGGGTGGCCAGTATCAACCAAAACACCGGCAG CACCTACTACCTGGACAGCGTGCGAGGCCGGTTCACCATCAGC CGGGACAACGCCAAGAACAGCCTGTACCTGCAGATGAACAGC CTGCGGGCCGAGGACACCGCCGTGTACTACTGCGCCAGAGGCG ATTACTACGGCACCACCTACTGGTACTTCGACGTGTGGGGCCA GGGCACCACCGTGACCGTCAGCTCAGCTAGCACCAAGGGCCCC AGCGTGTTCCCCCTGGCCCCCAGCAGCAAGAGCACCAGCGGCG GCACAGCCGCCCTGGGCTGCCTGGTGAAGGACTACTTCCCCGA GCCCGTGACCGTGTCCTGGAACAGCGGAGCCCTGACCTCCGGC GTGCACACCTTCCCCGCCGTGCTGCAGAGCAGCGGCCTGTACA GCCTGTCCAGCGTGGTGACAGTGCCCAGCAGCAGCCTGGGCAC CCAGACCTACATCTGCAACGTGAACCACAAGCCCAGCAACACC AAGGTGGACAAGAGAGTGGAGCCCAAGAGCTGCGACAAGACC CACACCTGCCCCCCCTGCCCAGCCCCAGAGCTGCTGGGCGGAC CCTCCGTGTTCCTGTTCCCCCCCAAGCCCAAGGACACCCTGATG ATCAGCAGGACCCCCGAGGTGACCTGCGTGGTGGTGGACGTGA GCCACGAGGACCCTGAGGTGAAGTTCAACTGGTACGTGGACG GCGTGGAGGTGCACAACGCCAAGACCAAGCCCAGAGAGGAGC AGTACAACAGCACCTACAGGGTGGTGTCCGTGCTGACCGTGCT GCACCAGGACTGGCTGAACGGCAAGGAATACAAGTGCAAGGT CTCCAACAAGGCCCTGCCAGCCCCCATCGAAAAGACCATCAGC AAGGCCAAGGGCCAGCCACGGGAGCCCCAGGTGTACACCCTG CCCCCCTCCCGGGAGGAGATGACCAAGAACCAGGTGTCCCTGA CCTGTCTGGTGAAGGGCTTCTACCCCAGCGACATCGCCGTGGA GTGGGAGAGCAACGGCCAGCCCGAGAACAACTACAAGACCAC CCCCCCAGTGCTGGACAGCGACGGCAGCTTCTTCCTGTACAGC |

TABLE 1-continued

Examples of anti- cKIT Antibodies

|  |  |  |
|---|---|---|
|  |  | AAGCTGACCGTGGACAAGTCCAGGTGGCAGCAGGGCAACGTG<br>TTCAGCTGCAGCGTGATGCACGAGGCCCTGCACAACCACTACA<br>CCCAGAAGAGCCTGAGCCTGTCCCCCGGCAAG |
| SEQ ID NO 121: (Kabat) | LCDR1 | RASQSISSYLN |
| SEQ ID NO 122: (Kabat) | LCDR2 | YTSRLQS |
| SEQ ID NO 123: (Kabat) | LCDR3 | QQGRRLWS |
| SEQ ID NO 124:<br>(Chothia) | LCDR1 | SQSISSY |
| SEQ ID NO 125:<br>(Chothia) | LCDR2 | YTS |
| SEQ ID NO 126:<br>(Chothia) | LCDR3 | GRRLW |
| SEQ ID NO 127: | VL | DIQMTQSPSSLSASVGDRVTITCRASQSISSYLNWYQQKPGKAPKL<br>LIYYTSRLQSGVPSRFSGSGSGTDFTLTISSLQPEDFATYYCQQGRR<br>LWSFGGGTKVEIK |
| SEQ ID NO 128: | Light<br>Chain | DIQMTQSPSSLSASVGDRVTITCRASQSISSYLNWYQQKPGKAPKL<br>LIYYTSRLQSGVPSRFSGSGSGTDFTLTISSLQPEDFATYYCQQGRR<br>LWSFGGGTKVEIKRTVAAP SVFIFPPSDEQLKSGTASVVCLLNNFY<br>PREAKVQWKVDNALQSGNSQESVTEQDSKDSTYSLSSTLTLSKA<br>DYEKHKVYACEVTHQGLSSPVTKSFNRGEC |
| SEQ ID NO 129: | DNA<br>Light<br>Chain | GATATCCAGATGACCCAGAGCCCCAGCAGCCTGAGCGCCAGCG<br>TGGGCGACAGAGTGACCATCACCTGTCGGGCCAGCCAGAGCAT<br>CAGCAGCTACCTGAACTGGTATCAGCAGAAGCCCGGCAAGGCC<br>CCCAAGCTGCTGATCTACTACACCAGCCGGCTGCAGAGCGGCG<br>TGCCCAGCAGATTTTCTGGCAGCGGCAGCGGCACCGACTTCAC<br>CCTGACCATCAGCAGCCTGCAGCCCGAGGACTTCGCCACCTAC<br>TACTGCCAGCAGGGCCGCCGCCTGTGGTCCTTCGGCGGAGGCA<br>CCAAGGTGGAAATCAAGCGTACGGTGGCCGCTCCCAGCGTGTT<br>CATCTTCCCCCCCAGCGACGAGCAGCTGAAGAGCGGCACCGCC<br>AGCGTGGTGTGCCTGCTGAACAACTTCTACCCCCGGGAGGCCA<br>AGGTGCAGTGGAAGGTGGACAACGCCCTGCAGAGCGGCAACA<br>GCCAGGAGAGCGTCACCGAGCAGGACAGCAAGGACTCCACCT<br>ACAGCCTGAGCAGCACCCTGACCCTGAGCAAGGCCGACTACGA<br>GAAGCATAAGGTGTACGCCTGCGAGGTGACCCACCAGGGCCTG<br>TCCAGCCCCGTGACCAAGAGCTTCAACAGGGGCGAGTGC |

20376

| SEQ ID NO 130: (Kabat) | HCDR1 | SYAIS |
| SEQ ID NO 131: (Kabat) | HCDR2 | GIIPMSGRTTYAQKFQG |
| SEQ ID NO 132: (Kabat) | HCDR3 | DYGPEAPDYGQSTSYFWYYAFDP |
| SEQ ID NO 133:<br>(Chothia) | HCDR1 | GGTFSSY |
| SEQ ID NO 134:<br>(Chothia) | HCDR2 | IPMSGR |
| SEQ ID NO 135:<br>(Chothia) | HCDR3 | DYGPEAPDYGQSTSYFWYYAFDP |
| SEQ ID NO 136: | VH | QVQLVQSGAEVKKPGSSVKVSCKASGGTFSSYAISWVRQAPGQG<br>LEWMGGIIPMSGRTTYAQKFQGRVTITADESTSTAYMELSSLRSE<br>DTAVYYCARDYGPEAPDYGQSTSYFWYYAFDPWGQGTLVTVSS |
| SEQ ID NO 137: | Heavy<br>Chain | QVQLVQSGAEVKKPGSSVKVSCKASGGTFSSYAISWVRQAPGQG<br>LEWMGGIIPMSGRTTYAQKFQGRVTITADESTSTAYMELSSLRSE<br>DTAVYYCARDYGPEAPDYGQSTSYFWYYAFDPWGQGTLVTVSS<br>ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPELLGGPSVFLFPPKPKDTLMIS<br>RTPEVTCVVVDVSHEDPEVKFNWYVDGVEVHNAKTKPREEQYN<br>STYRVVSVLTVLHQDWLNGKEYKCKVSNKALPAPIEKTISKAKG<br>QPREPQVYTLPPSREEMTKNQVSLTCLVKGFYPSDIAVEWESNGQ<br>PENNYKTTPPVLDSDGSFFLYSKLTVDKSRWQQGNVFSCSVMHE<br>ALHNHYTQKSLSLSPGK |

TABLE 1-continued

Examples of anti- cKIT Antibodies

| | | |
|---|---|---|
| SEQ ID NO 138: | DNA Heavy Chain | CAGGTGCAGCTGGTGCAGTCAGGCGCCGAAGTGAAGAAACCC GGCTCTAGCGTGAAAGTCAGCTGTAAAGCTAGTGGGGGCACCT TCTCTAGCTACGCTATTAGCTGGGTCAGACAGGCCCCAGGTCA AGGCTTGGAGTGGATGGGCGGAATTATCCCTATGAGCGGTAGA ACTACCTACGCTCAGAAATTTCAGGGTAGAGTGACTATCACCG CCGACGAGTCTACTAGCACCGCCTATATGGAACTGAGTTCTCT GAGGTCAGAGGACACCGCCGTCTACTACTGCGCTAGAGACTAC GGCCCCGAGGCCCCCGACTACGGTCAATCAACTAGCTACTTCT GGTACTACGCCTTCGACCCTTGGGGTCAAGGCACCCTGGTCAC CGTGTCTTCAGCTAGCACTAAGGGCCCAAGTGTGTTTCCCCTGG CCCCCAGCAGCAAGTCTACTTCCGGCGGAACTGCTGCCCTGGG TTGCCTGGTGAAGGACTACTTCCCCGAGCCCGTGACAGTGTCC TGGAACTCTGGGGCTCTGACTTCCGGCGTGCACACCTTCCCCGC CGTGCTGCAGAGCAGCGGCCTGTACAGCCTGAGCAGCGTGGTG ACAGTGCCCTCCAGCTCTCTGGGAACCCAGACCTATATCTGCA ACGTGAACCACAAGCCCAGCAACACCAAGGTGGACAAGAGAG TGGAGCCCAAGAGCTGCGACAAGACCCACACCTGCCCCCCCTG CCCAGCTCCAGAACTGCTGGGAGGGCCTTCCGTGTTCCTGTTCC CCCCCAAGCCCAAGGACACCCTGATGATCAGCAGGACCCCCGA GGTGACCTGCGTGGTGGTGGACGTGTCCCACGAGGACCCAGAG GTGAAGTTCAACTGGTACGTGGACGGCGTGGAGGTGCACAACG CCAAGACCAAGCCCAGAGAGGAGCAGTACAACAGCACCTACA GGGTGGTGTCCGTGCTGACCGTGCTGCACCAGGACTGGCTGAA CGGCAAAGAATACAAGTGCAAAGTCTCCAACAAGGCCCTGCC AGCCCCAATCGAAAAGACAATCAGCAAGGCCAAGGGCCAGCC ACGGGAGCCCCAGGTGTACACCCTGCCCCCCAGCCGGGAGGA GATGACCAAGAACCAGGTGTCCCTGACCTGTCTGGTGAAGGGC TTCTACCCCAGCGATATCGCCGTGGAGTGGGAGAGCAACGGCC AGCCCGAGAACAACTACAAGACCACCCCCCCAGTGCTGGACA GCGACGGCAGCTTCTTCCTGTACAGCAAGCTGACCGTGGACAA GTCCAGGTGGCAGCAGGGCAACGTGTTCAGCTGCAGCGTGATG CACGAGGCCCTGCACAACCACTACACCCAGAAGTCCCTGAGCC TGAGCCCCGGCAAG |
| SEQ ID NO 139: (Kabat) | LCDR1 | SGDNIPSYFVH |
| SEQ ID NO 140: (Kabat) | LCDR2 | DDNDRPS |
| SEQ ID NO 141: (Kabat) | LCDR3 | SSWDQDTVV |
| SEQ ID NO 142: (Chothia) | LCDR1 | DNIPSYF |
| SEQ ID NO 143: (Chothia) | LCDR2 | DDN |
| SEQ ID NO 144: (Chothia) | LCDR3 | WDQDTV |
| SEQ ID NO 145: | VL | DIELTQPPSVSVSPGQTASITCSGDNIPSYFVHWYQQKPGQAPVLVI YDDNDRPSGIPERFSGSNSGNTATLTISGTQAEDEADYYCSSWDQ DTVVFGGGTKLTVL |
| SEQ ID NO 146: | Light Chain | DIELTQPPSVSVSPGQTASITCSGDNIPSYFVHWYQQKPGQAPVLVI YDDNDRPSGIPERFSGSNSGNTATLTISGTQAEDEADYYCSSWDQ DTVVFGGGTKLTVLGQPKAAPSVTLFPPSSEELQANKATLVCLISD FYPGAVTVAWKADSSPVKAGVETTTPSKQSNNKYAASSYLSLTPE QWKSHRSYSCQVTHEGSTVEKTVAPTECS |
| SEQ ID NO 147: | DNA Light Chain | GATATCGAGCTGACTCAGCCCCCTAGCGTCAGCGTCAGCCCTG GTCAAACCGCCTCTATCACCTGTAGCGGCGATAATATCCCTAG CTACTTCGTGCACTGGTATCAGCAGAAGCCCGGTCAAGCCCCC GTGCTGGTGATCTACGACGATAACGATAGACCTAGCGGAATCC CCGAGCGGTTTAGCGGCTCTAATAGCGGTAACACCGCTACCCT GACTATTAGCGGCACTCAGGCCGAGGACGAGGCCGACTACTAC TGCTCTAGCTGGGATCAGGACACCGTGGTGTTCGGCGGAGGCA CTAAGCTGACCGTGCTGGGTCAACCTAAGGCTGCCCCCAGCGT GACCCTGTTCCCCCCCAGCAGCGAGGAGCTGCAGGCCAACAAG GCCACCCTGGTGTGCCTGATCAGCGACTTCTACCCAGGCGCCG TGACCGTGGCCTGGAAGGCCGACAGCAGCCCCGTGAAGGCCG GCGTGGAGACCACCACCCCCAGCAAGCAGAGCAACAACAAGT ACGCCGCCAGCAGCTACCTGAGCCTGACCCCCGAGCAGTGGAA GAGCCACAGGTCCTACAGCTGCCAGGTGACCCACGAGGGCAG CACCGTGGAAAAGACCGTGGCCCCAACCGAGTGCAGC |

Other antibodies of the present disclosure include those where the amino acids or nucleic acids encoding the amino acids have been mutated, yet have at least 60, 70, 80, 90 or 95 percent identity to the sequences described in Table 1. In some aspects, it includes mutant amino acid sequences wherein no more than 1, 2, 3, 4 or 5 amino acids have been mutated in the variable regions when compared with the variable regions depicted in the sequence described in Table 1, while retaining substantially the same therapeutic activity.

Since each of these antibodies can bind to cKIT, the VH, VL, full length light chain, and full length heavy chain sequences (amino acid sequences and the nucleotide sequences encoding the amino acid sequences) can be "mixed and matched" to create other cKIT-binding antibodies. Such "mixed and matched" cKIT-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise, a full length light chain sequence from a particular full length heavy chain/full length light chain pairing should be replaced with a structurally similar full length light chain sequence. Accordingly, in one aspect, the disclosure provides for an isolated monoclonal antibody or antigen binding region thereof having: a heavy chain variable region comprising an amino acid sequence selected from the group consisting of SEQ ID NOs: 9, 28, 46, 64, 82, 100, 118 or 136 (Table 1); and a light chain variable region comprising an amino acid sequence selected from the group consisting of SEQ ID NOs: 18, 37, 55, 73, 91, 109, 127 or 145 (Table1); wherein the antibody specifically binds to cKIT.

In another aspect, the disclosure provides (i) an isolated monoclonal antibody having: a full length heavy chain comprising an amino acid sequence that has been optimized for expression in the cell of a mammalian selected from the group consisting of SEQ ID NOs: 11, 29, 47, 65, 83, 101, 119, or 137; and a full length light chain comprising an amino acid sequence that has been optimized for expression in the cell of a mammalian selected from the group consisting of SEQ ID NOs: 20, 21, 38, 56, 74, 92, 110, 128, or 146; or (ii) a functional protein comprising an antigen binding portion thereof.

In another aspect, the present disclosure provides cKIT-binding antibodies that comprise the heavy chain and light chain CDR1s, CDR2s and CDR3s as described in Table 1, or combinations thereof. The amino acid sequences of the VH CDR1s of the antibodies are shown in SEQ ID NOs: 3, 22, 40, 58, 76, 94, 112 and 130. The amino acid sequences of the VH CDR2s of the antibodies and are shown in SEQ ID NOs: 4, 23, 41, 59, 77, 95, 113 and 131. The amino acid sequences of the VH CDR3s of the antibodies are shown in SEQ ID NOs: 5, 24, 42, 60, 78, 96, 114 and 132. The amino acid sequences of the VL CDR1s of the antibodies are shown in SEQ ID NOs: 12, 31, 49, 67, 85, 103, 121 and 139. The amino acid sequences of the VL CDR2s of the antibodies are shown in SEQ ID NOs 13, 32, 50, 68, 86, 104, 122 and 140. The amino acid sequences of the VL CDR3s of the antibodies are shown in SEQ ID NOs:14, 33, 51, 69, 87, 105, 123 and 141.

Given that each of these antibodies can bind to cKIT and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other C5-binding binding molecules. Such "mixed and matched" cKIT-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure.

Accordingly, the present disclosure provides an isolated monoclonal antibody or antigen binding region thereof comprising a heavy chain CDR1 comprising an amino acid sequence selected from the group consisting of SEQ ID NOs: 3, 22, 40, 58, 76, 94, 112 and 130; a heavy chain CDR2 comprising an amino acid sequence selected from the group consisting of SEQ ID NOs: 4, 23, 41, 59, 77, 95, 113 and 131; a heavy chain CDR3 comprising an amino acid sequence selected from the group consisting of SEQ ID NOs: 5, 24, 42, 60, 78, 96, 114 and 132; a light chain CDR1 comprising an amino acid sequence selected from the group consisting of SEQ ID NOs: 12, 31, 49, 67, 85, 103, 121 and 139; a light chain CDR2 comprising an amino acid sequence selected from the group consisting of SEQ ID NOs: 13, 32, 50, 68, 86, 104, 122 and 140; and a light chain CDR3 comprising an amino acid sequence selected from the group consisting of SEQ ID NOs: 14, 33, 51, 69, 87, 105, 123 and 141; wherein the antibody specifically binds cKIT.

In a specific aspect, an antibody or antibody fragment (e.g., antigen binding fragments) that specifically binds to cKIT comprising a heavy chain CDR1 of SEQ ID NO:3, a heavy chain CDR2 of SEQ ID NO: 4; a heavy chain CDR3 of SEQ ID NO:5; a light chain CDR1 of SEQ ID NO:12; a light chain CDR2 of SEQ ID NO: 13; and a light chain CDR3 of SEQ ID NO: 14.

In a specific aspect, an antibody or antibody fragment (e.g., antigen binding fragments) that specifically binds to cKIT comprising a heavy chain CDR1 of SEQ ID NO:22, a heavy chain CDR2 of SEQ ID NO: 23; a heavy chain CDR3 of SEQ ID NO:24; a light chain CDR1 of SEQ ID NO:31; a light chain CDR2 of SEQ ID NO: 32; and a light chain CDR3 of SEQ ID NO: 33.

In a specific aspect, an antibody or antibody fragment (e.g., antigen binding fragments) that specifically binds to cKIT comprising a heavy chain CDR1 of SEQ ID NO:40, a heavy chain CDR2 of SEQ ID NO: 41; a heavy chain CDR3 of SEQ ID NO:42; a light chain CDR1 of SEQ ID NO:49; a light chain CDR2 of SEQ ID NO: 50; and a light chain CDR3 of SEQ ID NO: 51.

In a specific aspect, an antibody or antibody fragment (e.g., antigen binding fragments) that specifically binds to cKIT comprising a heavy chain CDR1 of SEQ ID NO:58, a heavy chain CDR2 of SEQ ID NO: 59; a heavy chain CDR3 of SEQ ID NO:60; a light chain CDR1 of SEQ ID NO:67; a light chain CDR2 of SEQ ID NO: 68; and a light chain CDR3 of SEQ ID NO: 69.

In a specific aspect, an antibody or antibody fragment (e.g., antigen binding fragments) that specifically binds to cKIT comprising a heavy chain CDR1 of SEQ ID NO:76, a heavy chain CDR2 of SEQ ID NO: 77; a heavy chain CDR3 of SEQ ID NO:78; a light chain CDR1 of SEQ ID NO:85; a light chain CDR2 of SEQ ID NO: 86; and a light chain CDR3 of SEQ ID NO: 87.

In a specific aspect, an antibody or antibody fragment (e.g., antigen binding fragments) that specifically binds to cKIT comprising a heavy chain CDR1 of SEQ ID NO:94, a heavy chain CDR2 of SEQ ID NO: 95; a heavy chain CDR3 of SEQ ID NO:96; a light chain CDR1 of SEQ ID NO:103; a light chain CDR2 of SEQ ID NO: 104; and a light chain CDR3 of SEQ ID NO: 105.

In a specific aspect, an antibody or antibody fragment (e.g., antigen binding fragments) that specifically binds to cKIT comprising a heavy chain CDR1 of SEQ ID NO:112, a heavy chain CDR2 of SEQ ID NO: 113; a heavy chain CDR3 of SEQ ID NO:114; a light chain CDR1 of SEQ ID NO:121; a light chain CDR2 of SEQ ID NO: 122; and a light chain CDR3 of SEQ ID NO: 123.

In a specific aspect, an antibody or antibody fragment (e.g., antigen binding fragments) that specifically binds to cKIT comprising a heavy chain CDR1 of SEQ ID NO:130, a heavy chain CDR2 of SEQ ID NO: 131; a heavy chain CDR3 of SEQ ID NO:132; a light chain CDR1 of SEQ ID NO:139; a light chain CDR2 of SEQ ID NO: 140; and a light chain CDR3 of SEQ ID NO: 141.

In certain aspects, an antibody that specifically binds to cKIT is an antibody or antibody fragment (e.g., antigen binding fragment) that is described in Table 1.

1. Identification of Epitopes and Antibodies that Bind to the Same Epitope

The present disclosure provides antibodies and antibody fragments (e.g., antigen binding fragments) that bind to an epitope of within the extracellular domain of the cKIT receptor. In certain aspects the antibodies and antibody fragments can bind to epitopes with domains 1-3 of the cKIT extracellular domain.

The present disclosure also provides antibodies and antibody fragments (e.g., antigen binding fragments) that bind to the same epitope as do the anti-cKIT antibodies described in Table 1. Additional antibodies and antibody fragments (e.g., antigen binding fragments) can therefore be identified based on their ability to cross-compete (e.g., to competitively inhibit the binding of, in a statistically significant manner) with other antibodies in cKIT binding assays. The ability of a test antibody to inhibit the binding of antibodies and antibody fragments (e.g., antigen binding fragments) of the present disclosure to a cKIT protein (e.g., human cKIT) demonstrates that the test antibody can compete with that antibody or antibody fragment (e.g., antigen binding fragments) for binding to cKIT; such an antibody may, according to non-limiting theory, bind to the same or a related (e.g., a structurally similar or spatially proximal) epitope on the cKIT protein as the antibody or antibody fragment (e.g., antigen binding fragments) with which it competes. In a certain aspect, the antibody that binds to the same epitope on cKIT as the antibodies or antibody fragments (e.g., antigen binding fragments) of the present disclosure is a human or humanized monoclonal antibody. Such human or humanized monoclonal antibodies can be prepared and isolated as described herein.

2. Further Alteration of the Framework of Fc Region

The present disclosure provides site-specific labeled immunoconjugates. These immunoconjugates can comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

Figure 4:
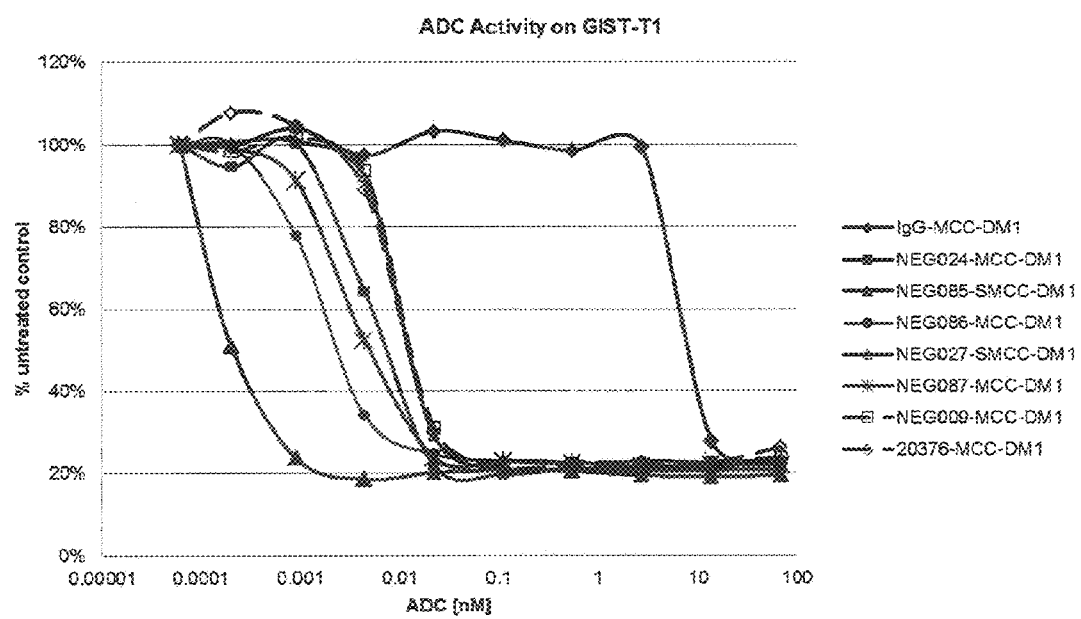
FIG. 4 shows the ability of c-Kit-MCC-DM1 ADCs to inhibit the proliferation of GIST-T1 (Imatinib-sensitive) cells.
Figure 5:
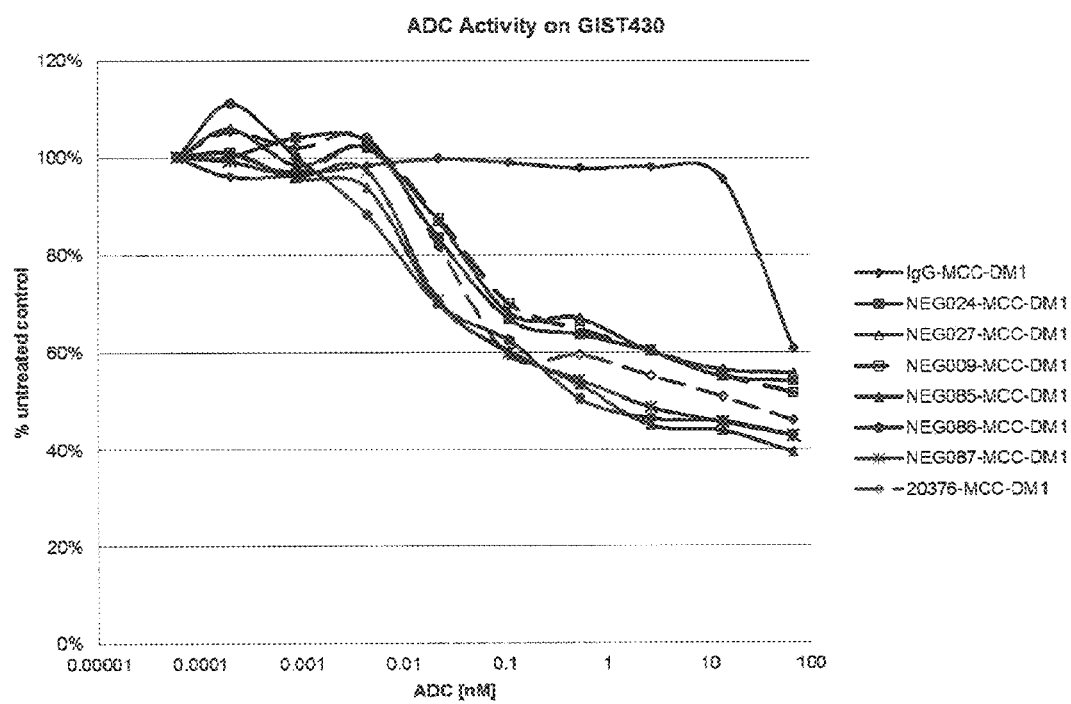
FIG. 5 shows the ability of c-Kit-MCC-DM1 ADCs to inhibit the proliferation of GIST430 (Imatinib-resistant) cells.
Figure 6:
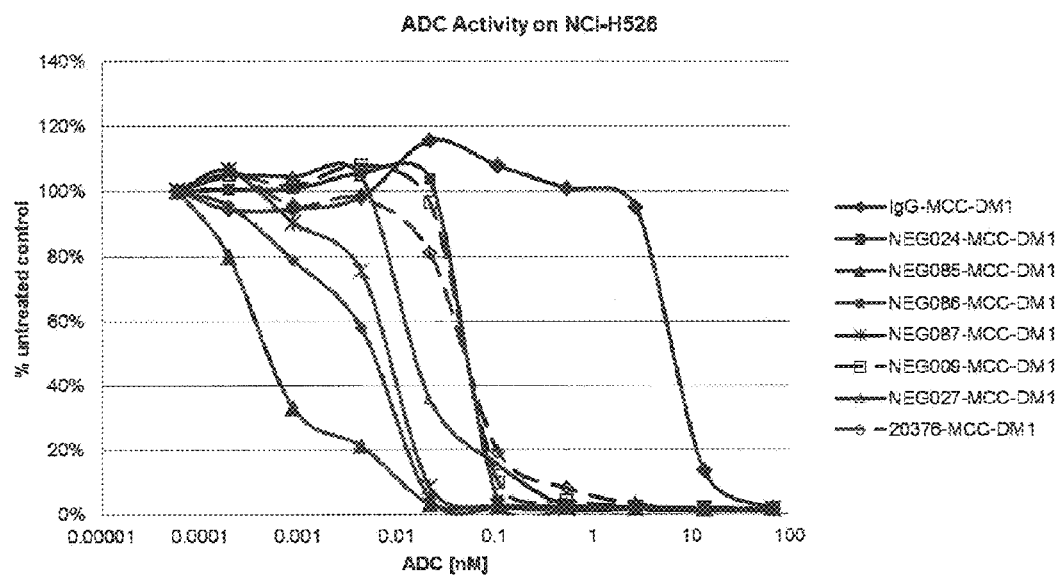
FIG. 6 shows the ability of c-Kit-MCC-DM1 ADCs to inhibit the proliferation of NCI-H526 (higher c-Kit expressing SCLC) cells.
Figure 7:
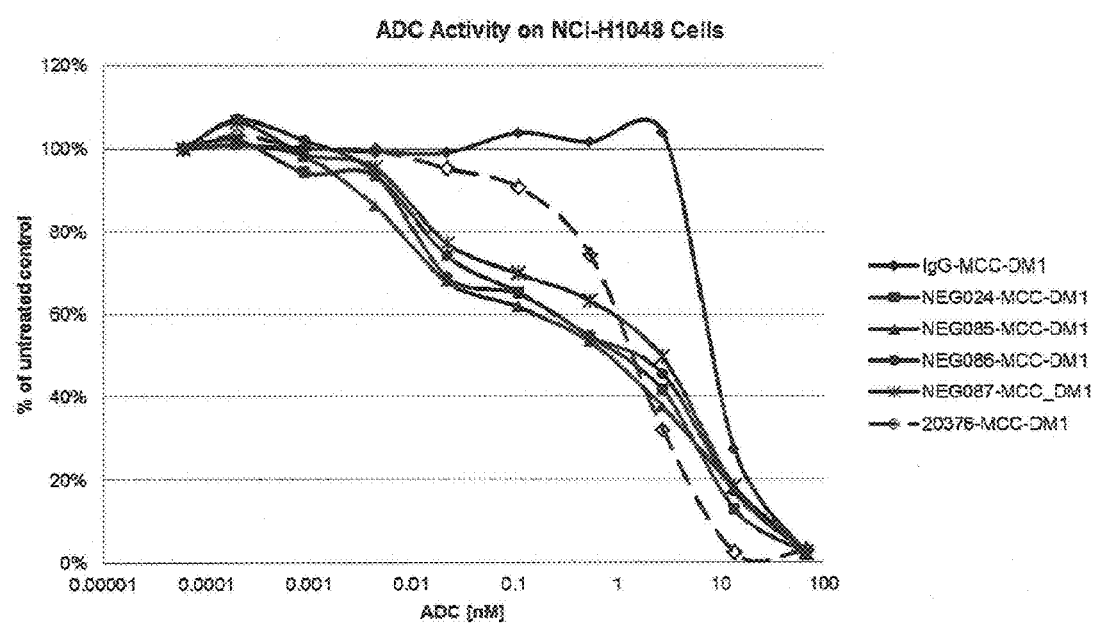
FIG. 7 shows the ability of c-Kit-MCC-DM1 ADCs to inhibit the proliferation of NCI-H1048 (lower c-Kit expressing SCLC) cells.
Figure 8:
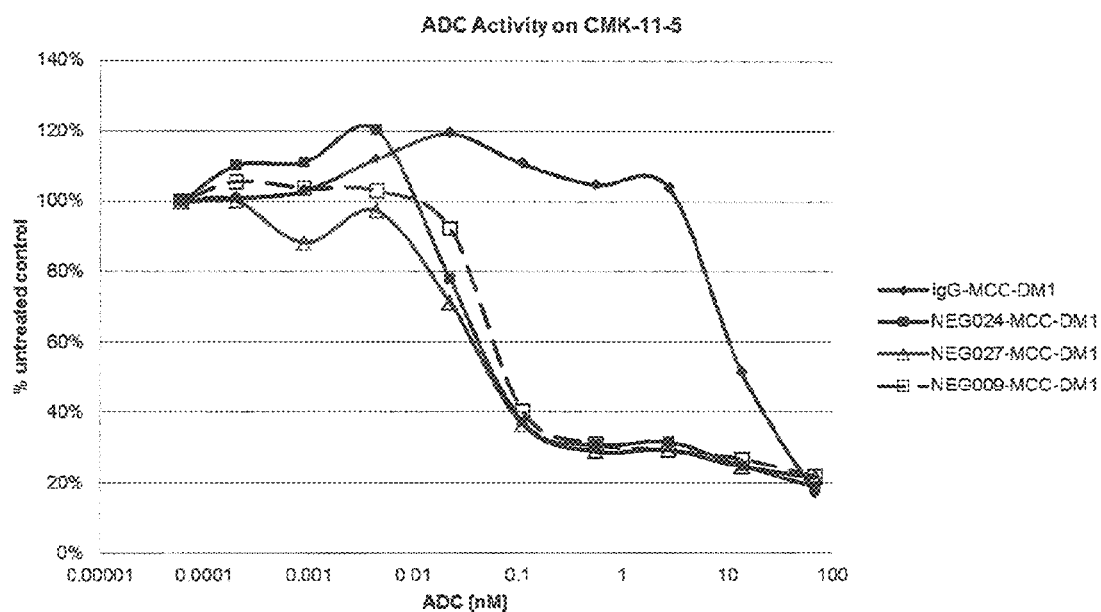
FIG. 8 shows the ability of c-Kit-MCC-DM1 ADCs to inhibit the proliferation of CMK11-5 (high c-Kit expressing AML) cells.
Figure 9:
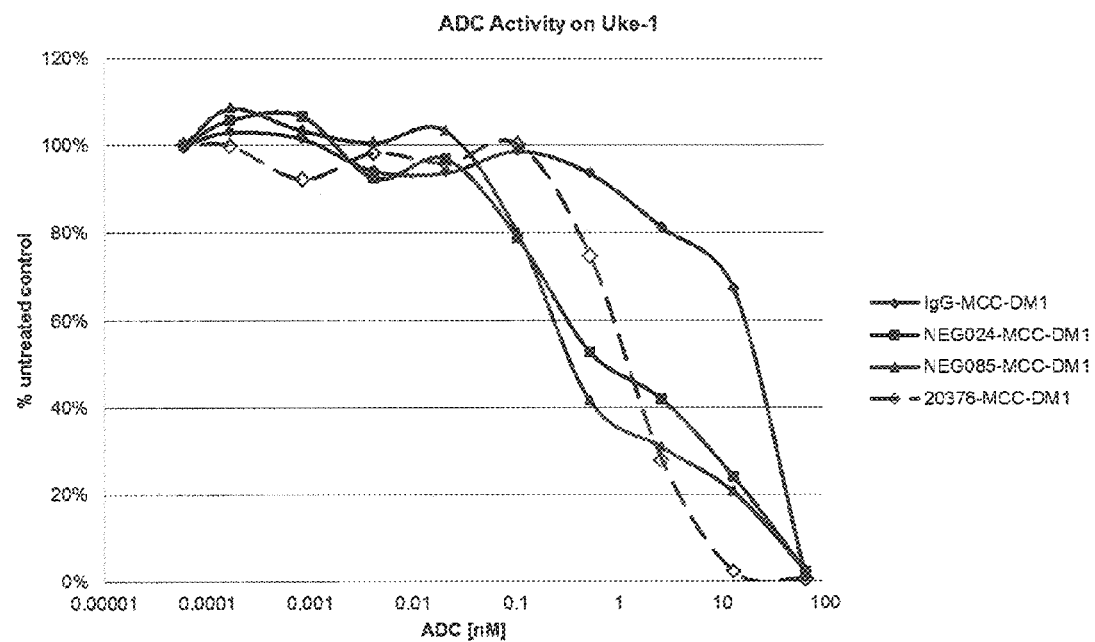
FIG. 9 shows the ability of c-Kit-MCC-DM1 ADCs to inhibit the proliferation of Uke-1 (lower c-Kit expressing AML) cells.

In another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen binding fragment thereof of the present disclosure are replaced by one or more allotypic amino acid residues, such as those shown in FIG. 4 for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγR1, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

3. Production of the cKIT Antibodies

Anti-cKIT antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 30, 48, 66, 84, 102, 120 and 137. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs:39, 57, 75, 93, 111, 129 and 147.

In some aspects, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 30, 48, 66, 84, 102, 120. In some aspects, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 39, 57, 75, 93, 111, 129 and 147.

The polynucleotides of the present disclosure can encode only the variable region sequence of an anti-cKIT antibody. They can also encode both a variable region and a constant region of the antibody. Some of the polynucleotide sequences encode a polypeptide that comprises variable regions of both the heavy chain and the light chain of one of an exemplified anti-cKIT antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-cKIT antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the present disclosure are expression vectors and host cells for producing the anti-cKIT antibodies described above. Various expression vectors can be employed to express the polynucleotides encoding the anti-cKIT antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the anti-cKIT polynucleotides and polypeptides in mammalian (e.g., human) cells include pThioHis A, B & C, pcDNA3.1/H is, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-cKIT antibody chain or fragment. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-cKIT antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-cKIT antibody sequences. More often, the inserted anti-cKIT antibody sequences are linked to a signal sequences before inclusion in the vector. Vectors to be used to receive sequences encoding anti-cKIT antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-cKIT antibody chains can be either prokaryotic or eukaryotic. E. coli is one prokaryotic host useful for cloning and expressing the polynucleotides of the present disclosure. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-cKIT polypeptides. Insect cells in combination with baculovirus vectors can also be used.

In other aspects, mammalian host cells are used to express and produce the anti-cKIT polypeptides of the present disclosure. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-cKIT antibody chains or binding fragments can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments), and antibody drug conjugates of the present disclosure are useful in a variety of applications including, but not limited to, treatment of cancer, such as solid cancers. In certain aspects, the antibodies, antibody fragments (e.g., antigen binding fragments), and antibody drug conjugates are useful for inhibiting tumor growth, inducing differentiation, reducing tumor volume, and/or reducing the tumorigenicity of a tumor. The methods of use can be in vitro, ex vivo, or in vivo methods.

In one aspect, the antibodies, antibody fragments (e.g., antigen binding fragments), and antibody drug conjugates are useful for detecting the presence of cKIT in a biological sample. The term "detecting" as used herein encompasses quantitative or qualitative detection. In certain aspects, a biological sample comprises a cell or tissue. In certain aspects, such tissues include normal and/or cancerous tissues that express cKIT at higher levels relative to other tissues.

In one aspect, the present disclosure provides a method of detecting the presence of cKIT in a biological sample. In certain aspects, the method comprises contacting the biological sample with an anti-cKIT antibody under conditions permissive for binding of the antibody to the antigen, and detecting whether a complex is formed between the antibody and the antigen.

Also included is a method of diagnosing a disorder associated with increased expression of cKIT. In certain aspects, the method comprises contacting a test cell with an anti-cKIT antibody; determining the level of expression (either quantitatively or qualitatively) of cKIT on the test cell by detecting binding of the anti-cKIT antibody to the cKIT antigen; and comparing the level of expression of cKIT in the test cell with the level of expression of cKIT in a control cell (e.g., a normal cell of the same tissue origin as the test cell or a cell that expresses cKIT at levels comparable to such a normal cell), wherein a higher level of expression of cKIT on the test cell as compared to the control cell indicates the presence of a disorder associated with increased expression of cKIT. In certain aspects, the test cell is obtained from an individual suspected of having a disorder associated with increased expression of cKIT. In certain aspects, the disorder is a cell proliferative disorder, such as a cancer or a tumor.

In certain aspects, a method of diagnosis or detection, such as those described above, comprises detecting binding of an anti-cKIT antibody to cKIT expressed on the surface of a cell or in a membrane preparation obtained from a cell expressing cKIT on its surface. An exemplary assay for detecting binding of an anti-cKIT antibody to cKIT expressed on the surface of a cell is a "FACS" assay.

Certain other methods can be used to detect binding of anti-cKIT antibodies to cKIT. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain aspects, anti-cKIT antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain aspects, anti-cKIT antibodies are immobilized on an insoluble matrix. Immobilization entails separating the anti-cKIT antibody from any cKIT proteins that remains free in solution. This conventionally is accomplished by either insolubilizing the anti-cKIT antibody before the assay procedure, as by adsorption to a water-insoluble matrix or surface (Bennich et al, U.S. Pat. No. 3,720,760), or by covalent coupling (for example, using glutaraldehyde crosslinking), or by insolubilizing the anti-cKIT antibody after formation of a complex between the anti-cKIT antibody and cKIT protein, e.g., by immunoprecipitation.

Any of the above aspects of diagnosis or detection can be carried out using an immunoconjugate of the present disclosure in place of or in addition to an anti-cKIT antibody.

In one aspect, the disclosure provides for a method of treating, preventing or ameliorating a disease comprising administering the antibodies, antibody fragments (e.g., antigen binding fragments), and antibody drug conjugates to a patient, thereby treating the disease. In certain aspects, the disease treated with the antibodies, antibody fragments (e.g., antigen binding fragments), and antibody drug conjugates is a cancer. Examples of diseases which can be treated and/or prevented include, but are not limited to, gastrointestinal stromal tumors (GIST), small cell lung cancer (SCLC), acute myelod leukemia (AML), melanoma, mast cell leukemia (MCL), mastocytosis, neurofibromatosis, breast cancer, non-small cell lung cancer (NSCLC), and pancreatic cancer. In certain aspects, the cancer is characterized by cKIT expressing cells to which the antibodies, antibody fragments (e.g., antigen binding fragments), and antibody drug conjugates can specifically bind.

The present disclosure provides for methods of treating cancer comprising administering a therapeutically effective amount of the antibodies, antibody fragments (e.g., antigen binding fragments), or antibody drug conjugates. In certain aspects, the cancer is a solid cancer. In certain aspects, the subject is a human.

In certain aspects, the method of inhibiting tumor growth comprises administering to a subject a therapeutically effective amount of the antibodies, antibody fragments (e.g., antigen binding fragments), or antibody drug conjugates. In certain aspects, the subject is a human. In certain aspects, the subject has a tumor or has had a tumor removed.

In certain aspects, the tumor expresses the cKIT to which the anti-cKIT antibody binds. In certain aspects, the tumor overexpresses the human cKIT.

For the treatment of the disease, the appropriate dosage of the antibodies, antibody fragments (e.g., antigen binding fragments), or antibody drug conjugates depend on various factors, such as the type of disease to be treated, the severity and course of the disease, the responsiveness of the disease, previous therapy, patient's clinical history, and so on. The antibody or agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody, antibody fragment (e.g., antigen binding fragment), or antibody drug conjugates. In certain aspects, dosage is from 0.01 mg to 10 mg (e.g., 0.01 mg, 0.05 mg, 0.1 mg, 0.5 mg, 1 mg, 2 mg, 3 mg, 4 mg, 5 mg, 7 mg, 8 mg, 9 mg, or 10 mg) per kg of body weight, and can be given once or more daily, weekly, monthly or yearly. In certain aspects, the antibody, antibody fragment (e.g., antigen binding fragment), or antibody drug conjugate of the present disclosure is given once every two weeks or once every three weeks. The treating physician can estimate repetition rates for dosing based on measured residence times and concentrations of the drug in bodily fluids or tissues.

Combination Therapy

In certain instances, an antibody, antibody fragment (e.g., antigen binding fragment), or antibody drug conjugate of the present disclosure is combined with other therapeutic agents, such as other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), *phoenix* (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one aspect, an antibody, antibody fragment (e.g., antigen binding fragment), or antibody drug conjugate of the present disclosure is combined in a pharmaceutical combination formulation, or dosing regimen as combination therapy, with a second compound having anti-cancer properties. The second compound of the pharmaceutical combination formulation or dosing regimen can have complementary activities to the antibody or immunoconjugate of the combination such that they do not adversely affect each other. For example, an antibody, antibody fragment (e.g., antigen binding fragment), or antibody drug conjugate of the present disclosure can be administered in combination with, but not limited to, a chemotherapeutic agent, a tyrosine kinase inhibitor, for example, Imatinib, and other cKIT pathway inhibitors.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating cancer by administering to a subject in need thereof an antibody drug conjugate in combination with one or more tyrosine kinase inhibitors, including but not limited to, EGFR inhibitors, Her2 inhibitors, Her3 inhibitors, IGFR inhibitors, and Met inhibitors.

For example, tyrosine kinase inhibitors include but are not limited to, Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2, 4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); nilotinib (Tasigna®); Regorafenib (Stivarga®) and Imatinib or Imatinib mesylate (Gilvec® and Gleevec®).

Epidermal growth factor receptor (EGFR) inhibitors include but are not limited to, Erlotinib hydrochloride (Tarceva®), Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

EGFR antibodies include but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1).

Human Epidermal Growth Factor Receptor 2 (HER2 receptor) (also known as Neu, ErbB-2, CD340, or p185) inhibitors include but are not limited to, Trastuzumab (Herceptin®); Pertuzumab (Omnitarg®); Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,1-f][1,2,4]triazin-5-yl)methyl)piperidin-3-ol (BMS690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8).

HER3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MEDI-573, and BI836845. See e.g., Yee, JNCI, 104; 975 (2012) for review.

In another aspect, the present disclosure provides a method of treating cancer by administering to a subject in need thereof an antibody drug conjugate in combination with one or more FGF downstream signaling pathway inhibitors, including but not limited to, MEK inhibitors, Braf inhibitors, PI3K/Akt inhibitors, SHP2 inhibitors, and also mTor.

For example, mitogen-activated protein kinase (MEK) inhibitors include but are not limited to, XL-518 (also known as GDC-0973, Cas No. 1029872-29-4, available from ACC Corp.); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-[4-(Ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); and Trametinib dimethyl sulfoxide (GSK-1120212, CAS 1204531-25-80).

Phosphoinositide 3-kinase (PI3K) inhibitors include but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6).

mTor include but are not limited to, Temsirolimus (Torisel®); Ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23, 29,35-hexamethyl-2,3,10,14,20- pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1).

In yet another aspect, the present disclosure provides a method of treating cancer by administering to a subject in need thereof an antibody drug conjugate in combination with one or more pro-apoptotics, including but not limited to, IAP inhibitors, Bcl2 inhibitors, MCl1 inhibitors, Trail agents, Chk inhibitors.

For examples, IAP inhibitors include but are not limited to, LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134,679, all of which are incorporated herein by reference.

BCL-2 inhibitors include but are not limited to, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155,386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl] sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (Sha et al., Mol. Cancer. Ther. 2007; 6(1):147-153), and CBP501 ((d-Bpa)sws(d-Phe-F5)(d-Cha)rrrqrr).

In one aspect, the present disclosure provides a method of treating cancer by administering to a subject in need thereof an antibody drug conjugate in combination with one or more FGFR inhibitors. For example, FGFR inhibitors include but are not limited to, Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)-2-aminopropanoate); Vargatef (BIBF1120, CAS 928326-83-4); Dovitinib dilactic acid (TKI258, CAS 852433-84-2); 3-(2,6-Dichloro-3,5-dimethoxy-phenyl)-1-{6-[4-(4-ethyl-piperazin-1-yl)-phenylamino]-pyrimidin-4-yl}-1-methyl-urea (BGJ398, CAS 872511-34-7); Danusertib (PHA-739358); and (PD173074, CAS 219580-11-7). In a specific aspect, the present disclosure provides a method of treating cancer by administering to a subject in need thereof an antibody drug conjugate in combination with an FGFR2 inhibitor, such as 3-(2,6-dichloro-3,5-dimethoxyphenyl)-1-(6((4-(4-ethylpiperazin-1-yl)phenyl)amino)pyrimidin-4-yl)-1-methylurea (also known as BGJ-398); or 4-amino-5-fluoro-3-(5-(4-methylpiperazinl-yl)-1H-benzo[d]imidazole-2-yl)quinolin-2(1H)-one (also known as dovitinib or TKI-258). AZD4547 (Gavine et al., 2012, Cancer Research 72, 2045-56, N-[5-[2-(3,5-Dimethoxyphenyl)ethyl]-2H-pyrazol-3-yl]-4-(3R, 5S)-diemthylpiperazin-1-yl)benzamide), Ponatinib (AP24534; Gozgit et al., 2012, Mol Cancer Ther., 11; 690-99; 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide, CAS 943319-70-8)

Pharmaceutical Compositions

To prepare pharmaceutical or sterile compositions including immunoconjugates, the immunoconjugates of the present disclosure are mixed with a pharmaceutically acceptable carrier or excipient. The compositions can additionally contain one or more other therapeutic agents that are suitable for treating or preventing cancer gastrointestinal stromal tumors (GIST), small cell lung cancer (SCLC), acute myelod leukemia (AML), melanoma, mast cell leukemia (MCL), mastocytosis, neurofibromatosis, breast cancer, non-small cell lung cancer (NSCLC) and pancreatic cancer.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, NY, 1993; Lieberman, et al. (eds.), Pharmaceutical Dosage Forms: Tablets, Marcel Dekker, NY, 1990; Lieberman, et al. (eds.) Pharmaceutical Dosage Forms: Disperse Systems, Marcel Dekker, NY, 1990; Weiner and Kotkoskie, Excipient Toxicity and Safety, Marcel Dekker, Inc., New York, N.Y., 2000).

In a specific aspect, the clinical service form (CSF) of the antibody drug conjugates of the present disclosure is a lyophilisate in vial containing the ADC, sodium succinate, and polysorbate 20. The lyophilisate can be reconstitute with water for injection, the solution comprises the ADC, sodium succinate, sucrose, and polysorbate 20 at a pH of about 5.0. For subsequent intravenous administration, the obtained solution will usually be further diluted into a carrier solution.

Selecting an administration regimen for a therapeutic depends on several factors, including the serum or tissue turnover rate of the entity, the level of symptoms, the immunogenicity of the entity, and the accessibility of the target cells in the biological matrix. In certain aspects, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions antibody drug conjugates can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion, or by doses at intervals of, e.g., one day, one week, or 1-7 times per week. Doses can be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the immunoconjugates of the present disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof can be calculated using the patient's weight in kilograms (kg) multiplied by the dose to be administered in mg/kg.

Doses of the immunoconjugates the can be repeated and the administrations may be separated by at least 1 day, 2 days, 3 days, 5 days, 10 days, 15 days, 30 days, 45 days, 2 months, 75 days, 3 months, or at least 6 months. In a specific aspect, doses of the immunoconjugates of the present disclosure are repeated every 3 weeks.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure can also be administered via one or more routes of administration using one or more of a variety of methods known in the art. As will be appreciated by the skilled artisan, the route and/or mode of administration will vary depending upon the desired results. Selected routes of administration for the immunoconjugates include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically. In one aspect, the immunoconjugates of the present disclosure are administered by infusion. In another aspect, the immunoconjugates are administered subcutaneously.

If the immunoconjugates of the present disclosure are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the immunoconjugates (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more immunoconjugates of the present disclosure. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the immunoconjugates of the disclosure are administered topically, they can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the immunoconjugates are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the immunoconjugates of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the immunoconjugates of the present disclosure. The two or more therapies may be administered within one same patient visit.

In certain aspects, immunoconjugates can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522, 811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The present disclosure provides protocols for the administration of pharmaceutical composition comprising immunoconjugates alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the immunoconjugates can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various aspects, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other aspects, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1

Generation of cKIT Abs by Hybridoma Technology

Antigen and Other Proteins

A transient expression cell line secreting human cKIT protein was generated by transfection of 293 Freestyle™ cells (Invitrogen, Carlsbad, Calif.). Briefly, the cells cultivated in Freestyle™ medium (Invitrogen) were transfected using 293Fectin™ transfection reagent and a recombinant plasmid containing the ECD of the human cKIT cDNA and either a His6 tag at the C-terminus of the sequence, or a murine Fc (pFUSE, Invivogen, San Diego, Calif.). 48-72 hours later the media is centrifuged to remove the cells, sterile filtered, and the cleared lysate used for protein purification.

For the His6 tagged cKIT: The resulting concentrate was applied to a NiNTA His-Bind Superflow column at 0.5 mL/min. After baseline washing with PBS, bound material was eluted with PBS with a stepwise gradient of Imidazole (10-500 mM). The resulting eluate was dialyzed against PBS, pH 7.3, sterile filtered and aliquotted. For Fc-cKit fusion, Protein G fastFlow columns were used (instead of NiNTA) as outlined above, and eluted with a pH 3 Glycine buffer, which was neutralized with Tris, pH 8.

Hybridoma Generation

Immunization of Mice and Production of Hybridomas

Purified cKIT was diluted 1:1 with Freunds Complete Adjuvant prior to immunization of Bcl-2 transgenic mice (C57BL/6-Tgn (bcl-2) 22 Wehi strain). Mice were immunized using a procedure that calls for Repetitive Immunization at Multiple Sites (RIMMS) (McIntyre G D., Hybridoma, 1997). Briefly, mice were injected with 1-3 µg of antigen at 8 specific sites proximal to peripheral lymph nodes (PLN). This procedure was repeated 8 times over a 12-day period. On Day 12, a test bleed was collected and the serum antibody titer was analyzed by ELISA. Pooled PLN were removed from high titer mice on Day 15. To harvest lymphocytes, PLN were washed twice with plain DMEM and then dissociated by passage through a 0.22 micron screen (Falcon #352350, BD Bioscience, San Jose, Calif.). The resulting lymphocytes were washed 2 additional times prior to fusion. F0 myeloma cells were mixed with lymphocytes at a ratio of 2.5 lymphocytes to 1 F0 cell. The cell mixture was centrifuged and 1 mL of PEG 1500 was subsequently added dropwise to the cell pellet for 1 min. After 30 seconds, 1 mL of DMEM was slowly added, and 1 min later, 19 mL of DMEM was added for 5 min. Fused cells were pelleted, suspended at a density of $2 \times 10^5$ cells/mL in HAT media (DMEM+20% FBS, Pen/Strep/Glu, 1×NEAA, 1×HAT, 0.5×HFCS), and placed at 37° C. for one hr. The cells were then plated in 384-well plates at 60 µL/well.

Screening of Hybridomas Secreting Antibodies to cKIT

Ten days after fusion, hybridoma plates were screened for the presence of cKIT specific antibodies. For the ELISA screen, Maxisorp 384-well plates (Nunc #464718) were coated with 50 µL of cKIT (diluted to 15 ng/well in PBS) and incubated overnight at 4° C. The remaining protein was aspirated and wells were blocked with 1% BSA in PBS. After 30 min incubation at room temperature, the wells were washed four times with PBS+0.05% Tween (PBST). 15 µL of hybridoma supernatant was transferred to the ELISA plates. 15 µL of mouse serum, taken at the time of PLN removal, was diluted 1:1000 in PBS and added as a positive control. 50 µL of secondary antibody (goat anti mouse IgG-HRP (Jackson Immuno Research #115-035-071, West Grove, Pa.), diluted 1:5000 in PBS) was added to all wells on the ELISA plates. After incubation at room temperature for 1 h, the plates were washed eight times with PBST. 25 µL of TMB (KPL #50-76-05) was added and after 30 min incubation at room temperature; the plates were read at an absorbance of 605 nm. Cells from positive wells were expanded into 24-well plates in HT media (DMEM+20% FBS, Pen/Strep/Glu, 1×NEAA, 1×HT, 0.5×HFCS).

Antibody Purification

Supernatant containing cKIT antibodies were purified using protein G (Upstate #16-266 (Billerica, Mass.)). Prior to loading the supernatant, the resin was equilibrated with 10 column volumes of PBS. Following binding of the sample, the column was washed with 10 column volumes of PBS, and the antibody was then eluted with 5 column volumes of 0.1 M Glycine, pH 2.0. Column fractions were immediately neutralized with 1/10th volume of Tris HCl, pH 9.0. The OD280 of the fractions was measured, and positive fractions were pooled and dialyzed overnight against PBS, pH 7.2.

Example 2

Humanization and Affinity Maturation of Anti-cKIT Antibodies

Design of Humanization

VH and VL sequences of hybridoma derived anti-cKIT antibody 9P3 are SEQ ID NO. 9 and SEQ ID NO. 18, respectively. Amino acid sequences of human IgG1 constant domains used to generate full IgG1 are SEQ ID NO. 10 for the heavy chain and SEQ ID NO. 19 for the light chain. Humanization of the heavy chain was accomplished by grafting the 3 CDR regions (GFTFSDYYMA (SEQ ID NO. 148)) (NINYDGSSTYYLDS (SEQ ID NO. 149)) and (GDYYGTTYWYFDV (SEQ ID NO. 150) from anti-cKIT antibody 9P3, onto human germline acceptor framework VH3_3-07 (vBASE database). Humanization of the light chain was accomplished by either grafting the 3 CDR regions (RASQDISNYLN (SEQ ID NO. 151)), (YTSRLQS (SEQ ID NO. 152)) and (QQGKKLWS (SEQ ID NO. 153)) from anti-cKIT antibody 9P3, onto human germline acceptor framework VK3-L25 (vBASE database) or grafting 2 CDR regions (SEQ ID NO. 152 and SEQ ID NO. 153) onto human germline acceptor framework VK1-O12 (vBASE database). In addition to the CDR regions, one framework residue of the variable light chain domain, i.e. VL #71 and in the case of VK3-L25 VL #79 (residue numbering based on SEQ ID NO. 21) was retained from the 9P3 sequence. Further, the human J elements JH4 and JK4 were used for the heavy and light chain, respectively. The resulting amino acid sequences of the humanized antibody heavy chain is SEQ ID NO. 11 and for the two light chains SEQ ID NO. 20 (VK1-O12) and SEQ ID NO. 21 (VK3-L6).

We hypothesized that the amino acid motif aspartate followed by glycine (DG) may be susceptible to post-translational modification (iso-aspartate formation) and that lysines within the CDRs may decrease the fraction of active antibody after antibody-drug conjugation. Further, we intended to affinity mature the humanized antibody. A combination of random mutagenesis (i.e. error-prone PCR) and directed mutagenesis was applied to optimize the humanized antibodies.

Generation of Humanized Sequences

DNA sequences coding for humanized VL and VH domains were ordered at GeneArt (Life Technologies Inc. Regensburg, Germany) including codon optimization for *homo sapiens*. Sequences coding for VL and VH domains were subcloned by cut and paste from the GeneArt derived vectors into expression vectors suitable for secretion in mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

Expression and Purification of Humanized Antibodies

Human Embryonic Kidney cells constitutively expressing the SV40 large T antigen (HEK293-T ATCC11268) are one of the preferred host cell lines for transient expression of humanized and/or optimized IgG proteins. Transfection is performed using PEI (Polyethylenimine, MW 25.000 linear, Polysciences, USA Cat. No. 23966) as transfection reagent. The PEI stock solution is prepared by carefully dissolving 1 g of PEI in 900 ml cell culture grade water at room temperature (RT). To facilitate dissolution of PEI, the solution is acidified by addition of HCl to pH 3-5, followed by neutralization with NaOH to a final pH of 7.05. Finally, the volume is adjusted to 1 L and the solution is filtered through a 0.22 μm filter, aliquotted and frozen at −80° C. until further use. Once thawed, an aliquot can be re-frozen up to 3 times at −20° C. but should not be stored long term at −20° C. HEK 293T cells are cultivated using a Novartis proprietary serum-free culture medium for transfection and propagation of the cells, and ExCell VPRO serum-free culture medium (SAFC Biosciences, USA, Cat. No. 24561C) as production/feed medium. Cells prepared for transient transfections are cultivated in suspension culture. For small scale (<5 L) transfections, cells are grown in Corning shake flasks (Corning, Tewksbury, Mass.) on an orbital shaker (100-120 rpm) in a humidified incubator at 5% CO2 (seed flasks). Cells in the seed cultures should be maintained in the exponential growth phase (cell densities between $5\times10^5$ and $3\times10^6$/mL) and display a viability of >90% for transfection. Cell densities outside of this range will result in either a lag phase after dilution or reduced transfection efficiency. For small scale (<5 L) transfection an aliquot of cells is taken out of the seed cultures and adjusted to $1.4\times10^6$ cells/mL in 36% of the final volume with Novartis serum-free culture medium. The DNA solution (Solution 1: 0.5 mg of heavy chain and 0.5 mg of light chain expression plasmid for a 1 L transfection) is prepared by diluting the DNA to 1 mg/L (final volume) in 7% of the final culture volume followed by gentle mixing. To prevent bacterial contamination, this solution is filtered using a 0.22 μm filter (e.g. Millipore Stericup). Then 3 mg/L (final volume) of PEI solution is also diluted in 7% of final culture volume and mixed gently (Solution 2). Both solutions are incubated for 5-10 min at room temperature (RT). Thereafter solution 2 is added to solution 1 with gentle mixing and incubated for another 5-15 minutes at room temperature. The transfection mix is then added to the cells and the cultivation of cells is continued for 4 to 6 hours. Finally, the remaining 50% of total production volume are achieved by addition of ExCell® VPRO serum-free culture medium. The cell cultivation is continued for eleven days post transfection. The culture is harvested by centrifugation at 4500 rpm for 20 minutes at 4° C. (Heraeus®, Multifuge 3S-R, Thermo Scientific, Rockford, Ill.). The cell supernatant recovered is sterile filtered through a stericup filter (0.22 μm) and stored at 4° C. until further processing.

Purification was performed on an "ÄKTA 100 explorer Air" chromatography system at 4° C. in a cooling cabinet, using a freshly sanitized (0.25 M NaOH) HiTrap ProtA MabSelect®SuRe, 5 ml column. The column was equilibrated with 5 CV of PBS (Gibco, Life Technologies, Carlsbad, Calif.), and then the sterile filtered supernatant (2 L) was loaded at 4.0 ml/min. The column was washed with 8 CV of PBS to elute the unbound sample and again washed with 5 CV of PBS. Antibody was eluted with 5 CV of 50 mM citrate, 70 mM NaCl pH 3.2. The eluate was collected in 3 ml fractions; fractions were pooled and adjusted at pH 7 with 1 M Tris HCl pH10. The pools were pooled and sterile filtered (Millipore Steriflip, 0.22 um), the OD 280 nm was measured in a Spectrophotometer ND-1000 (NanoDrop), and the protein concentration was calculated based on the sequence data. The eluate was tested for aggregation (SEC-MALS) and purity (SDS-PAGE, LAL and MS). For the second purification step, if needed, pools from the first purification were loaded into a freshly sanitised (0.5 M NaOH) SPX (Hi Load 16/60 Superdex 200 grade 120 mL (GE-Helthcare). The column was equilibrated with PBS and the run was done with PBS buffer at 1 ml/min, the eluate was collected in 1.2 ml fractions and analyzed as described for the first purification step.

Example 3

Screening for Anti-cKIT Antibodies

HuCAL PLATINUM™ Pannings

For selection of antibodies recognizing human cKIT multiple panning strategies were employed. Therapeutic antibodies against human cKIT proteins were generated by selection of clones having high affinity binding affinities, using as the source of antibody variant proteins a commercially available phage display library, the Morphosys HuCAL PLATINUM® library (Morphosys, Munich Del.). The phagemid library is based on the HuCAL® concept (Knappik et al., (2000) J Mol Biol 296: 57-86) and employs the CysDisplay® technology for displaying the Fab on the phage surface (Lohning, WO 01/05950). For isolation of anti-cKIT antibodies, standard panning strategies were performed using solid phase, solution, whole cell and differential whole cell panning approaches.

Solid Phase Panning Against cKIT

An 96-well Maxisorp™ plate was coated with human or mouse cKIT Fc fusion protein o/n at 4° C. For each panning, about $4 \times 10^{13}$ HuCAL PLATINUM® phage-antibodies were added to each antigen coated and incubated for 2 h at RT on a microtiter plate shaker. Afterwards, unspecific bound phages were washed off by several washing steps and specifically bound phages, were eluted using 25 mM DTT in 10 mM Tris/HCl pH 8.

The eluate was transferred into 14 ml of E. coli bacteria and incubated for phage infection. The infected bacteria were resuspended in 2×YT medium, plated on LB/Cam agar plates and incubated o/n. Colonies were scraped off the plates and were used for phage rescue, polyclonal amplification of selected clones, and phage production. With purified phage the next panning round was started.

The second and third round of solid phase panning was performed according to the protocol of the first round except for decreased amounts of antigen and more stringent washing conditions.

Capture Panning Against cKIT

For capture panning, the antigen cKIT/murine Fc fusion proteins were immobilized on a 96-well Maxisorp™ plate via an goat anti-mouse Fc capture antibody. During phage blocking, human and mouse γ globulin were added to the blocking buffer to avoid selection of antibodies against the capture antibody and mouse Fc part of the antigen. The antigen coating and phage blocking procedures in the capture panning was performed as described in the Solid Phase Panning protocol (see above).

Solution Panning Protocol with Streptavidin-Coupled Magnetic Beads

Solution pannings were performed in two different modes ("classical" and "alternative"). For each panning, about $4 \times 10^{13}$ HuCAL PLATINUM® phage-antibodies were blocked with an equal volume of 2× Chemiblocker/0.1% Tween20. For removal of Streptavidin- or bead-binding phage, pre-adsorption of blocked phage particles was performed twice using 1 mg blocked Streptavidin beads each.

a) "Classical" mode: Biotinylated 16P23 mAb was incubated with human cKIT ECD-H is protein and was added to the blocked phage particles. The 16P23 antibody is an internally generated hybridoma and was used in various screening protocols as a capture antibody to expose different domains on the ECD of cKIT. The 16P23 antibody was also used for antibody binning purposes. After incubation the phage-antigen complexes were captured using Streptavidin beads and phage particles bound to the Streptavidin beads were collected with a magnetic separator.

b) "Alternative" mode: Biotinylated 16P23 mAb was added to streptavidin beads and the antibody-bead mix was incubated on a rotator at RT for 30 min. Beads were washed and resuspended in PBS containing human cKIT ECD-His protein. Subsequently, the phages were added and the antibody-bead-antigen-phage complex was rotated for an additional 1 h at RT on a rotator. After this last incubation step the beads were captured with a magnetic separator and the supernatants were discarded.

Using both display methods unspecific bound phage were washed off by several washing steps using PBS/0.05% Tween20 and PBS. Specifically bound phages were eluted from Streptavidin beads by using 25 mM DTT in 10 mM Tris/HCl pH 8. Subsequent phage infection and phage production was performed according to the Solid Phase Panning protocol.

The second and third round of the solution panning was performed according to the protocol of the first round except for decreased amounts of antigen and more stringent washing conditions.

Whole Cell Panning Against cKIT

Target cells expressing antigen human, mouse or rat cKIT were used as antigens and were contacted with HuCAL PLATINUM® phage-antibodies for pannings. The phage-cell complexes were washed three times in PBS/5% FCS. Elution of specifically bound phage from target cells was performed with 0.1 M glycine-HCl/0.5 M NaCl, pH 2.2. Subsequent phage infection and phage production was performed according to the Solid Phase Panning protocol. The second and third round of the whole cell panning was performed according to the protocol of the first round.

Differential Whole Cell Panning Against cKIT

In the differential whole cell panning, the selection was done alternating on cells and purified protein. The selection rounds on purified antigen were performed as described in the Solid Phase Panning protocol For the selection rounds on cells please refer to the procedure in the Whole Cell Panning Against cKIT section.

Maturation Pannings

In order to obtain specific antibodies with increased affinities, maturation pannings were performed (Prassler et al., Future Med. Immuno. 2009 1(4):571-583). For this purpose, sequenced clones already tested for cKIT specific binding were used for LCDR3 or HCDR2 cassette exchange. Afterwards two rounds of solid phase pannings were performed with human and/or mouse cKIT Fc fusion protein as described in the Solid Phase Panning protocol.

a) For LCDR3RapMAT®: Fab-encoding fragments of phage derived pMORPH30® vector DNA (Morphosys, Munich Del.) were enzymatically digested and inserts were replaced with TRIM™ LCDR3 maturation cassettes (Virnekaes et al., NAR 1994 22(25):5600-5607). Subsequently, 1.25 µg pMORPH30® display vector was ligated with the insert fragment carrying the diversified LCDR3s.

b) For HCDR2RapMAT®: After the 2nd round of panning, Fab-encoding fragments of phage derived pMORPH30® vector DNA were enzymatically digested and inserts were replaced with TRIM™ HCDR2 maturation cassettes (Virnekas et al., supra). Subsequently, 1.25 µg pMORPH30® display vector was ligated with the insert fragment carrying the diversified HCDR2s.

The generated libraries were amplified and subjected to two rounds of panning with either increased stringency and reduced antigen concentration or alternation of human and mouse cKIT antigen to identify affinity improved clones.

Preparation of Fab Containing Bacterial Lysates for ELISA Screening

For initial screening and characterization an o/n culture of individual Fab-expressing *E. coli* clones were lysed using lysozyme, 4 mM EDTA and 10 U/µl Benzonase. Fab containing *E. coli* lysates were used for ELISA, FACS and SET screening.

Screening of Fab-Containing Raw Bacterial Lysates
ELISA Screening

Using ELISA screening, single Fab clones are identified from panning output for binding to the target antigen. Fabs are tested using Fab containing crude *E. coli* lysates.

Fab Expression Check ELISA

For verification of Fab expression in the prepared *E. coli* lysates, Maxisorp™ 384 well plates (Nunc, Sigma-Aldrich, St. Louis Mo.) were coated with Fd fragment specific sheep anti-human IgG diluted 1:1000 in PBS. After blocking with 5% skim milk powder in PBS containing 0.05% Tween20, Fab-containing *E. coli* lysates were added. Subsequently the bound HuCAL®-Fab fragments were detected by incubation with F(ab)$_2$ specific goat anti-human IgG conjugated to alkaline phosphatase (diluted 1:5000) followed by addition of AttoPhos® fluorescence substrate (Roche, #11681982001, Mannheim, Del.). Fluorescence emission at 535 nm was recorded with excitation at 430 nm.

ELISA Screening on Directly Coated Antigen

Maxisorp™ 384 well plates were coated with mFc tagged human cKIT ECD protein at a concentration of 10 µg/ml in PBS. After blocking of plates with 5% skim milk powder in PBS, Fab-containing *E. coli* lysates were added. Binding of Fabs was detected by F(ab)$_2$ specific goat anti-human IgG conjugated to alkaline phosphatase (diluted 1:5000) using Attophos® fluorescence substrate (Roche, #11681982001, Mannheim, Del.). Fluorescence emission at 535 nm was recorded with excitation at 430 nm.

Epitope Binning with Fab BEL Lysates

To identify potential ligand binding competitors prior to affinity maturation, a competition ELISA screening with Fab *E. coli* lysates and 16P23 antibody, a known ligand binding competitor, was performed. For this purpose, Maxisorp™ 384 well plates were coated with mFc tagged human cKIT ECD protein and blocked as described above (ELISA Screening on Directly Coated Antigen).

16P23 mAb was added at a final concentration of 5 µg/ml followed by incubation with Fab-containing *E. coli* lysates. Finally, binding of Fabs was detected with an anti-FLAG alkaline phosphatase-conjugated antibody (Sigma A-9469, diluted to 1:10000) using Attophos® fluorescence substrate (Roche, #11681982001). Fluorescence emission at 535 nm was recorded with excitation at 430 nm.

FACS Screening

In FACS screening, single Fab clones binding to cell surface expressed antigen are identified from the panning output. Fabs are tested using Fab containing crude *E. coli* lysates.

FACS Screening was performed either in 96- or 384-well plate format:

a) In 96-well plate format using a BD FACS array device, 100 µl of cell-suspension were transferred into a fresh 96-well plate (resulting in 1×10$^5$ cells/well). Target cell suspension containing plate was centrifuged and supernatant was discarded. Remaining cell pellet was resuspended and 50 µl of Fab containing BEL extracts was added to the corresponding wells. Plate was incubated on ice for 1 hour. Following incubation, cells were spun down and washed three times with 200 µl FACS buffer (PBS, 3% FCS). After each washing step, cells were centrifuged and carefully resuspended. Secondary detection antibody (PE conjugated goat anti human IgG; Dianova, Hamburg, Del.) was added and samples were incubate on ice and subsequently washed according to Fab incubation. Finally, cell pellets were resuspended in 150 µl FACS buffer per well and samples were analyzed in BD FACS array.

b) In 384-well plate format using a BD Calibur® HTS device (BD Biosciences, San Jose, Calif.), 20 µl of cell-suspension were transferred into a fresh 384 round well plate (resulting in 4×10$^4$ cells/well). Target cell suspension containing plate was centrifuged and supernatant was discarded. Remaining cell pellet was resuspended and 20 µl of Fab containing extracts was added to the corresponding wells. Plate was incubated for 1 hour shaking at 4° C. Following incubation, cells were spun down and washed three times with 40 µl FACS buffer (PBS, 3% FCS). After each washing step, cells were centrifuged and carefully resuspended. 40 µl of PE conjugated goat anti human detection antibody was added and samples were incubated on ice and subsequently washed according to Fab incubation. Finally, cell pellets were resuspended in 35 µl FACS buffer per well and samples were measured with BD FACS Calibur/HTS device.

Affinity Determination

For K$_D$ determinations, monomer fractions of antibody protein were used (at least 90% monomer content, analyzed by analytical SEC; Superdex 75 PC3.2/30 (GE Healthcare, Pittsburgh, Pa.) for Fab, or Tosoh TSKgel G3000 SW$_{XL}$ (7.8 mm/30.0 cm) (Tosoh Bioscience GmbH, Stuttgart, Del.) for IgG, respectively).

Solution Equilibrium Titration (SET) Method for KD Determination Using Sector Imager 6000 (MSD)

Affinity determination in solution was basically performed as described in the literature (Friquet et al., J. Immuno. Meth. 1985; 77:305-319). In order to improve the sensitivity and accuracy of the SET method, it was transferred from classical ELISA to ECL based technology (Haenel et al., 2005). 1 mg/ml goat-anti-human (Fab)$_2$ fragment specific antibodies (Dianova) were labeled with MSD Sulfo-TAG™ NHS-Ester (Meso Scale Discovery, Gaithersburg, Md., USA) according to the manufacturer's instructions. MSD plates were coated with antigen and the equilibrated samples were transferred to those plates. After washing, 30 µl per well of the MSD-Sulfo-tag labeled detection antibody (anti-human (Fab)$_2$) was added to the MSD plate and incubated on a shaker. After washing the MSD plate and adding 30 µl/well MSD Read Buffer T with surfactant, electrochemiluminescence signals were detected using a Sector Imager 6000 (Meso Scale Discovery, Gaithersburg, Md., USA).

The data was evaluated with XLfit (IDBS) software applying customized fitting models. For $K_D$ determination of Fab molecules the following fit model was used (according to (Haenel et al., Anal. Biochem 2005; 339(1):182-184), modified according to (Abraham et al., J. Mol. Recogn 1996; 9:456-461)):

$$y = B_{max} - \left( \frac{B_{max}}{2[Fab]_t} \left( [Fab]_t + x + K_D - \sqrt{([Fab]_t + x + K_D)^2 - 4x[Fab]_t} \right) \right)$$

$[Fab]_t$: applied total Fab concentration
x: applied total soluble antigen concentration (binding sites)
$B_{max}$: maximal signal of Fab without antigen
$K_D$: affinity For $K_D$ determination of IgG molecules the following fit model for IgG was used (modified according to (Piehler et al., 1997)):

$$y = \frac{2B_{max}}{[IgG]} \left( \frac{[IgG]}{2} - \frac{\left( \frac{x + [IgG] + K_D}{2} - \sqrt{\frac{(x + [IgG] + K_D)^2}{4} - x[IgG]} \right)^2}{2[IgG]} \right)$$

[IgG]: applied total IgG concentration
x: applied total soluble antigen concentration (binding sites)
$B_{max}$: maximal signal of IgG without antigen
$K_D$: affinity Experimental Settings:

$K_D$ determination of HuCAL® anti cKIT IgGs was basically performed as follows: human cKIT-Fc was coated at 0.1 µg/ml in PBS o/n at 4° C. on standard MSD plates/assay buffer for 1 h at RT on streptavidin MSD plates. Subsequently MSD plates were blocked with PBS with 3% BSA for 1 h at RT. Streptavidin plates were blocked o/n at 4° C. with PBS with 5% BSA before antigen coating. For titration of antigen human cKIT-His was applied.

Subsequently, the concentration of unbound Fab was quantified via ECL detection using the Sector Imager 6000 (Meso Scale Discovery, Gaithersburg, Md., USA). Results were processed using XLfit (IDBS) software, applying the corresponding fit model to estimate affinities and thus identify clones most improved by the maturation.

In Vitro Biochemical Assays (Cross-Reactivity and Domain-Binding Analysis)

Purified IgGs were tested in ELISA for binding to human, cyno and mouse cKIT full-length ECD proteins as well as human cKIT ECD domain constructs D1-3 and D4-5. For this purpose plates were coated with antigen at a concentration of 5 µg/ml in PBS over night at 4° C. Binding of IgGs was detected by anti-human or anti-mouse F(ab)$_2$ conjugated to alkaline phosphatase (diluted 1:5000 in 1% MPBS) using Attophos® as substrate. Fluorescence emission was measured at an excitation of 430 nm and an emission of 535 nm.

Epitope Binning of Purified IgGs

Purified IgG candidates were tested for competition with internally generated tool antibodies, previously shown to define individual bins on the extracellular domain of cKIT. For this purpose, IgGs were coated at constant amounts on Maxisorp™ plates and tested for competition with increasing amounts of competitor IgG in solution. As positive control, the coated IgG was analyzed for competition with itself in solution. All tested IgGs were preincubated in 50× excess with glycobiotinylated human cKIT-Fc fusion for 1 h at RT in solution. Antigen/antibody complexes were then added to the coated antibodies and detection of bound complexes occurred via the biotinylated antigen. In general, signals at high IgG concentration could only be obtained when the coated IgG was able to bind to accessible epitopes on the antigen different to the tested IgG in solution (i.e. a non competitive antibody). In contrast, for competitive antibodies, antibodies with partially overlapping epitopes or antibodies that block the epitope by steric hindrance, binding signals at high IgG concentration were significantly decreased in contrast to controls.

Respective wells of Maxisorp™ plates were coated with 20 µl/well of IgG dilution at a concentration of 1.2 µg/ml in PBS, incubated overnight at 4° C. and then washed 3× with PBST. Plates were blocked with 90 µl 3% BSA/PBS well for 1 h at RT and washed 3× with PBST.

EC50 Determination on Cells Via FACS

Purified IgGs were tested at a single concentration or titrated in FACS to determine EC50 values for binding to cell surface expressed human, mouse or rat cKIT. For this purpose, Mole, P815 or RBL-2H3 cells were harvested with Accutase® (Life Technologies, Carlsbad, Calif.) and diluted to 1×10$^6$/ml in FACS buffer. All subsequent steps were done on ice to prevent internalization of the receptor. The cell suspension was filled with 100 µl/well into a 96 well U bottom plate. After centrifugation at 210 g for 5 min at 4° C., buffer was discarded. 100 µl of the specific mAbs diluted in FACS buffer was then added per well at a concentration of 15 µg/ml or in titration experiments at a serial dilution of antibody concentrations (1:3 dilution steps, starting concentration of 15 µg/ml). After 1 h incubation on ice, cells were washed three times with 150 µl FACS buffer. Secondary PE conjugated goat anti human detection antibody (diluted 1:200 in FACS buffer) was added to the cells with 100 µl/well and incubated on ice for 1 h. Cells were washed three times with 150 µl FACS buffer. Finally, cell pellets were resuspended in 200 µl FACS buffer per well and samples were analyzed in BD FACS array.

In Vitro Bio-Assays

SCF-Dependent Proliferation Assay

Proliferation assays were performed on the Mole cell line (human acute megakaryoblastic leukemia, DSMZ no.: ACC 104) cultured in RPMI1640 with stable glutamine (PAN #P04-18500), 10% FCS and 10 ng/ml SCF (R&D CAT#255-SC; Lot#CM2810061, R&D Corp, Berkeley Calif.).

In the SCF-dependent proliferation assay purified IgGs or IgG containing cell culture supernatants were tested. In both experimental settings cells were harvested and resuspended in 50 ml starve medium (culture medium without SCF) at a concentration of 0.5×10$^6$ cells/ml and incubated at 37° C. for 18 h. Cells were then resuspended at a concentration of 1×10$^6$ cells/ml in starving medium with 60 ng/ml SCF (2× concentrated, final concentration after addition of antibody is 30 ng/ml). 50 µl of cells (5×10$^4$ cells/well) and 50 µl of 2× concentrated purified antibodies or undiluted cell culture supernatants were added per well of a white 96-well flat with clear bottom plates. For negative and positive controls, cells w/o SCF and w/o antibody or cells with SCF and w/o antibody were included. Plates were incubated for 48 h at 37° C. and finally cell numbers were determined using CellTiter-Glo® (Promega #G7571, Promega, Madison, Wis.) according to the manufacturer's instructions.

Fab-ZAP ADC Piggyback Assay

To test the ability of antibodies to internalize after receptor binding, an ADC assay was performed mixing Fab-ZAP reagent (goat anti-hu-mAb-saporin-coupled; ATS Biotechnology, Cat# IT-51-250, ATS Bio, San Diego, Calif.) either with purified IgGs or with IgG containing cell culture supernatants. Cytotoxic potential was tested on the cancer cell line CMK-11-5 (acute megakaryoblastic leukemia cells, cultured in RPMI1640+10% FCS) as these cells show high expression of cKIT.

Cells in culture were counted and diluted in medium to a concentration of $1 \times 10^5$ cells/ml. 50 µl cell suspension (5000 cells/well) were transferred to 96-well plates (Flat Clear Bottom White Plate TC-Treated, Corning Cat#3903, Corning, Tewksbury, Mass.). In a separate plate (96 Well V bottom, Nunc, Cat#249946, Nunc Sigma-Aldrich, St. Louis, Mo.) IgGs were diluted in medium. IgG containing cell culture supernatants were diluted 1:125 and purified IgGs to a concentration of 0.4 nM resulting in a total volume of 60 µl/well. An equal volume of FabZAP solution at a concentration of 5 nm was added and the plate was incubated for 60 min at 37° C. 50 µl of antibody/Fab-ZAP conjugates were transferred to CMK-11-5 cells (total volume 100 µl). For controls, wells with cells only (=100% viability control) and cells only incubated with Fab-ZAP (to check for unspecific killing of the secondary reagent) were prepared. Final concentration of Fab-ZAP was 1.25 nM. Plates were incubated for 72 h at 37° C. and 5% $CO_2$. Cell numbers were determined using CellTiter-Glo® (Promega #G7571) according to the manufacturer's instructions. Viability was normalized to the cells only control.

Summary

In Screening for cKIT Antibodies, 2 Different Strategies were Performed:

Strategy 1:

Candidates with human/cyno x-reactivity (217 HCDR3 families) were selected on high affinity and after IgG conversion clones were screened for functionality in CMK-11-5 FabZAP ADC assay and Mole proliferation assay. Based on functional activity and diversity candidates were selected for exploratory scale expression.

Strategy 2:

Candidates with human/cyno/mouse x-reactivity (5 HCDR3 families) were affinity matured and after IgG conversion candidates were selected for expression.

In summary, 82 purified IgG candidates from strategy 1 and 2 were subjected to in-depth characterization. From this pool of 82, 26 IgG candidates were selected for upscaled production, toxin conjugation and subsequent testing as antibody drug conjugates in in vitro and in vivo experiments.

Upon in-depth characterization, the 26 antibodies (14 candidates from strategy 1 and 12 candidates from strategy 2) belonging to 16 different HCDR3 families were selected for upscaled production and testing as antibody-DM1 conjugate. Candidates were selected according to following criteria: 1) Potent killing of wildtype and mutant cKIT expressing cells in Fab-DM1 piggyback assay with EC50 in the sub- to low-nanomolar range, 2) the KD values of 24/26 IgGs for cyno cKIT are within 3-fold range to that determined for the human cKIT. In addition, 12/26 IgGs cross-react with mouse and rat cKIT expressed on cells.

Selected candidates from this screening could be assigned to different epitope bins:
1) 19/26 IgGs belong to Bin 1 or Bin 6 (binding to cKIT D1-3, ligand binding domains)
2) 6/26 IgGs belong to Bin 8 (binding to cKIT D4-5, dimerization domains)
3) 1/26 IgGs belong to Bin 2, which had high affinity to human cKIT but had only weak affinity to cyno cKIT. An example of an antibody to come from this type of screening protocol is antibody 20376.

Example 4

Constructs for Human, Cyno, Mouse and Rat cKIT ECD Proteins

Human, mouse and rat cKIT extracellular domains were gene synthesized based on amino acid sequences from the GenBank or Uniprot databases (see Table 2 below). Cynomolgus cKIT and 1 ECD cDNA template were gene synthesized based on amino acid sequences information generated using mRNA from various cyno tissues (e.g. Zyagen Laboratories; Table 2 below). All synthesized DNA fragments were cloned into appropriate expression vectors e.g. hEF1-HTLV based vector (pFUSE-mIgG2A-Fc2) with C-terminal tags to allow for purification.

TABLE 2

| Name | Description | Accession Number | SEQ ID NO |
|---|---|---|---|
| Human cKIT D1-5 | Human cKIT tr. variant 2, residues 26-520-TAG<br>QPSVSPGEPSPPSIHPGKSDLIVRVGDEIRLLCTDPGFVK<br>WTFEILDETNENKQNEWITEKAEATNTGKYTCTNKHG<br>LSNSIYVFVRDPAKLFLVDRSLYGKEDNDTLVRCPLTD<br>PEVTNYSLKGCQGKPLPKDLRFIPDPKAGIMIKSVKRA<br>YHRLCLHCSVDQEGKSVLSEKFILKVRPAFKAVPVVS<br>VSKASYLLREGEEFTVTCTIKDVSSSVYSTWKRENSQT<br>KLQEKYNSWHHGDFNYERQATLTISSARVNDSGVFM<br>CYANNTFGSANVTTTLEVVDKGFINIFPMINTTVFVND<br>GENVDLIVEYEAFPKPEHQQWIYMNRTFTDKWEDYPK<br>SENESNIRYVSELHLTRLKGTEGGTYTFLVSNSDVNAA<br>IAFNVYVNTKPEILTYDRLVNGMLQCVAAGFPEPTID<br>WYFCPGTEQRCSASVLPVDVQTLNSSGPPFGKLVVQS<br>SIDSSAFKHNGTVECKAYNDVGKTSAYFNFAFKEQIHP<br>HTLFTPRSHHHHHH | NM_001093772 | (SEQ ID NO. 154) |
| Human cKIT D1-3 | Human cKIT tr. Variant 1, residues 26-311-TAG<br>QPSVSPGEPSPPSIHPGKSDLIVRVGDEIRLLCTDPGFVK<br>WTFEILDETNENKQNEWITEKAEATNTGKYTCTNKHG<br>LSNSIYVFVRDPAKLFLVDRSLYGKEDNDTLVRCPLTD | NM_000222 | (SEQ ID NO. 155) |

TABLE 2-continued

| Name | Description | Accession Number | SEQ ID NO |
|---|---|---|---|
| | PEVTNYSLKGCQGKPLPKDLRFIPDPKAGIMIKSVKRA YHRLCLHCSVDQEGKSVLSEKFILKVRPAFKAVPVVS VSKASYLLREGEEFTVTCTIKDVSSSVYSTWKRENSQT KLQEKYNSWHHGDFNYERQATLTISSARVNDSGVFM CYANNTFGSANVTTTLEVVDKGRSHHHHHH | | |
| Human cKIT D4-5 | Human cKIT tr. variant 1, residues 311-524-TAG GFINIFPMINTTVFVNDGENVDLIVEYEAFPKPEHQQWI YMNRTFTDKWEDYPKSENESNIRYVSELHLTRLKGTE GGTYTFLVSNSDVNAAIAFNVYVNTKPEILTYDRLVN GMLQCVAAGFPEPTIDWYFCPGTEQRCSASVLPVDVQ TLNSSGPPFGKLVVQSSIDSSAFKHNGTVECKAYNDVG KTSAYFNFAFKGNNKEQIHPHTLFTPRSHHHHHH | NM_000222 | (SEQ ID NO. 156) |
| Cynomolgus monkey cKIT D1-5 | Cynomolgus monkey cKIT, residues 25-520-TAG | Not applicable. | (see below) |
| Mouse cKIT D1-5 | Mouse cKIT tr. variant 1, residues 26-527-TAG SQPSASPGEPSPPSIHPAQSELIVEAGDTLSLTCIDPDFV RWTFKTYFNEMVENKKNEWIQEKAEATRTGTYTCSN SNGLTSSIYVFVRDPAKLFLVGLPLFGKEDSDALVRCP LTDPQVSNYSLIECDGKSLPTDLTFVPNPKAGITIKNVK RAYHRLCVRCAAQRDGTWLHSDKFTLKVRAAIKAIPV VSVPETSHLLKKGDTFTVVCTIKDVSTSVNSMWLKMN PQPQHIAQVKHNSWHRGDFNYERQETLTISSARVDDS GVFMCYANNTFGSANVTTTLKVVEKGFINISPVKNTT VFVTDGENVDLVVEYEAYPKPEHQQWIYMNRTSANK GKDYVKSDNKSNIRYVNQLRLTRLKGTEGGTYTFLVS NSDASASVTFNVYVNTKPEILTYDRLINGMLQCVAEG FPEPTIDWYFCTGAEQRCTTPVSPVDVQVQNVSVSPFG KLVVQSSIDSSVFRHNGTVECKASNDVGKSSAFFNFAF KEQIQAHTLFTPLEVLFQGPRSPRGPTIKPCPPCKCPAP NLLGGPSVFIFPPKIKDVLMISLSPIVTCVVVDVSEDDP DVQISWFVNNVEVHTAQTQTHREDYNSTLRVVSALPI QHQDWMSGKEFKCKVNNKDLPAPIERTISKPKGSVRA PQVYVLPPPEEEMTKKQVTLTCMVTDFMPEDIYVEWT NNGKTELNYKNTEPVLDSDGSYFMYSKLRVEKKNWV ERNSYSCSVVHEGLHNHHTTKSFSRTPGK | NM_001122733 | (SEQ ID NO. 157) |
| Rat cKIT D1-5 | Rat cKIT, residues 25-526-TAG SQPSASPGEPSPPSIQPAQSELIVEAGDTIRLTCTDPAFV KWTFEILDVRIENKQSEWIREKAEATHTGKYTCVSGSG LRSSIYVFVRDPAVLFLVGLPLFGKEDNDALVRCPLTD PQVSNYSLIECDGKSLPTDLKFVPNPKAGITIKNVKRA YHRLCIRCAAQREGKWMRSDKFTLKVRAAIKAIPVVS VPETSHLLKEGDTFTVICTIKDVSTSVDSMWIKLNPQP QSKAQVKRNSWHQGDFNYERQETLTISSARVNDSGVF MCYANNTFGSANVTTTLKVVEKGFINIFPVKNTTVFVT DGENVDLVVEFEAYPKPEHQQWIYMNRTPTNRGEDY VKSDNQSNIRYVNELRLTRLKGTEGGTYTFLVSNSDVS ASVTFDVYVNTKPEILTYDRLMNGRLQCVAAGFPEPTI DWYFCTGAEQRCTVPVPPVDVQIQNASVSPFGKLVVQ SSIDSSVFRHNGTVECKASNAVGKSSAFFNFAFKGNSK EQIQPHTLFTPRSLEVLFQGPGSPPLKECPPCAAPDLLG GPSVFIFPPKIKDVLMISLSPMVTCVVVDVSEDDPDVQI SWFVNNVEVHTAQTQTHREDYNSTLRVVSALPIQHQD WMSGKEFKCKVNNRALPSPIEKTISKPRGPVRAPQVY VLPPPAEEMTKKEFSLTCMITGFLPAEIAVDWTSNGRT EQNYKNTATVLDSDGSYFMYSKLRVQKSTWERGSLF ACSVVHEGLHNHLTTKTISRSLGK | NM_022264 | (SEQ ID NO. 158) |

TABLE 3

Sequences of cynomolgus cKIT protein

| Construct | Amino acid sequence in one letter code, signal peptide underlined | SEQ ID NO |
|---|---|---|
| Cynomolgus monkey cKIT D1-5 | MYRMQLLSCIALSLALVTNSQPSVSPGEPSPPSIHPAKSELIVRVGNEIRLLC IDPGFVKWTFEILDETNENKQNEWITEKAEATNTGKYTCTNKHGLSSSIYV FVRDPAKLFLVDRSLYGKEDNDTLVRCPLTDPEVTSYSLKGCQGKPLPKD LRFVPDPKAGITIKSVKRAYHRLCLHCSADQEGKSVLSDKFILKVRPAFKA VPVVSVSKASYLLREGEEFTVTCTIKDVSSSVYSTWKRENSQTKLQEKYNS WHHGDFNYERQATLTISSARVNDSGVFMCYANNTFGSANVTTTLEVVDK GFINIFPMINTTVFVNDGENVDLIVEYEAFPKPEHQQWIYMNRTFTDKWED YPKSENESNIRYVSELHLTRLKGTEGGTYTFLVSNSDVNASIAFNVYVNTK PEILTYDRLVNGMLQCVAAGFPEPTIDWYFCPGTEQRCSASVLPVDVQTL NASGPPFGKLVVQSSIDSSAFKHNGTVECKAYNDVGKTSAYFNFAFKGNN KEQIHPHTLFTPRSHHHHHH | (SEQ ID NO. 159) |

Expression of Recombinant cKIT Proteins

The desired cKIT recombinant proteins were expressed in HEK293 derived cell lines (293FS) previously adapted to suspension culture and grown in serum-free medium FreeStyle-293 (Gibco, catalogue #12338018). Both small scale and large scale protein production were via transient transfection and was performed in multiple shaker flasks (Nalgene), up to 1 L each, with 293Fectin (Life Technologies, catalogue #12347019) as a plasmid carrier. Total DNA and 293Fectin was used at a ratio of 1:1.5 (w:v). DNA to culture ratio was 1 mg/L. The cell culture supernatants were harvested 3-4 days post transfection, centrifuged and sterile filtered prior to purification.

Example 5

Purification of Human, Cyno, Mouse and Rat cKIT ECD Protein, and of cKIT Subdomains 1-3, and 4-5

Tagged Protein Purification

Recombinant Fc-tagged cKIT extracellular domain proteins (e.g., human cKIT ECD-Fc, human cKIT (ECD subdomains 1-3, 4-5)-Fc, cyno cKIT-mFc, rat cKIT-mFc, mouse cKIT-mFc) were purified from the cell culture supernatant. The clarified supernatant was passed over a Protein A Sepharose column which had been equilibrated with PBS. After washing to baseline, the bound material was eluted with Pierce Immunopure low pH Elution Buffer, or 100 mM glycine (pH 2.7) and immediately neutralized with ⅛$^{th}$ the elution volume of 1 M Tris pH 9. The pooled protein was concentrated if necessary using Amicon Ultra 15 mL centrifugal concentrators with 10 kD or 30 kD nominal molecular weight cut-offs. The pools were then purified by SEC using a Superdex 200 26/60 column to remove aggregates. The purified protein was then characterized by SDS-PAGE and SEC-MALLS (Multi-angle laser light scattering). Concentration was determined by absorbance at 280 nm, using the theoretical absorption coefficients calculated from the sequence by Vector NTI.

Example 6

Binding of cKIT Abs to cKIT ECD Subdomains

To help define the binding sites of the cKIT Abs, the human cKIT ECD was divided into subdomains 1-3 (ligand binding domain) and subdomains 4-5 (dimerization domain). To determine which subdomains were bound, a sandwich ELISA assay was employed. 1 ug/ml of ECD diluted in 1× Phosphate buffered saline corresponding to cKIT subdomains 1-3, subdomains 4-5 or full-length cKIT ECD were coated on 96 well Immulon 4-HBX plates (Thermo Scientific Cat#3855, Rockford, Ill.) and incubated overnight at 4° C. Plates were washed three times with wash buffer (1× Phosphate buffered saline (PBS) with 0.01% Tween-20 (Bio-Rad 101-0781)). Plates were blocked with 280 ul/well 3% Bovine Serum Albumin diluted in 1×PB S for 2 hrs at room temperature. Plates were washed three times with wash buffer. Antibodies were prepared at 2 ug/ml in wash buffer with 5-fold dilutions for 8 points and added to ELISA plates at 100 ul/well in triplicate. Plates were incubated on an orbital shaker shaking at 200 rpm for 1 hr at room temperature. Assay plates were washed three times with wash buffer. Secondary antibody F(ab')$_2$ Fragment Goat anti-human IgG (H+L) (Jackson Immunoresearch Cat#109-036-088, West Grove, Pa.) was prepared 1:10,000 in wash buffer and added to ELISA plates at 100 ul/well. Plates were incubated with secondary antibody for 1 hr at room temperature shaking at 200 rpm on an orbital shaker. Assay plates were washed three times with wash buffer. To develop the ELISA signal, 100 ul/well of Sure Blue® TMB substrate (KPL Cat#52-00-03, Gaithersburg, Md.) was added to plates and allowed to incubate for 10 mins at room temperature. To stop the reaction 50 ul of 1N Hydrochloric Acid was added to each well. Absorbance was measured at 450 nM using a Molecular Devices SpectraMax M5 plate reader. To determine the binding response of each antibody the optical density measurements were averaged, standard deviation values generated and graphed using Excel. The binding domains of each individual anti-cKIT antibody is found in Table 5 below.

Example 7

Affinity Measurements of cKIT Abs

Affinity of the antibodies to cKIT species orthologues and also to cKIT was determined using SPR technology using a Biacore® 2000 instrument (GE Healthcare, Pittsburgh, Pa.) and with CM5 sensor chips.

Briefly, HBS-P (0.01 M HEPES, pH 7.4, 0.15 M NaCl, 0.005% Surfactant P20) supplemented with 2% Odyssey® blocking buffer (Li-Cor Biosciences, Lincoln, Nebr.) was used as the running buffer for all the experiments. The immobilization level and analyte interactions were measured by response unit (RU). Pilot experiments were performed to test and confirm the feasibility of the immobilization of the anti-human Fc antibody (Catalog number BR100839, GE Healthcare, Pittsburgh, Pa.) and the capture of the test antibodies.

For kinetic measurements, the experiments were performed in which the antibodies were captured to the sensor chip surface via the immobilized anti-human Fc antibody and the ability of the cKIT proteins to bind in free solution was determined Briefly, 25 mg/ml of anti-human Fc antibody at pH 5 was immobilized on a CM5 sensor chip through amine coupling at flow rate of 5 µl/minute on all two flow cells to reach 10,500 RUs. 0.1-1 µg/ml of test antibodies were then injected at 10 µl/min for 1 minute. Captured levels of the antibodies were generally kept below 200 RUs. Subsequently, 3.125-50 nM of cKIT receptor extracellular domains (ECD) were diluted in a 2-fold series and injected at a flow rate of 40 µl/min for 3 min over both reference and test flow cells. Table of tested ECDs is listed below. Dissociation of the binding was followed for 10 min. After each injection cycle, the chip surface was regenerated with 3 M $MgCl_2$ at 10 µl/min for 30 s. All experiments were performed at 25° C. and the response data were globally fitted with a simple 1:1 interaction model (using Scrubber 2® software version 2.0b (BioLogic Software) to obtain estimates of on rate ($k_a$), off-rate ($k_d$) and affinity ($K_D$).

TABLE 4

ECD isotype and source

| ECD Isotype | Tag | Source |
|---|---|---|
| Human | C-terminal 6x His | NVS |
| Cyno | C-terminal 6x His | NVS |
| Mouse | C-terminal 6x His | Sino Biological Inc (Catalog number: 50530-M08H) |
| Rat | C-terminal mFc | NVS |

Table 5 lists the domain binding and affinity. As shown in the Table, the antibodies 9p3, NEG024, NEG027, NEG085, NEG086, NEG087 and 20376 all react with human cKIT at the nanomolar level, and have similar affinities for those tested against cynomolgus monkey ECD. However, only 20376 cross reacted with mouse. None of the antibodies tested cross-reacted with rat cKIT.

TABLE 5

| Ab | Domain binding | Affinity human cKIT (nM) | Affinity cyno cKIT (nM) | Affinity mouse cKIT (nM) | Affinity to rat cKIT (nM) |
|---|---|---|---|---|---|
| 9P3 | d1-3 | 20 | not determined | Not reactive | Not reactive |
| NEG024 | d1-3 | 1.31 | 1.15 | Not reactive | Not reactive |
| NEG026 | d1-3 | not determined | not determined | Not reactive | Not reactive |
| NEG027 | d1-3 | 1.34 | not determined | Not reactive | Not reactive |
| NEG085 | d1-3 | 8.4 | 6.14 | Not reactive | Not reactive |
| NEG086 | d1-3 | 1.44 | 1.34 | Not reactive | Not reactive |
| NEG087 | d1-3 | 1.13 | 1.39 | Not reactive | Not reactive |
| 20376 | d1-3 | 9.1 | 4.8 | 2.5 | Not reactive |

Example 8

Preparation of ADCs

Preparation of the DM1 Conjugates by One-Step Process

Individual cKIT antibodies were diafiltered into a reaction buffer (15 mM potassium phosphate, 2 mM EDTA, pH 7.6) via Tangential Flow Filtration (TFF#1) prior to the start of the conjugation reaction. Subsequently, a cKIT antibody (about 5.0 mg/mL) was mixed with DM1 (5.6-fold molar excess relative to the amount of antibody) and then with SMCC (about 5.0-fold excess relative to the amount of antibody). The reaction was performed at 20° C. in 15 mM potassium phosphate buffer (pH 7.6) containing 2 mM EDTA and 10% DMA for approximately 16 hours. The reaction was quenched by adding 1 M acetic acid to adjust the pH to 5.50. After pH adjustment, the reaction mixture was filtered through a multi-layer (0.45/0.22 µm) PVDF filter and purified and diafiltered into a 20 mM succinate buffer (pH 5.0) containing 8.22% sucrose using Tangential Flow Filtration (TFF#2). An example of the instrument parameters for the Tangential Flow Filtration are listed in Table 6 below.

TABLE 6

Instrument parameters for the Tangential Flow Filtration

| TFF Parameter | TFF#1 Set Point | TFF#2 Set Point |
|---|---|---|
| Bulk Concentration (Cb - g/L) | 20 | 20 |
| TMP (psi) | 12-18 | 12-18 |
| Feed Flow rate (LMH) | 324 | 324 |
| Membrane Load (g/m2) | 110-150 | 110-150 |
| Diavolumes | 10 | 14 |
| Diafiltration Buffer | 15 mM potassium phosphate, 2 mM EDTA, pH 7.6 | 20 mM Succinate, 8.22% Sucrose, pH 5.0 |
| Temperature (° C.) | RT (20-25) | RT (20-25) |

Conjugates obtained from the process described above was analyzed by: UV spectroscopy for cytotoxic agent loading (Maytansinoid to Antibody Ratio, MAR); SEC-HPLC for determination of conjugate monomer; and reverse-phase HPLC or hydrophobic shielded phase (Hisep)-HPLC for free maytansinoid percentage.

Preparation of DM1 Conjugates by In Situ Process

The anti-cKIT antibodies can also be conjugated by an in situ process according to the following procedures. cKIT antibodies were conjugated to DM1 using the sulfosuccinimidyl 4-(N-maleimidomethyl)cyclohexane-1-carboxylate (sulfo-SMCC) linker. Stock solutions of DM1 and sulfo-SMCC heterobifunctional linker were prepared in DMA. Sulfo-SMCC and DM1 thiol were mixed together to react for 10 minutes at 25° C. in DMA containing 40% v/v of aqueous 50 mM succinate buffer, 2 mM EDTA, pH 5.0, at the ratio of DM1 to linker of 1.3:1 mole equivalent and a final concentration of DM1 of 1.95 mM. The antibody was then reacted with an aliquot of the reaction to give a mole equivalent ratio of SMCC to Ab of around 6.5:1 under final conjugation conditions of 2.5 mg/mL of Ab in 50 mM EPPS, pH 8.0 and 10% DMA (v/v). After approximately 18 hours at 25° C., the conjugation reaction mixture was purified using a SEPHADEX™ G25 column equilibrated with 10 mM succinate, 250 mM glycine, 0.5% sucrose, 0.01% Tween 20, pH 5.5.

Either method is useful in the conjugation of antibodies. The Table below provides an example of cKIT ADCs.

TABLE 7

Properties of DM1-conjugated antibodies

| Ab | MAR | Monomer (%) | Yield (%) | Free drug (%) |
| --- | --- | --- | --- | --- |
| 9P3 | 3.6 | 99 | | none detected |
| NEG024 | 4 | 98 | 70 | 0.7 |
| NEG026 | 4 | 98 | 71 | 1.2 |
| NEG027 | 4 | 98 | 68 | 1.2 |
| NEG085 | 3.5 | 99 | 88 | 0.7 |
| NEG086 | 3.5 | 99 | 83 | 1.5 |
| NEG087 | 3.6 | 99 | 90 | 1.1 |
| 20376 | 3.8 | 99 | 84 | none detected |

Preparation of ADCs with the SPDB Linker

Anti-cKIT antibodies, for example, antibody 9P3, (8 mg/ml) were modified with N-succinimidyl 4-(2-pyridyldithio)butanoate (SPDB, 5.0, 5.5 and 4.9 fold molar excess respectively) for 120 minutes at 25° C. in 50 mM potassium phosphate buffer (pH 7.5) containing 50 mM NaCl, 2 mM EDTA, and 5% DMA. The modified Ab without purification was subsequently conjugated to DM4 (1.7 fold molar excess over the unbound linker) at a final modified antibody concentration of 4 mg/mL in 50 mM potassium phosphate buffer (pH 7.5) containing 50 mM NaCl, 2 mM EDTA, and 5% DMA for 18 hours at 25° C. The conjugation reaction mixture was purified using a SEPHADEX™ G25 column equilibrated and eluted with 10 mM succinate, 250 mM glycine, 0.5% sucrose, 0.01% Tween 20, pH 5.5.

Preparation of ADCs with the CX1-1 Linker

Anti-cKIT antibodies, for example, antibody 9P3 (5.0 mg/mL) were mixed with DM1 (7.15-fold molar excess relative to the amount of antibody) and then with CX1-1 (5.5-fold excess relative to the amount of antibody). The reaction was performed at 25° C. in 60 mM EPPS [4-(2-Hydroxyethyl)-1-piperazinepropanesulfonic acid] buffer (pH 8.5) containing 2 mM EDTA and 5% DMA for approximately 16 hours. The reaction mixture was then purified using a SEPHADEX™ G25 column equilibrated and eluted in 10 mM succinate, 250 mM glycine, 0.5% sucrose, 0.01% Tween 20, pH 5.5.

An example comparing the in vitro efficacies of antibody-MCC-DM1, antibody-SPDB-DM4 and antibody-CX1-1-DM is shown in FIG. 2.

Example 9

Affinity of ADCs Relative to Parental Antibodies

The affinity of the antibodies to cKIT following conjugation to SMCC-DM1 was determined using Biacore technology using a Biacore® T100 instrument (GE Healthcare, Pittsburgh, Pa.) and CM5 sensor chips using similar methodology to that described in Example 7 above.

For the antibodies assessed, similar affinity estimates for binding to human cKIT were obtained for SMCC-DM1 conjugated antibodies relative to parental unconjugated antibodies, suggesting that conjugation does not appreciably impact antibody binding (Table 8).

TABLE 8

Affinities of unconjugated and MCC-DM1 conjugated antibodies

| | Human c-Kit ECD (nM) | |
| --- | --- | --- |
| | Unconjugated | -MCC-DM1 |
| NEG024 | 1.3 | 1.1 |
| NEG085 | 4.2 | 5.2 |
| NEG086 | 1.4 | 1.8 |
| 20376 | 9.1 | 11.2 |

Example 10

Activity of 9P3-MCC-DM1, 9P3-SPDB-DM4 and 9P3-CX1-1-DM1 on a Panel of Cell Lines Following conjugation to the MCC-DM1 linker-payload, the ability of the antibody drug conjugates (ADCs) to inhibit the proliferation of AML, SCLC, GIST, and melanoma cell lines was determined. The GIST-T1 cell line was generously provided by Dr. Takahiro Taguchi, Kochi U., Japan. The GIST430 and GIST882 cell lines were kindly provided by Dr. Jonathan Fletcher, Brigham and Women's Hospital, Boston, Mass.

For small cell lung cancer (SCLC), the NCI-H526 and the NCI-H1048 cell lines were used. NCI-H526 is a high cKIT expressor and was obtained from ATCC (CRL-5811, ATCC Manassas, Va.). NCI-H1048 expresses cKIT at a lower level, and was also obtained from the ATCC (CRL-5853). CMK-11-5 is an AML line that expresses high levels of cKIT ((JCRB Cat# IFO50430, Japan) see also Nagano et al., Int. J. Hematol. 1992; 56:67-78)). UKE-1 is also an AML cell line and it expresses low amounts of cKIT. The UKE-1 cell line was generously provided by Professor Walter Fiedler, University Hospital Eppendorf, Hamburg, Germany. Kasumi 1 was obtained from the ATCC (CRL-2724). Kasumi-6 was obtained from the ATCC (CRL-2775). MDA-MB-453 were obtained from ATCC (HTB-131). NCI-H889 and NCI-H1930 lines were purchased from ATCC (CRL-5817 and CRL-5906 respectively). Hel92.1.7 cells were obtained from Sigma-Aldrich (Cat#92111706-1VL, Sigma Aldrich, St. Louis, Mo.). The M-07e and SKNO1 cells were purchased from DSMZ, ACC-104 and ACC-690 respectively (DSMZ, Braunschweig, Del.) The OCI-M1 cell line is also from DSMZ (ACC-529).

Briefly, cells were cultured in a tissue culture incubator at 37° C. with 5% $CO_2$ in culture medium as recommended by the supplier. On the day of the assay, cells were washed twice with PBS (Cellgro, catalog #21-031-CV), prior to being treated with 0.1% trypsin-EDTA (in-house technical services) for 5 min and resuspended in the recommended culture medium. Cells were then counted and seeded in 96 well plates (Costar catalog #3603, Corning, Tewksbury, Mass.) at densities of 2,000-10,000 cells/well in 100 μl of cell culture medium. A duplicate plate was generated for a day 0 measurement and all plates were incubated in a tissue culture incubator at 37° C. with 5% $CO_2$ overnight. Medium only wells were also generated to act as negative controls. Following this incubation, 100 μl/well of Cell titer Glo® reagent (Promega catalog # G7573, Madison, Wis.) was added to the day 0 plates, which were then shaken gently for 2 min, incubated for 10 min, and the resulting luminescence intensity was measured using a Perkin Elmer Wallac Microbeta Trilux® plate reader (Perkin Elmer, Waltham, Mass.). Test ADCs were serially diluted to a 3x stock solution in the appropriate cell culture medium and 50 μl of 3× serially diluted ADCs were added (final assay concentration 0.0002-68 nM DM1 equivalents) prior to incubation in a tissue culture incubator at 37° C. with 5% $CO_2$ for 5 days. Following this incubation period, relative cell viability was determined via the addition of Cell titer Glo® reagent as described above. The effect of the ADCs on cell proliferation was calculated using the average of the duplicates as follows: (% Inhibition=(ADC treated−untreated)/(untreated−Day 0)*100). The % inhibition data was fitted to a 4-parameter logistic equation and $GI_{50}$ values were determined.

As shown in FIG. 1, cKIT ADCs were tested in a proliferation assay on a panel of GIST (GIST T-1, GIST882, GIST430), SCLC (NCI-H526, NCI-H1048) and AML (Kasumi-6, Kasumi-1) cell lines. IC50 and maximum killing values are listed in the table. MDA-MB453 (breast cancer cell line) does not express cKIT. IgG-MCC-DM1 is the isotype control. As demonstrated by FIG. 1, all of the cKIT ADCs had nanomolar to sub-nanomolar IC50s in the seven lines used. This indicates that the cKIT ADCs have a broad spectrum of indications, and could be used wherever a tumor is expressing appropriate levels of cKIT.

The ability of an anti-cKIT antibody (9P3) conjugated via the SPDB-DM4 and CX1-1-DM1 linker-payload was also evaluated and is shown in FIG. 2. These studies, which were conducted as described above, revealed that the anti-cKIT ADC evaluated was also a potent inhibitor of cell proliferation using SPDB-DM4 or CX1-1-DM1, suggesting that their ability to successfully deliver toxin to kill cells is not limited to MCC-DM1. FIG. 1 and FIG. 2 both provide for cKIT ADCs that are effective in the nanomolar to sub-nanomolar range.

In addition, FIG. 3 is a plot of anti-cKIT ADC GI50 against cKIT receptor level, and what indications (AML, GIST, melanoma and SCLC). As shown in FIG. 3, anti-cKIT ADC is efficacious across all of the listed indications.

Example 11

In Vitro Activity of cKIT-MCC-DNB ADCs on GIST, SCLC and AML Cell Lines

Following conjugation to the MCC-DM1 linker-payload, the ability of the antibody drug conjugates (ADCs) to inhibit the proliferation of AML, SCLC and GIST cell lines was determined. For a listing of the cells used in these experiments by supplier see Example 10 above.

Briefly, cells were cultured in a tissue culture incubator at 37° C. with 5% $CO_2$ in culture medium as recommended by the supplier. On the day of the assay, cells were washed twice with PBS (Cellgro, Cat #21-031-CV, Corning Tewksbury, Mass.), prior to being treated with 0.1% trypsin-EDTA (in-house technical services) for 5 min and resuspended in the recommended culture medium. Cells were then counted and seeded in 96 well plates (Costar catalog #3603, Corning, Tewksbury, Mass.) at densities of 5,000 cells/well for AML and SCLC cells and 10,000 cells/well for GIST cells in 100 μl of cell culture medium. A duplicate plate was generated for a day 0 measurement and all plates were incubated in a tissue culture incubator at 37° C. with 5% $CO_2$ overnight. Following this incubation, 100 μl/well of Cell titer Glo® reagent (Promega catalog # G7573, Promega, Madison, Wis.) was added to the day 0 plates, which were then shaken gently for 2 min, incubated for 10 min, and the resulting luminescence intensity was measured using a Perkin Elmer Wallac Microbeta® Trilux plate reader (Perkin Elmer, Waltham, Mass.). Test ADCs were serially diluted to a 3× stock solution in the appropriate cell culture medium and 50 μl of 3× serially diluted ADCs were added (final assay concentration of 0.0002-68 nM DM1 equivalents) prior to incubation in a tissue culture incubator at 37° C. with 5% $CO_2$ for 5 to 8 days. Following this incubation period, relative cell viability was determined via the addition of Cell titer Glo® reagent as described above. The effect of the ADCs on cell proliferation was calculated using the average of the duplicates as follows: (% of maximum affection ($A_{MAX}$)=(untreated−highest ADC concentration treated)*100).

The % inhibition data was fitted to a 4-parameter logistic equation and $GI_{50}$ values were determined. This data is shown in FIGS. 4-9. As shown in the graphs, an IgG-MCC-DM1 conjugate is used as control. All of the ADCs tested have greater activity than the control antibody. As demonstrated by the curves in FIGS. 4-9, the anti-cKIT ADCs, for example, the NEG085, NEG024 and 20376 antibodies were very effective in reducing cell proliferation, and thus would efficacious in the treatment of GIST, AML and SCLC.

Example 12

Quantitation of cKIT Surface Receptor Density on Cell Lines by FACS (Fluoresence Activated Cell Sorting)

Quantum Simply Cellular Beads (Bangs Laboratories, Inc. Catalog #815, Fishers, Ind.) were used as standards. Antibody Binding Capacity of bead standards range from 0 to about 310,000. Beads or five hundred thousand cells were centrifuged and washed two times with 100 μl/sample of FACS buffer (PBS, 0.2% BSA, 0.1% NaAz). After each washing step, beads or cells were centrifuged and carefully re-suspended. Following washes, FACS buffer was added and 10 μg/ml of APC-Mouse Anti-Human CD117 (BD Pharmigen Catalog #550412, BD Biosciences, San Jose, Calif.) or 10 μg/ml of APC-Mouse IgG κ Isotype Control (BD Pharmigen Catalog #554681) was added to the corresponding wells, for a final volume of 100 μl/sample.

The cell-antibody suspensions were then incubated on ice for 1 hour. Following incubation, cells were spun down and washed two times with 100 μl FACS buffer. After each washing step, beads or cells were centrifuged and carefully re-suspended.

Non-viable cells were excluded by re-suspension in 100 μl/sample 7-AAD (BD Pharmigen Catalog #559925)-containing FACS buffer. Samples were incubated on ice for 10 minutes and were analyzed in BD FACS Canto II® (BD Biosciences, San Jose, Calif.). Geomean of signal per sample was determined using FlowJo® software, and antigen densities were determined as described in the Quantum Simply Cellular manual. Analyses of in vitro cell line sensitivity to ADCs and cell line receptor density were done in TIBCO Spotfire 4.0.

This receptor density is shown on the Y-axis of FIG. 3. A receptor density analysis is useful in this aspect as an initial biomarker for patient stratification. For example, in FIG. 3, a high receptor density is correlating with efficacy of the anti-cKIT ADC GI50 shown on the X-axis. Analysis of receptor density is useful in a clinical setting, for determining which patients should receive an anti-cKIT ADC therapeutic.

Example 13

Epitope Mapping of cKIT to 9P3 Antibody by Deuterium Exchange Mass Spectrometry (HDx-MS)

Deuterium exchange mass spectrometry (HDx-MS) measures the deuterium uptake on the amide backbone of a protein. These measurements are sensitive to the amide's solvent accessibility and to changes in the hydrogen bonding network of the backbone amides. HDx-MS is often used to compare proteins in two different states, such as apo and ligand-bound, and coupled with rapid digestion with pepsin. In such experiments one can locate regions, typically of 10 to 15 amino acids, that show differential deuterium uptake between two different states. Regions that are protected are either directly involved in ligand binding or allosterically affected by binding of the antibody to the ligand.

In these experiments, the deuterium uptake of cKIT extra-cellular domain (SEQ ID NO:160, see below) was measured in the absence and presence of a therapeutic mAb, 9P3. Regions in cKIT that show a decrease in deuterium uptake upon binding of the antibody are likely to be involved in the epitope; however, due to the nature of the measurement it is also possible to detect changes remote from the direct binding site (allosteric effects). Usually, the regions that have the greatest amount of protection are involved in direct binding although this may not always be the case. In order to delineate direct binding events from allosteric effects orthogonal measurements (e.g. X-ray crystallography, alanine mutagenesis) are necessary.

TABLE 9 cKIT extra-cellular domain construct

SEQ ID NO: 160
LENGTH: 503 amino acids
TYPE: Protein
ORGANISM: Human
QPSVSPGEPSPPSIHPGKSDLIVRVGDEIRLLCTDPGFVKWTFEILDETNENKQNEWITEKAEAT

NTGKYTCTNKHGLSNSIYVFVRDPAKLFLVDRSLYGKEDNDTLVRCPLTDPEVTNYSLKGCQ

GKPLPKDLRFIPDPKAGIMIKSVKRAYHRLCLHCSVDQEGKSVLSEKFILKVRPAFKAVPVVS

VSKASYLLREGEEFTVTCTIKDVSSSVYSTWKRENSQTKLQEKYNSWHHGDFNYERQATLTIS

SARVNDSGVFMCYANNTFGSANVTTTLEVVDKGFINIFPMINTTVFVNDGENVDLIVEYEAFP

KPEHQQWIYMNRTFTDKWEDYPKSENESNIRYVSELHLTRLKGTEGGTYTFLVSNSDVNAAI

AFNVYVNTKPEILTYDRLVNGMLQCVAAGFPEPTIDWYFCPGTEQRCSASVLPVDVQTLNSS

GPPFGKLVVQSSIDSSAFKHNGTVECKAYNDVGKTSAYFNFAFKEQIHPHTLFTPRSHHHHHH

The cKIT epitope mapping experiments are performed on a Waters Synapt® G2 HDx-MS platform, which includes LEAP® robot system, nanoACQUITY® UPLC System, and Synapt® G2 mass spectrometer. In this method, triplicate control experiments are carried out as follows. 300 pmol (1.4 mg/ml) of cKIT antigen is diluted into 110 ul of 95% deuterated PBS buffer (pH 7.4) and incubates at room temperature on a bench rotator for 25 minutes (% D=85.5%). Deuterium exchange is quenched by 1:1 dilution with cold quench buffer (6M Urea and 1M TCEP pH=2.5) on ice for 5 min. After quenching the tube is transferred onto a LEAP system (Thermo box is set at 2° C.) and the quenched sample is injected by the LEAP system onto the UPLC system for analysis. The UPLC system incorporates an immobilized pepsin column 2.1 mm×30 mm (Life Technologies 2-3131-00) that is maintained at 12° C. An 8-minute 2 to 35% acetonitrile gradient and Waters UPLC CSH C18 1.0×100 mm column is used for separation. Next, triplicate experiments are carried out using the antibody. 300 pmol of 9P3 antibody is immobilized on Protein G agarose beads (Thermo Scientific Cat#22851) using standard techniques. Briefly, the antibody is centrifuged to remove a storage buffer. Then 200 ul of PBS buffer (pH 7.4) and 300 pmol of cKIT are added to the immobilized Ab and incubate for 30 min at room temperature. After incubation, the complex is centrifuged and washed with 200 ul PBS buffer and centrifuged again. For deuterium exchange, 200 ul of deuterated PBS is added to the antigen-antibody complex for incubation at room temperature for 25 minutes (% D=85.5%). Deuterium buffer is then removed, and immediately, 125 ul ice cold quench buffer is added. After quenching for 5 minutes, the column is centrifuged and the flow-through is transferred into a prechilled HPLC vial. The sample is analyzed using the same on-line pepsin digestion/LC-MS setup as the control experiment.

Figure 10:
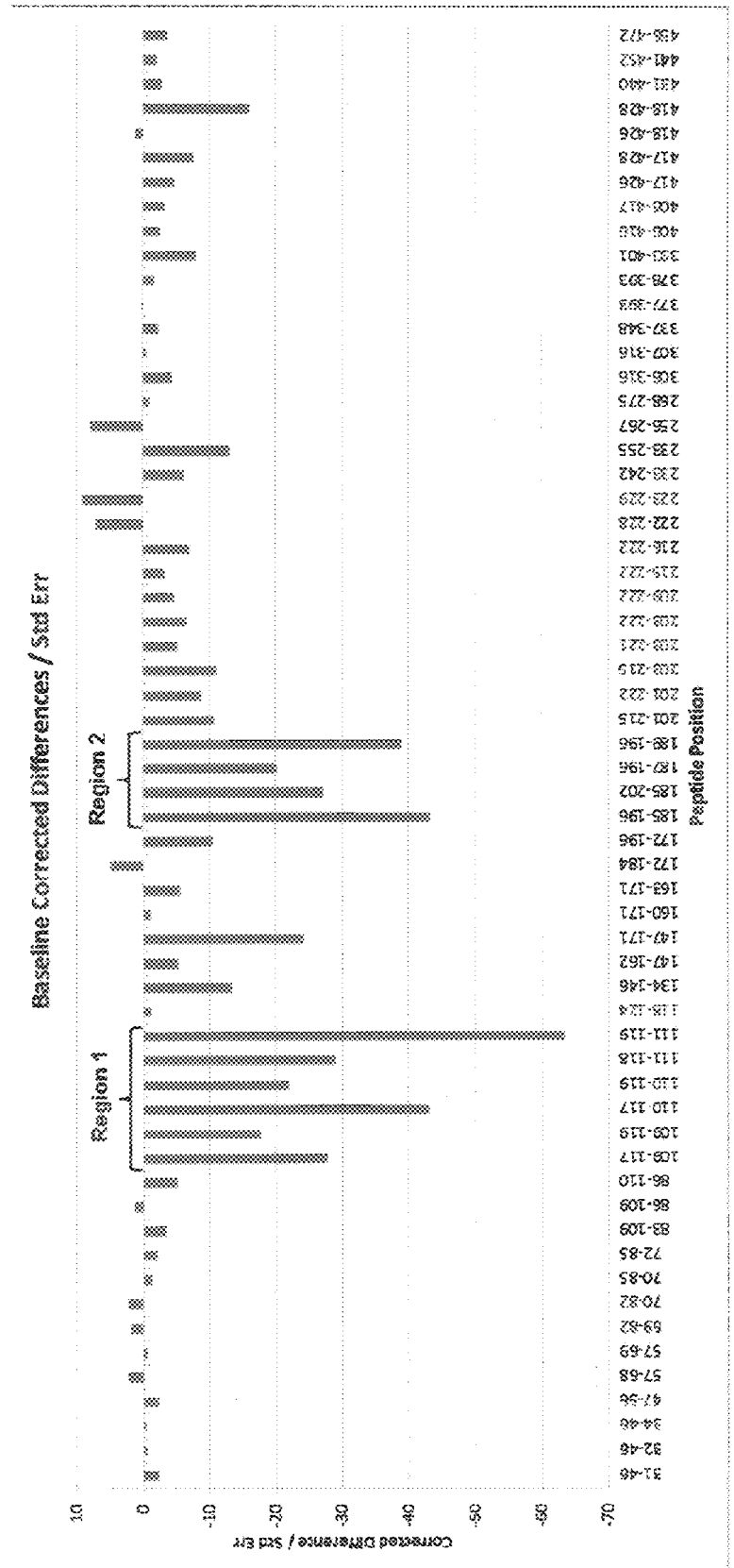
FIG. 10 is HDx-MS raw data plotted as the corrected difference over the standard error in measurement. A more negative value indicates more protection from deuterium exchange upon binding of 9P3 to c-Kit antigen. The two most significant regions of protection are denoted as Region 1 and Region 2.
Figure 11:
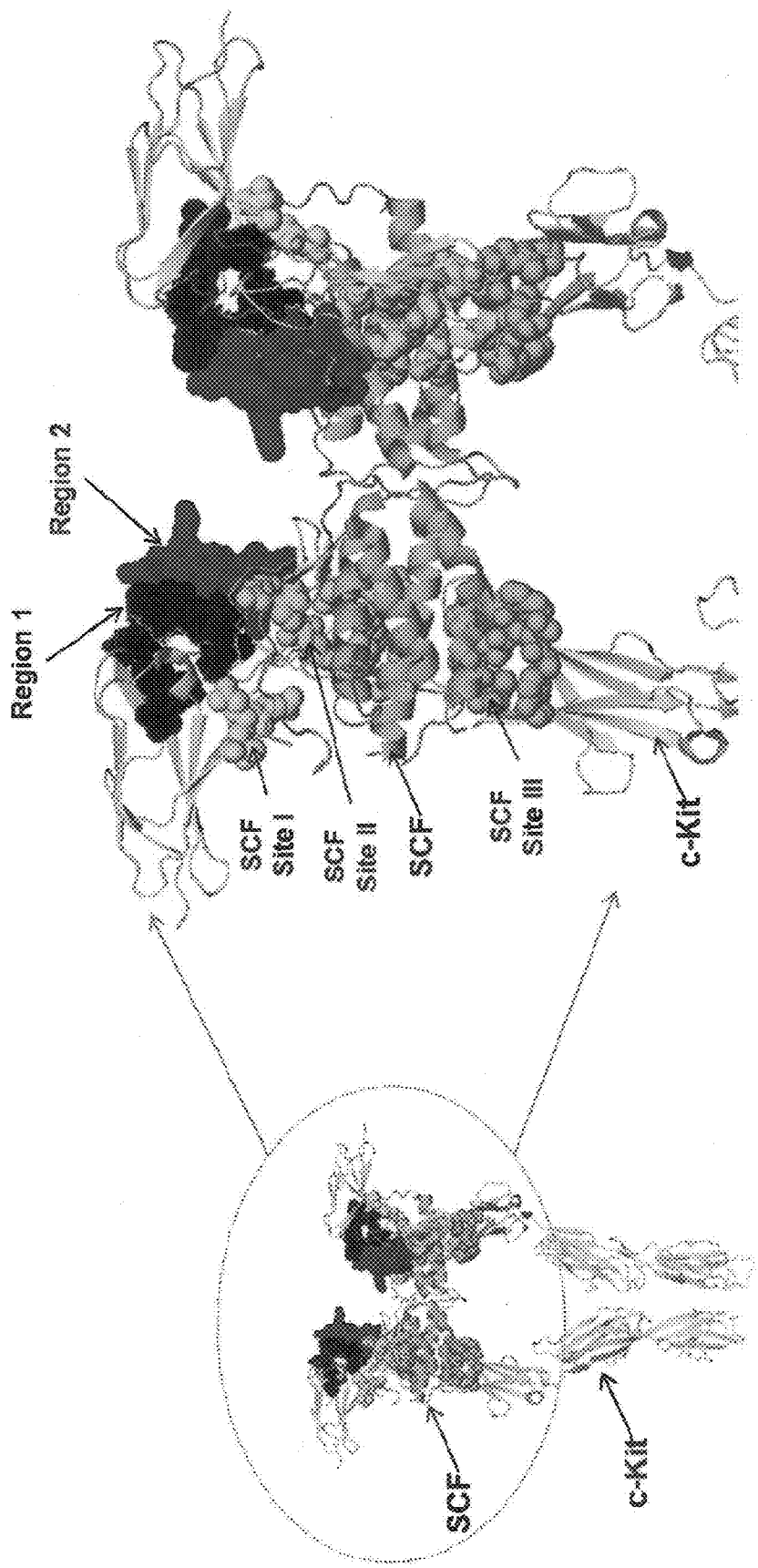
FIG. 11 shows regions of HDx-MS protection are mapped using surface fill: region 1 (black) and region 2 (dark grey). SCF binding sites are denoted as Site I (light grey spheres), Site II (medium grey spheres), and Site III (darker grey spheres).

The results of these measurements are summarized in FIG. 10 and FIG. 11. FIG. 10 shows the baseline corrected differences between the control and 9P3 antibody bound sample divided by the standard error in the measurement. In this plot the more negative value indicates a greater amount of protection in a given region upon binding of 9P3 antibody to cKIT antigen. Upon binding of 9P3 to cKIT we observe the most significant amounts of protection in the following two regions of cKIT: VFVRDPAKLFL ((Region 1, 109-119 (SEQ ID NO. 161)) and HCSDQEGKSLV ((Region 2, 185-196 (SEQ ID NO. 162)). Region 1 comprises residues 109-119 and is part of the D1 and D2 domains. Region 2 comprises residues 185-196 and is part of the D2 domain. In FIG. 11, we have mapped the two most protected regions (see FIG. 10) onto the crystal structure of cKIT extra-cellular domain (PDB ID 2e9w). In addition, we have also labeled the SCF binding sites on cKIT as site I, II, and III using literature values (Yuzawa et al., Cell 2007; 130: 323-334). There are two key findings from FIG. 11. First, regions 1 and 2 are very close together in the crystal structure even though they are far apart in primary sequence space. This observation suggests that both could potentially be part of the epitope and if so, the epitope for 9P3 is discontinuous. Second, regions 1 and 2 are remote from the SCF binding sites reported in literature. This is an important observation because it suggests that 9P3 antibody does not directly interfere with ligand binding. Instead the antibody might sterically interfere with ligand binding and/or with the dimerization of the receptor upon ligand binding. In separate competition assays, using ELISA and FACS we observed partial blocking of SCF binding to cKIT by 9P3 so there appears to be partial steric interference. In conclusion, the HDx-MS data indicate that the epitope for 9P3 antibody consists of a discontinuous epitope that is remote from the SCF binding sites. NEG024, NEG085, NEG086, NEG027 and NEG087 are expected to have the same mechanism of action.

Example 14

The Ability of cKIT ADCs to Act as (Monists was Evaluated Using a cKIT Wild Type Cell Line Mo7e and a cKIT Mutant Cell Line GIST T-1

To evaluate the potential agonistic properties of cKIT ADCs, $2\times10^6$ of GIST T-1 (kindly provided by Dr. Takahiro Taguchi, Kochi U., Japan) or Mo7e (DSMZ, ACC-104) cells were serum starved overnight at 37° C. with 5% $CO_2$ (DMEM for GIST T-1 and RPMI for Mo7e supplemented with 0.1% FBS) in 6-well plate (NUNC catalog #14067). Cells were treated with 10 ng/ml rh-SCF (R&D, Cat#255-SC, R&D, Berkeley, Calif.), 5 ug/ml NEG085-MCC-DM1, NEG024-MCC-DM1, and 20376-MCC-DM1 for 15 minutes at 37° C. One well was designated as untreated (UT). Cells were harvested in 1 ml PBS. The cell pellets were lysed on ice for 60 mins in 30 ul lysis buffer: 20 mM Tris-HCl; pH7.5, 137 mM NaCl, 1% Triton X-100, 15% Glycerol, protease and phosphatase inhibitors. Lysates were then spun down for 40 mins at 12,000 rpm at 4° C. 20 μg of each sample was boiled for 10 min at 75° C. and loaded on a 12-well NuPAGE® 4-12% Bis-Tris gel (Life Technologies, NP0322BOX, Carlsbad, Calif.). After protein transfer to membrane blots, membranes were blocked in TBST-5% milk at room temperature for 1 hour and then probed with primary antibodies overnight at 4° C. Blots were washed in TBST (4×5 mins) on the next day. Blots were incubated in the secondary antibody (goat-anti rabbit-HRP 1:30,000, Santa Cruz) for 1 hr at room temperature. Blots were washed in TBST (4×5 mins) and developed.

The primary antibodies used for Western blotting were α-cKIT, Tyr703 (Cell Signaling Technology Cat#3073, Beverly, Mass.), α-cKIT Tyr721 (NOVUS, Cat# NBP1-51412, Novus, Littleton, Colo.), AKT Ser473 (Cell Signaling Technology Cat#9271), AKT (Cell Signaling Technology Cat#4691), ERK Thr202/Tyr204 (Cell Signaling Technology Cat#9101), ERK (Cell Signaling Technology Cat#9102), and GAPDH (Cell Signaling Technology Cat#3683).

Figure 12:
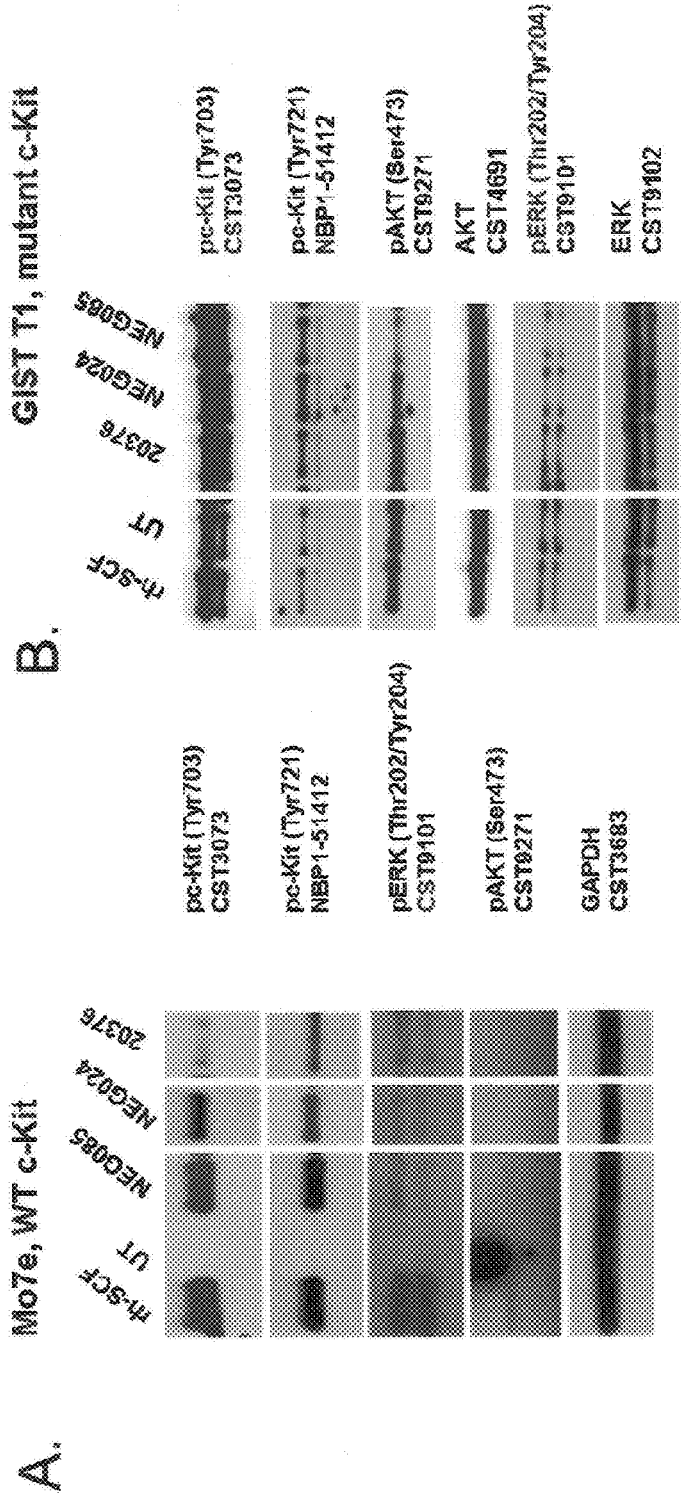
FIG. 12 is a Western blot showing the ability of SCF, NEG085-MCC-DM1, NEG024-MCC-DM1 and 20376-MCC-DM1 to modulate phosphorylation of c-Kit in a wild-type c-Kit cell line (Mo7e, A) or mutant c-Kit cell line (GIST-T1, B) after 15 minutes.

As shown in FIG. 12, the cKIT antibodies NEG085, NEG024 and 20376 can mediate phosphorylation of cKIT in the absence of ligand (SCF). However, downstream signaling pathways are not affected, as the signal does not transduce to phospho ERK or phosphor AKT.

Figure 13:
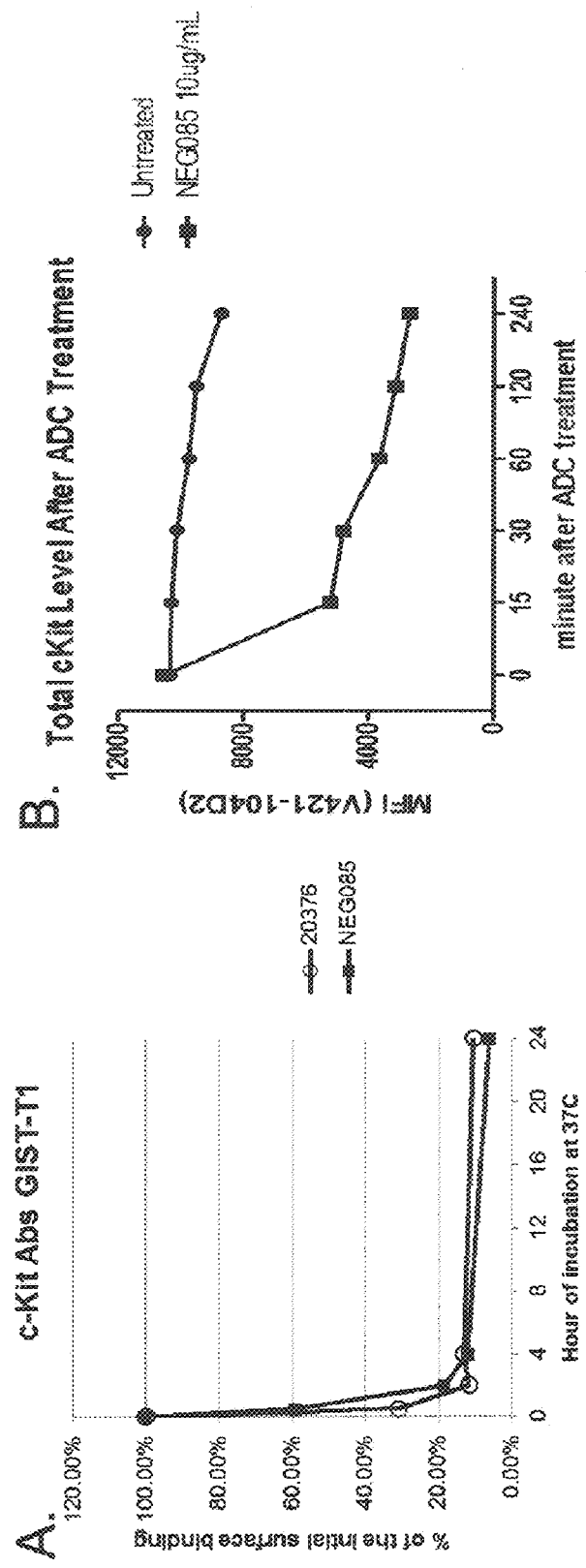
FIG. 13 shows that NEG085 and 20376 Abs mediate rapid internalization of surface c-Kit on GIST-T1 cells (A) and on human bone marrow cells (B)

Example 15 cKIT Ab-Mediated Internalization of Surface cKIT on GIST-T1 Cells as Determined by Flow Cytometry The kinetics of cKIT antibody mediated internalization was evaluated by treating with antibody in a cell monolayer using a temperature shift method and flow cytometry readout. GIST-T1 (kindly provided by Dr. Takahiro Taguchi, Kochi U., Japan) cells were seeded at 2.5×10E5 cells/well in five 12-well tissue culture treated plates (BD Falcon 353043). The cells were incubated in a tissue culture incubator at 37° C. with 5% $CO_2$ overnight. The following day medium was removed and replaced with 450 ul fresh medium. The cKIT antibodies NEG085, 20376 and an isotype control were prepared at 10×10 μg/ml concentration in appropriate cell culture medium and 50 μl of test cKIT antibody or isotype was added per well with final concentration of 10 ug/ml. All cells were incubated for 1 hr on ice, followed by two washes with 1 mL 1× Phosphate buffered saline (PBS) and resuspended in 500 μl cell culture medium. Plates #2-5 were transferred to 37° C. and harvested at time points; 30 min, 2 hr, 4 hr and 24 hr at 37° C. with 5% $CO_2$. 100 μl of cell dissociation buffer (Gibco Cat#13150-016, Life Technologies, Carlsbad, Calif.) was added to plate#1 (4° C. binding control) and incubated at 37° C. until cells were detached. Cells were neutralized with 100 μl of medium and transferred to a 96 well V-bottom tissue culture treated plate (Costar 3894). Cells were centrifuged and washed twice with FACS Buffer (1× Phosphate Buffered Saline, 2% Fetal Bovine Serum, 0.1% Sodium Azide). The Phycoerythrin conjugated goat anti-human IgG secondary Ab (Invitrogen H10104, Life Technologies, Carlsbad, Calif.) was prepared at a1 to 100 ratio in FACS buffer. Secondary antibody was added to cells at 100 μl/well and incubated with cells on ice for 45 min. At the end of the incubation period, cells were centrifuged and washed with FACS Buffer three times. Cells were fixed with 100 μl/well of 1% paraformaldehyde and stored at 4° C. in the dark. Repeat cell disassociation, secondary antibody incubation and fixation steps for the cells incubated at 37° C. for the various time points. The following day, all samples were analyzed using the BD FACSCanto II® equipment using a HTS system (BD Biosciences, San Jose, Calif.). Samples were analyzed with FlowJo software to obtain the Geometric Mean values of fluorescence for the Phycoerythrin channel. FIG. 13A is a plot of % of initial cell surface binding vs Geometric Mean-PE 4° C. binding/Geometric Mean-PE timepoint at 37° C.×100. As demonstrated in FIG. 13A, both antibodies NEG085 and 20376 bind cKIT on the cell surface and are rapidly internalized into the cell. This indicates that the cKIT ADCs disclosed would be rapidly internalized, thus delivering the toxin into the cell efficiently.

In another internalization experiment, the impact of NEG085 on cKit receptor levels was evaluated on human bone marrow cells. Normal human CD34+ bone marrow cells (All Cells, Cat #ABM022F, Emeryville, Calif.) were thawed and washed with 10 mL of StemPro®-34 SFM medium (Gibco, Life Technologies, Carlsbad, Calif.). Cells were resuspended in 1.25 mL of StemPro-34 SFM medium at $4\times10^5$ cells/mL and split equally into two tubes. One tube was untreated, and the other was treated with 10 μg/ml of NEG085 and both were incubated at 37 C, 5% CO2. 100 μL of cell suspension was collected at each timepoint (0, 15, 30, 60, 120, and 240 min) from each condition, and placed into an ice cold collection tube to cease internalization. Cells were washed with 3 mL of ice-cold FBS stain buffer and resuspended in 100 μL of FBS stain buffer. 5 mL of 104D2-BV421 (mouse anti-human IgG1 k, Biolegend) was added to each tube and incubated on ice for 1 hour. Following another wash with FBS stain buffer, total cKit receptors were measured by flow cytometry by assessing the mean fluorescence intensity of BV421 on a FACS Canto II® (BD Biosciences, San Jose, Calif.).

As shown in FIG. 13B, cKIT is rapidly internalized upon binding of NEG085, with the bulk of the internalization happening rapidly (15 minutes) and then continuing to steadily decline the amount of cKIT on the surface until the endpoint of 4 hours.

Example 16

Assessment of the Ability of NEG085-MCC-DM1 to Modulate cKIT Degradation in a Wildtype cKIT Cell Line (NCI-H526) or a Mutant cKIT Cell Line (GIST-T1)

Figure 14:
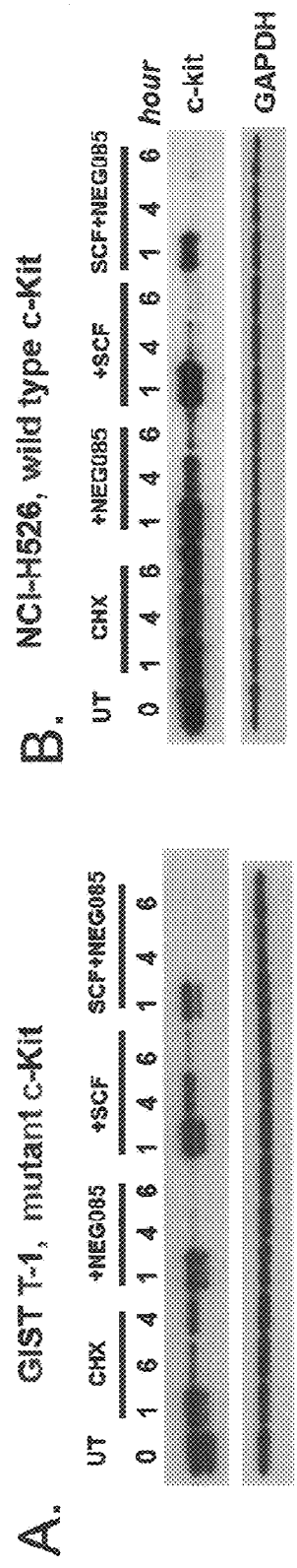
FIG. 14 are Western blots showing the ability of SCF or NEG085-MCC-DM1 to accelerate c-Kit degradation in a mutant c-Kit cell line (GIST-T1, A) and wildtype c-Kit cell line (NCI-H526, B) over a timecourse.

$5\times10^6$ of GIST-T1 (kindly provided by Dr. Takahiro Taguchi, Kochi U., Japan) or NCI-H526 (ATCC CRL-5811) cells were seeded in growth media (DMEM, 10% FBS for GIST T-1 and RPMI, 10% FBS for NCI-H526) the night before at 37° C. with 5% $CO_2$. Cells were then treated with 100 mM cycloheximide (CHX) (Cat#090M4009, Sigma-Aldrich, St. Louis, Mo.) in methionine free medium (GIBCO: DMEM, 21013-024; RPMI, A14517-01, Life Technologies, Carlsbad, Calif.). Cells were either treated with 5 µg/ml ADC (NEG085-MCC-DM1), 10 ng/ml rh-SCF (R&D, 255-SC), or both ADC and rh-SCF for 1, 4 or 6 hours at 37° C. with 5% $CO_2$. Cells were harvested at 1 hour, 4 hour, and 6 hour post treatment in 1 ml PBS. The cell pellets were lysed on ice for 60 mins in 50 ul lysis buffer (20 mM Tris-HCl; pH7.5, 137 mM NaCl, 1% Triton X-100, 15% Glycerol, protease and phosphatase inhibitors). Lysates were then spun down for 40 mins at 12,000 rpm at 4° C. Five µg of each sample was boiled for 10 min at 75° C. and loaded on a 15-well NuPAGE® 4-12% Bis-Tris gel (NP0323BOX Life Technologies, Carlsbad, Calif.). After protein transfer to membrane blots, membranes were blocked in TBST-5% milk at room temperature for 1 hour and then probed with anti cKIT antibody (Cell Signaling Technology Cat#3074, Beverly, Mass.) overnight at 4° C. Blots were washed in TBST (4×5 mins) the next day. The blot was incubated in the secondary antibody (goat-anti rabbit-HRP 1:30,000, Santa Cruz Biotechnologies, Dallas, Tex.) for 1 hour at room temperature. The blot was washed in TBST (4×5 mins) and developed. The primary antibodies used for Western blotting were α-cKIT (Cell Signaling Technology Cat#3074) and GAPDH (Cell Signaling Technology Cat#3683). FIGS. 14 A/B show a timecourse of cKIT receptor degradation mediated by NEG085-MCC-DM1. The degradation was rapid with levels becoming very low/undetectable after 6 hours. Note that the degradation of the cKIT receptor happens faster than SCF with NEG085-MCC-DM1 in the GIST T1 cells which express a mutant cKIT receptor (panel 14A). Also, the NEG085-MCC-DM1 does not block the cKIT receptor from binding SCF, as the addition of NEG085-MCC-DM1 and SCF provides for faster degradation, as seen in FIG. 14B. If the NEG085-MCC-DM1 were a ligand blocker, there would be no difference between NEG085-MCC-DM1 and NEG085-MCC-DM1 with SCF.

Example 17

Unconjugated NEG085 and 20376 do not Inhibit the Proliferation of Mo7e, a SCF-Dependent Cell Line To evaluate the potential antagonistic properties of the naked antibodies and the ability of the antibody drug conjugates (ADCs) to inhibit the proliferation of a cKIT-expressing cell line, MO7e (DSMZ, Catalog # ACC-104, Braunschweig, Del.) were grown in the presence or absence of cKIT ligand, Stem Cell Factor (SCF), for survival. MO7e cells were grown in either 10 ng/ml human granulocyte-macrophage colony-stimulating factor GM-CSF (R&D Systems Cat#215-GM, Minneapolis, Minn.) or 10 ng/ml human Stem Cell Factor SCF (R&D Systems Cat#255-SC) prior to seeding in 96 well plates (Costar Cat #3904, Corning, Tewksbury, Mass.) at 5000 cells/well in 100 µl dilution medium. A duplicate plate was generated for a day 0 measurement and all plates were incubated in a tissue culture incubator at 37° C. with 5% $CO_2$ overnight. Following this incubation, an additional 50 µl of dilution medium was added, followed by 90 µl/well of Cell titer Glo® reagent (Promega Cat# G7573, Madison, Wis.) to each well of the designated "day 0" plate. Assay plates were shaken gently for 20 min and the resulting luminescence intensity was measured using a Perkin Elmer 1450 Microbeta TriLux® plate reader (Perkin Elmer, Waltham, Mass.). Test naked Abs and ADCs were prepared at 3× concentration; 30 µg/ml in the appropriate cell culture medium and diluted serially 5-fold for 8 points. Medium only wells were also generated to act as negative controls. 50 ul of 3× serially diluted antibodies or ADCs were added (final assay concentration 0.0009-68 nM) prior to incubation in a tissue culture incubator at 37° C. with 5% $CO_2$ for 5 days. Following this incubation period, relative cell viability was determined via the addition of Cell titer Glo reagent as described above. The effect of the ADCs on cell proliferation was calculated using the average of the duplicates as follows: (% Inhibition= (ADC or Ab treated)/(untreated)*100) The % inhibition data was fitted to a 4-parameter logistic equation and $IC_{50}$ values were determined.

Figure 15:
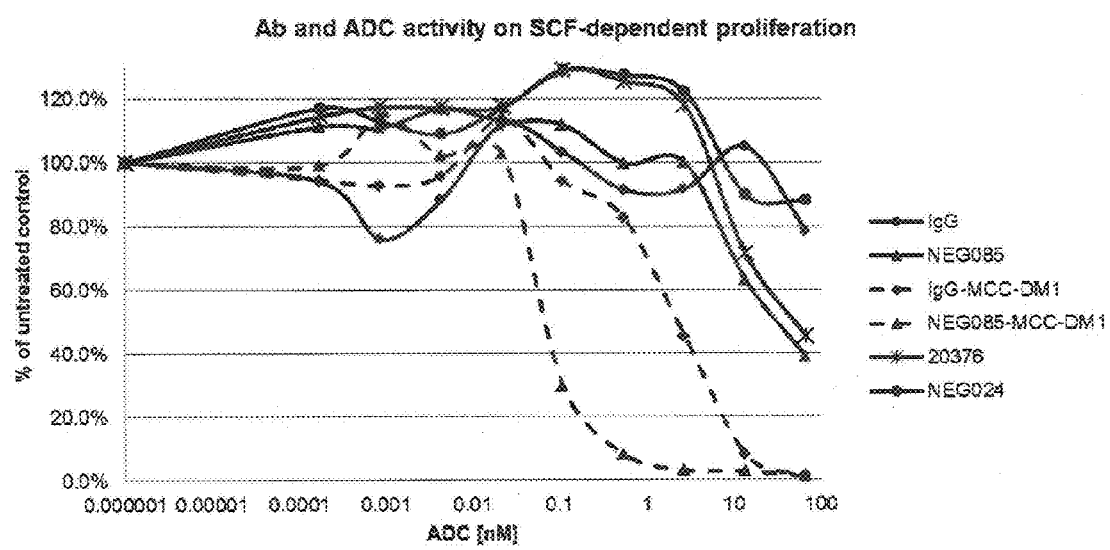
FIG. 15 shows the ability of NEG085, NEG024, 20376, NEG085-MCC-DM1 to inhibit the SCF-dependent proliferation of Mo7e cells.
Figure 16:
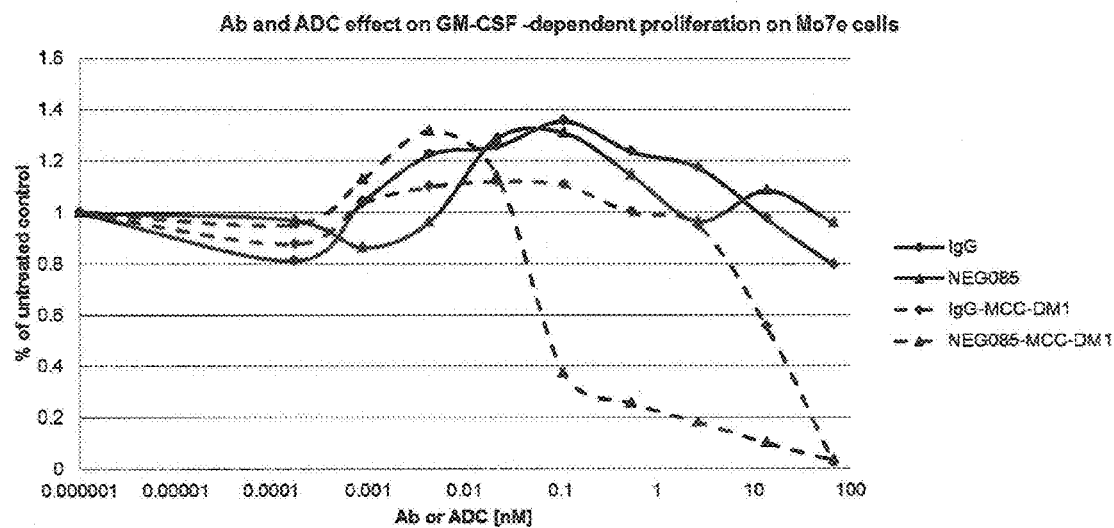
FIG. 16 shows the ability of NEG085 and NEG085-MCC-DM1 to inhibit SCF-independent proliferation of Mo7e cells.

As shown in FIG. 15 and FIG. 16, the naked anti-cKIT antibodies do not inhibit cell proliferation. In FIG. 15, the NEG085-MCC-DM1 is compared with unconjugated NEG085, NEG024 and 20376. As shown clearly in the graph, NEG085-MCC-DM1 inhibits cell proliferation of M07e cells at a low concentration, while the unconjugated antibodies do not have this effect. The IgG-MCC-DM1 control has a greater anti-proliferative effect than unconjugated NEG085, NEG024 or 20376.

This is also seen in FIG. 16, where the experiment uses GM-CSF rather than SCF to negate the internalization effect on the cKIT receptor that the SCF ligand has. The result in FIG. 16 is consistent with that of FIG. 15, that an unconjugated NEG085 antibody has no detrimental effect on cell proliferation, similar to an unconjugated IgG control. In summary, the results shown on FIGS. 15 and 16 indicate that the reduction in cell proliferation is due to the conjugation of the anti-cKIT antibodies with the toxin.

Example 18

Evaluation of ADCC Activity In Vitro

The ability of the unconjugated anti-cKIT antibodies (NEG085, 20376) to mediate antibody dependent cellular cytotoxicity was determined versus Uke-1 cells (target cells; generously provided by Professor Walter Fiedler, University Hospital Eppendorf, Hamburg, Germany) in co-incubation with NK3.3 cells (killer cells or effector cells; kindly provided by Jacky Kornbluth from Saint Louis University). In brief, Uke-1 cells were stained with Calcein acetoxy-methyl ester (Calcein-AM; Sigma-Aldrich catalog #17783-5MG, St. Louis, Mo.), washed twice, pipetted into a 96-well microtiterplate (96 well, U-bottomed, clear plastic; Corning Costar, catalog #650 160, Tewksbury, Mass.) at a concentration of 5000 cells per well and pre-incubated for 10 min with a serial dilution of the above mentioned antibodies and proteins (from 50,000 to 0.003 µg per ml) before adding the effector NK3.3 cells for 1 hour in an effector to target ratio of 20 to 1. In order to calculate the antibody specific lysis of the target cells, a parallel incubation of target cells only without antibody or effector cells served as a baseline and negative control, whereas the positive control or maximal lysis or hundred percent specific lysis was determined by lysis of target cells only with a 1% Triton-X 100 solution. As an additional positive control, MabCampath® (Sanofi, Paris, FR) was used, recognizing CD52 on the Uke-1cells. Following a co-incubation of target and effector cells, the microtiterplate was centrifuged and an aliquot of the supernatant fluid was transferred to another microtiterplate (96 well, flat-bottomed, black with clear bottom; Corning Costar, catalog #3904, Tewksbury, Mass.) and the concentration of free Calcein in solution was determined with a fluorescence counter (Victor 3® multilabel counter, Perkin Elmer, Waltham, Mass.).

Figure 17:
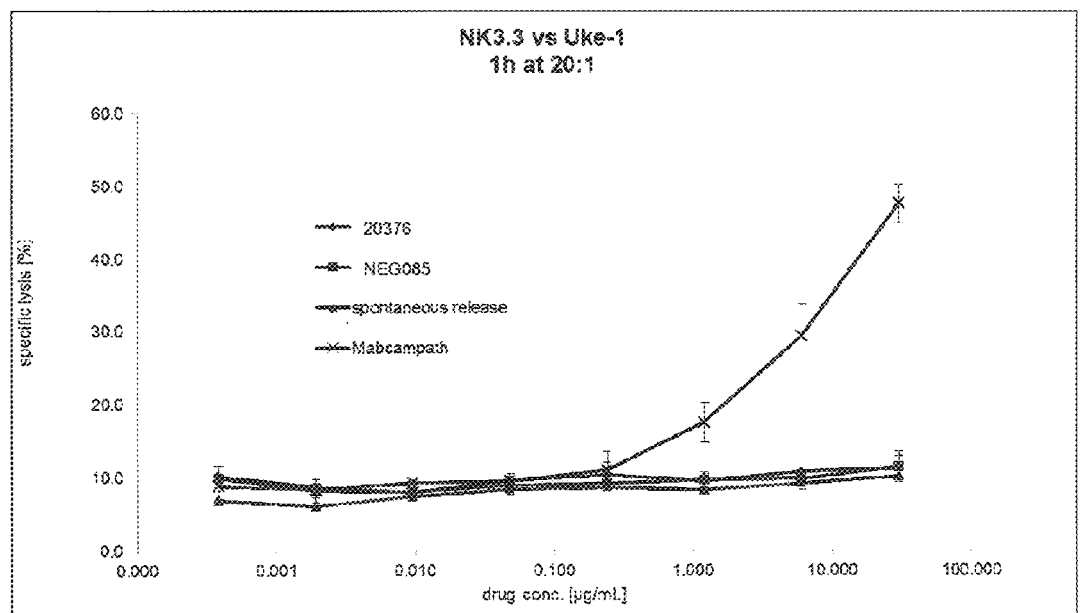
FIG. 17 shows the assessment of the ability of Campath (-CD52 Ab), NEG085 or 20376 antibodies to induce ADCC in vitro in Uke-1 cells.

Results are presented in FIG. 17. Antibody Dependent Cell Mediated Cytotoxicity (ADCC) is a mechanism of cell mediated immunity, whereby an effector cell lyses a target cell that has been bound by specific antibodies. In this experiment, MabCampath® as well as the anti-cKIT antibodies 20376 and NEG085 are unconjugated human IgG1 antibodies. As shown in FIG. 17, only the MabCampath antibody mediated ADCC killing of the target cells. Both 20376 and NEG085 were not able to induce ADCC even at higher concentrations. As such, any cell killing seen when one of the ADCs is used, for example, NEG085-MCC-DM1, is not due to an ADCC mechanism of action.

Example 19

The Ability of NEG085 and 20376 to Cause Mast Cell Apoptosis was Investigated Using Primary Human Mast Cells Primary human mast cells were cultured from peripheral human blood according to the methods described by Saito et al., Nature Protocols 2006; 1(4):2178-2183. Mast cells, which had been in liquid culture for a minimum of one week, were incubated with increasing concentrations (0.05-100 nM) of the anti-human cKIT Abs, NEG085 and 20376, or an isotype control IgG, in the presence of 1.6 nM rhSCF (Genscript, Cat # Z00400, Piscataway, N.J.), for 48 h at 37° C. before the addition of the Caspase-Glo® 3/7 reagent (Promega, Cat# G8093, Madison, Wis.) to measure apoptosis. Following 30 min incubation at RT, luminescence was recorded on the BioTek® Synergy plate reader (BioTek, Winooski, Vt.).

Figure 18:
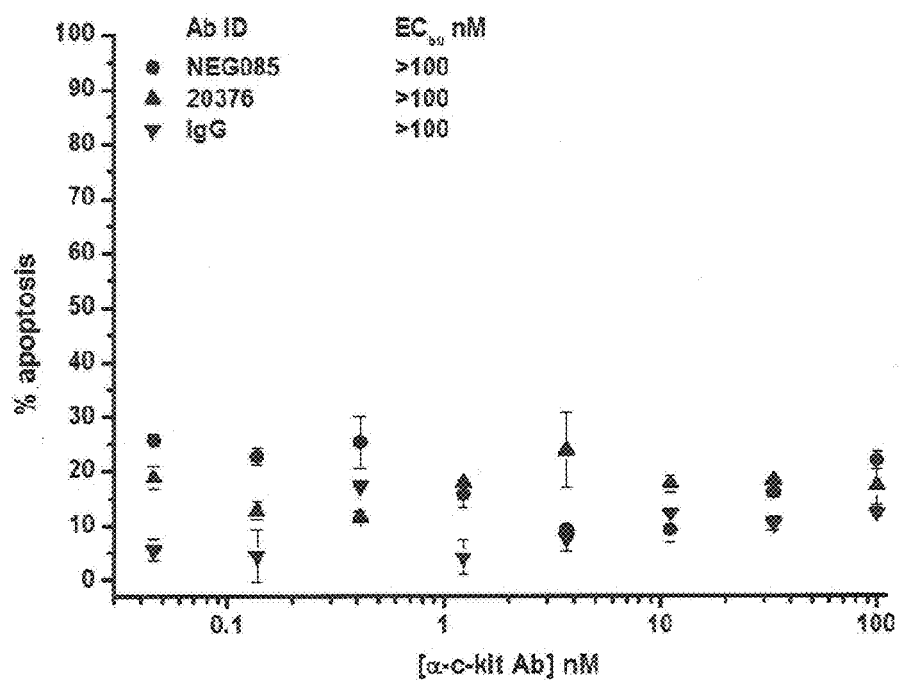
FIG. 18 shows the assessment of the ability of NEG085 and 20376 to mediate primary human mast cell apoptosis.

As cKIT is expressed on mast cells, any therapeutic anti cKIT antibodies should not cause depletion of mast cells. FIG. 18 shows an apoptosis assay with primary human mast cells following treatment with either anti-human cKIT Abs or an isotype control Ab, in the presence of 1.6 nM rhSCF. Primary human mast cells were incubated with increasing concentrations of the anti cKIT antibodies, NEG085 and 20376, or an isotype control IgG. As seen in FIG. 18, both the NEG085 and 20376 unconjugated antibodies do not lead to apoptosis of human primary mast cells ex vivo.

Example 20

The Ability of NEG085 and 20376 to Mediate Mast Cell Degranulation was Determined Using Primary Human Mast Cells Primary human mast cells were cultured from peripheral human blood according to the methods described by Saito et al., (supra). Mast cells, which had been in liquid culture for a minimum of one week, were pre-treated with 5% Ag-specific IgE JW8 (in-house batch ACE 27283), 95% non-specific monoclonal human IgE (Abbiotec, Cat #12030635, San Diego, Calif.) and 10 ng/mL rhIL-4 (R&D Systems Cat #204-IL, Minneapolis, Minn.) for 5 days at 37° C. The cells were then incubated with increasing concentrations (0.05-100 nM) of an isotype control IgG, the anti-human cKIT Abs, 20376 and NEG085, the anti-IgE Ab, LE27, or the NIP(5)BSA antigen, in the presence of a goat anti-human IgG (H+L) Fc-specific Ab (Jackson ImmunoResearch, Cat #109-005-008-JIR, West Grove, Pa.) for 90 min at 37° C. Cells were then centrifuged and the supernatants were transferred into 96-well black-walled plates prior to the addition of the β-hexosaminidase substrate. Following 90 min incubation at 37° C., the reaction was stopped by the addition of tris-base (Sigma, Cat # T1503-500G, pH 12, St. Louis, Mo.) and the fluorescence intensity was recorded on the Envision® plate reader.

Figure 19:
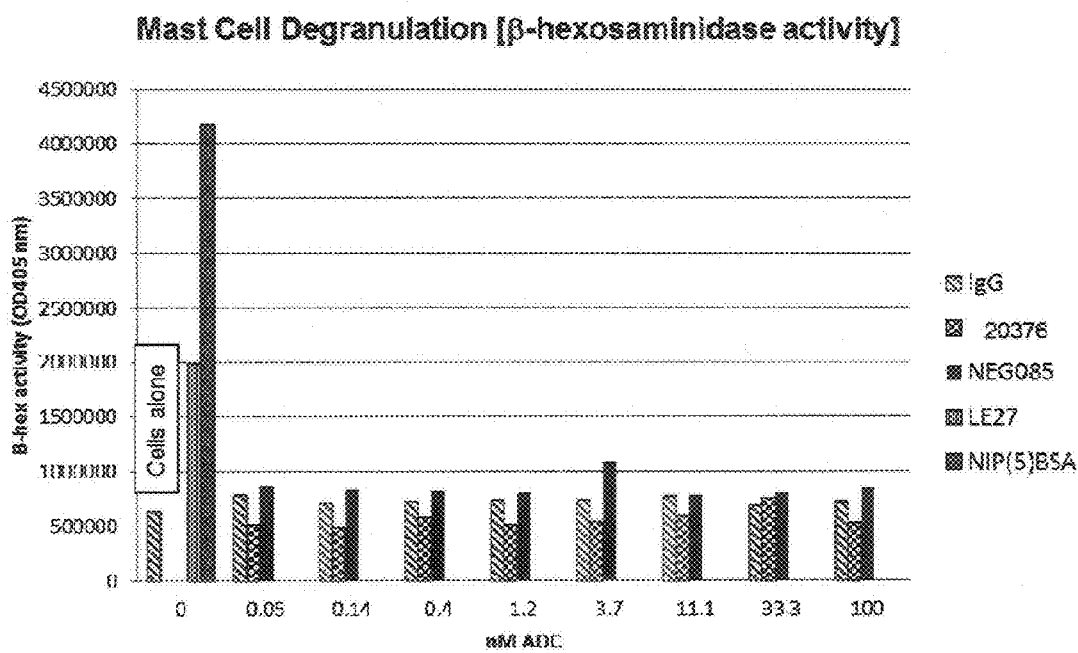
FIG. 19 shows the assessment of the ability of NEG085 and 20376 to mediate primary human mast cell degranulation.

As in the previous experiment in Example 19, it is important to assess any detrimental effect of anti-cKIT antibodies on mast cells. Where the previous experiment examined apoptosis of mast cells, here the experiments are directed to mast cell degranulation. As shown in FIG. 19, the positive controls NIP(5) and LE27 show high levels of mast cell degranulation. In contrast, anti-cKIT antibodies NEG085 and 20376 do not induce mast cell degranulation of human primary mast cells ex vivo.

Example 21

In Vivo On-Target Pharmacodynamic Marker Modulation by cKIT ADCs

Studies were conducted to assess the ability of the cKIT ADC NEG027-MCC-DM1 to modulate pharmacodynamic markers in vivo, including an examination of the co-localization of NEG027 antibody to the pharmacodynamics (PD) event of mitotic arrest in the mutant cKIT expressing GIST T1 tumor xenograft. The goal of these studies was to evaluate the degree and duration of G2/M cell cycle arrest.

Presence of ADC was indirectly estimated by detecting human IgG antibody (which is NEG027 in the mouse) in the tumor using an immunohistochemical approach. An affinity purified rabbit anti-human IgG (H+L) was obtained from Jackson ImmunoResearch Laboratories (Cat#309-005-082, West Grove, Pa.). The antibody reacts with whole molecule human IgG and the light chains of other human immunoglobulins with minimal cross-reaction to mouse serum proteins. Briefly, the IHC protocol included heat and standard exposure to Ventana Cell Conditioning #1 antigen retrieval reagent. The primary antibody was diluted to a working concentration of 2 ug/ml and incubated for 32 minutes at room temperature. Subsequently, incubation with Ventana UltraMap pre-diluted HRP-conjugated anti-rabbit antibody (Cat #760-4315, Ventana, Tucson, Ariz.) was performed for 32 minutes.

Accumulation of pHH3 positive nuclei, as assessed by immunohistochemistry, was used as a marker of G2/M arrest. A rabbit polyclonal antibody produced by immunizing animals with a synthetic phosphopeptide corresponding to residues surrounding Ser10 of human histone H3 (pHH3) was obtained from Cell Signaling Technology (Danvers, Mass., Cat#9701). Briefly, the IHC protocol included heat and standard exposure to Ventana Cell Conditioning #1 antigen retrieval reagent. The primary antibody was diluted to 1:50 and incubated for 60 minutes at room temperature.

Subsequently, incubation with Jackson ImmunoResearch Laboratories goat anti-rabbit biotinylated secondary antibody (Cat#111-065-144, West Grove, Pa.) was performed for 32 minutes.

To assess anti-cKIT ADC induced PD marker changes in the GIST T1 subcutaneous tumor xenograft model, female SCID-beige mice were implanted subcutaneously with $10 \times 10^6$ cells in a suspension containing 50% Matrigel™ (BD Biosciences) in Hank's balanced salt solution. The total injection volume containing cells in suspension was 200 µl. Mice were randomly assigned to receive a single i.v. dose of either NEG027-MCC-DM1 (2.5 mg/kg), non-specific IgG1-MCC-DM1 isotype control (2.5 mg/kg) or tris-buffered saline (TBS; 5 ml/kg) once tumors reached between 300 and 500 mm³ (n=3/group). Immunostaining for human IgG shows where NEG027 is located and this correlates with areas of a greater density of pHH3 immunostaining (representative images shown in FIG. 20, providing support for colocalization of the antibody with the pharmacodynamic effect. Consistent with the expected mechanism of action of the maytansinoid payload, NEG027-MCC-DM1 yielded a marked, time-dependent increase in the percentage of cells positive for pHH3 positivity, peaking at 33 and 48 h post dose relative to the non-specific isotype IgG1-MCC-DM1 or PBS treated controls, with signal back to baseline at around a week (representative images shown in FIG. 21, graph shown in FIG. 22). Time dependent changes in cleaved caspase 3 were also evaluated. In these studies, a rabbit polyclonal antibody produced by immunizing animals with a synthetic peptide corresponding to amino-terminal residues adjacent to (Asp175) in human caspase-3 was obtained from EMD Millipore (Cat#PC679). The IHC protocol included Heat and Standard exposure to Ventana Cell Conditioning #1 antigen retrieval reagent. The primary antibody was diluted to 20 ug/ml and incubated for 32 minutes at room temperature. Subsequently, incubation with Jackson ImmunoResearch Laboratories goat anti-rabbit biotinylated secondary antibody (Cat#111-065-144, West Grove, Pa.) was performed for 32 minutes.

Figure 22:
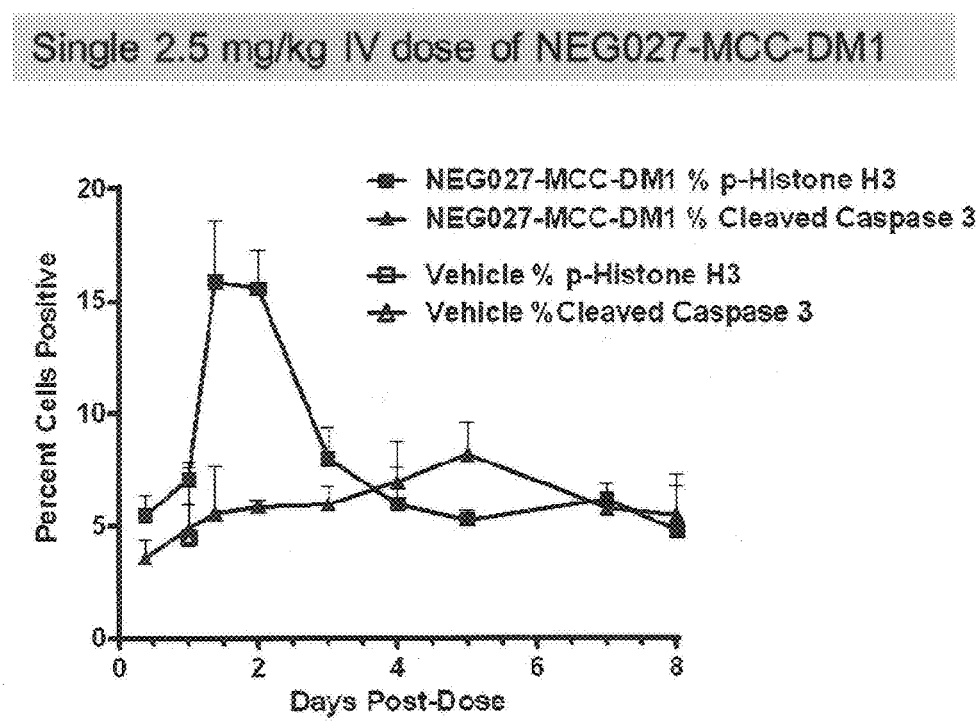
FIG. 22 graphically represents mitotic arrest and apoptosis induction 8 days post single dose of c-Kit ADC.

Similar to pHH3, time dependent changes in cleaved caspase 3 were also observed (representative images shown in FIG. 21, graph shown in FIG. 22). These data demonstrate that the cKIT ADC NEG027-MCC-DM1 is capable of eliciting robust in vivo cellular PD effects consistent with the mechanism of action of the maytansinoid payload.

A representative photo of cKIT immunostaining on the GIST T1 tumor is shown to visualize the staining pattern in this xenograft model (FIG. 21). A rabbit polyclonal antibody produced by immunizing animals with a synthetic peptide corresponding to amino acids 963 to 976 at the cytoplasmic c-terminal part of cKIT was obtained from Dako (Cat# A4502). Briefly, the IHC protocol included heat and standard exposure to Ventana Cell Conditioning #1 antigen retrieval reagent. The primary antibody was diluted to a working concentration of 14 ug/ml and incubated for 60 minutes at room temperature. Subsequently, incubation with Ventana UltraMap pre-diluted HRP-conjugated anti-rabbit antibody (Cat #760-4315) was performed for 16 minutes.

Example 22

In Vivo Efficacy of Anti-cKIT ADCs Against Gastrointestinal Stromal Tumor (GIST) in Mice The anti-tumor activity of anti-cKIT ADCs was evaluated in several tumor xenograft models. The dose dependent antitumor activity and pharmacokinetics (PK) of a non-mouse cKIT cross-reactive anti-human cKIT ADC NEG027-MCC-DM1 was evaluated in the mutant cKIT expressing GIST T1 subcutaneous tumor xenograft model. Female SCID-beige mice were implanted subcutaneously with $10 \times 10^6$ cells containing 50% Matrigel™ (BD Biosciences) in Hank's balanced salt solution. The total injection volume containing cells in suspension was 200 µl.

Mice were enrolled in the study 10 days post implantation with average tumor volume of 207 mm³. After being randomly assigned to one of five groups (n=9/group), mice were administered a single i.v. dose of TBS, the ADC vehicle (5 ml/kg), a non-specific isotype control IgG1-MCC-DM1 (2.5 mg/kg), or NEG027-MCC-DM1 (0.625, 1.25 or 2.5 mg/kg). Tumor volumes and body weights were measured twice weekly. The control IgG1-MCC-DM1 was not significantly active at 2.5 mg/kg. NEG027-MCC-DM1 at 0.625 showed statistically significant efficacy compared to the TBS treated group, however 1.25 and 2.5 mg/kg induced even greater efficacy, both inducing similar tumor volume stasis as per caliper measurements, although a histological assessment did not show presence of tumor cells. Instead a mixture of connective tissue, adipose tissue and segments of peripheral nerves and striated muscle were the main tissue components in these sections. This supports a histological regression in the tumor (FIGS. 23-26).

From this study serum was also collected at 1 hour, 24 hours and 4, 7, 11 and 21 days post-dose to measure antibody/ADC concentration over time using an anti-human IgG1 ELISA and an anti-DM ELISA, respectively. To assess PK parameters, serum was collected via retro-orbital bleeds and analyzed via ELISA. The total antibody PK assay measures total antibody concentration, with/without DM1 by colorimetric ELISA. Plates are coated with anti-human IgG (Fc specific), and detection is with anti-human IgG-HRP before being read on an appropriate plate-reader. The conjugate PK assay measures antibody that is bound to at least 1 DM1 molecule by colorimetric ELISA. In this format, plates are coated with anti-maytansine antibody, and detected with anti-human IgG-HRP. PK is dose proportional with an approximate serum half-life of seven days (FIGS. 23-24).

Figure 28:
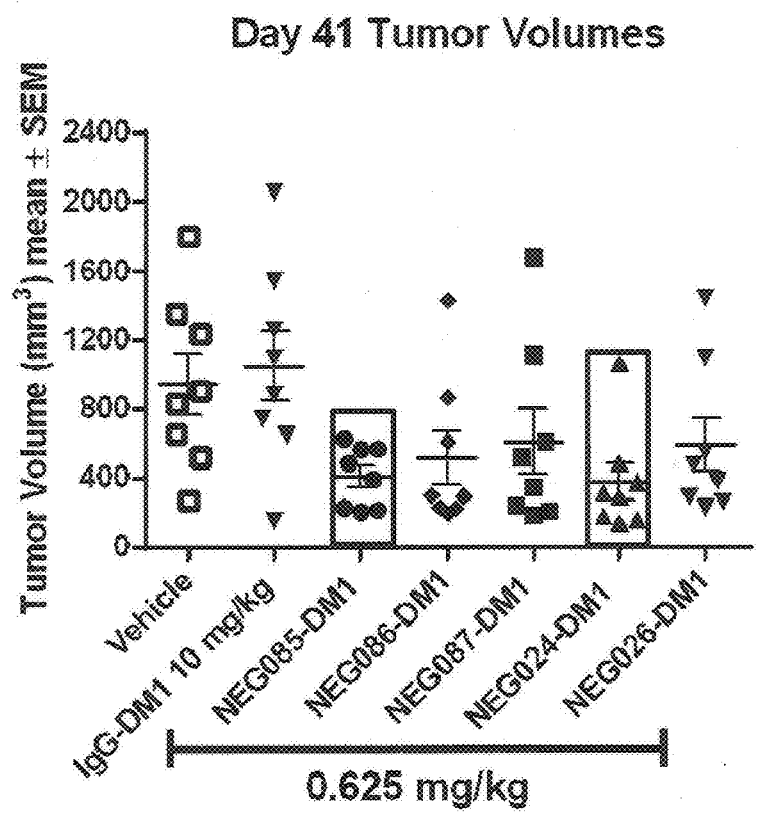
FIG. 28 shows clustering of day 41 after administration of single dose of anti-c-Kit ADC to a GIST T1 xenograft mouse.

Since a single 0.625 mg/kg dose of NEG027-MCC-DM1 only caused GIST T1 tumor growth delay, thus providing a dynamic range to assess differing ADC activities, this dose level was selected to assess efficacy of a set of closely related ADCs, also derived from the original murine 9P3-MCC-DM1 ADC. Female SCID-beige mice were implanted subcutaneously with $10 \times 10^6$ cells containing 50% Matrigel™ (BD Biosciences, San Jose, Calif.) in Hank's balanced salt solution. The total injection volume containing cells in suspension was 200 µl. Mice were enrolled in the study 10 days post implantation with average tumor volume of 195 mm³. After being randomly assigned to groups (n=8/group), mice were administered a single i.v. dose of TBS (8 ml/kg), a non-specific isotype control IgG1-MCC-DM1 (10 mg/kg), NEG085-MCC-DM1 (0.625 mg/kg), NEG086-MCC-DM1 (0.625 mg/kg), NEG087-MCC-DM1 (0.625 mg/kg), NEG024-MCC-DM1 (0.625 mg/kg), or NEG026-MCC-DM1 (0.625 mg/kg). Tumor volumes and body weights were measured twice weekly (FIG. 27-29). The control IgG1-MCC-DM1 even at the high dose of 10 mg/kg was not active. The anti-cKIT ADCs dosed at 0.625 mg/kg were not statistically different from each other. NEG085-MCC-DM1 and NEG024-MCC-DM1 treated groups had the smallest tumor volumes in the tightest range.

From this study serum was also collected at 1 hour, 24 hours and 3, 7, 10, 14 and 21 days post-dose to measure antibody/ADC concentration over time using an anti-human IgG1 ELISA and an anti-DM ELISA, respectively. To assess PK parameters, serum was collected via retro-orbital bleeds and analyzed via ELISA. The total antibody PK assay measures total antibody concentration, with/without DM1 by colorimetric ELISA. Plates are coated with anti-human IgG (Fc specific), and detection is with anti-human IgG-HRP before being read on an appropriate plate-reader. The conjugate PK assay measures antibody that is bound to at least 1 DM1 molecule by colorimetric ELISA. In this format, plates are coated with anti-maytansine antibody, and detected with anti-human IgG-HRP. These ADCs showed similar serum exposures (FIG. 30).

Example 23

In Vivo Efficacy of Anti-cKIT ADCs Against Small Cell Lung Cancer in Mice

Antitumor activity of a set of ADCs were assessed in the NCI-H1048 small cell lung cancer xenograft model with moderate cKIT immunostaining that exhibits greater heterogeneity compared to GIST T1 tumor xenografts (FIG. 21-FIG. 30). NEG085-MCC-DM1 was compared to a set of cKIT ADCs that are strong antagonists of cKIT signaling, none of which bind to mouse cKIT. Female SCID-beige mice were implanted subcutaneously with $10 \times 10^6$ cells containing 50% Matrigel™ (BD Biosciences) in Hank's balanced salt solution. The total injection volume containing cells in suspension was 200 µl. Mice were enrolled in the study 15 days post implantation with average tumor volume of about 120 mm³. All treated groups received a single intravenous dose of 2 mg/kg. After being randomly assigned to groups (n=8/group), mice were administered a single i.v. dose of TBS (5 ml/kg), a non-specific isotype control IgG1-MCC-DM1 (2 mg/kg), NEG024-MCC-DM1, NEG085-MCC-DM1, and NEG086-MCC-DM1. Tumor volumes and body weights were measured twice weekly (FIG. 31, 32). The control IgG1-MCC-DM1 was not active. NEG085-MCC-DM1 trended toward efficacy with a low AT/AC of 9%, but was not statistically different from the vehicle at this 2 mg/kg dose. NEG024-MCC-DM1 and NEG026-MCC-DM1 were significantly efficacious.

Antitumor efficacy of cKIT ADCs were also NCI-H1048 small cell lung cancer xenograft model, dose dependent antitumor activity of NEG085-MCC-DM1 was assessed. Female SCID-beige mice were implanted subcutaneously with $10 \times 10^6$ cells containing 50% Matrigel™ (BD Biosciences) in Hank's balanced salt solution. The total injection volume containing cells in suspension was 200 µl. Mice were enrolled in the study 11 days post implantation with average tumor volume of about 150-200 mm³. After being randomly assigned to groups (n=8/group), mice were administered a single i.v. dose of TBS (5 ml/kg), a non-specific isotype control IgG1-MCC-DM1 (10 mg/kg), or NEG085-MCC-DM1 (2.5, 5 and 10 mg/kg). Tumor volumes and body weights were measured twice weekly (FIG. 33, 34). The control IgG1-MCC-DM1 was not active, nor was the 2.5 mg/kg dose of NEG085-MCC-DM1. However, the 5 and 10 mg/kg doses were significantly efficacious.

Antitumor activity of two anti-cKIT ADCs were assessed in a second small cell lung cancer xenograft model with higher cKIT levels, similar to the GIST T1 tumor xenografts (representative photos on FIG. 21 and graphs in FIG. 35). Female SCID-beige mice were implanted subcutaneously with $6 \times 10^6$ cells containing 50% Matrigel™ (BD Biosciences) in Hank's balanced salt solution. The total injection volume containing cells in suspension was 200 µl. Mice were enrolled in the study 6 days post implantation with average tumor volume of about 150 mm³. After being randomly assigned to groups (n=9/group), mice were administered a single i.v. dose of TBS (8 ml/kg), a non-specific isotype control IgG1-MCC-DM1 (10 mg/kg), NEG024-MCC-DM1 (2.5, 5 and 10 mg/kg) and a mouse cross-reactive ADC 20376-MCC-DM1 (10 mg/kg). Tumor volumes and body weights were measured twice weekly (FIG. 35 and FIG. 36). The control IgG1-MCC-DM1 was not active. 20376-MCC-DM1 at 10 mg/kg initially regressed tumors, however after the initial regression, tumor recurrence was seen. Significant dose dependent efficacy was observed with the three doses of NEG024-MCC-DM1, with sustained long term regression at 10 mg/kg, with tumors starting to regrow after 60 days, suggesting 20376-MCC-DM1 may require more than the single dose administered in this study. The serum exposure of a 10 mg/kg dose of 20376-MCC-DM1 and NEG024-MCC-DM1 were about equivalent.

Example 24

In Vivo Efficacy of Anti-cKIT ADCs Against Acute Myelogenous Leukemia in Mice

Figure 37:
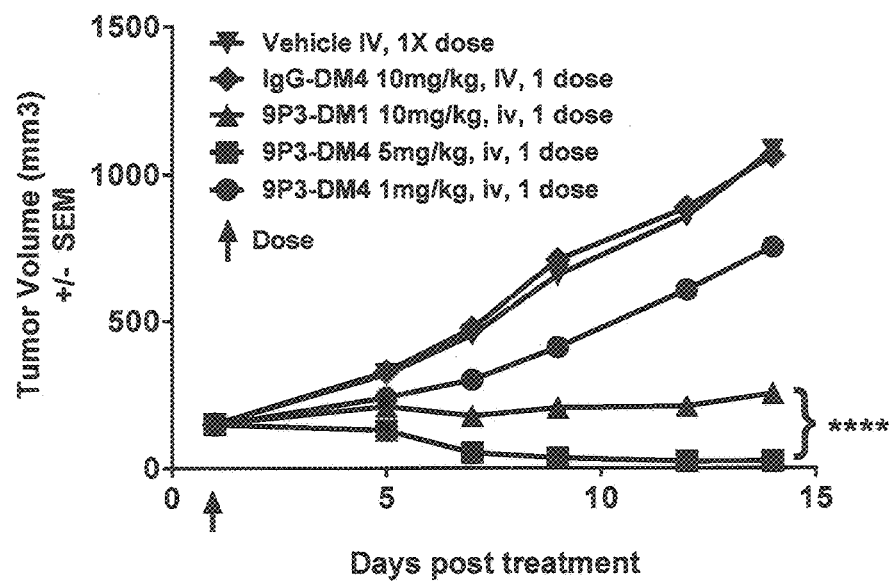
FIG. 37 shows anti-cKIT ADC efficacy in an AML xenograft model (Kasumi-1).

The dose dependent antitumor activity of anti-cKIT ADC murine 9P3-MCC-DM1 and 9P3-SPDB-DM4 was evaluated in the mutant cKIT expressing acute myelogenous leukemia Kasumi-1 subcutaneous tumor xenograft model. Female SCID-beige mice were transplanted subcutaneously with 2-3 pieces of 1 mm³ fragmented Kasumi-1 tumor tissues on the right flank with Matrigel™ (BD Biosciences). Mice with Kasumi-1 tumors were enrolled in the study 21 days post implantation with average tumor volume of 150 mm³. After being randomly assigned to one of eight groups (n=8/group), mice were administered a single i.v. dose of PBS (200 ul), a non-specific isotype control IgG1-SPDB-DM4 (10 mg/kg), 9P3-SMCC-DM1 (10 mg/kg) and 9P3-SPDB-DM4 (1 or 5 mg/kg). Tumor volumes and body weights were measured three times weekly (FIG. 37). The control IgG1-SPDB-DM4 was not significantly active at 10 mg/kg. Tumor growth regression was observed with 9P3-SPDB-DM4 at 5 mg/kg and 10 mg/kg doses.

TABLE 10

Kasumi-1 Efficacy

| Drug | Dose | Schedule | Tumor Response Mean change of tumor volume vs control ($\Delta T/\Delta C$) (%) | Host Response Percent body weight loss (%) | Survival (Survivors/total) |
|---|---|---|---|---|---|
| PBS | 0 mg/kg | single dose IV | 100 | 6.36 | 8/8 |
| IgG-SPDB-DM4 | 10 mg/kg | single dose IV | 98 | 3.06 | 8/8 |

TABLE 10-continued

Kasumi-1 Efficacy

| Drug | Dose | Schedule | Tumor Response Mean change of tumor volume vs control (ΔT/ΔC) (%) | Host Response Percent body weight loss (%) | Survival (Survivors/total) |
|---|---|---|---|---|---|
| 9P3-MCC-DM1 | 10 mg/kg | single dose IV | 11 | −0.62 | 8/8 |
| 9P3-SPDB-DM4 | 1 mg/kg | single dose IV | 65 | −0.05 | 8/8 |
| 9P3-SPDB-DM4 | 5 mg/kg | single dose IV | −83 | −1.72 | 8/8 |

Example 25

In Vivo Efficacy of Anti-cKIT ADCs Against Mastocytosis in Mice

The antitumor activity of anti-cKIT ADC murine 9P3-MCC-DM1 and 9P3-SPDB-DM4 was evaluated in the mutant cKIT expressing HMC-1.2 subcutaneous tumor xenograft model. The HMC-1.2 cell line was kindly provided by Dr. Joseph Butterfield, Mayo Clinic, Rochester, Minn. Female Foxn-1 nude mice were implanted subcutaneously with 3, 5, and 10×10$^6$ cells containing 50% Matrigel™ (BD Biosciences) in FBS-free DMEM media. The total injection volume containing cells in suspension was 100 μl.

Figure 38:
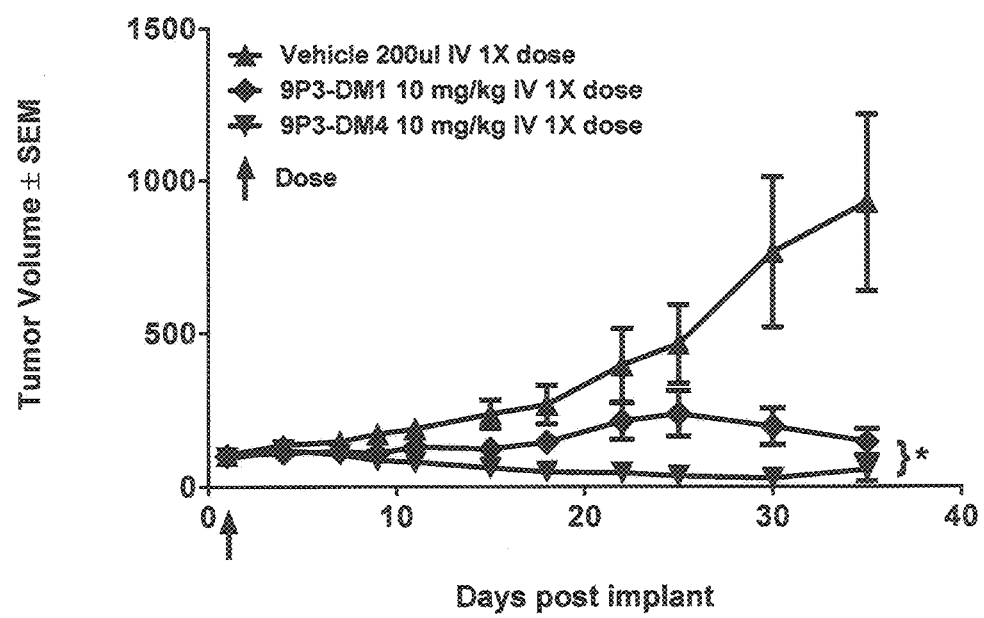
FIG. 38 shows anti-cKIT ADC efficacy in a HMC-1 mastocytosis xenograft mouse model.

HMC-1.2 tumor bearing mice in this study were enrolled 33 days post implantation with average tumor volume of 100 mm$^3$. After being randomly assigned to one of three groups (n=4/group), mice were administered a single i.v. dose of PBS (200 μl), 9P3-MCC-DM1 (10 mg/kg) or 9P3-SPDB-DM4 (10 mg/kg). Tumor volumes and body weights were measured three times weekly (FIG. 38). Tumor regression was observed at 9P3-SPDB-DM4 and 9P3-SMCC-DM1 at 10 mg/kg.

TABLE 11

HMC-1 Study

| Drug | Dose | Schedule | Tumor Response Mean change of tumor volume vs control (ΔT/ΔC) (%) | Host Response Percent body weight loss (%) | Survival (Survivors/total) |
|---|---|---|---|---|---|
| PBS | 0 mg/kg | single dose IV | 100 | 13.49 | 4/4 |
| 9P3-MCC-DM1 | 10 mg/kg | single dose IV | 6 | 7.71 | 4/4 |
| 9P3-SPDB-DM4 | 10 mg/kg | single dose IV | −40 | 3.25 | 4/4 |

Example 26

In Vivo Efficacy of a Mouse Cross-Reactive cKIT ADC20376-MCC-DM1

The dose dependent antitumor activity and pharmacokinetics (PK) of the mouse cKIT cross-reactive anti-human cKIT ADC 20376-MCC-DM1 was evaluated in the mutant cKIT expressing GIST T1 subcutaneous tumor xenograft model. Female SCID-beige mice were enrolled in the study 10 days post implantation with average tumor volume of about 200 mm$^3$. After being randomly assigned to one of five groups (n=9/group), mice were administered a single i.v. dose of TBS (5 ml/kg), a non-specific isotype control IgG1-MCC-DM1 (10 mg/kg), NEG085-MCC-DM1 (0.625 mg/kg) or 20376-MCC-DM1 (0.625, 2.5, 5 or 10 mg/kg). Tumor volumes and body weights were measured twice weekly (FIGS. 39-41). The control IgG1-MCC-DM1 was not significantly active at 10 mg/kg. 203786-MCC-DM1 was also ineffective, while NEG085-MCC-DM1 at 0.625 showed what may be a hint of efficacy, although also not statistically significant. 20376-MCC-DM1 at 2.5, 5 and 10 mg/kg were all significantly efficacious.

From this study serum was also collected at 1 hour, 24 hours and 4, 7, 11 and 21 days post-dose to measure antibody/ADC concentration over time using an anti-human IgG1 ELISA and an anti-DM ELISA, respectively. To assess PK parameters, serum was collected via retro-orbital bleeds and analyzed via ELISA. The total antibody PK assay measures total antibody concentration, with/without DM1 by colorimetric ELISA. Plates are coated with anti-human IgG (Fc specific), and detection is with anti-human IgG-HRP before being read on an appropriate plate-reader. The conjugate PK assay measures antibody that is bound to at least 1 DM1 molecule by colorimetric ELISA. In this format, plates are coated with anti-maytansine antibody, and detected with anti-human IgG-HRP. With the mouse cKIT cross reactive ADC 20376-MCC-DM1 the PK was not dose proportional due to the ADC binding mouse cKIT in normal tissues affecting the exposure (tissue mediated drug disposition), and thus there is a clear difference in serum concentrations between 20376-MCC-DM1 and the non-mouse cKIT cross-reactive ADC NEG085-MCC-DM1 (FIG. 40). This accounts for the difference in efficacy between the two ADCs at the low dose of 0.625 mg/kg. At the higher doses, the tissue mediated drug disposition effect is less pronounced and efficacy becomes apparent in the GIST T1 tumor xenograft model in mice.

Example 28

In Vivo Efficacy of cKIT ADCs with the SPDB-DM4 Linker/Payload Against Gastrointestinal Stromal Tumors The dose dependent antitumor activity of the murine 9P3 ADCs (from which NEG024 and NEG085 were derived) with the MCC-DM1 (non-cleavable) and SPDB-DM4 (cleavable) linkers/payloads was compared in the mutant cKIT expressing GIST T1 subcutaneous tumor xenograft model. Female SCID-beige mice were enrolled in the study 18 days post implantation with average tumor volume of about 170 mm³. After being randomly assigned to groups (n=8/group), mice were administered a single i.v. dose of TBS (5 ml/kg), unconjugated murine 9P3 antibody (10 mg/kg), a non-specific isotype control IgG1-MCC-DM1 (5 mg/kg), non-specific isotype control IgG1-MCC-DM1 (5 mg/kg), non-specific isotype control IgG1-SPDB-DM4 (10 mg/kg), 9P3-MCC-DM1 (5 and 10 mg/kg or 9P3-SPDB-DM4 (2.5 and 5 mg/kg. Tumor volumes and body weights were measured twice weekly (FIGS. 42, 43). Neither the control non-specific IgG1 ADCs nor the unconjugated 9P3 were efficacious. All the 9P3. ADCs were efficacious at the tested dose levels; however, tumors from the 2.5 mg/kg 9P3-SPDB-DM4 treated group appeared slightly less effective than the other groups.

The dose dependent antitumor activity of the murine 9P3 ADCs (from which NEG024 and NEG085 were derived) with the MCC-DM1 (non-cleavable) and SPDB-DM4 (cleavable) linkers/payloads was compared in a second tumor xenograft model of mutant cKIT expressing gastrointestinal stromal tumor, GIST430. Female SCID-beige mice were enrolled in the study 11 days post implantation with average tumor volume of about 200 mm³. After being randomly assigned to groups (n=9/group), mice were administered a single i.v. dose of TBS (5 ml/kg), unconjugated murine 9P3 antibody (10 mg/kg), a non-specific isotype control IgG1-MCC-DM1 (5 mg/kg), non-specific isotype control IgG1-MCC-DM1 (10 mg/kg), non-specific isotype control IgG1-SPDB-DM4 (5 mg/kg), 9P3-MCC-DM1 (10 mg/kg) or 9P3-SPDB-DM4 (5 mg/kg). Tumor volumes and body weights were measured twice weekly (FIGS. 44, 45). Neither control non-specific IgG1 ADC was efficacious. However, both 9P3 ADCs were similar efficacious at the tested dose levels.

Example 29

Formulation

The clinical service form (CSF) of the ADC is a lyophilisate in vial containing 50 mg anti-cKIT-MCC-DM1, 16.2 mg sodium succinate, 410.8 mg sucrose and 1 mg polysorbate 20 (without considering the overfill of 10% to allow for withdrawal of the declared content). After reconstitution of the lyophilizate with 5 mL water for injection, a solution containing 10 mg/mL anti-cKIT-MCC-DM1, 20 mM sodium succinate, 240 mM Sucrose and 0.02% polysorbate 20 at a pH of 5.0 is obtained.

For subsequent intravenous administration, the obtained solution will usually be further diluted into a carrier solution to the ready-to-use ADC solution for infusion.

For the CSF, an ADC concentration of 10 mg/mL was chosen based on preliminary stability testing. A sucrose concentration of 240 mM was selected in order to create an isotonic formulation, to maintain an amorphous lyophilizate cake structure and to afford protein stabilization.

Important stability-indicating analytical methods to select the most stable formulation encompassed, amongst others, size-exclusion chromatography to determine aggregation levels, subvisible particulate matter testing, free Toxin determination and potency testing.

The pre-screening study showed that polysorbate 20 at a concentration of 0.02% provides sufficient stabilization against mechanical stress. The liquid and lyophilized stability studies at real-time and accelerated stability conditions (25° C. and 40° C.) demonstrated that a succinate pH 5.0 formulation provides the overall best storage stability. Most notably in this formulation the best balance of all tested formulations between aggregation and release of the free Toxin could be met. After three months at 40° C. no noteworthy increase in degradation products could be determined.

It is understood that the examples and aspects described herein are for illustrative purposes only and that various modifications or changes in light thereof will be suggested to persons skilled in the art and are to be included within the spirit and purview of this application and scope of the appended claims.

What is claimed is:

1. An antibody drug conjugate of the formula

Ab-(L-(D)$_m$)$_n$ or a pharmaceutically acceptable salt thereof; wherein
Ab is an antibody or antigen binding fragment thereof that comprises a heavy chain variable region that comprises: (a) a VH CDR1 of SEQ ID NO: 76, (b) a VH CDR2 of SEQ ID NO: 77, (c) a VH CDR3 of SEQ ID NO: 78; and a light chain variable region that comprises: (d) a VL CDR1 of SEQ ID NO: 85, (e) a VL CDR2 of SEQ ID NO: 86, and (f) a VL CDR3 of SEQ ID NO: 87 and specifically binds to an epitope of human cKIT at domains 1-3 (SEQ ID NO. 155);
L is a linker;
D is a drug moiety;
m is an integer from 1 to 8; and
n is an integer from 1 to 10.

2. The antibody drug conjugate of claim 1, wherein said n is 3 or 4.

3. The antibody drug conjugate of claim 1, wherein said linker is selected from the group consisting of a cleavable linker, a non-cleavable linker, a hydrophilic linker, a procharged linker and a dicarboxylic acid based linker.

4. The antibody drug conjugate of claim 3, wherein the linker is derived from a cross-linking reagent selected from the group consisting of N-succinimidyl-3-(2-pyridyldithio) propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

5. The antibody drug conjugate of claim 4, wherein said linker is derived from the cross-linking reagent N-succinimidyl 4-(maleimidomethyl) cyclohexanecarboxylate (SMCC).

6. The antibody drug conjugate of claim 5, wherein the drug moiety is a maytansinoid.

7. The antibody drug conjugate of claim 6, wherein the maytansinoid is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

8. An antibody drug conjugate of the formula

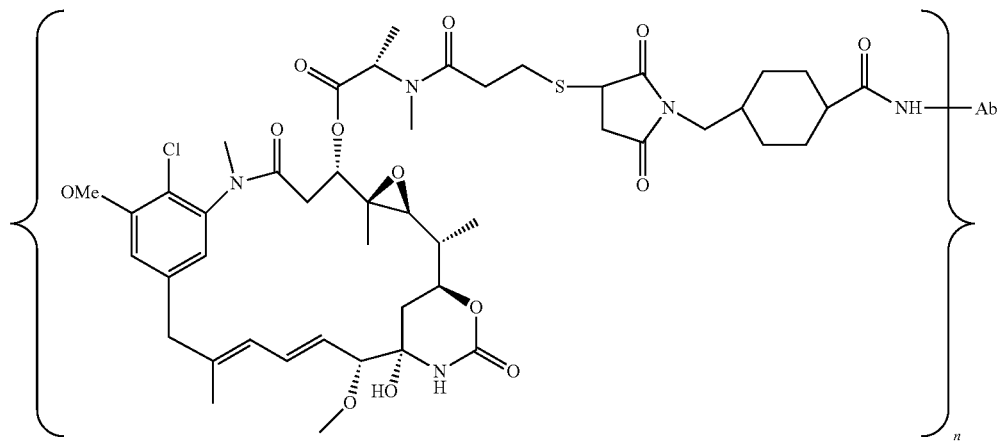

or a pharmaceutically acceptable salt thereof; wherein
Ab is an antibody or antigen binding fragment thereof that comprises a heavy chain variable region that comprises: (a) a VH CDR1 of SEQ ID NO: 76, (b) a VH CDR2 of SEQ ID NO: 77, (c) a VH CDR3 of SEQ ID NO: 78; and a light chain variable region that comprises: (d) a VL CDR1 of SEQ ID NO: 85, (e) a VL CDR2 of SEQ ID NO: 86, and (f) a VL CDR3 of SEQ ID NO: 87, specifically binds to human cKIT, and comprises at least n number of primary amines; and
n is an integer from 1 to 10.

9. The antibody drug conjugate of claim 8, wherein said n is 3 or 4.

10. The antibody drug conjugate of claim 8, wherein said antibody is a human or humanized antibody.

11. The antibody drug conjugate of claim 8, wherein said antibody is a monoclonal antibody.

12. A pharmaceutical composition comprising the antibody drug conjugate of claim 1 and a pharmaceutically acceptable carrier.

13. The pharmaceutical composition of claim 12 wherein said composition is prepared as a lyophilisate.

14. The pharmaceutical composition of claim 13, wherein said lyophilisate comprises the antibody drug conjugate of claim 1, sodium succinate, and polysorbate 20.

15. The antibody or antigen binding fragment of claim 1, wherein said antibody or antigen binding fragment is a single chain antibody (scFv).

* * * * *

SEQUENCE LISTING

<160> NUMBER OF SEQ ID NOS: 162

<210> SEQ ID NO 1
<211> LENGTH: 5084
<212> TYPE: DNA
<213> ORGANISM: Homo sapiens

<400> SEQUENCE: 1

```
gatcccatcg cagctaccgc gatgagaggc gctcgcggcg cctgggattt tctctgcgtt      60
ctgctcctac tgcttcgcgt ccagacaggc tcttctcaac catctgtgag tccaggggaa     120
ccgtctccac catccatcca tccaggaaaa tcagacttaa tagtccgcgt gggcgacgag     180
```

-continued

```
attaggctgt tatgcactga tccgggcttt gtcaaatgga cttttgagat cctggatgaa    240
acgaatgaga ataagcagaa tgaatggatc acggaaaagg cagaagccac caacaccggc    300
aaatacacgt gcaccaacaa acacggctta agcaattcca tttatgtgtt tgttagagat    360
cctgccaagc ttttccttgt tgaccgctcc ttgtatggga agaagacaa cgacacgctg     420 gtccgctgtc ctctcacaga cccagaagtg accaattatt ccctcaaggg gtgccagggg    480
aagcctcttc ccaaggactt gaggtttatt cctgacccca aggcgggcat catgatcaaa    540
agtgtgaaac gcgcctacca tcggctctgt ctgcattgtt ctgtggacca ggagggcaag    600
tcagtgctgt cggaaaaatt catcctgaaa gtgaggccag ccttcaaagc tgtgcctgtt    660
gtgtctgtgt ccaaagcaag ctatcttctt agggaagggg aagaattcac agtgacgtgc    720
acaataaaag atgtgtctag ttctgtgtac tcaacgtgga aaagagaaaa cagtcagact    780
aaactacagg agaaatataa tagctggcat cacggtgact tcaattatga acgtcaggca    840
acgttgacta tcagttcagc gagagttaat gattctggag tgttcatgtg ttatgccaat    900 aatactttg gatcagcaaa tgtcacaaca accttggaag tagtagataa aggattcatt     960
aatatcttcc ccatgataaa cactacagta tttgtaaacg atggagaaaa tgtagatttg    1020
attgttgaat atgaagcatt ccccaaacct gaacaccagc agtggatcta tatgaacaga    1080
accttcactg ataaatggga agattatccc aagtctgaga tgaaagtaa tatcagatac     1140 gtaagtgaac ttcatctaac gagattaaaa ggcaccgaag gaggcactta cacattccta    1200
gtgtccaatt ctgacgtcaa tgctgccata gcatttaatg tttatgtgaa tacaaaacca    1260
gaaatcctga cttacgacag gctcgtgaat ggcatgctcc aatgtgtggc agcaggattc    1320
ccagagccca caatagattg gtattttgt ccaggaactg agcagagatg ctctgcttct     1380
gtactgccag tggatgtgca gacactaaac tcatctgggc caccgtttgg aaagctagtg    1440
gttcagagtt ctatagattc tagtgcattc aagcacaatg gcacggttga atgtaaggct    1500
tacaacgatg tgggcaagac ttctgcctat tttaactttg catttaaagg taacaacaaa    1560
gagcaaatcc atccccacac cctgttcact cctttgctga ttggtttcgt aatcgtagct    1620
ggcatgatgt gcattattgt gatgattctg acctacaaat atttcagaa acccatgtat     1680 gaagtacagt ggaaggttgt tgaggagata aatggaaaca attatgttta catagaccca    1740
acacaacttc cttatgatca caaatgggag tttcccagaa acaggctgag ttttgggaaa    1800
accctgggtg ctggagcttt cgggaaggtt gttgaggcaa ctgcttatgg cttaattaag    1860
tcagatgcgg ccatgactgt cgctgtaaag atgctcaagc cgagtgccca tttgacagaa    1920
cgggaagccc tcatgtctga actcaaagtc ctgagttacc ttggtaatca catgaatatt    1980
gtgaatctac ttgagcctg caccattgga gggcccaccc tggtcattac agaatattgt    2040
tgctatggtg atcttttgaa ttttttgaga agaaacgtg attcatttat ttgttcaaag     2100
caggaagatc atgcagaagc tgcactttat aagaatcttc tgcattcaaa ggagtcttcc    2160
tgcagcgata gtactaatga gtacatggac atgaaacctg gagtttctta tgttgtccca    2220
accaaggccg acaaaaggag atctgtgaga ataggctcat acatagaaag agatgtgact    2280
cccgccatca tggaggatga cgagttggcc ctagacttag aagacttgct gagcttttct    2340
taccaggtgg caaagggcat ggctttcctc gcctccaaga attgtattca cagagacttg    2400
gcagccagaa atatcctcct tactcatggt cggatcacaa agatttgtga ttttggtcta    2460
gccagagaca tcaagaatga ttctaattat gtggttaaag gaaacgctcg actacctgtg    2520
```

-continued

```
aagtggatgg cacctgaaag cattttcaac tgtgtataca cgtttgaaag tgacgtctgg    2580
tcctatggga ttttttctttg ggagctgttc tctttaggaa gcagcccta tcctggaatg    2640 ccggtcgatt ctaagttcta caagatgatc aaggaaggct tccggatgct cagccctgaa    2700
cacgcacctg ctgaaatgta tgacataatg aagacttgct gggatgcaga tccctaaaa    2760 agaccaacat tcaagcaaat tgttcagcta attgagaagc agatttcaga gagcaccaat    2820
catatttact ccaacttagc aaactgcagc cccaaccgac agaagcccgt ggtagaccat    2880
tctgtgcgga tcaattctgt cggcagcacc gcttcctcct cccagcctct gcttgtgcac    2940
gacgatgtct gagcagaatc agtgtttggg tcacccctcc aggaatgatc tcttcttttg    3000
gcttccatga tggttatttt cttttctttc aacttgcatc caactccagg atagtgggca    3060
ccccactgca atcctgtctt tctgagcaca ctttagtggc cgatgatttt tgtcatcagc    3120
caccatccta ttgcaaaggt tccaactgta tatattccca atagcaacgt agcttctacc    3180
atgaacagaa acattctga tttggaaaaa gagagggagg tatggactgg gggccagagt    3240
cctttccaag gcttctccaa ttctgcccaa aaatatggtt gatagtttac ctgaataaat    3300
ggtagtaatc acagttggcc ttcagaacca tccatagtag tatgatgata caagattaga    3360
agctgaaaac ctaagtcctt tatgtggaaa acagaacatc attagaacaa aggacagagt    3420
atgaacacct gggcttaaga aatctagtat ttcatgctgg gaatgagaca taggccatga    3480
aaaaaatgat ccccaagtgt gaacaaaaga tgctcttctg tggaccactg catgagcttt    3540
tatactaccg acctggtttt taaatagagt ttgctattag agcattgaat tggagagaag    3600
gcctccctag ccagcacttg tatatacgca tctataaatt gtccgtgttc atacatttga    3660
ggggaaaaca ccataaggtt tcgtttctgt atacaaccct ggcattatgt ccactgtgta    3720
tagaagtaga ttaagagcca tataagtttg aaggaaacag ttaataccat tttttaagga    3780
aacaatataa ccacaaagca cagtttgaac aaaatctcct cttttagctg atgaacttat    3840
tctgtagatt ctgtggaaca agcctatcag cttcagaatg gcattgtact caatggatttt   3900 gatgctgttt gacaaagtta ctgattcact gcatggctcc cacaggagtg ggaaaacact    3960
gccatcttag tttggattct tatgtagcag gaaataaagt ataggtttag cctccttcgc    4020
aggcatgtcc tggacaccgg gccagtatct atatatgtgt atgtacgttt gtatgtgtgt    4080 agacaaaatat ttggaggggt atttttttgccc tgagtccaag agggtccttt agtacctgaa  4140
aagtaacttg gctttcatta ttagtactgc tcttgtttct tttcacatag ctgtctagag    4200
tagcttacca gaagcttcca tagtggtgca gaggaagtgg aaggcatcag tcccctatgta   4260 tttgcagttc acctgcactt aaggcactct gttatttaga ctcatcttac tgtacctgtt    4320
ccttagacct tccataatgc tactgtctca ctgaaacatt taaattttac cctttagact    4380
gtagcctgga tattattctt gtagtttacc tctttaaaaa caaacaaaa caaacaaaa       4440 aactccccctt cctcactgcc aatataaaa ggcaaatgtg tacatggcag agttgtgtg     4500 ttgtcttgaa agattcaggt atgttgcctt tatggtttcc cccttctaca tttcttagac    4560
tacatttaga gaactgtggc cgttatctgg aagtaaccat ttgcactgga gttctatgct    4620
ctcgcacctt tccaaagtta acagattttg ggttgtgtt gtcacccaag agattgttgt     4680
ttgccatact ttgtctgaaa aattcctttg tgtttctatt gacttcaatg atagtaagaa    4740
aagtggttgt tagttataga tgtctaggta cttcaggggc acttcattga gagttttgtc    4800
ttgccatact ttgtctgaaa aattcctttg tgtttctatt gacttcaatg atagtaagaa    4860
aagtggttgt tagttataga tgtctaggta cttcaggggc acttcattga gagttttgtc    4920
```

```
aatgtctttt gaatattccc aagcccatga gtccttgaaa atattttta tatatacagt    4980 aactttatgt gtaaatacat aagcggcgta agtttaaagg atgttggtgt tccacgtgtt    5040
ttattcctgt atgttgtcca attgttgaca gttctgaaga attc                     5084
```

<210> SEQ ID NO 2
<211> LENGTH: 976
<212> TYPE: PRT
<213> ORGANISM: Homo sapiens

<400> SEQUENCE: 2

```
Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
```

```
                340             345                 350
Arg Thr Phe Thr Asp Lys Trp Glu Asp Tyr Pro Lys Ser Glu Asn Glu
            355                 360                 365

Ser Asn Ile Arg Tyr Val Ser Glu Leu His Leu Thr Arg Leu Lys Gly
        370                 375             380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410             415

Thr Tyr Asp Arg Leu Val Asn Gly Met Leu Gln Cys Val Ala Ala Gly
            420                 425             430

Phe Pro Glu Pro Thr Ile Asp Trp Tyr Phe Cys Pro Gly Thr Glu Gln
        435                 440             445

Arg Cys Ser Ala Ser Val Leu Pro Val Asp Val Gln Thr Leu Asn Ser
        450                 455             460

Ser Gly Pro Pro Phe Gly Lys Leu Val Val Gln Ser Ser Ile Asp Ser
465                 470              475                480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
        530                 535             540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605

Tyr Gly Leu Ile Lys Ser Asp Ala Ala Met Thr Val Ala Val Lys Met
        610                 615             620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
        675                 680             685

Phe Ile Cys Ser Lys Gln Glu Asp His Ala Glu Ala Leu Tyr Lys
        690                 695             700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
        755                 760                 765
```

```
Leu Leu Ser Phe Ser Tyr Gln Val Ala Lys Gly Met Ala Phe Leu Ala
    770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
        835                 840                 845

Glu Ser Asp Val Trp Ser Tyr Gly Ile Phe Leu Trp Glu Leu Phe Ser
    850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Tyr Tyr Met Ala
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Ile Asn Tyr Asp Gly Ser Ser Thr Tyr Tyr Leu Asp Ser Leu Lys
1               5                   10                  15

Ser

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Gly Asp Tyr Tyr Gly Thr Thr Tyr Trp Tyr Phe Asp Val
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Thr Phe Ser Asp Tyr
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Tyr Asp Gly Ser Ser
1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Asp Tyr Tyr Gly Thr Thr Tyr Trp Tyr Phe Asp Val
1               5                   10

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Arg Leu Val Glu Ser Gly Gly Leu Val Gln Pro Arg Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Gly Asp Tyr Tyr Gly Thr Thr Tyr Trp Tyr Phe Asp Val Trp
            100                 105                 110
```

```
Gly Thr Gly Thr Thr Val Thr Val Ser Ser
        115                 120
```

<210> SEQ ID NO 10
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Val Ala Ala Pro Ser Val Phe Ile Phe Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105
```

<210> SEQ ID NO 11
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Tyr Asp Gly Ser Ser Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Ser Gln Asp Ile Ser Asn Tyr Leu Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

```
Tyr Thr Ser Arg Leu Gln Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Gly Lys Lys Leu Trp Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gln Asp Ile Ser Asn Tyr
1               5

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Thr Ser
1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Lys Lys Leu Trp
1               5

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45
```

```
Tyr Tyr Thr Ser Arg Leu Gln Ser Gly Val Pro Ser Arg Phe Ser Gly
     50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Lys Lys Leu Trp Ser
                 85                  90                  95

Phe Gly Gly Gly Thr Lys Leu Glu Ile Lys Arg
            100                 105
```

<210> SEQ ID NO 19
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Lys Lys Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 21
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45
```

```
Tyr Tyr Thr Ser Arg Leu Gln Ser Gly Ile Pro Ala Arg Phe Ser Gly
         50                  55                  60

Ser Gly Ser Gly Thr Asp Tyr Thr Leu Thr Ile Ser Ser Leu Glu Pro
 65                  70                  75                  80

Glu Asp Phe Ala Val Tyr Tyr Cys Gln Gln Gly Lys Lys Leu Trp Ser
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Tyr Tyr Met Ala
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Ile Asn Gln Ile Ala Gly Ser Thr Tyr Tyr Leu Asp Ser Val Arg
1               5                   10                  15

Gly

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Asp Tyr Tyr Gly Thr Thr Tyr Trp Tyr Phe Asp Val
1               5                   10
```

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Gly Phe Thr Phe Ser Asp Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Asn Gln Ile Ala Gly Ser
1               5

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Gly Asp Tyr Tyr Gly Thr Thr Tyr Trp Tyr Phe Asp Val
1               5                   10

<210> SEQ ID NO 28
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Tyr Met Ala Trp Val Arg Gln Ala Pro Gly Lys Gly Leu Glu Trp Val
            35                  40                  45

Ala Asn Ile Asn Gln Ile Ala Gly Ser Thr Tyr Tyr Leu Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser
        115                 120

<210> SEQ ID NO 29
<211> LENGTH: 452

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Gln Ile Ala Gly Ser Thr Tyr Tyr Leu Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
            450

<210> SEQ ID NO 30
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gaagtgcaat tggtggaaag cggcggaggc ctggtgcagc ctggcggctc tctgagactg      60
agctgtgccg ccagcggctt caccttcagc gactactaca tggcctgggt ccgacaggcc    120
cctggcaagg gcctggaatg ggtggccaat atcaaccaaa tcgccggcag cacctactac    180
ctggacagcg tgagaggccg gttcaccatc agccgggaca acgccaagaa cagcctgtac    240
ctgcagatga acagcctgcg ggccgaggac accgccgtgt actactgcgc cagaggcgat    300
tactacggca ccacctactg gtacttcgac gtgtggggcc agggcaccac cgtgaccgtc    360
agctcagcta gcaccaaggg ccccagcgtg ttccccctgg cccccagcag caagagcacc    420
agcggcggca cagccgccct gggctgcctg gtgaaggact acttccccga gcccgtgacc    480
gtgtcctgga cagcggagc cctgacctcc ggcgtgcaca ccttcccccgc cgtgctgcag    540 agcagcggcc tgtacagcct gtccagcgtg gtgacagtgc cagcagcag cctgggcacc    600 cagacctaca tctgcaacgt gaaccacaag cccagcaaca ccaaggtgga caagagagtg    660
gagcccaaga gctgcgacaa gacccacacc tgccccccct gcccagcccc agagctgctg    720
ggcggaccct ccgtgttcct gttccccccc aagcccaagg acaccctgat gatcagcagg    780
acccccgagg tgacctgcgt ggtggtggac gtgagccacg aggacccaga ggtgaagttc    840
aactggtacg tggacggcgt ggaggtgcac aacgccaaga ccaagccag agaggagcag    900 tacaacagca cctacagggt ggtgtccgtg ctgaccgtgc tgcaccagga ctggctgaac    960
ggcaaggaat acaagtgcaa ggtctccaac aaggccctgc cagcccccat cgaaaagacc   1020
atcagcaagg ccaagggcca gccacgggag ccccaggtgt acaccctgcc ccctcccgg    1080 gaggagatga ccaagaacca ggtgtccctg acctgtctgg tgaagggctt ctaccccagc   1140
gacatcgccg tggagtggga gagcaacggc cagcccgaga caactacaa gaccaccccc   1200 ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga gagcctgag cctgtccccc ggcaag                              1356

<210> SEQ ID NO 31
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 31

Arg Ala Ser Gln Asp Ile Ser Asn Tyr Leu Asn
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Thr Ser Arg Leu Gln Ser
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Gly Lys Lys Leu Trp Ser
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Gln Asp Ile Ser Asn Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Thr Ser
1

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Lys Lys Leu Trp
1               5
```

```
<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ile Val Met Thr Gln Ser Pro Ala Thr Leu Ser Leu Ser Pro Gly
1               5                  10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys
            100                 105

<210> SEQ ID NO 38
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Met Thr Gln Ser Pro Ala Thr Leu Ser Leu Ser Pro Gly
1               5                  10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

Asn Arg Gly Glu Cys
    210

<210> SEQ ID NO 39
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gagatcgtga tgacccagag ccccgccacc ctgagcctga gccctggcga aagagccacc     60
ctgtcctgca gagccagcca ggacatcagc aactacctga actggtatca gcagaagccc    120
ggccaggccc ccagactgct gatctactac accagccggc tgcagagcgg catccccgcc    180
agattttctg gcagcggcag cggcaccgac tacaccctga ccatcagcag cctggaaccc    240
gaggacttcg ccgtgtacta ctgccagcag ggcaagaagc tgtggtcctt cggcggaggc    300
accaaggtgg aaatcaagcg tacggtggcc gctcccagcg tgttcatctt cccccccagc    360
gacgagcagc tgaagagcgg caccgccagc gtggtgtgcc tgctgaacaa cttctacccc    420
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                           639

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Tyr Tyr Met Ala
1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asn Ile Asn Gln Asn Thr Gly Ser Thr Tyr Tyr Val Asp Ser Val Gln
1               5                   10                  15

Gly

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Gly Asp Tyr Tyr Gly Thr Thr Tyr Trp Tyr Phe Asp Val
1               5                   10
```

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Gly Phe Thr Phe Ser Asp Tyr
1               5
```

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Asn Gln Asn Thr Gly Ser
1               5
```

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Gly Asp Tyr Tyr Gly Thr Thr Tyr Trp Tyr Phe Asp Val
1               5                   10
```

<210> SEQ ID NO 46
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Gln Asn Thr Gly Ser Thr Tyr Tyr Val Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser
        115                 120
```

<210> SEQ ID NO 47
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Gln Asn Thr Gly Ser Thr Tyr Tyr Val Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
```

|   |   |   |   |   |   |   |   |   |   |   |   |
|---|---|---|---|---|---|---|---|---|---|---|---|
|   |   | 355 |   |   |   | 360 |   |   |   | 365 |   |
| Ser | Leu | Thr | Cys | Leu | Val | Lys | Gly | Phe | Tyr | Pro | Ser | Asp | Ile | Ala | Val |
|   | 370 |   |   |   | 375 |   |   |   | 380 |   |   |
| Glu | Trp | Glu | Ser | Asn | Gly | Gln | Pro | Glu | Asn | Asn | Tyr | Lys | Thr | Thr | Pro |
| 385 |   |   |   | 390 |   |   |   | 395 |   |   |   | 400 |
| Pro | Val | Leu | Asp | Ser | Asp | Gly | Ser | Phe | Phe | Leu | Tyr | Ser | Lys | Leu | Thr |
|   |   |   | 405 |   |   |   | 410 |   |   |   | 415 |   |
| Val | Asp | Lys | Ser | Arg | Trp | Gln | Gln | Gly | Asn | Val | Phe | Ser | Cys | Ser | Val |
|   | 420 |   |   |   | 425 |   |   |   | 430 |   |   |
| Met | His | Glu | Ala | Leu | His | Asn | His | Tyr | Thr | Gln | Lys | Ser | Leu | Ser | Leu |
|   | 435 |   |   |   | 440 |   |   |   | 445 |   |   |
| Ser | Pro | Gly | Lys |
|   | 450 |   |   |

<210> SEQ ID NO 48
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

| gaagtgcaat tggtggaaag cggcggaggc ctggtgcagc ctggcggctc tctgagactg | 60 |
| agctgtgccg ccagcggctt caccttcagc gactactaca tggcctgggt ccgacaggcc | 120 |
| cctggcaagg gcctggaatg gtggccaat atcaaccaaa acaccggcag cacctactac | 180 |
| gtggacagcg tgcaaggccg gttcaccatc agccgggaca cgccaagaa cagcctgtac | 240 |
| ctgcagatga acagcctgcg ggccgaggac accgccgtgt actactgcgc cagaggcgat | 300 |
| tactacggca ccacctactg gtacttcgac gtgtggggcc agggcaccac cgtgaccgtc | 360 |
| agctcagcta gcaccaaggg ccccagcgtg ttccccctgg ccccagcag caagagcacc | 420 |
| agcggcggca gccgcccct gggctgcctg gtgaaggact acttccccga gcccgtgacc | 480 |
| gtgtcctgga cagcggagc cctgacctcc ggcgtgcaca ccttcccgc cgtgctgcag | 540 |
| agcagcggcc tgtacagcct gtccagcgtg gtgacagtgc ccagcagcag cctgggcacc | 600 |
| cagacctaca tctgcaacgt gaaccacaag cccagcaaca ccaaggtgga caagagagtg | 660 |
| gagcccaaga gctgcgacaa gacccacacc tgccccccct gcccagcccc agagctgctg | 720 |
| ggcggaccct ccgtgttcct gttccccccc aagcccaagg acaccctgat gatcagcagg | 780 |
| acccccgagg tgacctgcgt ggtggtggac gtgagccacg aggacccaga ggtgaagttc | 840 |
| aactggtacg tggacggcgt ggaggtgcac aacgccaaga ccaagcccag agaggagcag | 900 |
| tacaacagca cctacagggt ggtgtccgtg ctgaccgtgc tgcaccagga ctggctgaac | 960 |
| ggcaaggaat acaagtgcaa ggtctccaac aaggccctgc cagcccccat cgaaaagacc | 1020 |
| atcagcaagg ccaagggcca gccacgggag ccccaggtgt acaccctgcc ccctcccgg | 1080 |
| gaggagatga ccaagaacca ggtgtccctg acctgtctgg tgaagggctt ctaccccagc | 1140 |
| gacatcgccg tggagtggga gagcaacggc cagcccgaga caactacaa gaccaccccc | 1200 |
| ccagtgctgg acagcgacgg cagcttcttc ctgtacagca agctgaccgt ggacaagtcc | 1260 |
| aggtggcagc agggcaacgt gttcagctgc agcgtgatgc acgaggccct gcacaaccac | 1320 |
| tacacccaga agagcctgag cctgtccccc ggcaag | 1356 |

<210> SEQ ID NO 49

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ala Ser Gln Asp Ile Ser Asn Tyr Leu Asn
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Thr Ser Arg Leu Gln Ser
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Gly Lys Lys Leu Trp Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Gln Asp Ile Ser Asn Tyr
1               5

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Thr Ser
1

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

Gly Lys Lys Leu Trp
1               5

<210> SEQ ID NO 55
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys
            100                 105

<210> SEQ ID NO 56
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 57
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gagatcgtga tgacccagag ccccgccacc ctgagcctga gccctggcga aagagccacc        60
ctgtcctgca gagccagcca ggacatcagc aactacctga actggtatca gcagaagccc       120
ggccaggccc ccagactgct gatctactac accagccggc tgcagagcgg catccccgcc       180 agatttctg gcagcggcag cggcaccgac tacaccctga ccatcagcag cctggaaccc        240
gaggacttcg ccgtgtacta ctgccagcag ggcaagaagc tgtggtcctt cggcggaggc       300
accaaggtgg aaatcaagcg tacggtggcc gctcccagcg tgttcatctt ccccccagc        360 gacgagcagc tgaagagcgg caccgccagc gtggtgtgcc tgctgaacaa cttctacccc       420
cgggaggcca aggtgcagtg gaaggtggac aacgccctgc agagcggcaa cagccaggag       480
agcgtcaccg agcaggacag caaggactcc acctacagcc tgagcagcac cctgaccctg       540
agcaaggccg actacgagaa gcataaggtg tacgcctgcg aggtgaccca ccagggcctg       600
tccagccccg tgaccaagag cttcaacagg ggcgagtgc                              639

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Tyr Tyr Met Ala
1               5

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Ile Asn Gln Asn Thr Gly Ser Thr Tyr Tyr Leu Asp Ser Val Arg
1               5                   10                  15

Gly

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic

```
<400> SEQUENCE: 60

Gly Asp Tyr Tyr Gly Thr Thr Tyr Trp Tyr Phe Asp Val
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Phe Thr Phe Ser Asp Tyr
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Gln Asn Thr Gly Ser
1               5

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Asp Tyr Tyr Gly Thr Thr Tyr Trp Tyr Phe Asp Val
1               5                   10

<210> SEQ ID NO 64
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Gln Asn Thr Gly Ser Thr Tyr Tyr Leu Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
```

```
                100             105             110
Gly Gln Gly Thr Thr Val Thr Val Ser Ser
            115                 120

<210> SEQ ID NO 65
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Gln Asn Thr Gly Ser Thr Tyr Tyr Leu Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335
```

```
Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 66
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gaagtgcaat tggtggaaag cggcggaggc ctggtgcagc ctggcggctc tctgagactg        60
agctgtgccg ccagcggctt caccttcagc gactactaca tggcctgggt ccgacaggcc      120
cctggcaagg gcctggaatg ggtggccagt atcaaccaaa acaccggcag cacctactac      180
ctggacagcg tgcgaggccg gttcaccatc agccgggaca cgccaagaa cagcctgtac       240 ctgcagatga acagcctgcg ggccgaggac accgccgtgt actactgcgc cagaggcgat      300
tactacggca ccacctactg gtacttcgac gtgtggggcc agggcaccac cgtgaccgtc      360
agctcagcta gcaccaaggg ccccagcgtg ttccccctgg cccccagcag caagagcacc      420
agcggcggca cagccgccct gggctgcctg gtgaaggact acttccccga gcccgtgacc      480
gtgtcctgga cagcggagc cctgacctcc ggcgtgcaca ccttccccgc cgtgctgcag       540
agcagcggcc tgtacagcct gtccagcgtg gtgacagtgc ccagcagcag cctgggcacc      600
cagacctaca tctgcaacgt gaaccacaag cccagcaaca ccaaggtgga caagagagtg      660
gagcccaaga gctgcgacaa gacccacacc tgccccccct gcccagcccc agagctgctg      720
ggcggaccct ccgtgttcct gttccccccc aagcccaagg acaccctgat gatcagcagg      780
acccccgagg tgacctgcgt ggtggtggac gtgagccacg aggacccaga ggtgaagttc      840
aactggtacg tggacggcgt ggaggtgcac aacgccaaga ccaagcccag agaggagcag      900
tacaacagca cctacagggt ggtgtccgtg ctgaccgtgc tgcaccagga ctggctgaac      960
ggcaaggaat acaagtgcaa ggtctccaac aaggccctgc cagcccccat cgaaaagacc     1020
atcagcaagg ccaagggcca gccacgggag ccccaggtgt acaccctgcc ccctcccgg     1080 gaggagatga ccaagaacca ggtgtccctg acctgtctgg tgaagggctt ctaccccagc     1140
gacatcgccg tggagtggga gagcaacggc cagcccgaga caactacaa gaccacccc     1200 ccagtgctgg acagcgacgg cagcttcttc ctgtacagca agctgaccgt ggacaagtcc     1260
aggtggcagc agggcaacgt gttcagctgc agcgtgatgc acgaggccct gcacaaccac     1320
```

-continued tacacccaga agagcctgag cctgtccccc ggcaag       1356

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ala Ser Gln Asp Ile Ser Asn Tyr Leu Asn
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Tyr Thr Ser Arg Leu Gln Ser
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Gly Lys Lys Leu Trp Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Gln Asp Ile Ser Asn Tyr
1               5

<210> SEQ ID NO 71
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Thr Ser
1

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 72

Gly Lys Lys Leu Trp
1               5

<210> SEQ ID NO 73
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys
            100                 105

<210> SEQ ID NO 74
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 75
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gagatcgtga tgacccagag ccccgccacc ctgagcctga gccctggcga aagagccacc      60
ctgtcctgca gagccagcca ggacatcagc aactacctga actggtatca gcagaagccc     120
ggccaggccc ccagactgct gatctactac accagcggc tgcagagcgg catccccgcc      180
agattttctg gcagcggcag cggcaccgac tacaccctga ccatcagcag cctggaaccc     240
gaggacttcg ccgtgtacta ctgccagcag ggcaagaagc tgtggtcctt cggcggaggc     300
accaaggtgg aaatcaagcg tacggtggcc gctcccagcg tgttcatctt cccccccagc     360
gacgagcagc tgaagagcgg caccgccagc gtggtgtgcc tgctgaacaa cttctacccc     420
cgggaggcca aggtgcagtg gaaggtggac aacgccctgc agagcggcaa cagccaggag     480
agcgtcaccg agcaggacag caaggactcc acctacagcc tgagcagcac cctgaccctg     540
agcaaggccg actacgagaa gcataaggtg tacgcctgcg aggtgaccca ccagggcctg     600
tccagccccg tgaccaagag cttcaacagg ggcgagtgc                             639

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Tyr Tyr Met Ala
1               5

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asn Ile Asn Tyr Pro Gly Ser Ser Thr Tyr Tyr Leu Asp Ser Val Lys
1               5                   10                  15

Gly

<210> SEQ ID NO 78
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Asp Tyr Tyr Gly Thr Thr Tyr Trp Tyr Phe Asp Val
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Phe Ala Phe Ser Gly Tyr
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Tyr Pro Gly Ser Ser
1               5

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Asp Tyr Tyr Gly Thr Thr Tyr Trp Tyr Phe Asp Val
1               5                   10

<210> SEQ ID NO 82
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Gly Tyr
            20                  25                  30

Tyr Met Ala Trp Val Arg Gln Ala Pro Gly Lys Gly Leu Glu Trp Val
        35                  40                  45

Ala Asn Ile Asn Tyr Pro Gly Ser Ser Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser
        115                 120

<210> SEQ ID NO 83
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Gly Tyr
            20                  25                  30

Tyr Met Ala Trp Val Arg Gln Ala Pro Gly Lys Gly Leu Glu Trp Val
        35                  40                  45

Ala Asn Ile Asn Tyr Pro Gly Ser Ser Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

```
Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 84
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
gaagtgcaat tggtggaaag cggcggaggc ctggtgcagc ctggcggctc tctgagactg      60
agctgtgccg ccagcggctt cgccttcagc ggctactaca tggcctgggt ccgacaggcc    120
cctggcaagg gcctggaatg ggtggccaac atcaactacc ccggcagcag cacctactac    180
ctggacagcg tgaagggccg gttcaccatc agccgggaca cgccaagaa cagcctgtac    240 ctgcagatga acagcctgcg ggccgaggac accgccgtgt actactgcgc cagaggcgat    300
tactacggca ccacctactg gtacttcgac gtgtggggcc agggcaccac cgtgaccgtc    360
agctcagcta gcaccaaggg cccccagcgtg ttccccctgg cccccagcag caagagcacc    420
agcggcggca cagccgccct gggctgcctg gtgaaggact acttccccga gcccgtgacc    480
gtgtcctgga acagcggagc cctgacctcc ggcgtgcaca ccttccccgc cgtgctgcag    540
agcagcggcc tgtacagcct gtccagcgtg gtgacagtgc ccagcagcag cctgggcacc    600
cagacctaca tctgcaacgt gaaccacaag cccagcaaca ccaaggtgga caagagagtg    660
gagcccaaga gctgcgacaa gacccacacc tgcccccct gcccagcccc agagctgctg    720
ggcggaccct ccgtgttcct gttcccccc aagcccaagg acaccctgat gatcagcagg    780
acccccgagg tgacctgcgt ggtggtggac gtgagccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaggaat acaagtgcaa ggtctccaac aaggccctgc cagcccccat cgaaaagacc   1020
atcagcaagg ccaagggcca gccacgggag ccccaggtgt acaccctgcc ccctcccgg   1080 gaggagatga ccaagaacca ggtgtccctg acctgtctgg tgaagggctt ctaccccagc   1140
gacatcgccg tggagtggga gagcaacggc cagcccgaga caactacaa gaccaccccc   1200
```

```
ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga agagcctgag cctgtccccc ggcaag                              1356
```

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

```
Arg Ala Ser Gln Ser Ile Ser Ser Tyr Leu Asn
1               5                   10
```

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Tyr Thr Ser Arg Leu Gln Ser
1               5
```

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Gln Gln Gly Arg Arg Leu Trp Ser
1               5
```

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Ser Gln Ser Ile Ser Ser Tyr
1               5
```

<210> SEQ ID NO 89
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Tyr Thr Ser
1
```

<210> SEQ ID NO 90
<211> LENGTH: 5

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Arg Arg Leu Trp
1               5

<210> SEQ ID NO 91
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Arg Leu Trp Ser
                85                  90                  95

Phe Gly Gly Gly Thr Lys Val Glu Ile Lys
            100                 105

<210> SEQ ID NO 92
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Arg Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
```

```
                    130                 135                 140
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 93
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gatatccaga tgacccagag ccccagcagc ctgagcgcca gcgtgggcga cagagtgacc      60
atcacctgtc gggccagcca gagcatcagc agctacctga actggtatca gcagaagccc    120
ggcaaggccc ccaagctgct gatctactac accagcggc tgcagagcgg cgtgcccagc     180 agatttctg gcagcggcag cggcaccgac ttcaccctga ccatcagcag cctgcagccc     240
gaggacttcg ccacctacta ctgccagcag ggccgccgcc tgtggtcctt cggcggaggc    300
accaaggtgg aaatcaagcg tacggtggcc gctcccagcg tgttcatctt cccccccagc    360
gacgagcagc tgaagagcgg caccgccagc gtggtgtgcc tgctgaacaa cttctacccc    420
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                           639

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Tyr Tyr Met Ala
1               5

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asn Ile Asn Gln Ile Ala Gly Ser Thr Tyr Tyr Val Asp Ser Val Gln
1               5                   10                  15

Gly
```

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Asp Tyr Tyr Gly Thr Thr Tyr Trp Tyr Phe Asp Val
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Phe Thr Phe Ser Asp Tyr
1               5

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asn Gln Ile Ala Gly Ser
1               5

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Asp Tyr Tyr Gly Thr Thr Tyr Trp Tyr Phe Asp Val
1               5                   10

<210> SEQ ID NO 100
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Gln Ile Ala Gly Ser Thr Tyr Tyr Val Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser
            115                 120

<210> SEQ ID NO 101
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Gln Ile Ala Gly Ser Thr Tyr Tyr Val Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr

```
                290                 295                 300
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 102
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gaagtgcaat tggtggaaag cggcggaggc ctggtgcagc ctggcggctc tctgagactg      60
agctgtgccg ccagcggctt caccttcagc gactactaca tggcctgggt ccgacaggcc    120
cctggcaagg gcctggaatg ggtggccaat atcaaccaaa tcgccggcag cacctactac    180
gtggacagcg tgcaaggccg gttcaccatc agccgggaca cgccaagaa cagcctgtac    240 ctgcagatga acagcctgcg ggccgaggac accgccgtgt actactgcgc cagaggcgat    300
tactacggca ccacctactg gtacttcgac gtgtggggcc agggcaccac cgtgaccgtc    360
agctcagcta gcaccaaggg ccccagcgtg ttccccctgg ccccagcag caagagcacc    420 agcggcggca gcccgccct gggctgcctg gtgaaggact acttccccga gcccgtgacc    480
gtgtcctgga cagcggagc cctgacctcc ggcgtgcaca ccttccccgc cgtgctgcag    540
agcagcggcc tgtacagcct gtccagcgtg gtgacagtgc ccagcagcag cctgggcacc    600
cagacctaca tctgcaacgt gaaccacaag cccagcaaca ccaaggtgga caagagagtg    660
gagcccaaga gctgcgacaa gacccacacc tgccccccct gcccagcccc agagctgctg    720
ggcggaccct ccgtgttcct gttccccccc aagcccaagg acaccctgat gatcagcagg    780 accccgagg tgacctgcgt ggtggtggac gtgagccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaggaat acaagtgcaa ggtctccaac aaggccctgc cagcccccat cgaaaagacc   1020
atcagcaagg ccaagggcca gccacgggag ccccaggtgt acaccctgcc ccctcccgg   1080
```

-continued

```
gaggagatga ccaagaacca ggtgtccctg acctgtctgg tgaagggctt ctaccccagc   1140
gacatcgccg tggagtggga gagcaacggc cagcccgaga acaactacaa gaccaccccc   1200
ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga gagcctgag cctgtccccc ggcaag                              1356
```

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ala Ser Gln Ser Ile Ser Ser Tyr Leu Asn
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Tyr Thr Ser Arg Leu Gln Ser
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Gln Gly Arg Arg Leu Trp Ser
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Gln Ser Ile Ser Ser Tyr
1               5

<210> SEQ ID NO 107
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Thr Ser
1

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Arg Arg Leu Trp
1               5

<210> SEQ ID NO 109
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Arg Leu Trp Ser
                85                  90                  95

Phe Gly Gly Gly Thr Lys Val Glu Ile Lys
            100                 105

<210> SEQ ID NO 110
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Arg Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 111
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
gatatccaga tgacccagag ccccagcagc ctgagcgcca gcgtgggcga cagagtgacc        60
atcacctgtc gggccagcca gagcatcagc agctacctga actggtatca gcagaagccc       120
ggcaaggccc ccaagctgct gatctactac accagccggc tgcagagcgg cgtgcccagc       180 agatttctg gcagcggcag cggcaccgac ttcaccctga ccatcagcag cctgcagccc        240
gaggacttcg ccacctacta ctgccagcag ggccgccgcc tgtggtcctt cggcggaggc       300
accaaggtgg aaatcaagcg tacggtggcc gctcccagcg tgttcatctt ccccccagc       360 gacgagcagc tgaagagcgg caccgccagc gtggtgtgcc tgctgaacaa cttctacccc       420
cgggaggcca aggtgcagtg gaaggtggac aacgccctgc agagcggcaa cagccaggag       480
agcgtcaccg agcaggacag caaggactcc acctacagcc tgagcagcac cctgaccctg       540
agcaaggccg actacgagaa gcataaggtg tacgcctgcg aggtgaccca ccagggcctg       600
tccagccccg tgaccaagag cttcaacagg ggcgagtgc                               639

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Tyr Tyr Met Ala
1               5

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Ser Ile Asn Gln Asn Thr Gly Ser Thr Tyr Tyr Leu Asp Ser Val Arg
1               5                   10                  15

Gly

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Asp Tyr Tyr Gly Thr Thr Tyr Trp Tyr Phe Asp Val
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Phe Thr Phe Ser Asp Tyr
1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asn Gln Asn Thr Gly Ser
1               5

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Asp Tyr Tyr Gly Thr Thr Tyr Trp Tyr Phe Asp Val
1               5                   10

<210> SEQ ID NO 118
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
```

```
                35                  40                  45
Ala Ser Ile Asn Gln Asn Thr Gly Ser Thr Tyr Tyr Leu Asp Ser Val
         50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser
            115                 120

<210> SEQ ID NO 119
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Tyr Met Ala Trp Val Arg Gln Ala Pro Gly Lys Gly Leu Glu Trp Val
         35                  40                  45

Ala Ser Ile Asn Gln Asn Thr Gly Ser Thr Tyr Tyr Leu Asp Ser Val
         50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

| | | | | | | | | | | |
|---|---|---|---|---|---|---|---|---|---|---|
|His|Glu|Asp|Pro|Glu|Val|Lys|Phe|Asn|Trp|Tyr|Val|Asp|Gly|Val|Glu|
| | |275| | | |280| | | |285| | | | | |
|Val|His|Asn|Ala|Lys|Thr|Lys|Pro|Arg|Glu|Glu|Gln|Tyr|Asn|Ser|Thr|
| |290| | | | |295| | | | |300| | | | |
|Tyr|Arg|Val|Val|Ser|Val|Leu|Thr|Val|Leu|His|Gln|Asp|Trp|Leu|Asn|
|305| | | | |310| | | | |315| | | | |320|
|Gly|Lys|Glu|Tyr|Lys|Cys|Lys|Val|Ser|Asn|Lys|Ala|Leu|Pro|Ala|Pro|
| | | | |325| | | | |330| | | | |335| |
|Ile|Glu|Lys|Thr|Ile|Ser|Lys|Ala|Lys|Gly|Gln|Pro|Arg|Glu|Pro|Gln|
| | | |340| | | | |345| | | | |350| | |
|Val|Tyr|Thr|Leu|Pro|Pro|Ser|Arg|Glu|Glu|Met|Thr|Lys|Asn|Gln|Val|
| | |355| | | | |360| | | | |365| | | |
|Ser|Leu|Thr|Cys|Leu|Val|Lys|Gly|Phe|Tyr|Pro|Ser|Asp|Ile|Ala|Val|
| |370| | | | |375| | | | |380| | | | |
|Glu|Trp|Glu|Ser|Asn|Gly|Gln|Pro|Glu|Asn|Asn|Tyr|Lys|Thr|Thr|Pro|
|385| | | | |390| | | | |395| | | | |400|
|Pro|Val|Leu|Asp|Ser|Asp|Gly|Ser|Phe|Phe|Leu|Tyr|Ser|Lys|Leu|Thr|
| | | | |405| | | | |410| | | | |415| |
|Val|Asp|Lys|Ser|Arg|Trp|Gln|Gln|Gly|Asn|Val|Phe|Ser|Cys|Ser|Val|
| | | |420| | | | |425| | | | |430| | |
|Met|His|Glu|Ala|Leu|His|Asn|His|Tyr|Thr|Gln|Lys|Ser|Leu|Ser|Leu|
| | |435| | | | |440| | | | |445| | | |
|Ser|Pro|Gly|Lys| | | | | | | | | | | | |
| | |450| | | | | | | | | | | | | |

<210> SEQ ID NO 120
<211> LENGTH: 1356
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 120

```
gaagtgcaat tggtggaaag cggcggaggc ctggtgcagc ctggcggctc tctgagactg      60
agctgtgccg ccagcggctt caccttcagc gactactaca tggcctgggt ccgacaggcc     120
cctggcaagg gcctggaatg ggtggccagt atcaaccaaa acaccggcag cacctactac     180
ctggacagcg tgcgaggccg gttcaccatc agcggggaca cgccaagaa cagcctgtac     240
ctgcagatga acagcctgcg ggccgaggac accgccgtgt actactgcgc cagaggcgat     300
tactacggca ccacctactg gtacttcgac gtgtggggcc agggcaccac cgtgaccgtc     360
agctcagcta gcaccaaggg cccagcgtg ttccccctgg ccccagcag caagagcacc     420
agcggcggca gcccgccct gggctgcctg gtgaaggact acttcccga gcccgtgacc     480
gtgtcctgga acagcggagc cctgaccct ggcgtgcaca ccttcccgc cgtgctgcag     540
agcagcggcc tgtacagcct gtccagcgtg gtgacagtgc ccagcagcag cctgggcacc     600
cagacctaca tctgcaacgt gaaccacaag cccagcaaca ccaaggtgga caagagagtg     660
gagcccaaga gctgcgacaa gacccacacc tgcccccct gcccagcccc agagctgctg     720
ggcggaccct ccgtgttcct gttccccccc aagcccaagg acaccctgat gatcagcagg     780
acccccgagg tgacctgcgt ggtggtggac gtgagccacg aggacccaga ggtgaagttc     840
aactggtacg tggacggcgt ggaggtgcac aacgccaaga ccaagcccag agaggagcag     900
tacaacagca cctacagggt ggtgtccgtg ctgaccgtgc tgcaccagga ctggctgaac     960
```

```
ggcaaggaat acaagtgcaa ggtctccaac aaggccctgc cagcccccat cgaaaagacc    1020
atcagcaagg ccaagggcca gccacgggag ccccaggtgt acaccctgcc cccctcccgg    1080
gaggagatga ccaagaacca ggtgtccctg acctgtctgg tgaagggctt ctaccccagc    1140
gacatcgccg tggagtggga gagcaacggc cagcccgaga caactacaa gaccacccc     1200 ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga agagcctgag cctgtccccc ggcaag                              1356
```

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Ala Ser Gln Ser Ile Ser Ser Tyr Leu Asn
1               5                   10

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Tyr Thr Ser Arg Leu Gln Ser
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Gln Gly Arg Arg Leu Trp Ser
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Gln Ser Ile Ser Ser Tyr
1               5

<210> SEQ ID NO 125
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Tyr Thr Ser
1

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Arg Arg Leu Trp
1               5

<210> SEQ ID NO 127
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Arg Leu Trp Ser
                85                  90                  95

Phe Gly Gly Gly Thr Lys Val Glu Ile Lys
            100                 105

<210> SEQ ID NO 128
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Arg Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 129
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gatatccaga tgacccagag ccccagcagc ctgagcgcca gcgtgggcga cagagtgacc    60
atcacctgtc gggccagcca gagcatcagc agctacctga actggtatca gcagaagccc   120
ggcaaggccc ccaagctgct gatctactac accagccggc tgcagagcgg cgtgcccagc   180 agatttctg gcagcggcag cggcaccgac ttcaccctga ccatcagcag cctgcagccc   240
gaggacttcg ccacctacta ctgccagcag ggccgccgcc tgtggtcctt cggcggaggc   300
accaaggtgg aaatcaagcg tacggtggcc gctcccagcg tgttcatctt cccccccagc   360
gacgagcagc tgaagagcgg caccgccagc gtggtgtgcc tgctgaacaa cttctacccc   420
cgggaggcca aggtgcagtg gaaggtggac aacgccctgc agagcggcaa cagccaggag   480
agcgtcaccg agcaggacag caaggactcc acctacagcc tgagcagcac cctgaccctg   540
agcaaggccg actacgagaa gcataaggtg tacgcctgcg aggtgaccca ccagggcctg   600
tccagccccg tgaccaagag cttcaacagg ggcgagtgc                          639

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Tyr Ala Ile Ser
1               5

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Gly Ile Ile Pro Met Ser Gly Arg Thr Thr Tyr Ala Gln Lys Phe Gln
1               5                   10                  15

Gly

<210> SEQ ID NO 132
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Tyr Gly Pro Glu Ala Pro Asp Tyr Gly Gln Ser Thr Ser Tyr Phe
1               5                   10                  15

Trp Tyr Tyr Ala Phe Asp Pro
            20

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Gly Thr Phe Ser Ser Tyr
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ile Pro Met Ser Gly Arg
1               5

<210> SEQ ID NO 135
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Tyr Gly Pro Glu Ala Pro Asp Tyr Gly Gln Ser Thr Ser Tyr Phe
1               5                   10                  15

Trp Tyr Tyr Ala Phe Asp Pro
            20

<210> SEQ ID NO 136
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Met Ser Gly Arg Thr Thr Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Gly Pro Glu Ala Pro Asp Tyr Gly Gln Ser Thr Ser
            100                 105                 110

Tyr Phe Trp Tyr Tyr Ala Phe Asp Pro Trp Gly Gln Gly Thr Leu Val
        115                 120                 125

Thr Val Ser Ser
    130
```

<210> SEQ ID NO 137
<211> LENGTH: 462
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 137

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Met Ser Gly Arg Thr Thr Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Gly Pro Glu Ala Pro Asp Tyr Gly Gln Ser Thr Ser
            100                 105                 110

Tyr Phe Trp Tyr Tyr Ala Phe Asp Pro Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
        180                 185                 190

Gly Leu Tyr Ser Leu Ser Ser Val Val Thr Val Pro Ser Ser Ser Leu
    195                 200                 205
```

Gly Thr Gln Thr Tyr Ile Cys Asn Val Asn His Lys Pro Ser Asn Thr
            210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 138
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
caggtgcagc tggtgcagtc aggcgccgaa gtgaagaaac ccggctctag cgtgaaagtc      60
agctgtaaag ctagtggggg caccttctct agctacgcta ttagctgggt cagacaggcc     120
ccaggtcaag gcttggagtg gatgggcgga attatcccta tgagcggtag aactacctac     180
gctcagaaat ttcagggtag agtgactatc accgccgacg agtctactag caccgcctat     240
atggaactga gttctctgag gtcagaggac accgccgtct actactgcgc tagagactac     300
ggccccgagg cccccgacta cggtcaatca actagctact ctggtactac gccttcgac     360 ccttggggtc aaggcaccct ggtcaccgtg tcttcagcta gcactaaggg cccaagtgtg     420 tttccctgg cccccagcag caagtctact ccggcggaa ctgctgccct gggttgcctg     480
gtgaaggact acttccccga gcccgtgaca gtgtcctgga actctggggc tctgacttcc     540
ggcgtgcaca ccttccccgc cgtgctgcag agcagcggcc tgtacagcct gagcagcgtg     600

```
gtgacagtgc cctccagctc tctgggaacc cagacctata tctgcaacgt gaaccacaag    660
cccagcaaca ccaaggtgga caagagagtg gagcccaaga gctgcgacaa gacccacacc    720
tgcccccccT gcccagctcc agaactgctg ggagggcctt ccgtgttcct gttccccccc    780
aagcccaagg acaccctgat gatcagcagg accccgagg tgacctgcgt ggtggtggac     840
gtgtcccacg aggacccaga ggtgaagttc aactggtacg tggacggcgt ggaggtgcac    900
aacgccaaga ccaagcccag agaggagcag tacaacagca cctacagggt ggtgtccgtg    960
ctgaccgtgc tgcaccagga ctggctgaac ggcaaagaat acaagtgcaa agtctccaac   1020
aaggccctgc cagccccaat cgaaaagaca atcagcaagg ccaagggcca gccacgggag   1080
ccccaggtgt acaccctgcc ccccagccgg gaggagatga ccaagaacca ggtgtccctg   1140
acctgtctgg tgaagggctt ctaccccagc gatatcgccg tggagtggga gagcaacggc   1200
cagcccgaga caactacaa gaccaccccc ccagtgctgg acagcgacgg cagcttcttc   1260
ctgtacagca agctgaccgt ggacaagtcc aggtggcagc agggcaacgt gttcagctgc   1320
agcgtgatgc acgaggccct gcacaaccac tacacccaga gtccctgag cctgagcccc   1380 ggcaag                                                              1386

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Gly Asp Asn Ile Pro Ser Tyr Phe Val His
1               5                   10

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Asp Asn Asp Arg Pro Ser
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Ser Trp Asp Gln Asp Thr Val Val
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 142

Asp Asn Ile Pro Ser Tyr Phe
1               5

<210> SEQ ID NO 143
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Asp Asn
1

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Trp Asp Gln Asp Thr Val
1               5

<210> SEQ ID NO 145
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Pro Ser Tyr Phe Val
            20                  25                  30

His Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Asp Gln Asp Thr Val Val
                85                  90                  95

Phe Gly Gly Gly Thr Lys Leu Thr Val Leu
            100                 105

<210> SEQ ID NO 146
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Pro Ser Tyr Phe Val
            20                  25                  30

His Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Asp Gln Asp Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 147
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147
gatatcgagc tgactcagcc ccctagcgtc agcgtcagcc ctggtcaaac cgcctctatc      60
acctgtagcg gcgataatat ccctagctac ttcgtgcact ggtatcagca gaagcccggt    120
caagcccccg tgctggtgat ctacgacgat aacgatagac tagcggaat ccccgagcgg     180 tttagcggct ctaatagcgg taacaccgct accctgacta ttagcggcac tcaggccgag    240
gacgaggccg actactactg ctctagctgg gatcaggaca ccgtggtgtt cggcggaggc    300
actaagctga ccgtgctggg tcaacctaag gctgccccca gcgtgaccct gttccccccc    360
agcagcgagg agctgcaggc caacaaggcc accctggtgt gcctgatcag cgacttctac    420
ccaggcgccg tgaccgtggc ctggaaggcc gacagcagcc ccgtgaaggc cggcgtggag    480
accaccaccc ccagcaagca gagcaacaac aagtacgccg ccagcagcta cctgagcctg    540 accccccgagc agtggaagag ccacaggtcc tacagctgcc aggtgaccca cgagggcagc    600
accgtggaaa agaccgtggc cccaaccgag tgcagc                              636

<210> SEQ ID NO 148
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 148

Gly Phe Thr Phe Ser Asp Tyr Tyr Met Ala
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asn Ile Asn Tyr Asp Gly Ser Ser Thr Tyr Tyr Leu Asp Ser
1               5                   10

<210> SEQ ID NO 150
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Asp Tyr Tyr Gly Thr Thr Tyr Trp Tyr Phe Asp Val
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Arg Ala Ser Gln Asp Ile Ser Asn Tyr Leu Asn
1               5                   10

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Tyr Thr Ser Arg Leu Gln Ser
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Gln Gly Lys Lys Leu Trp Ser
1               5
```

```
<210> SEQ ID NO 154
<211> LENGTH: 503
<212> TYPE: PRT
<213> ORGANISM: Homo sapiens

<400> SEQUENCE: 154

Gln Pro Ser Val Ser Pro Gly Glu Pro Ser Pro Ser Ile His Pro
1               5                   10                  15

Gly Lys Ser Asp Leu Ile Val Arg Val Gly Asp Glu Ile Arg Leu Leu
                20                  25                  30

Cys Thr Asp Pro Gly Phe Val Lys Trp Thr Phe Glu Ile Leu Asp Glu
            35                  40                  45

Thr Asn Glu Asn Lys Gln Asn Glu Trp Ile Thr Glu Lys Ala Glu Ala
    50                  55                  60

Thr Asn Thr Gly Lys Tyr Thr Cys Thr Asn Lys His Gly Leu Ser Asn
65                  70                  75                  80

Ser Ile Tyr Val Phe Val Arg Asp Pro Ala Lys Leu Phe Leu Val Asp
                85                  90                  95

Arg Ser Leu Tyr Gly Lys Glu Asp Asn Asp Thr Leu Val Arg Cys Pro
                100                 105                 110

Leu Thr Asp Pro Glu Val Thr Asn Tyr Ser Leu Lys Gly Cys Gln Gly
            115                 120                 125

Lys Pro Leu Pro Lys Asp Leu Arg Phe Ile Pro Asp Pro Lys Ala Gly
    130                 135                 140

Ile Met Ile Lys Ser Val Lys Arg Ala Tyr His Arg Leu Cys Leu His
145                 150                 155                 160

Cys Ser Val Asp Gln Glu Gly Lys Ser Val Leu Ser Glu Lys Phe Ile
                165                 170                 175

Leu Lys Val Arg Pro Ala Phe Lys Ala Val Pro Val Val Ser Val Ser
                180                 185                 190

Lys Ala Ser Tyr Leu Leu Arg Glu Gly Glu Glu Phe Thr Val Thr Cys
            195                 200                 205

Thr Ile Lys Asp Val Ser Ser Ser Val Tyr Ser Thr Trp Lys Arg Glu
    210                 215                 220

Asn Ser Gln Thr Lys Leu Gln Glu Lys Tyr Asn Ser Trp His His Gly
225                 230                 235                 240

Asp Phe Asn Tyr Glu Arg Gln Ala Thr Leu Thr Ile Ser Ser Ala Arg
                245                 250                 255

Val Asn Asp Ser Gly Val Phe Met Cys Tyr Ala Asn Asn Thr Phe Gly
                260                 265                 270

Ser Ala Asn Val Thr Thr Thr Leu Glu Val Val Asp Lys Gly Phe Ile
            275                 280                 285

Asn Ile Phe Pro Met Ile Asn Thr Thr Val Phe Val Asn Asp Gly Glu
    290                 295                 300

Asn Val Asp Leu Ile Val Glu Tyr Glu Ala Phe Pro Lys Pro Glu His
305                 310                 315                 320

Gln Gln Trp Ile Tyr Met Asn Arg Thr Phe Thr Asp Lys Trp Glu Asp
                325                 330                 335

Tyr Pro Lys Ser Glu Asn Glu Ser Asn Ile Arg Tyr Val Ser Glu Leu
                340                 345                 350

His Leu Thr Arg Leu Lys Gly Thr Glu Gly Gly Thr Tyr Thr Phe Leu
            355                 360                 365

Val Ser Asn Ser Asp Val Asn Ala Ala Ile Ala Phe Asn Val Tyr Val
    370                 375                 380
```

Asn Thr Lys Pro Glu Ile Leu Thr Tyr Asp Arg Leu Val Asn Gly Met
385                 390                 395                 400

Leu Gln Cys Val Ala Ala Gly Phe Pro Glu Pro Thr Ile Asp Trp Tyr
            405                 410                 415

Phe Cys Pro Gly Thr Glu Gln Arg Cys Ser Ala Ser Val Leu Pro Val
            420                 425                 430

Asp Val Gln Thr Leu Asn Ser Ser Gly Pro Pro Phe Gly Lys Leu Val
            435                 440                 445

Val Gln Ser Ser Ile Asp Ser Ser Ala Phe Lys His Asn Gly Thr Val
        450                 455                 460

Glu Cys Lys Ala Tyr Asn Asp Val Gly Lys Thr Ser Ala Tyr Phe Asn
465                 470                 475                 480

Phe Ala Phe Lys Glu Gln Ile His Pro His Thr Leu Phe Thr Pro Arg
            485                 490                 495

Ser His His His His His His
            500

<210> SEQ ID NO 155
<211> LENGTH: 294
<212> TYPE: PRT
<213> ORGANISM: Homo sapiens

<400> SEQUENCE: 155

Gln Pro Ser Val Ser Pro Gly Glu Pro Ser Pro Ser Ile His Pro
1               5                   10                  15

Gly Lys Ser Asp Leu Ile Val Arg Val Gly Asp Glu Ile Arg Leu Leu
            20                  25                  30

Cys Thr Asp Pro Gly Phe Val Lys Trp Thr Phe Glu Ile Leu Asp Glu
        35                  40                  45

Thr Asn Glu Asn Lys Gln Asn Glu Trp Ile Thr Glu Lys Ala Glu Ala
    50                  55                  60

Thr Asn Thr Gly Lys Tyr Thr Cys Thr Asn Lys His Gly Leu Ser Asn
65                  70                  75                  80

Ser Ile Tyr Val Phe Val Arg Asp Pro Ala Lys Leu Phe Leu Val Asp
                85                  90                  95

Arg Ser Leu Tyr Gly Lys Glu Asp Asn Asp Thr Leu Val Arg Cys Pro
            100                 105                 110

Leu Thr Asp Pro Glu Val Thr Asn Tyr Ser Leu Lys Gly Cys Gln Gly
        115                 120                 125

Lys Pro Leu Pro Lys Asp Leu Arg Phe Ile Pro Asp Pro Lys Ala Gly
    130                 135                 140

Ile Met Ile Lys Ser Val Lys Arg Ala Tyr His Arg Leu Cys Leu His
145                 150                 155                 160

Cys Ser Val Asp Gln Glu Gly Lys Ser Val Leu Ser Glu Lys Phe Ile
                165                 170                 175

Leu Lys Val Arg Pro Ala Phe Lys Ala Val Pro Val Val Ser Val Ser
            180                 185                 190

Lys Ala Ser Tyr Leu Leu Arg Glu Gly Glu Glu Phe Thr Val Thr Cys
        195                 200                 205

Thr Ile Lys Asp Val Ser Ser Ser Val Tyr Ser Thr Trp Lys Arg Glu
    210                 215                 220

Asn Ser Gln Thr Lys Leu Gln Glu Lys Tyr Asn Ser Trp His His Gly
225                 230                 235                 240

Asp Phe Asn Tyr Glu Arg Gln Ala Thr Leu Thr Ile Ser Ser Ala Arg
                245                 250                 255

```
Val Asn Asp Ser Gly Val Phe Met Cys Tyr Ala Asn Asn Thr Phe Gly
            260                 265                 270

Ser Ala Asn Val Thr Thr Thr Leu Glu Val Val Asp Lys Gly Arg Ser
            275                 280                 285

His His His His His His
        290

<210> SEQ ID NO 156
<211> LENGTH: 222
<212> TYPE: PRT
<213> ORGANISM: Homo sapiens

<400> SEQUENCE: 156

Gly Phe Ile Asn Ile Phe Pro Met Ile Asn Thr Thr Val Phe Val Asn
1               5                   10                  15

Asp Gly Glu Asn Val Asp Leu Ile Val Glu Tyr Glu Ala Phe Pro Lys
            20                  25                  30

Pro Glu His Gln Gln Trp Ile Tyr Met Asn Arg Thr Phe Thr Asp Lys
        35                  40                  45

Trp Glu Asp Tyr Pro Lys Ser Glu Asn Glu Ser Asn Ile Arg Tyr Val
50                  55                  60

Ser Glu Leu His Leu Thr Arg Leu Lys Gly Thr Glu Gly Gly Thr Tyr
65                  70                  75                  80

Thr Phe Leu Val Ser Asn Ser Asp Val Asn Ala Ala Ile Ala Phe Asn
                85                  90                  95

Val Tyr Val Asn Thr Lys Pro Glu Ile Leu Thr Tyr Asp Arg Leu Val
            100                 105                 110

Asn Gly Met Leu Gln Cys Val Ala Ala Gly Phe Pro Glu Pro Thr Ile
        115                 120                 125

Asp Trp Tyr Phe Cys Pro Gly Thr Glu Gln Arg Cys Ser Ala Ser Val
130                 135                 140

Leu Pro Val Asp Val Gln Thr Leu Asn Ser Ser Gly Pro Pro Phe Gly
145                 150                 155                 160

Lys Leu Val Val Gln Ser Ser Ile Asp Ser Ser Ala Phe Lys His Asn
                165                 170                 175

Gly Thr Val Glu Cys Lys Ala Tyr Asn Asp Val Gly Lys Thr Ser Ala
            180                 185                 190

Tyr Phe Asn Phe Ala Phe Lys Gly Asn Asn Lys Glu Gln Ile His Pro
        195                 200                 205

His Thr Leu Phe Thr Pro Arg Ser His His His His His His
210                 215                 220

<210> SEQ ID NO 157
<211> LENGTH: 741
<212> TYPE: PRT
<213> ORGANISM: Mus musculus

<400> SEQUENCE: 157

Ser Gln Pro Ser Ala Ser Pro Gly Glu Pro Ser Pro Ser Ile His
1               5                   10                  15

Pro Ala Gln Ser Glu Leu Ile Val Glu Ala Gly Asp Thr Leu Ser Leu
            20                  25                  30

Thr Cys Ile Asp Pro Asp Phe Val Arg Trp Thr Phe Lys Thr Tyr Phe
        35                  40                  45

Asn Glu Met Val Glu Asn Lys Lys Asn Glu Trp Ile Gln Glu Lys Ala
50                  55                  60
```

```
Glu Ala Thr Arg Thr Gly Thr Tyr Thr Cys Ser Asn Ser Asn Gly Leu
 65                  70                  75                  80

Thr Ser Ser Ile Tyr Val Phe Val Arg Asp Pro Ala Lys Leu Phe Leu
             85                  90                  95

Val Gly Leu Pro Leu Phe Gly Lys Glu Asp Ser Asp Ala Leu Val Arg
            100                 105                 110

Cys Pro Leu Thr Asp Pro Gln Val Ser Asn Tyr Ser Leu Ile Glu Cys
            115                 120                 125

Asp Gly Lys Ser Leu Pro Thr Asp Leu Thr Phe Val Pro Asn Pro Lys
            130                 135                 140

Ala Gly Ile Thr Ile Lys Asn Val Lys Arg Ala Tyr His Arg Leu Cys
145                 150                 155                 160

Val Arg Cys Ala Ala Gln Arg Asp Gly Thr Trp Leu His Ser Asp Lys
                165                 170                 175

Phe Thr Leu Lys Val Arg Ala Ala Ile Lys Ala Ile Pro Val Val Ser
            180                 185                 190

Val Pro Glu Thr Ser His Leu Leu Lys Lys Gly Asp Thr Phe Thr Val
            195                 200                 205

Val Cys Thr Ile Lys Asp Val Ser Thr Ser Val Asn Ser Met Trp Leu
210                 215                 220

Lys Met Asn Pro Gln Pro Gln His Ile Ala Gln Val Lys His Asn Ser
225                 230                 235                 240

Trp His Arg Gly Asp Phe Asn Tyr Glu Arg Gln Glu Thr Leu Thr Ile
                245                 250                 255

Ser Ser Ala Arg Val Asp Asp Ser Gly Val Phe Met Cys Tyr Ala Asn
                260                 265                 270

Asn Thr Phe Gly Ser Ala Asn Val Thr Thr Thr Leu Lys Val Val Glu
            275                 280                 285

Lys Gly Phe Ile Asn Ile Ser Pro Val Lys Asn Thr Thr Val Phe Val
            290                 295                 300

Thr Asp Gly Glu Asn Val Asp Leu Val Val Glu Tyr Glu Ala Tyr Pro
305                 310                 315                 320

Lys Pro Glu His Gln Gln Trp Ile Tyr Met Asn Arg Thr Ser Ala Asn
                325                 330                 335

Lys Gly Lys Asp Tyr Val Lys Ser Asp Asn Lys Ser Asn Ile Arg Tyr
                340                 345                 350

Val Asn Gln Leu Arg Leu Thr Arg Leu Lys Gly Thr Glu Gly Gly Thr
            355                 360                 365

Tyr Thr Phe Leu Val Ser Asn Ser Asp Ala Ser Ala Ser Val Thr Phe
            370                 375                 380

Asn Val Tyr Val Asn Thr Lys Pro Glu Ile Leu Thr Tyr Asp Arg Leu
385                 390                 395                 400

Ile Asn Gly Met Leu Gln Cys Val Ala Glu Gly Phe Pro Glu Pro Thr
                405                 410                 415

Ile Asp Trp Tyr Phe Cys Thr Gly Ala Glu Gln Arg Cys Thr Thr Pro
            420                 425                 430

Val Ser Pro Val Asp Val Gln Val Gln Asn Val Ser Val Ser Pro Phe
            435                 440                 445

Gly Lys Leu Val Val Gln Ser Ser Ile Asp Ser Ser Val Phe Arg His
            450                 455                 460

Asn Gly Thr Val Glu Cys Lys Ala Ser Asn Asp Val Gly Lys Ser Ser
465                 470                 475                 480
```

Ala Phe Phe Asn Phe Ala Phe Lys Glu Gln Ile Gln Ala His Thr Leu
            485                 490                 495

Phe Thr Pro Leu Glu Val Leu Phe Gln Gly Pro Arg Ser Pro Arg Gly
            500                 505                 510

Pro Thr Ile Lys Pro Cys Pro Cys Lys Cys Pro Ala Pro Asn Leu
            515                 520                 525

Leu Gly Gly Pro Ser Val Phe Ile Phe Pro Pro Lys Ile Lys Asp Val
            530                 535                 540

Leu Met Ile Ser Leu Ser Pro Ile Val Thr Cys Val Val Asp Val
545                 550                 555                 560

Ser Glu Asp Asp Pro Asp Val Gln Ile Ser Trp Phe Val Asn Asn Val
                565                 570                 575

Glu Val His Thr Ala Gln Thr Gln Thr His Arg Glu Asp Tyr Asn Ser
            580                 585                 590

Thr Leu Arg Val Val Ser Ala Leu Pro Ile Gln His Gln Asp Trp Met
            595                 600                 605

Ser Gly Lys Glu Phe Lys Cys Lys Val Asn Asn Lys Asp Leu Pro Ala
            610                 615                 620

Pro Ile Glu Arg Thr Ile Ser Lys Pro Lys Gly Ser Val Arg Ala Pro
625                 630                 635                 640

Gln Val Tyr Val Leu Pro Pro Glu Glu Met Thr Lys Lys Gln
            645                 650                 655

Val Thr Leu Thr Cys Met Val Thr Asp Phe Met Pro Glu Asp Ile Tyr
            660                 665                 670

Val Glu Trp Thr Asn Asn Gly Lys Thr Glu Leu Asn Tyr Lys Asn Thr
            675                 680                 685

Glu Pro Val Leu Asp Ser Asp Gly Ser Tyr Phe Met Tyr Ser Lys Leu
            690                 695                 700

Arg Val Glu Lys Lys Asn Trp Val Glu Arg Asn Ser Tyr Ser Cys Ser
705                 710                 715                 720

Val Val His Glu Gly Leu His Asn His His Thr Thr Lys Ser Phe Ser
            725                 730                 735

Arg Thr Pro Gly Lys
            740

<210> SEQ ID NO 158
<211> LENGTH: 741
<212> TYPE: PRT
<213> ORGANISM: Rattus norvegicus

<400> SEQUENCE: 158

Ser Gln Pro Ser Ala Ser Pro Gly Glu Pro Ser Pro Ser Ile Gln
1               5                   10                  15

Pro Ala Gln Ser Glu Leu Ile Val Glu Ala Gly Asp Thr Ile Arg Leu
            20                  25                  30

Thr Cys Thr Asp Pro Ala Phe Val Lys Trp Thr Phe Glu Ile Leu Asp
            35                  40                  45

Val Arg Ile Glu Asn Lys Gln Ser Glu Trp Ile Arg Glu Lys Ala Glu
        50                  55                  60

Ala Thr His Thr Gly Lys Tyr Thr Cys Val Ser Gly Ser Gly Leu Arg
65                  70                  75                  80

Ser Ser Ile Tyr Val Phe Val Arg Asp Pro Ala Val Leu Phe Leu Val
                85                  90                  95

Gly Leu Pro Leu Phe Gly Lys Glu Asp Asn Asp Ala Leu Val Arg Cys
            100                 105                 110

```
Pro Leu Thr Asp Pro Gln Val Ser Asn Tyr Ser Leu Ile Glu Cys Asp
            115                 120                 125

Gly Lys Ser Leu Pro Thr Asp Leu Lys Phe Val Pro Asn Pro Lys Ala
        130                 135                 140

Gly Ile Thr Ile Lys Asn Val Lys Arg Ala Tyr His Arg Leu Cys Ile
145                 150                 155                 160

Arg Cys Ala Ala Gln Arg Glu Gly Lys Trp Met Arg Ser Asp Lys Phe
                165                 170                 175

Thr Leu Lys Val Arg Ala Ala Ile Lys Ala Ile Pro Val Val Ser Val
            180                 185                 190

Pro Glu Thr Ser His Leu Leu Lys Glu Gly Asp Thr Phe Thr Val Ile
        195                 200                 205

Cys Thr Ile Lys Asp Val Ser Thr Ser Val Asp Ser Met Trp Ile Lys
210                 215                 220

Leu Asn Pro Gln Pro Gln Ser Lys Ala Gln Val Lys Arg Asn Ser Trp
225                 230                 235                 240

His Gln Gly Asp Phe Asn Tyr Glu Arg Gln Glu Thr Leu Thr Ile Ser
                245                 250                 255

Ser Ala Arg Val Asn Asp Ser Gly Val Phe Met Cys Tyr Ala Asn Asn
            260                 265                 270

Thr Phe Gly Ser Ala Asn Val Thr Thr Thr Leu Lys Val Val Glu Lys
        275                 280                 285

Gly Phe Ile Asn Ile Phe Pro Val Lys Asn Thr Thr Val Phe Val Thr
290                 295                 300

Asp Gly Glu Asn Val Asp Leu Val Val Glu Phe Glu Ala Tyr Pro Lys
305                 310                 315                 320

Pro Glu His Gln Gln Trp Ile Tyr Met Asn Arg Thr Pro Thr Asn Arg
                325                 330                 335

Gly Glu Asp Tyr Val Lys Ser Asp Asn Gln Ser Asn Ile Arg Tyr Val
            340                 345                 350

Asn Glu Leu Arg Leu Thr Arg Leu Lys Gly Thr Glu Gly Gly Thr Tyr
        355                 360                 365

Thr Phe Leu Val Ser Asn Ser Asp Val Ser Ala Ser Val Thr Phe Asp
370                 375                 380

Val Tyr Val Asn Thr Lys Pro Glu Ile Leu Thr Tyr Asp Arg Leu Met
385                 390                 395                 400

Asn Gly Arg Leu Gln Cys Val Ala Ala Gly Phe Pro Glu Pro Thr Ile
                405                 410                 415

Asp Trp Tyr Phe Cys Thr Gly Ala Glu Gln Arg Cys Thr Val Pro Val
            420                 425                 430

Pro Pro Val Asp Val Gln Ile Gln Asn Ala Ser Val Ser Pro Phe Gly
        435                 440                 445

Lys Leu Val Val Gln Ser Ser Ile Asp Ser Ser Val Phe Arg His Asn
450                 455                 460

Gly Thr Val Glu Cys Lys Ala Ser Asn Ala Val Gly Lys Ser Ser Ala
465                 470                 475                 480

Phe Phe Asn Phe Ala Phe Lys Gly Asn Ser Lys Glu Gln Ile Gln Pro
                485                 490                 495

His Thr Leu Phe Thr Pro Arg Ser Leu Glu Val Leu Phe Gln Gly Pro
            500                 505                 510

Gly Ser Pro Pro Leu Lys Glu Cys Pro Pro Cys Ala Ala Pro Asp Leu
        515                 520                 525
```

```
Leu Gly Gly Pro Ser Val Phe Ile Phe Pro Pro Lys Ile Lys Asp Val
        530                 535                 540

Leu Met Ile Ser Leu Ser Pro Met Val Thr Cys Val Val Asp Val
545                 550                 555                 560

Ser Glu Asp Asp Pro Asp Val Gln Ile Ser Trp Phe Val Asn Asn Val
                565                 570                 575

Glu Val His Thr Ala Gln Thr Gln Thr His Arg Glu Asp Tyr Asn Ser
            580                 585                 590

Thr Leu Arg Val Val Ser Ala Leu Pro Ile Gln His Gln Asp Trp Met
        595                 600                 605

Ser Gly Lys Glu Phe Lys Cys Lys Val Asn Asn Arg Ala Leu Pro Ser
    610                 615                 620

Pro Ile Glu Lys Thr Ile Ser Lys Pro Arg Gly Pro Val Arg Ala Pro
625                 630                 635                 640

Gln Val Tyr Val Leu Pro Pro Ala Glu Glu Met Thr Lys Lys Glu
                645                 650                 655

Phe Ser Leu Thr Cys Met Ile Thr Gly Phe Leu Pro Ala Glu Ile Ala
            660                 665                 670

Val Asp Trp Thr Ser Asn Gly Arg Thr Glu Gln Asn Tyr Lys Asn Thr
        675                 680                 685

Ala Thr Val Leu Asp Ser Asp Gly Ser Tyr Phe Met Tyr Ser Lys Leu
    690                 695                 700

Arg Val Gln Lys Ser Thr Trp Glu Arg Gly Ser Leu Phe Ala Cys Ser
705                 710                 715                 720

Val Val His Glu Gly Leu His Asn His Leu Thr Thr Lys Thr Ile Ser
                725                 730                 735

Arg Ser Leu Gly Lys
            740

<210> SEQ ID NO 159
<211> LENGTH: 527
<212> TYPE: PRT
<213> ORGANISM: Macaca fascicularis

<400> SEQUENCE: 159

Met Tyr Arg Met Gln Leu Leu Ser Cys Ile Ala Leu Ser Leu Ala Leu
1               5                   10                  15

Val Thr Asn Ser Gln Pro Ser Val Ser Pro Gly Glu Pro Ser Pro Pro
            20                  25                  30

Ser Ile His Pro Ala Lys Ser Glu Leu Ile Val Arg Val Gly Asn Glu
        35                  40                  45

Ile Arg Leu Leu Cys Ile Asp Pro Gly Phe Val Lys Trp Thr Phe Glu
    50                  55                  60

Ile Leu Asp Glu Thr Asn Glu Asn Lys Gln Asn Glu Trp Ile Thr Glu
65                  70                  75                  80

Lys Ala Glu Ala Thr Asn Thr Gly Lys Tyr Thr Cys Thr Asn Lys His
                85                  90                  95

Gly Leu Ser Ser Ser Ile Tyr Val Phe Val Arg Asp Pro Ala Lys Leu
            100                 105                 110
```

-continued

Phe Leu Val Asp Arg Ser Leu Tyr Gly Lys Glu Asp Asn Asp Thr Leu
        115                 120                 125

Val Arg Cys Pro Leu Thr Asp Pro Glu Val Thr Ser Tyr Ser Leu Lys
130                 135                 140

Gly Cys Gln Gly Lys Pro Leu Pro Lys Asp Leu Arg Phe Val Pro Asp
145                 150                 155                 160

Pro Lys Ala Gly Ile Thr Ile Lys Ser Val Lys Arg Ala Tyr His Arg
                165                 170                 175

Leu Cys Leu His Cys Ser Ala Asp Gln Glu Gly Lys Ser Val Leu Ser
            180                 185                 190

Asp Lys Phe Ile Leu Lys Val Arg Pro Ala Phe Lys Ala Val Pro Val
        195                 200                 205

Val Ser Val Ser Lys Ala Ser Tyr Leu Leu Arg Glu Gly Glu Glu Phe
210                 215                 220

Thr Val Thr Cys Thr Ile Lys Asp Val Ser Ser Ser Val Tyr Ser Thr
225                 230                 235                 240

Trp Lys Arg Glu Asn Ser Gln Thr Lys Leu Gln Glu Lys Tyr Asn Ser
                245                 250                 255

Trp His His Gly Asp Phe Asn Tyr Glu Arg Gln Ala Thr Leu Thr Ile
            260                 265                 270

Ser Ser Ala Arg Val Asn Asp Ser Gly Val Phe Met Cys Tyr Ala Asn
        275                 280                 285

Asn Thr Phe Gly Ser Ala Asn Val Thr Thr Thr Leu Glu Val Val Asp
    290                 295                 300

Lys Gly Phe Ile Asn Ile Phe Pro Met Ile Asn Thr Thr Val Phe Val
305                 310                 315                 320

Asn Asp Gly Glu Asn Val Asp Leu Ile Val Glu Tyr Glu Ala Phe Pro
                325                 330                 335

Lys Pro Glu His Gln Gln Trp Ile Tyr Met Asn Arg Thr Phe Thr Asp
            340                 345                 350

Lys Trp Glu Asp Tyr Pro Lys Ser Glu Asn Glu Ser Asn Ile Arg Tyr
        355                 360                 365

Val Ser Glu Leu His Leu Thr Arg Leu Lys Gly Thr Glu Gly Gly Thr
370                 375                 380

Tyr Thr Phe Leu Val Ser Asn Ser Asp Val Asn Ala Ser Ile Ala Phe
385                 390                 395                 400

Asn Val Tyr Val Asn Thr Lys Pro Glu Ile Leu Thr Tyr Asp Arg Leu
                405                 410                 415

Val Asn Gly Met Leu Gln Cys Val Ala Ala Gly Phe Pro Glu Pro Thr
            420                 425                 430

Ile Asp Trp Tyr Phe Cys Pro Gly Thr Glu Gln Arg Cys Ser Ala Ser
        435                 440                 445

Val Leu Pro Val Asp Val Gln Thr Leu Asn Ala Ser Gly Pro Pro Phe
450                 455                 460

Gly Lys Leu Val Val Gln Ser Ser Ile Asp Ser Ser Ala Phe Lys His
465                 470                 475                 480

Asn Gly Thr Val Glu Cys Lys Ala Tyr Asn Asp Val Gly Lys Thr Ser
                485                 490                 495

Ala Tyr Phe Asn Phe Ala Phe Lys Gly Asn Asn Lys Glu Gln Ile His
            500                 505                 510

Pro His Thr Leu Phe Thr Pro Arg Ser His His His His His
        515                 520                 525

-continued

```
<210> SEQ ID NO 160
<211> LENGTH: 503
<212> TYPE: PRT
<213> ORGANISM: Homo sapiens

<400> SEQUENCE: 160

Gln Pro Ser Val Ser Pro Gly Glu Pro Ser Pro Ser Ile His Pro
1               5                   10                  15

Gly Lys Ser Asp Leu Ile Val Arg Val Gly Asp Glu Ile Arg Leu Leu
            20                  25                  30

Cys Thr Asp Pro Gly Phe Val Lys Trp Thr Phe Glu Ile Leu Asp Glu
        35                  40                  45

Thr Asn Glu Asn Lys Gln Asn Glu Trp Ile Thr Glu Lys Ala Glu Ala
    50                  55                  60

Thr Asn Thr Gly Lys Tyr Thr Cys Thr Asn Lys His Gly Leu Ser Asn
65                  70                  75                  80

Ser Ile Tyr Val Phe Val Arg Asp Pro Ala Lys Leu Phe Leu Val Asp
                85                  90                  95

Arg Ser Leu Tyr Gly Lys Glu Asp Asn Asp Thr Leu Val Arg Cys Pro
            100                 105                 110

Leu Thr Asp Pro Glu Val Thr Asn Tyr Ser Leu Lys Gly Cys Gln Gly
        115                 120                 125

Lys Pro Leu Pro Lys Asp Leu Arg Phe Ile Pro Asp Pro Lys Ala Gly
    130                 135                 140

Ile Met Ile Lys Ser Val Lys Arg Ala Tyr His Arg Leu Cys Leu His
145                 150                 155                 160

Cys Ser Val Asp Gln Glu Gly Lys Ser Val Leu Ser Glu Lys Phe Ile
                165                 170                 175

Leu Lys Val Arg Pro Ala Phe Lys Ala Val Pro Val Val Ser Val Ser
            180                 185                 190

Lys Ala Ser Tyr Leu Leu Arg Glu Gly Glu Glu Phe Thr Val Thr Cys
        195                 200                 205

Thr Ile Lys Asp Val Ser Ser Ser Val Tyr Ser Thr Trp Lys Arg Glu
    210                 215                 220

Asn Ser Gln Thr Lys Leu Gln Glu Lys Tyr Asn Ser Trp His His Gly
225                 230                 235                 240

Asp Phe Asn Tyr Glu Arg Gln Ala Thr Leu Thr Ile Ser Ser Ala Arg
                245                 250                 255

Val Asn Asp Ser Gly Val Phe Met Cys Tyr Ala Asn Asn Thr Phe Gly
            260                 265                 270

Ser Ala Asn Val Thr Thr Thr Leu Glu Val Val Asp Lys Gly Phe Ile
        275                 280                 285

Asn Ile Phe Pro Met Ile Asn Thr Thr Val Phe Val Asn Asp Gly Glu
    290                 295                 300

Asn Val Asp Leu Ile Val Glu Tyr Glu Ala Phe Pro Lys Pro Glu His
305                 310                 315                 320

Gln Gln Trp Ile Tyr Met Asn Arg Thr Phe Thr Asp Lys Trp Glu Asp
                325                 330                 335

Tyr Pro Lys Ser Glu Asn Glu Ser Asn Ile Arg Tyr Val Ser Glu Leu
            340                 345                 350

His Leu Thr Arg Leu Lys Gly Thr Glu Gly Gly Thr Tyr Thr Phe Leu
        355                 360                 365
```

```
Val Ser Asn Ser Asp Val Asn Ala Ala Ile Ala Phe Asn Val Tyr Val
    370                 375                 380

Asn Thr Lys Pro Glu Ile Leu Thr Tyr Asp Arg Leu Val Asn Gly Met
385                 390                 395                 400

Leu Gln Cys Val Ala Ala Gly Phe Pro Glu Pro Thr Ile Asp Trp Tyr
                405                 410                 415

Phe Cys Pro Gly Thr Glu Gln Arg Cys Ser Ala Ser Val Leu Pro Val
                420                 425                 430

Asp Val Gln Thr Leu Asn Ser Ser Gly Pro Pro Phe Gly Lys Leu Val
            435                 440                 445

Val Gln Ser Ser Ile Asp Ser Ser Ala Phe Lys His Asn Gly Thr Val
    450                 455                 460

Glu Cys Lys Ala Tyr Asn Asp Val Gly Lys Thr Ser Ala Tyr Phe Asn
465                 470                 475                 480

Phe Ala Phe Lys Glu Gln Ile His Pro His Thr Leu Phe Thr Pro Arg
                485                 490                 495

Ser His His His His His His
            500

<210> SEQ ID NO 161
<211> LENGTH: 11
<212> TYPE: PRT
<213> ORGANISM: Homo sapiens

<400> SEQUENCE: 161

Val Phe Val Arg Asp Pro Ala Lys Leu Phe Leu
1               5                   10

<210> SEQ ID NO 162
<211> LENGTH: 12
<212> TYPE: PRT
<213> ORGANISM: Homo sapiens

<400> SEQUENCE: 162

His Cys Ser Val Asp Gln Glu Gly Lys Ser Val Leu
1               5                   10
```